(12) United States Patent
Hu et al.

(10) Patent No.: US 11,833,137 B2
(45) Date of Patent: Dec. 5, 2023

(54) SUBSTITUTED CHROMENONES, IRE1 INHIBITORS, AND METHODS OF USING SAME

(71) Applicants: The Wistar Institute, Philadelphia, PA (US); University of South Florida, Tampa, FL (US)

(72) Inventors: Chih-Chi Andrew Hu, Philadelphia, PA (US); Juan R. Del Valle, Tampa, FL (US)

(73) Assignees: The Wistar Institute, Philadelphia, PA (US); University of South Florida, Tampa, FL (US)

( * ) Notice: Subject to any disclaimer, the term of this patent is extended or adjusted under 35 U.S.C. 154(b) by 252 days.

(21) Appl. No.: 17/041,529

(22) PCT Filed: Apr. 1, 2019

(86) PCT No.: PCT/US2019/025122
§ 371 (c)(1),
(2) Date: Sep. 25, 2020

(87) PCT Pub. No.: WO2019/195135
PCT Pub. Date: Oct. 10, 2019

(65) Prior Publication Data
US 2021/0008043 A1  Jan. 14, 2021

Related U.S. Application Data

(60) Provisional application No. 62/651,206, filed on Apr. 1, 2018, provisional application No. 62/651,201, filed on Apr. 1, 2018.

(51) Int. Cl.
| | | |
|---|---|---|
| *A61K 31/436* | (2006.01) | |
| *A61P 35/00* | (2006.01) | |
| *A61K 31/519* | (2006.01) | |
| *A61K 45/06* | (2006.01) | |
| *C07D 491/052* | (2006.01) | |

(52) U.S. Cl.
CPC .......... *A61K 31/436* (2013.01); *A61K 31/519* (2013.01); *A61K 45/06* (2013.01); *A61P 35/00* (2018.01); *C07D 491/052* (2013.01)

(58) Field of Classification Search
None
See application file for complete search history.

(56) References Cited

U.S. PATENT DOCUMENTS

| | | | |
|---|---|---|---|
| 2016/0083361 A1* | 3/2016 | Del Valle | A61K 31/395 514/249 |
| 2017/0144997 A1 | 5/2017 | Chen et al. | |
| 2017/0253590 A1 | 9/2017 | Glimcher et al. | |
| 2018/0059115 A1 | 3/2018 | Gabrilovich et al. | |

OTHER PUBLICATIONS

STN Next RN Record 2014 (Year: 2014).*
Tang et al. "Inhibition of ER stress-associated IRE-1/XBP-1 pathway reduces leukemic cell survival," J Clin Invest. 2014;124(6):2585-2598 (Year: 2014).*
International Search Report and Written Opinion, PCT/US2019/025122, dated Jun. 27, 2019.
Tang, et al., "Abstract 4756: Secretory IgM exacerbates tumor progression by inducing accumulations of myeloid-derived suppressor cells in mice", Cancer Research, vol. 78, Iss. 13 Supplement, Jul. 1, 2018 [retrieved on May 20, 2019] Retrieved from the internet: <URL: http://cancerres.aacrjournals.org/content/78/13_Supplemental/4756.short>.

* cited by examiner

*Primary Examiner* — Jeffrey S Lundgren
*Assistant Examiner* — Michael J Schmitt
(74) *Attorney, Agent, or Firm* — Saul Ewing LLP; Kathryn Doyle; Domingos J. Silva

(57) ABSTRACT

The present invention includes substituted chromenones that are useful to inhibit the IRE1/XBP-1 pathway. In certain embodiments, the compounds of the invention inhibit IRE1's RNase activity. In other embodiments, the compounds of the invention are useful to treat or prevent a cancer that involve activation of the ER stress response. The invention also relates, in certain aspects, to the discovery that secretory IgM (sIgM) can orchestrate an immunosuppressive microenvironment by recruiting myeloid-derived suppressor cells (MDSCs) into different tumor models, such as but not limited to solid tumors (such as but not limited to lung cancer) and tumors that have high levels of secreted IgM. In certain embodiments, sIgM produced by B cells or CLL cells can contribute to the accumulation of MDSCs in a tumor. In other embodiments, inhibition of the IRE1/XBP-1 pathway can ablate, minimize, or reduce MDSC levels in a tumor.

20 Claims, 80 Drawing Sheets

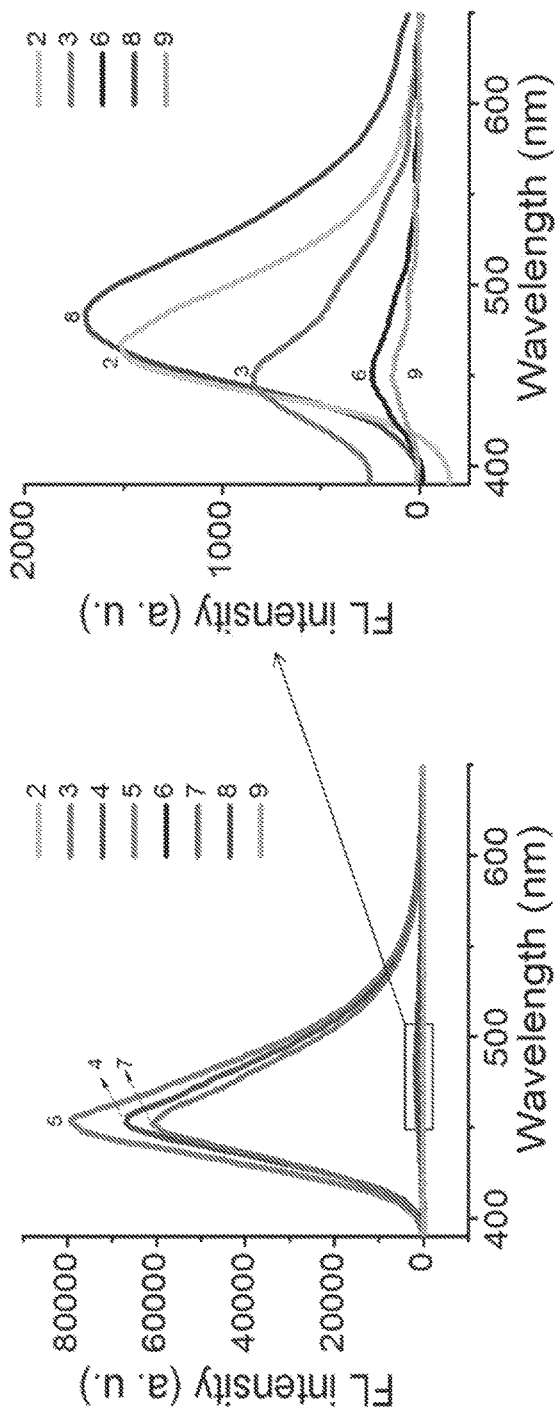
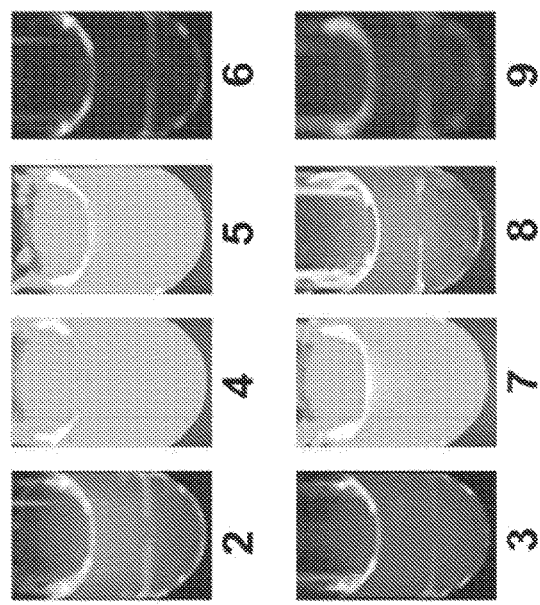
FIG. 1E
FIG. 1F
FIG. 1G $R^1$ = Amine substituent moiety
$R^2$ = Different protective group
$R^3$ = -OCH$_3$

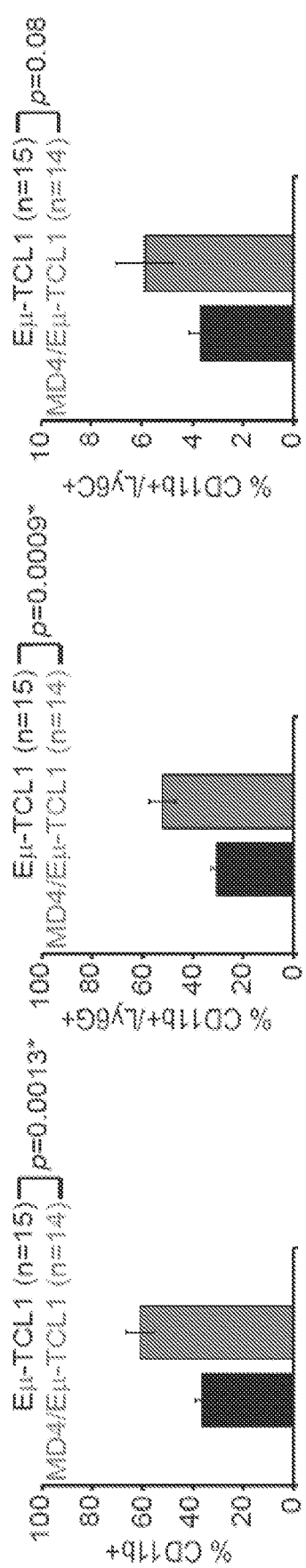
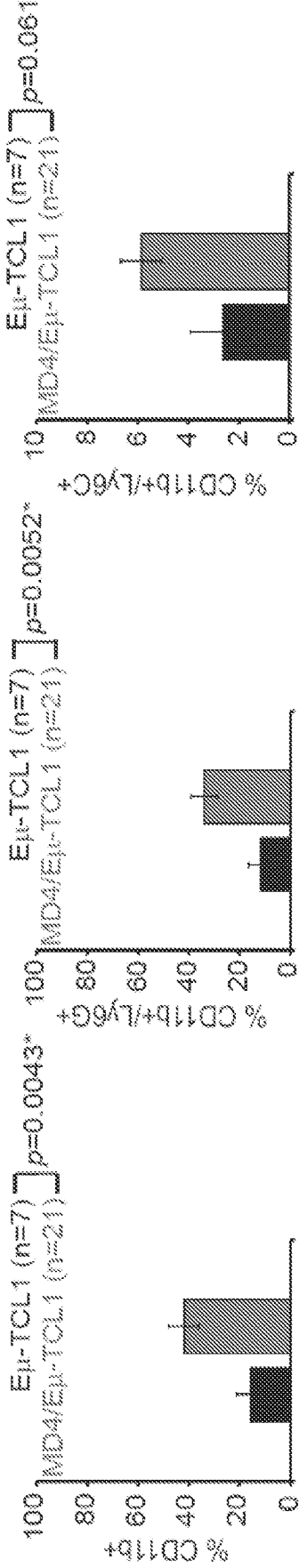
FIG. 21E  FIG. 21F  FIG. 21G
FIG. 21H  FIG. 21I  FIG. 21J

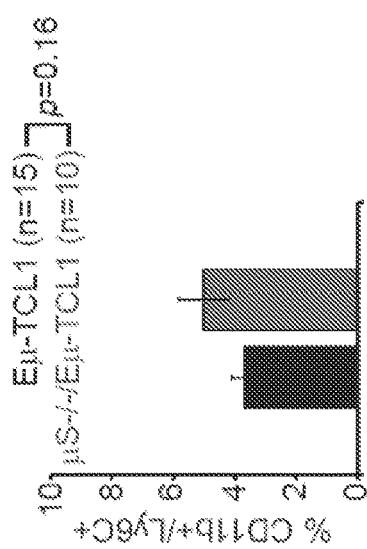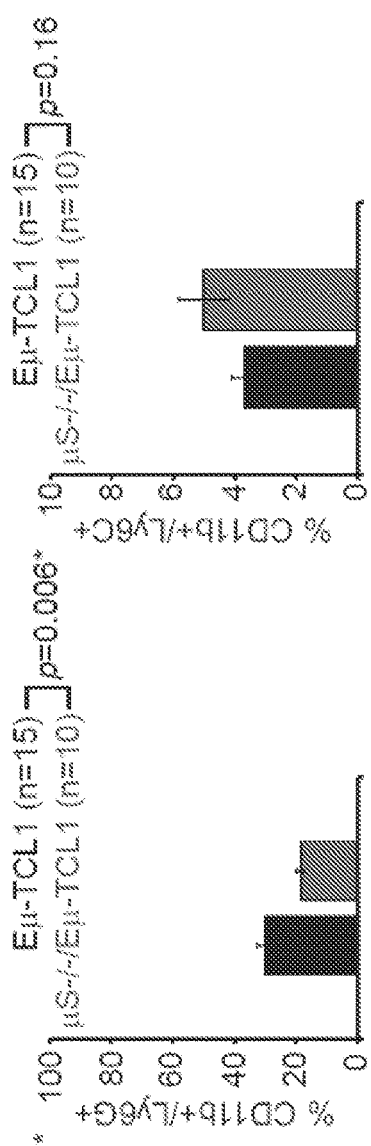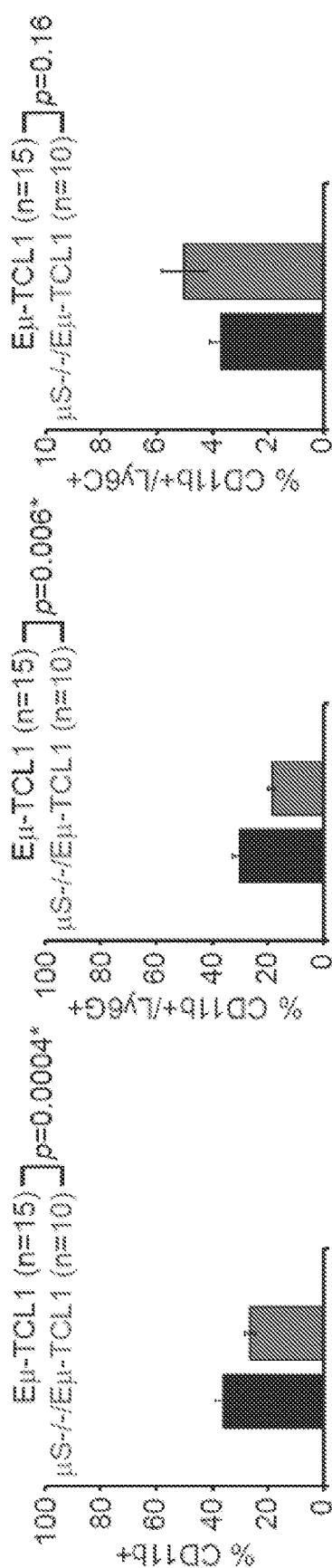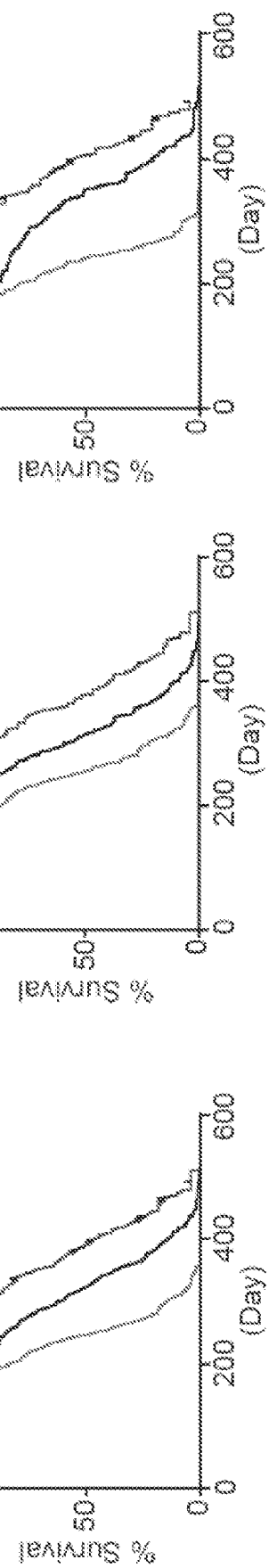
FIG. 22D  FIG. 22E  FIG. 22F
FIG. 22G  FIG. 22H  FIG. 22I

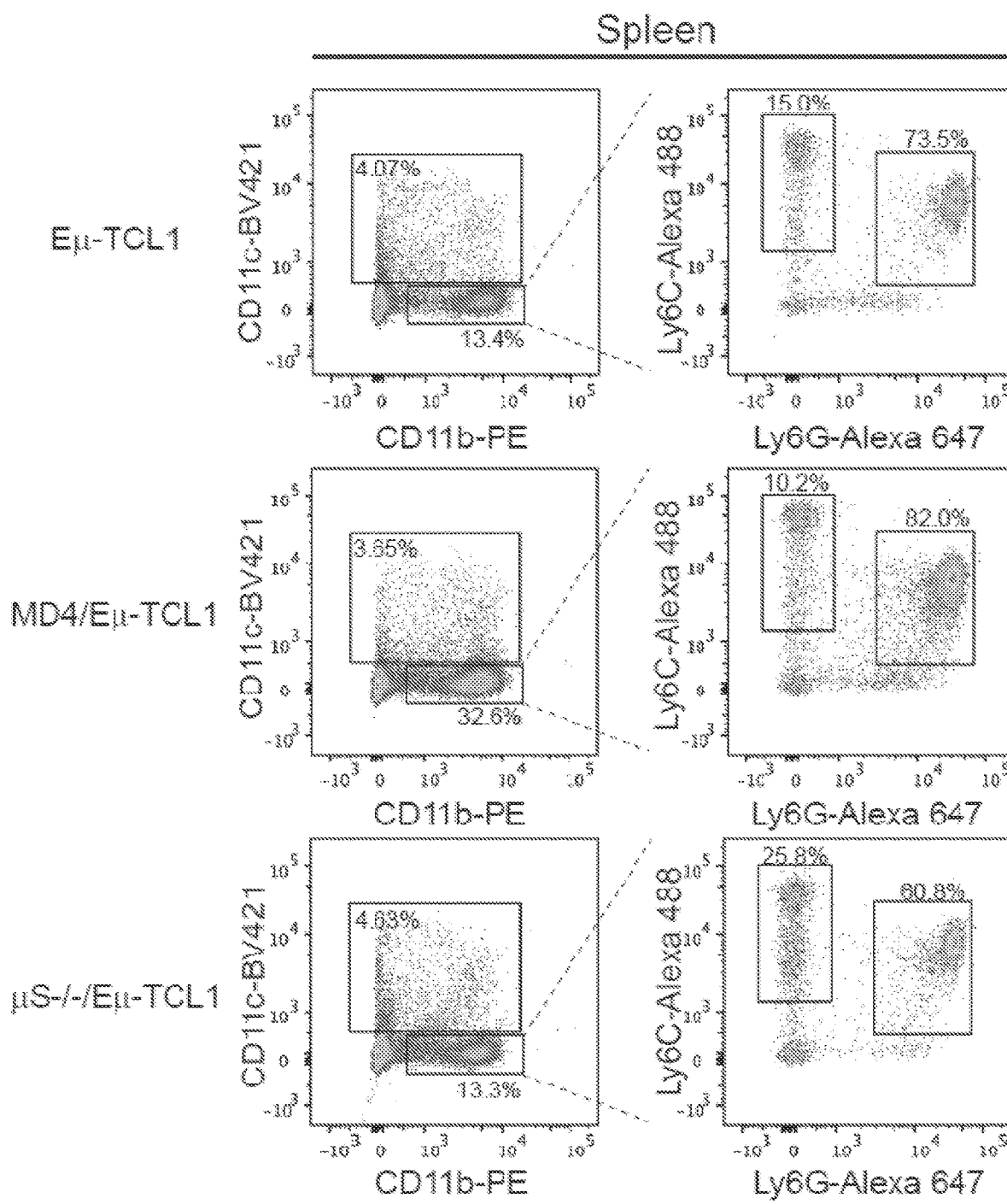

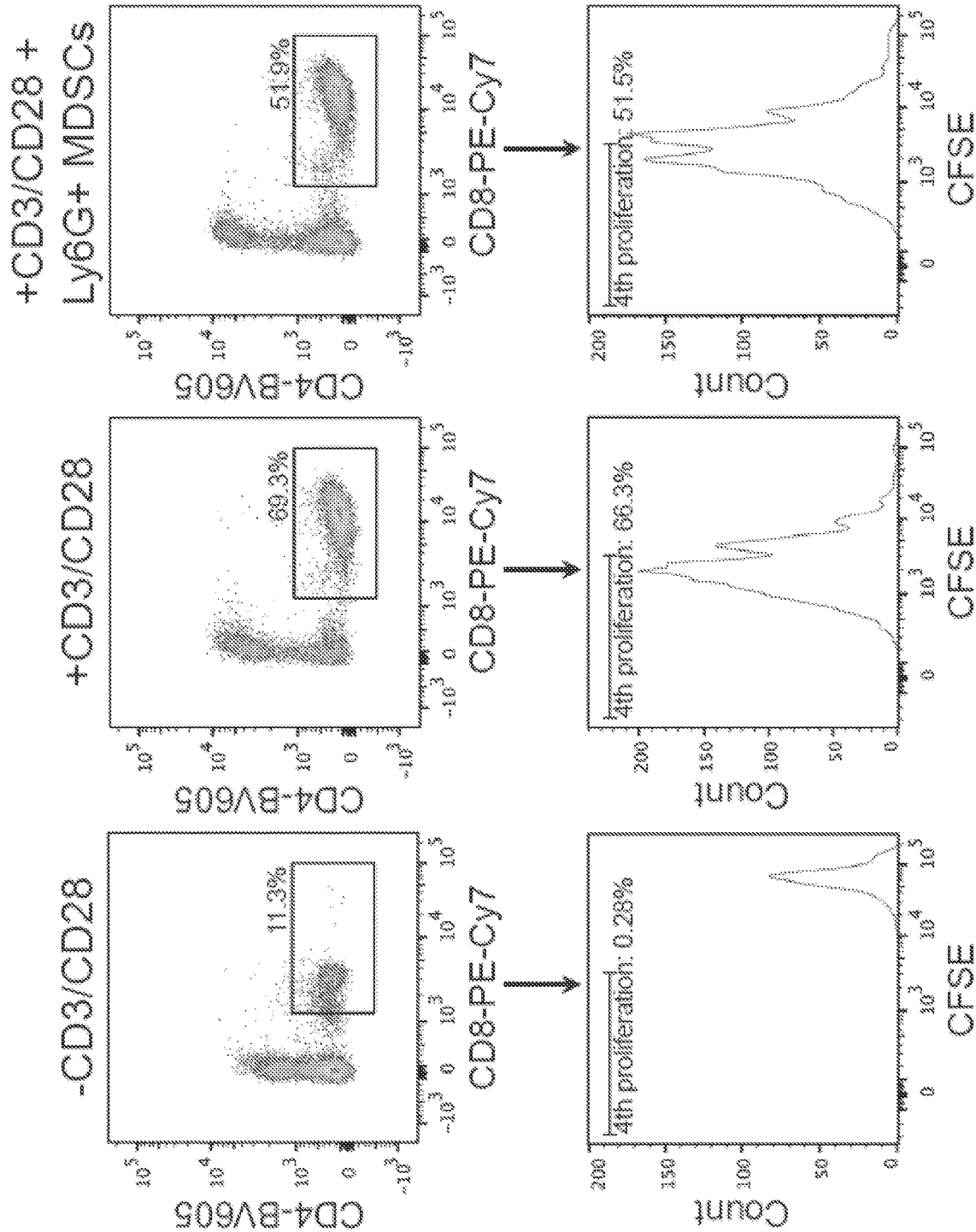

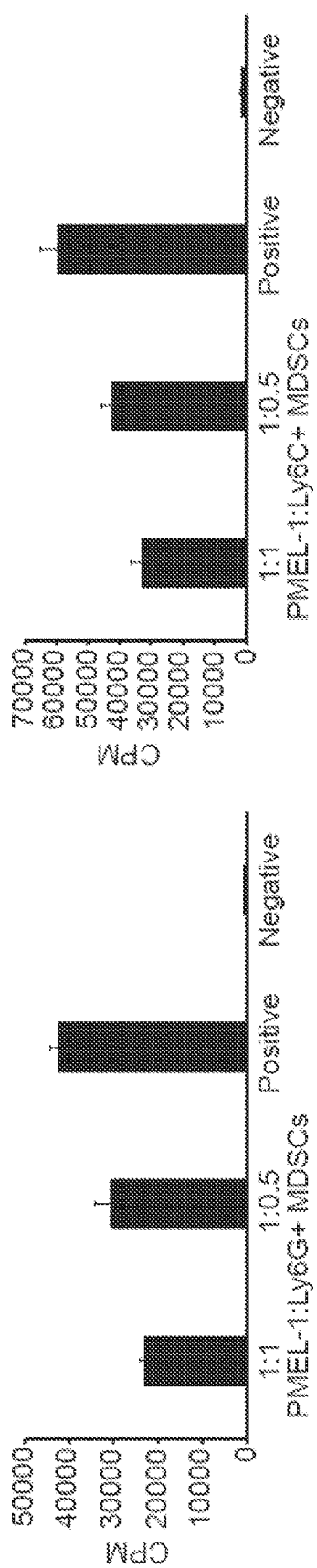
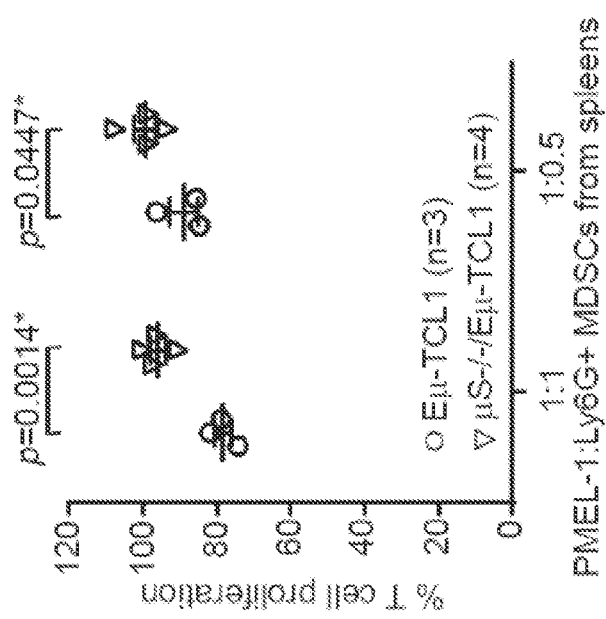
FIG. 23F
FIG. 23G
FIG. 23H

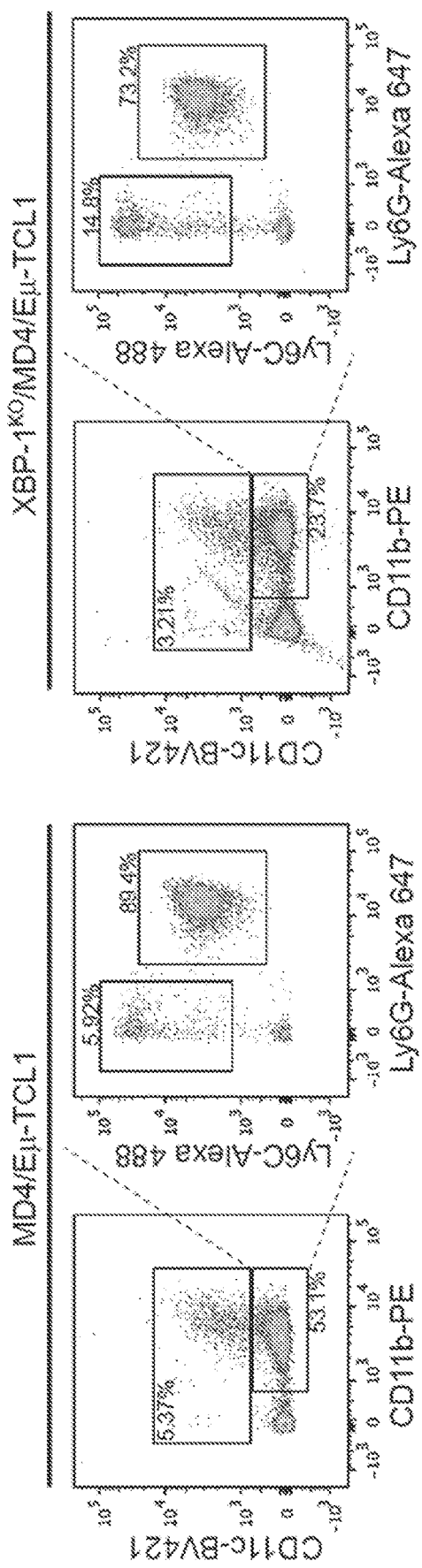
FIG. 24B
FIG. 24C
FIG. 24D

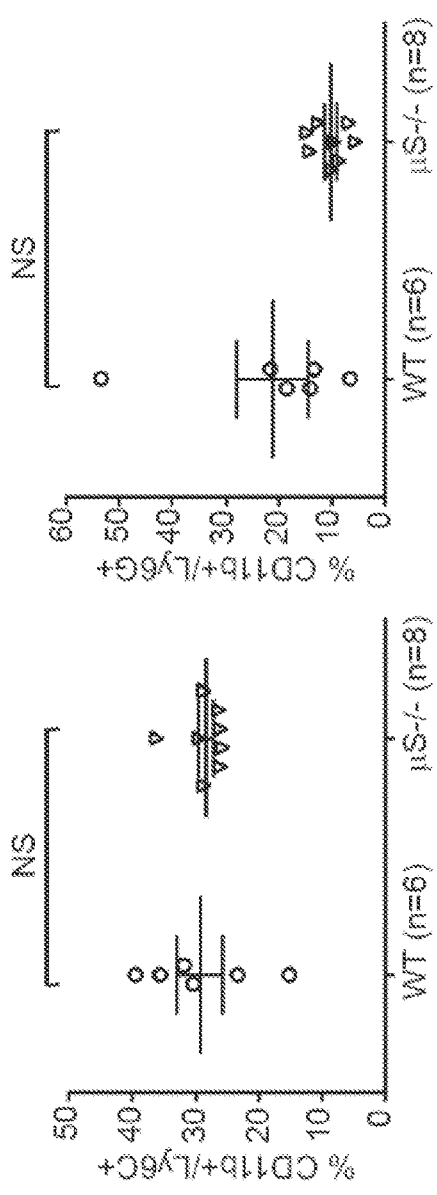
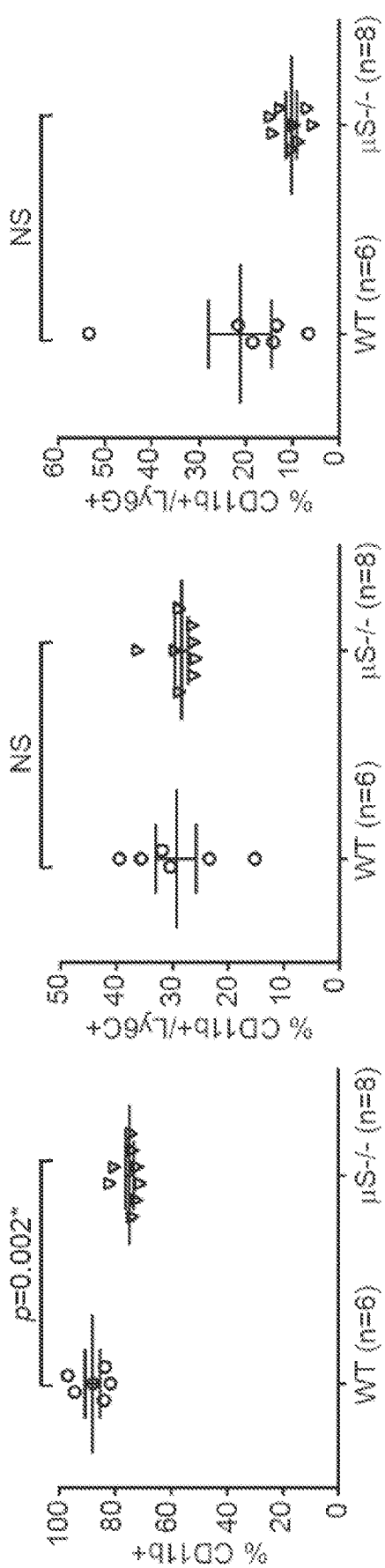
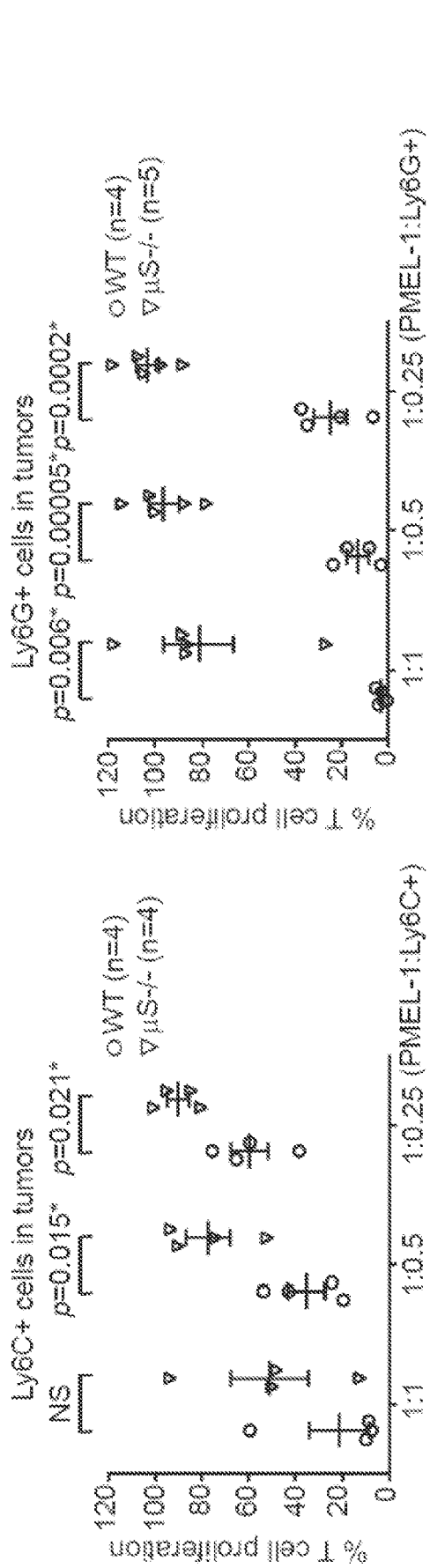
FIG. 25D  FIG. 25E  FIG. 25F  FIG. 25G  FIG. 25H

SUBSTITUTED CHROMENONES, IRE1 INHIBITORS, AND METHODS OF USING SAME

CROSS-REFERENCE TO RELATED APPLICATIONS

This application is a 35 U.S.C. § 371 national phase application from, and claiming priority to, International Application No. PCT/US2019/025122, filed Apr. 1, 2019, which claims priority under 35 U.S.C. § 119(e) of U.S. Provisional Patent Application Ser. No. 62/651,201, filed Apr. 1, 2018, and U.S. Provisional Patent Application Ser. No. 62/651,206, filed Apr. 1, 2018, all of which applications are incorporated herein by reference in their entireties.

STATEMENT REGARDING FEDERALLY SPONSORED RESEARCH OR DEVELOPMENT

This invention was made with government support under grant numbers CA163910, CA199553, CA190860, and CA100062 awarded by the National Institutes of Health. The government has certain rights in the invention.

BACKGROUND OF THE INVENTION

Cellular stress phenotypes in cancer result from the increased rates of metabolism, mitosis, protein synthesis, and DNA damage associated with tumor progression. Cytoprotective signaling pathways activated in response to these phenotypes have emerged as important non-oncogenic targets for therapy. The endoplasmic reticulum (ER) stress response is frequently hyperactivated in cancer due to an accumulation of unfolded proteins, hypoxic conditions, calcium imbalance, and other stimuli. Of note, the ER stress response can also be activated in response to the overexpression of oncogenes. The three branches of ER stress response are governed by the stress sensor proteins IRE-1, ATF6, and PERK.

Inositol-requiring enzyme 1 (denoted as IRE1 or IRE-1) is an endoplasmic reticulum (ER)-transmembrane protein and plays an essential role in the unfolded protein response (UPR) pathway, which is responsible for sensing and responding to ER stress. IRE1 contains an ER luminal stress-sensing domain and a cytoplasmic-facing RNase domain. Misfolded substrates activate IRE1, causing its oligomerization and activating its RNase activity. The main function of IRE1's RNase activity is the splicing of the transcription factor XBP1 mRNA (thus encoding a functional 54-kDa XBP-1s transcription factor). Splicing of XBP1 allows for the translation of functional transcription factor and the upregulation of target genes, including ER chaperones and ER-associated degradation components.

Chronic lymphocytic leukemia (CLL) represents 30% of adult leukemia and is an incurable B cell malignancy. Malignant CLL cells use a limited repertoire of immunoglobulin heavy and light chain genes to manufacture their B cell receptors (BCR), and are very responsive to in vitro anti-IgM stimulation. It is thus likely that antigen stimulation drives malignant progression of CLL. Unlike in multiple myeloma, leukemia and lymphoma cells do not expand their ERs. However, CLL was shown to require activation of the ER stress response for their survival. Thus, it is possible that inhibition of the ER stress response can be used to inhibit or kill these cancerous cells. In particular, the specific XBP-1 activation mechanism renders IRE1 a potential target for therapeutic intervention for cancer.

BCR signaling plays a critical role in supporting the survival of CLL cells, and targeting the BCR signaling molecules such as spleen tyrosine kinase (Syk) or Bruton's tyrosine kinase (BTK) has been proven useful to control human and mouse CLL.

The expression of the proto-oncoprotein, TCL1, is found in 90% of human CLL patients. Clinically, TCL1 overexpression is associated with constitutive BCR signal transduction, which allows CLL cells to undergo high-rate proliferation. The Eµ-TCL1 transgenic mouse was established with the TCL1 gene under the control of an immunoglobulin heavy chain promoter/enhancer to drive TCL1 overexpression in B cells. These mice develop CD19+/IgM+/B220$^{low}$/CD5+ CLL cells in the blood, spleen, lymph nodes, and bone marrow, and slowly progress to the full-blown monoclonal CLL stage with all clinical features of aggressive human CLL. CLL progress much slowly in Eµ-TCL1/IgHEL mice in which Eµ-TCL1 B cells also express the MD4 transgene to allow for the expression of a monoclonal BCR against hen egg lysozyme (HEL). The MD4 transgene allows Eµ-TCL1 B cells to produce not only HEL-reactive monoclonal BCR but also secretory IgM (sIgM). The role of sIgM in the progression of CLL has not been investigated.

Tumor growth was shown to decelerate in C57BL/6×C3H F1 mice injected with rabbit anti-mouse IgM serum to deplete B cells. When comparing SCID mice reconstituted with T cells or with both T and B cells, tumors were found to grow slower in and rejected more frequently by mice deficient of B cells. Mice deleted with an exon of the membrane-bound IgM are incapable of producing B cells. When these B-deficient mice were implanted with EL4 thymoma, MC38 colon carcinoma or B16 melanoma, significantly slower growth of all three tumors were observed. By crossing squamous cell carcinoma mouse model (K14-HPV16) with RAG-1$^{-/-}$ mice deficient for mature B and T cells, the growth of skin cancer was significantly slowed in HPV16/RAG-1$^{-/-}$ mice. Transfer of B cells or serum from HPV16 mice into HPV16/RAG-1$^{-/-}$ mice restored skin cancer growth. While B cells did not infiltrate premalignant HPV16 skin, IgG was later shown to engage IgG receptors (FcγRs) on mast cells and macrophages to promote squamous carcinogenesis. Although dendritic cells and myeloid-derived suppressor cells (MDSCs) express FcγRs, they do not exhibit immunosuppressive effects in this skin cancer mode.

MDSCs are pathologically activated immunosuppressive myeloid cells. Monocytic MDSCs (M-MDSCs) are morphologically and phenotypically similar to monocytes. Granulocytic MDSCs (G-MDSCs), also known as polymorphonuclear MDSC (PMN-MDSC), are morphologically and phenotypically similar to neutrophils. In mice, M-MDSCs and G-MDSCs are CD11b+/Ly6C+/Ly6G− and CD11b+/Ly6C$^{low}$/Ly6G+ populations, respectively. MDSC-mediated immunosuppressive effects are localization-dependent. Abundant evidence supports a close association between MDSC accumulations and clinical outcomes in human patients with various types of cancer, including CLL. While MDSCs can suppress the functions of immune cells, emerging new data in two studies suggest that MDSCs can be regulated by tumor-associated B cells or CLL cells.

There is thus a need in the art for the identification of novel compounds and compositions that can be used to treat and/or prevent cancer in a subject. In certain embodiments, such cancer is dependent on ER stress response. In other embodiments, the compound or composition inhibits IRE1 RNase activity. In certain embodiments, such cancers are characterized by secreted immunosuppressive agents. The present invention addresses this need.

BRIEF DESCRIPTION OF THE DRAWINGS

The following detailed description of illustrative embodiments of the invention will be better understood when read in conjunction with the appended drawings. For the purpose of illustrating the invention, certain illustrative embodiments are shown in the drawings. It should be understood, however, that the invention is not limited to the precise arrangements and instrumentalities of the embodiments shown in the drawings.

FIGS. 1A-1G illustrate potent tricyclic chromenone inhibitors of IRE1 that were developed by installing various amine substituents and protective moieties. IRE1 inhibitors with 1,3-dioxane acetal protective groups emit strong fluorescence. (FIG. 1A) Chemical structures of 1, 2, and 3 with different amine substituent groups ($R^1$). (FIG. 1B) Recombinant puritin-His-IRE-1 was immobilized to a CMS sensor chip using an amine coupling kit (GE Healthcare) and single-cycle kinetics were run by sequential injection of 2 or 3. Data fitted with a 1:1 binding model were used to determine the $K_d$ values. (FIG. 1C) 5TGM1 cells were treated with 1, 2, and 3 at 10 μM for 0, 3, 6, 12, or 24 h, lysed, and analyzed for indicated proteins by immunoblots. (FIG. 1D) Chemical structures of derivatives of 2 and 3 carrying different protecting groups ($R^2$). (FIG. 1E) The fluorescence intensity of 2 and 3 derivatives with different protecting groups in aqueous solution was measured from 380 to 650 nm (10 μM, DMSO/PBS mixture (v/v=1:99), $E_x$=360 nm). (FIG. 1F) The enlarged fluorescence spectra of 2, 3, 6, 8, and 9 in aqueous solution (10 μM, DMSO/PBS mixture (v/v=1:99), $E_x$=360 nm) were shown. (FIG. 1G) Fluorescence images of 2 and 3 derivatives with different protecting groups in aqueous solution (10 μM, DMSO/PBS mixture (v/v=1:99)) were illuminated at 365 nm.

(FIG. 2A) 5TGM1 cells were treated with 2, 4, 3, or 7 at 10 μM for a course of 3 days, lysed, and analyzed for indicated proteins by immunoblots. (FIG. 2B) 5TGM1 cells were treated with DMSO or with 20 μM 2, 4, 3, or 7 dissolved in DMSO for 3 days and subjected to XTT assays. Percentages of growth were determined by comparing treated groups with control groups (DMSO). Each data point derived from four independent groups receiving exactly the same treatment was plotted as mean±SD. Results are representative of three independent experiments. (FIG. 2C) 5TGM1 cells were treated with 4 or 5 using indicated concentrations for 24 h, lysed, and analyzed for indicated proteins by immunoblots. (FIG. 2D) Fluorescence stability of 4 in aqueous solution at 37° C. from 0 to 48 h (10 μM, DMSO/PBS mixture (v/v=1:99), $E_x$=360 nm). The values of $I/I_0$ were plotted as a function of time and shown in the inset. $I_0$ was the initial fluorescence intensity of 4 at 0 h. (FIG. 2E) Fluorescence stability of 5 in aqueous solution at 37° C. from 0 to 48 h (10 μM, DMSO/PBS mixture (v/v=1:99), $E_x$=360 nm). The values of $I/I_0$ were plotted as a function of time and shown in the inset. $I_0$ was the initial fluorescence intensity of 5 at 0 h. (FIG. 2F) 5TGM1 cells were treated with 6, 4, 7, 8, or 9 at 2.5 μM for 1, 2, or 4 h, lysed, and analyzed for indicated proteins by immunoblots. (FIG. 2G) The decomposition rates of 7 and 8 were plotted as a function of time in RPMI media incubated at 37° C. Aliquots were analyzed by HPLC and the peaks integrated.

(FIG. 3A) Chemical structures of IRE1 inhibitors carrying a methoxy group. (FIG. 3B) 5TGM1 cells were treated with 3, 8 or 10 at 2.5 μM for 1, 2, or 4 h, lysed, and analyzed for indicated proteins by immunoblots. (FIG. 3C) 5TGM1 cells were treated with 3, 8 or 10 at 10 μM for a course of 3 days, lysed, and analyzed for indicated proteins by immunoblots. (FIG. 3D) 5TGM1 cells were treated with indicated inhibitors at 10 μM for a course of 3 days, lysed, and analyzed for indicated proteins by immunoblots. (FIG. 3E) 5TGM1 cells were treated with DMSO or with 20 μM 3, 7 or D-F07 dissolved in DMSO for 3 days and subjected to XTT assays. Percentages of growth were determined by comparing treated groups with control groups (DMSO). Each data point derived from four independent groups receiving exactly the same treatment was plotted as mean±SD. Results are representative of three independent experiments. (FIG. 3F) WaC3 cells were treated for 3 days with DMSO or with 20 μM 7, 8, 10 or D-F07 dissolved in DMSO and subjected to XTT assays. Percentages of growth were determined by comparing treated groups with control groups (DMSO). Each data point derived from four independent groups receiving the same treatment was plotted as means±SD. Results are representative of three independent experiments. (FIG. 3G) The fluorescence intensity of 10, 11 and D-F07 was measured in aqueous solution (10 μM, DMSO/PBS mixture (v/v=1:99), $E_x$=360 nm).

(FIG. 4A) A scheme showing that installation of a photo-caged group to the hydroxyl group of D-F07 completely stabilizes the 1,3-dioxane acetal protective group to allow for UV-mediated release of intact D-F07. (FIG. 4B) The fluorescence of PC-D-F07 (10 μM in DMSO/PBS solution (v/v=1:99), $E_x$=360 nm) can be gradually 'turned on' by increasing exposure time to UV irradiation (0.55 W/cm²). The inset shows gradually enhanced blue fluorescence images, resulted from gradually liberated D-F07 by UV irradiation. (FIG. 4C) 5TGM1 cells were treated with D-F07 or PC-D-F07 at 10 μM, immediately subjected to UV irradiation (0.55 W/cm²) for 0, 3, 5, or 10 min, cultured for additional 4 h, lysed, and analyzed for indicated proteins by immunoblots. (FIG. 4D) 5TGM1 cells were treated with DMSO or PC-D-F07 (10 μM) for 4 h, washed with PBS for 3 times, fixed and analyzed by confocal microscopy. The fluorescence spectrum-scan was recorded in the range of 498-650 nm, $\lambda_{ex}$=488 nm. Scale bar=10 μm. (FIG. 4E) The fluorescence intensities in the cytoplasmic regions of 95 DMSO-treated (control) and 185 PC-D-F07-treated 5TGM1 cells with unsaturated fluorescence were used to calculate for the averaged fluorescence intensities. The fluorescence intensities at 10 s (I) were compared with background fluorescence at 0 s ($I_0$, DAPI filtered). Data ($I/I_0$) were plotted as mean±SD. (FIGS. 4F-4G) The decomposition rates of D-F07 and PC-D-F07 were plotted as a function of time in PBS (FIG. 4F) or RPMI media (FIG. 4G) at 37° C. Aliquots were analyzed by HPLC and the peaks integrated. (FIG. 4H) 5TGM1 cells were treated with D-F07 or PC-D-F07 at 10 μM for 4 h, washed three times with cold PBS, resuspended in fresh RPMI media, subjected to UV irradiation (4 W, 1 mW/cm²) for 10 min, cultured for additional 8 h, lysed, and analyzed for indicated proteins by immunoblots.

(FIG. 5A) A scheme showing that installation of a boronate-caged group stabilizes the 1,3-dioxane acetal protective group to allow for $H_2O_2$-mediated release of intact D-F07. (FIG. 5B) The fluorescence of BC-D-F07a (2.5 µM in the DMSO/PBS solution (v/v=1:99), $E_x$=360 nm) increases upon incubation with 0 to 200 µM hydrogen peroxide at room temperature for 1 h. (FIG. 5C) The fluorescence of BC-D-F07b (2.5 µM in the DMSO/PBS solution (v/v=1:99), $E_x$=360 nm) increases upon incubation with 0 to 2 mM hydrogen peroxide at 37° C. for 1 h. (FIG. 5D) Fluorescence stability of D-F07, BC-D-F07a and BC-D-F07b at 37° C. was monitored from 0 to 48 h (10 µM, DMSO/PBS mixture (v/v=1:99), $E_x$=360 nm). $I_0$ was the initial fluorescence intensity of D-F07, BC-D-F07a or BC-D-F07b at 0 h. (FIG. 5E) The levels of hydrogen peroxide produced by 5TGM1, 72-h LPS-stimulated primary CLL, MEC2, and WaC3 cells were measured by Amplex Red with or without the addition of extracellular catalase (500 U/mL). (FIG. 5F) 5TGM1 cells were treated with BC-D-F07a at increasing concentrations for 24 h, lysed, and analyzed for the expression of indicated proteins by immunoblots. (FIG. 5G) CD5+ CLL cells purified from spleens of Eµ-TCL1 mice were stimulated with LPS or 48 h, subsequently treated with BC-D-F07a at 20 µM for 16 h, and then incubated with hydrogen peroxide at indicated concentrations for another 4 h. Cells were lysed and analyzed for the expression of indicated proteins by immunoblots. (FIG. 5H) MEC2 cells were treated with BC-D-F07a at 20 µM for 16 h and subsequently incubated with hydrogen peroxide at indicated concentrations for additional 4 h. Cells were lysed and analyzed for the expression of indicated proteins by immunoblots. (FIGS. 5I-5J) 5TGM1 (I) or MEC2 (J) cells were treated with DMSO, 20 µM D-F07 or 20 µM BC-D-F07a for 2 days, and subjected to XTT assays. Percentages of growth were determined by comparing treated groups with control groups (DMSO). Each data point derived from four independent groups receiving the same treatment was plotted as means±SD. Results are representative of three independent experiments.

(FIG. 6A) A schematic diagram showing that installation of a thiol-reactive cage on the hydroxy group can stabilize the 1,3-dioxane acetal protecting group and allow for thiol-mediated release of D-F07. (FIG. 6B) The fluorescence of TC-D-F07 (2.5 µM in DMSO/PBS solution (v/v=1:99), $E_x$=360 nm) increases upon incubation with 0 to 1 mM GSH at room temperature for 10 min. (FIG. 6C) Fluorescence readouts of TC-D-F07 (2.5 µM in DMSO/PBS solution (v/v=1:99), $E_x$=360 nm) after incubation with increasing concentrations of cysteine, GSH, methionine and glycine at room temperature for 10 min. $I_0$ was the initial fluorescence intensity of TC-D-F07 at 2.5 µM. (FIG. 6D) The decomposition rates of D-F07 and TC-D-F07 were plotted as a function of time in PBS at 37° C. Aliquots were analyzed by HPLC and the peaks integrated. (FIG. 6E) 5TGM1 cells were treated with TC-D-F07 at indicated concentrations for 3 h, lysed, and analyzed for the expression of indicated proteins by immunoblots. (FIG. 6F) 5TGM1 cells were treated with D-F07 or TC-D-F07 at indicated concentrations for 0, 3, 6, or 12 h, lysed, and analyzed for the expression of indicated proteins by immunoblots. (FIG. 6G) 5TGM1 cells were treated with TC-D-F07 or 12 at 10 µM for 0, 3, 6, 12, or 24 h, lysed, and analyzed for the expression of indicated proteins by immunoblots. (FIG. 6H) 5TGM1 or (FIG. 6I) MEC2 cells were treated with DMSO, D-F07, TC-D-F07, or 12 at indicated concentrations for 24 h, and subjected to XTT assays. Percentages of growth were determined by comparing treated groups with control groups (DMSO). Each data point derived from four independent groups receiving the same treatment was plotted as means±SD. Results are representative of three independent experiments. (FIG. 6J) Compound concentrations in serum samples from three mice after a single intraperitoneal injection of D-F07 or TC-D-F07 were plotted as means±SEM (p<0.05 was asterisked).

(FIG. 19A) Splenocytes isolated from MD4$^{+/-}$/Eµ-TCL1$^{+/+}$ mice of indicated age groups were stained with CD3-APC-Cy7, IgM-PE-Cy7, CD5-APC, B220-FITC, HEL-Alexa 568 and DAPI. Live splenocytes were analyzed for precancerous CD5−/B220+ B cells and CD5+/B220+ CLL cells on gated CD3−/IgM+ B cell populations. CD5−/B220+ B cells (red line) and CD5+/B220$^{lo}$ CLL cells (blue line) were further analyzed for their HEL-binding capability, shown in the histograms. (FIG. 19B) A representative enlarged spleen of 8-month-old MD4$^{+/-}$/Eµ-

Figure 1A:
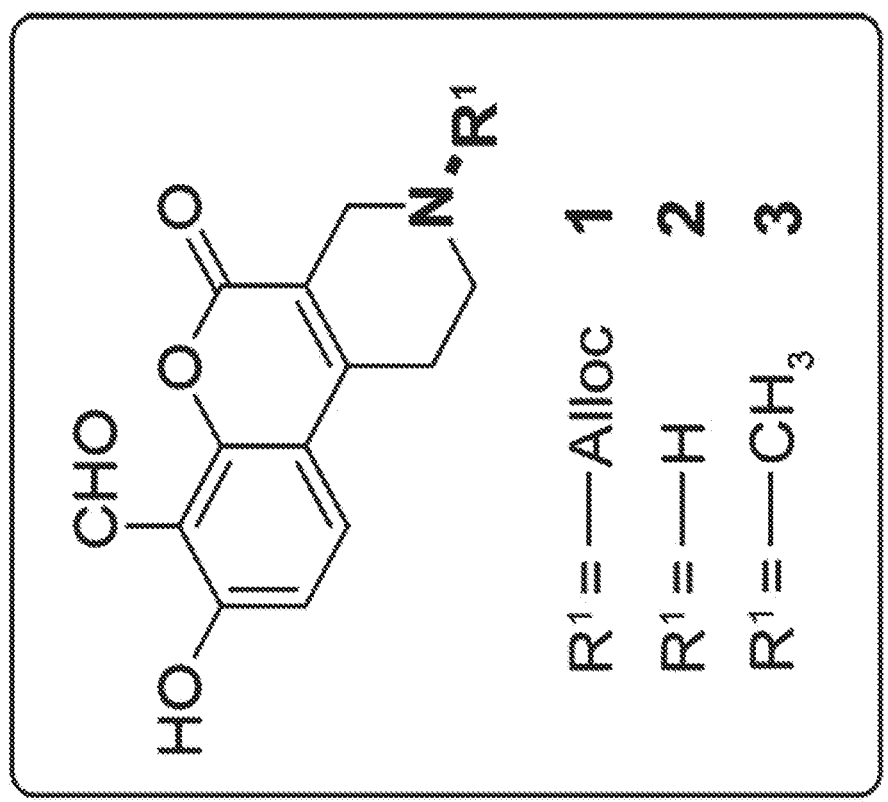

TCL1$^{+/+}$ mice (right), compared with a representative spleen from 6-week-old MD4$^{+/-}$/Eμ-TCL1$^{+/+}$ mice (left).

FIGS. 20A-20D illustrate the finding that MD4$^{+/-}$/Eμ-TCL1$^{+/+}$ CLL cells can be activated by F(ab')2 and secrete IgM. (FIG. 20A) CD5−/B220+ B cells purified from 6-week-old MD4$^{+/-}$ and MD4$^{+/-}$/Eμ-TCL1$^{+/+}$ mice were stimulated with oligomeric HEL (5 μg/mL) for indicated times, and lysed for analysis of indicated proteins by immunoblots. (FIG. 20B) CD5−/B220+ B cells purified from 3-month-old MD4$^{+/-}$ and MD4$^{+/-}$/Eμ-TCL1$^{+/+}$ mice were stimulated with oligomeric HEL (5 μg/mL) for indicated times, and lysed for analysis of indicated proteins by immunoblots. (FIG. 20C) CD5−/B220+ B cells purified from 6-week-old MD4$^{+/-}$/Eμ-TCL1$^{+/+}$ mice and CD5+/B220+ CLL cells from 11-month-old CLL-bearing MD4$^{+/-}$/Eμ-TCL1$^{+/+}$ mice were stimulated with F(ab')2 (20 μg/mL) for indicated time, and lysed for analysis of indicated proteins by immunoblots. (FIG. 20D) CD5−/B220+ B cells were purified from 7-month-old MD4$^{+/-}$ mice and 8-week-old MD4$^{+/-}$/Eμ-TCL1$^{+/+}$ mice. CD5+/B220+ CLL cells were purified from 7-month-old CLL-bearing MD4$^{+/-}$/Eμ-TCL1$^{+/+}$ mice. These cells were treated with CpG-1826 (0.5 μM) or LPS (20 μg/mL) for 3 days, and lysed for analysis of indicated proteins. Data in this figure are representative of three independent experiments.

FIGS. 21A-21J illustrate the finding that MD4$^{+/-}$/Eμ-TCL1$^{+/+}$ CLL mice generate significantly increased numbers of CD11b+/Ly6G+ granulocytic cells. (FIG. 21A) Lymphocyte, (FIG. 21B) granulocyte and (FIG. 21C) monocyte counts in the peripheral blood of approximately 6-month-old Eμ-TCL1$^{+/+}$ and MD4$^{+/-}$/Eμ-TCL1$^{+/+}$ mice were analyzed using a HemaTrue Hematology Analyzer (HESKA). Leukemia in mice: the number of lymphocytes in the peripheral blood is >5000 cells/4. Data were plotted as mean±SEM. (FIG. 21D) Blood cells collected from Eμ-TCL1$^{+/+}$ and MD4$^{+/-}$/Eμ-TCL1$^{+/+}$ mice were treated with RBC lysis buffer, and stained with CD11c-BV421, CD11b-PE, Ly6C-Alexa 488 and Ly6G-Alexa 647. Gated CD11c−/CD11b+ populations were analyzed for Ly6C$^{intermediate}$/Ly6G+ granulocytic and Ly6C+/Ly6G− monocytic cells. (FIG. 21E) Percentages of CD11b+ myeloid cells in the blood of age-matched 6-month-old Eμ-TCL1$^{+/+}$ and MD4$^{+/-}$/Eμ-TCL1$^{+/+}$ mice were plotted as mean±SEM. (FIG. 21F) Percentages of CD11b+/Ly6C$^{intermediate}$/Ly6G+ granulocytic cells in the blood of age-matched 6-month-old Eμ-TCL1$^{+/+}$ and MD4$^{+/-}$/Eμ-TCL1$^{+/+}$ mice were plotted as mean±SEM. (FIG. 21G) Percentages of CD11b+/Ly6C+/Ly6G− monocytic cells in the blood of age-matched 6-month-old Eμ-TCL1$^{+/+}$ and MD4$^{+/-}$/Eμ-TCL1$^{+/+}$ mice were plotted as mean±SEM. (FIG. 21H) Percentages of CD11b+ myeloid cells in the blood of age-matched 8-month-old Eμ-TCL1$^{+/+}$ and MD4$^{+/-}$/Eμ-TCL1$^{+/+}$ mice were plotted as mean±SEM. (FIG. 21I) Percentages of CD11b+/Ly6C$^{intermediate}$/Ly6G+ granulocytic cells in the blood of age-matched 8-month-old Eμ-TCL1$^{+/+}$ and MD4$^{+/-}$/Eμ-TCL1$^{+/+}$ mice were plotted as mean±SEM. (FIG. 21J) Percentages of CD11b+/Ly6C+/Ly6G− monocytic cells in the blood of age-matched 8-month-old Eμ-TCL1$^{+/+}$ and MD4$^{+/-}$/Eμ-TCL1$^{+/+}$ mice were plotted as mean±SEM.

FIGS. 22A-22I illustrate the finding that deleting the capability of Eγ-TCL1$^{+/+}$ mice in producing sIgM leads to decreased numbers of CD11b+/Ly6G+ granulocytic cells and prolonged survival of the mice. (FIG. 22A) The levels of sIgM in the sera of Eγ-TCL1$^{+/+}$ and μS$^{-/-}$/Eμ-TCL1$^{+/+}$ mice were determined by ELISA. (FIG. 22B) CD5+/B220+ CLL cells purified from CLL-bearing Eμ-TCL1$^{+/+}$ and μS$^{-/-}$/Eμ-TCL1$^{+/+}$ mice were stimulated with LPS for a course of 3 days, and lysed for analysis of indicated proteins by immunoblots. Data in this panel are representative of three independent experiments. (FIG. 22C) Blood cells collected from Eμ-TCL1$^{+/+}$ and μS$^{-/-}$/Eμ-TCL1$^{+/+}$ mice were treated with RBC lysis buffer, and stained with CD11c-BV421, CD11b-PE, Ly6C-Alexa 488 and Ly6G-Alexa 647. Gated CD11c−/CD11b+ populations were analyzed for Ly6C$^{intermediate}$/Ly6G+ granulocytic cells and Ly6C+/Ly6G− monocytic cells. (FIG. 22D) Percentages of CD11b+ myeloid cells in the blood of age-matched 6-month-old Eμ-TCL1$^{+/+}$ and μS$^{-/-}$/Eμ-TCL1$^{+/+}$ mice were plotted as mean±SEM. (FIG. 22E) Percentages of CD11b+/Ly6C$^{intermediate}$/Ly6G+ granulocytic cells in the blood of age-matched 6-month-old Eμ-TCL1$^{+/+}$ and μS$^{-/-}$/Eμ-TCL1$^{+/+}$ mice were plotted as mean±SEM. (FIG. 22F) Percentages of CD11b+/Ly6C+/Ly6G− monocytic cells in the blood of age-matched 6-month-old Eμ-TCL1$^{+/+}$ and μS$^{-/-}$/Eμ-TCL1$^{+/+}$ mice were plotted as mean±SEM. (FIG. 22G) The Kaplan-Meier survival analysis of Eμ-TCL1$^{+/+}$, μS$^{-/-}$/Eμ-TCL1$^{+/+}$ and MD4$^{+/-}$/Eμ-TCL1$^{+/+}$ mice. (FIG. 4H) The Kaplan-Meier survival analysis of female Eμ-TCL1$^{+/+}$, μS$^{-/-}$/Eμ-TCL1$^{+/+}$ and MD4$^{+/-}$/Eμ-TCL1$^{+/+}$ mice. (FIG. 22I) The Kaplan-Meier survival analysis of male Eμ-TCL1$^{+/+}$, μS$^{-/-}$/Eμ-TCL1$^{+/+}$ and MD4$^{+/-}$/Eμ-TCL1$^{+/+}$ mice.

FIGS. 23A-23H illustrate the finding that CD11b+/Ly6G+ granulocytic cells purified from spleens of MD4$^{+/-}$/Eμ-TCL1$^{+/+}$ and Eμ-TCL1$^{+/+}$ mice can suppress proliferation of T cells. (FIG. 23A) Splenocytes from age-matched 6-month-old Eμ-TCL1$^{+/+}$, MD4$^{+/-}$/Eμ-TCL1$^{+/+}$, and μS$^{-/-}$/Eμ-TCL1$^{+/+}$ mice were stained with CD11c-BV421, CD11b-PE, Ly6C-Alexa 488 and Ly6G-Alexa 647. Gated CD11c−/CD11b+ populations were analyzed for Ly6C$^{intermediate}$/Ly6G+ granulocytic cells and Ly6C+/Ly6G− monocytic cells. (FIG. 23B) Percentages of CD11b+ myeloid cells in spleens of age-matched 6-month-old Eμ-TCL1$^{+/+}$, MD4$^{+/-}$/Eμ-TCL1$^{+/+}$ and μS$^{-/-}$/Eμ-TCL1$^{+/+}$ mice were plotted as mean±SEM. (FIG. 23C) Percentages of CD11b+/Ly6C$^{intermediate}$/Ly6G+ granulocytic cells in spleens of age-matched 6-month-old Eμ-TCL1$^{+/+}$, MD4$^{+/-}$/Eμ-TCL1$^{+/+}$ and μS$^{-/-}$/Eμ-TCL1$^{+/+}$ mice were plotted as mean±SEM. (FIG. 23D) Percentages of CD11b+/Ly6C+/Ly6G− monocytic cells in spleens of age-matched 6-month-old Eμ-TCL1$^{+/+}$, MD4$^{+/-}$/Eμ-TCL1$^{+/+}$ and μS$^{-/-}$/Eμ-TCL1$^{+/+}$ mice were plotted as mean±SEM. (FIG. 23E) CFSE-stained mouse splenocytes (1×10$^5$ cells) were unstimulated (left panel), or stimulated with anti-mouse CD3ε antibody (1 μg/mL) and anti-mouse CD28 antibody (0.5 μg/mL) in the absence (middle panel) or presence (right panel) of 1×10$^5$ CD11b+/Ly6C$^{intermediate}$/Ly6G+ granulocytic cells purified from spleens of MD4$^{+/-}$/Eμ-TCL1$^{+/+}$ mice for 72 h, and subsequently stained with CD4-BV605 and CD8-PE-Cy7. CD8+ T cells were gated and analyzed for the frequency of cell division by CFSE dye dilution. (FIGS. 23F-23G) Splenocytes from PMEL-1 mice were mixed with splenocytes from naïve mice at the 1:4 ratio. In each well, 1×10$^5$ mixed splenocytes were incubated with 0.5 or 1×10$^5$ CD11b+/Ly6C$^{intermediate}$/Ly6G+ granulocytic cells (FIG. 23F) or CD11b+/Ly6C+/Ly6G− monocytic cells (FIG. 23G) purified from spleens of MD4$^{+/-}$/Eμ-TCL1$^{+/+}$ mice, in the absence or presence of the gp100 peptide (0.1 μg/mL). After incubation for 48 h, cells were radiolabeled with $^3$H-thymidine for additional 6 h. The $^3$H-thymidine uptake was measured (counts per minute; CPM) and plotted as mean±SD. (FIG. 23H) Splenocytes from PMEL-1 mice were mixed with splenocytes from naïve mice at the 1:4 ratio. In each well, 1×10$^5$ mixed splenocytes were incubated with 0.5 or 1×10$^5$ CD11b+/Ly6C$^{intermediate}$/Ly6G+ granulocytic cells purified from spleens of 8-month-old Eµ-TCL1$^{+/+}$ and µS$^{-/-}$/Eµ-TCL1$^{+/+}$ mice, in the presence of the gp100 peptide. After incubation for 48 h, cells were radiolabeled with $^3$H-thymidine for additional 6 h. The $^3$H-thymidine uptake was measured, and the percentages of proliferation were calculated by comparing to the positive control and plotted as mean±SEM.

FIGS. 24A-24J illustrate the finding that targeting XBP-1s in CLL cells of MD4$^{+/-}$/Eµ-TCL1$^{+/+}$ mice leads to reduced production of sIgM, and decreased numbers and function of granulocytic MDSCs. (FIG. 24A) The levels of IgM in the sera of MD4$^{+/-}$/Eµ-TCL1$^{+/+}$ and XBP-1$^{KO}$/MD4$^{+/-}$/Eµ-TCL1$^{+/+}$ mice were determined by ELISA. (FIG. 24B) Blood cells collected from MD4$^{+/-}$/Eµ-TCL1$^{+/+}$ and XBP-1$^{KO}$/MD4$^{+/-}$/Eµ-TCL1$^{+/+}$ mice were treated with RBC lysis buffer, and stained with CD11c-BV421, CD11b-PE, Ly6C-Alexa 488 and Ly6G-Alexa 647. Gated CD11c-/CD11b+ populations were analyzed for Ly6C$^{intermediate}$/Ly6G+ granulocytic MDSCs and Ly6C+/Ly6G- monocytic MDSCs. (FIG. 24C) Percentages of CD11b+ myeloid cells in the blood of MD4$^{+/-}$/Eµ-TCL1$^{+/+}$ and XBP-1$^{KO}$/MD4$^{+/-}$/Eµ-TCL1$^{+/+}$ mice were plotted as mean±SEM. (FIG. 24D) Percentages of CD11b+/Ly6C$^{intermediate}$/Ly6G+ granulocytic MDSCs in the blood of MD4$^{+/-}$/Eµ-TCL1$^{+/+}$ and XBP-1$^{KO}$/MD4$^{+/-}$/Eµ-TCL1$^{+/+}$ mice were plotted as mean±SEM. (FIG. 24E) Splenocytes from MD4$^{+/-}$/Eµ-TCL1$^{+/+}$ and XBP-1$^{KO}$/MD4$^{+/-}$/Eµ-TCL1$^{+/+}$ mice were treated with RBC lysis buffer, and stained with CD11b-BV605, Ly6C-Alexa 488, Ly6G-Alexa 647 and Arg-1-PE. Gated CD11b+/Ly6C$^{intermediate}$/Ly6G+ granulocytic MDSCs were analyzed for the expression of Arg-1. (FIG. 24F) Mean fluorescence intensity (MFI) of Arg-1 in gated CD11b+/Ly6C$^{intermediate}$/Ly6G+ granulocytic MDSCs from spleens of 5 MD4$^{+/-}$/Eµ-TCL1$^{+/+}$ and 5 XBP-1$^{KO}$/MD4$^{+/-}$/Eµ-TCL1$^{+/+}$ mice was plotted as mean±SEM. (FIG. 24G) Splenocytes from OT-I mice were mixed with splenocytes from naïve mice at the 1:4 ratio. In each well, 1×10$^5$ mixed splenocytes were incubated with 0.25, 0.5 or 1×10$^5$ CD11b+/Ly6C$^{intermediate}$/Ly6G+ granulocytic cells purified from spleens of 5 MD4$^{+/-}$/Eµ-TCL1$^{+/+}$ and 5 XBP-1$^{KO}$/MD4$^{+/-}$/Eµ-TCL1$^{+/+}$ mice, in the presence of the OVA peptide (0.1 µg/mL). After incubation for 48 h, cells were radiolabeled with $^3$H-thymidine for additional 6 h. The $^3$H-thymidine uptake was measured, and the percentages of proliferation were calculated by comparing to the positive control and plotted as mean±SEM. (FIG. 24H) MD4$^{+/-}$/Eµ-TCL1$^{+/+}$ mice with high percentage of CLL cells in the peripheral blood were identified and injected intraperitoneally with B-I09 (50 mg/kg; n=4) on days 1~5 and days 8~12. The percentage of CLL cells in PBMCs for each mouse was determined by flow cytofluorometry on day 6 and day 13, and compared with the CLL burden data of the mouse on day 0 (100%). Data derived from 4 mice receiving exactly the same treatment were plotted as mean±SEM. (FIG. 24I) MFI of Arg-1 in gated CD11b+/Ly6C$^{intermediate}$/Ly6G+ granulocytic MDSCs from spleens of 4 DMSO-treated and 4 B-I09-treated MD4$^{+/-}$/Eµ-TCL1$^{+/+}$ mice was plotted as mean±SEM. (FIG. 24J) Splenocytes from OT-I mice were mixed with splenocytes from naïve mice at the 1:4 ratio. In each well, 1×10$^5$ mixed splenocytes were incubated with 0.25, 0.5 or 1×10$^5$ CD11b+/Ly6C$^{intermediate}$/Ly6G+ granulocytic cells purified from spleens of untreated or B-I09-treated MD4$^{+/-}$/Eµ-TCL1$^{+/+}$ mice, in the presence of the OVA peptide. After incubation for 48 h, cells were radiolabeled with $^3$H-thymidine for additional 6 h. The $^3$H-thymidine uptake was measured, and the percentages of proliferation were calculated by comparing to the positive control and plotted as mean±SEM.

FIGS. 25A-25J illustrate the finding that reduced growth of Lewis lung carcinoma (LLC) in µS$^{-/-}$ mice is a result of reduced capabilities of MDSCs in suppressing proliferation of anti-tumor CD8+ T cells. (FIG. 25A) Eight-week-old wild-type (WT) and µS$^{-/-}$ mice were subcutaneously injected with LLC cells on day 0. The size of tumor was measured on days 11, 14, 18 and 24, and data were plotted as mean±SEM. (FIG. 25B) On day 24, the weight of carefully dissected tumors was recorded and plotted as mean±SEM. (FIG. 25C) Tumors dissected from WT and µS$^{-/-}$ mice on day 24 were cut into pieces, digested with the mouse tumor dissociation kit, and stained with CD45-PE, CD11b-BV605, Ly6C-Alexa 488 and Ly6G-Alexa 647. Gated CD45+ hematopoietic cells were further gated for CD11b+ myeloid populations, which were then analyzed for Ly6C$^{intermediate}$/Ly6G+ granulocytic MDSCs and Ly6C+/Ly6G- monocytic MDSCs. (FIG. 25D) Percentages of CD11b+ myeloid cells in the LLC tumors of WT and µS$^{-/-}$ mice were plotted as mean±SEM. (FIG. 25E) Percentages of CD11b+/Ly6C+/Ly6G- monocytic MDSCs in the LLC tumors of WT and µS$^{-/-}$ mice were plotted as mean±SEM. (FIG. 25F) Percentages of CD11b+/Ly6C$^{intermediate}$/Ly6G+ granulocytic MDSCs in the LLC tumors of WT and µS$^{-/-}$ mice were plotted as mean±SEM. (FIG. 25G) Splenocytes from PMEL-1 mice were mixed with splenocytes from nave mice at the 1:4 ratio. 1×10$^5$ mixed splenocytes were incubated with 0.25, 0.5 or 1×10$^5$ CD11b+/Ly6C+/Ly6G- monocytic MDSCs purified from the LLC tumors in WT and µS$^{-/-}$ mice, in the presence of the gp100 peptide (0.1 µg/mL). After incubation for 48 h, cells were radiolabeled with $^3$H-thymidine for additional 6 h. The $^3$H-thymidine uptake was measured, and the percentages of proliferation were calculated by comparing to the positive control and plotted as mean±SEM. (FIG. 25H) Similar to (FIG. 25G), 1×10$^5$ mixed splenocytes were incubated with 0.25, 0.5 or 1×10$^5$ CD11b+/Ly6C$^{intermediate}$/Ly6G+ granulocytic MDSCs purified from the LLC tumors in WT and µS$^{-/-}$ mice, in the presence of the gp100 peptide. After incubation for 48 h, cells were radiolabeled with $^3$H-thymidine for additional 6 h. The $^3$H-thymidine uptake was measured, and the percentages of proliferation were calculated by comparing to the positive control and plotted as mean±SEM. (FIG. 25I) Two days (−day 2) before LLC cells were subcutaneously injected on day 0, eight-week-old WT and µS$^{-/-}$ mice were injected intraperitoneally with the anti-mouse CD8α monoclonal antibody (100 µg per mouse) or the isotype control monoclonal antibody (100 µg per mouse). These mice received 5 subsequent antibody injections on days 1, 5, 8, 12, and 15. The size of tumor was measured and recorded starting from day 11 to day 22, and data were plotted as mean±SEM. (FIG. 25J) On day 22, the weight of dissected tumors from (FIG. 25I) was recorded and plotted as mean±SEM.

Figure 26A:
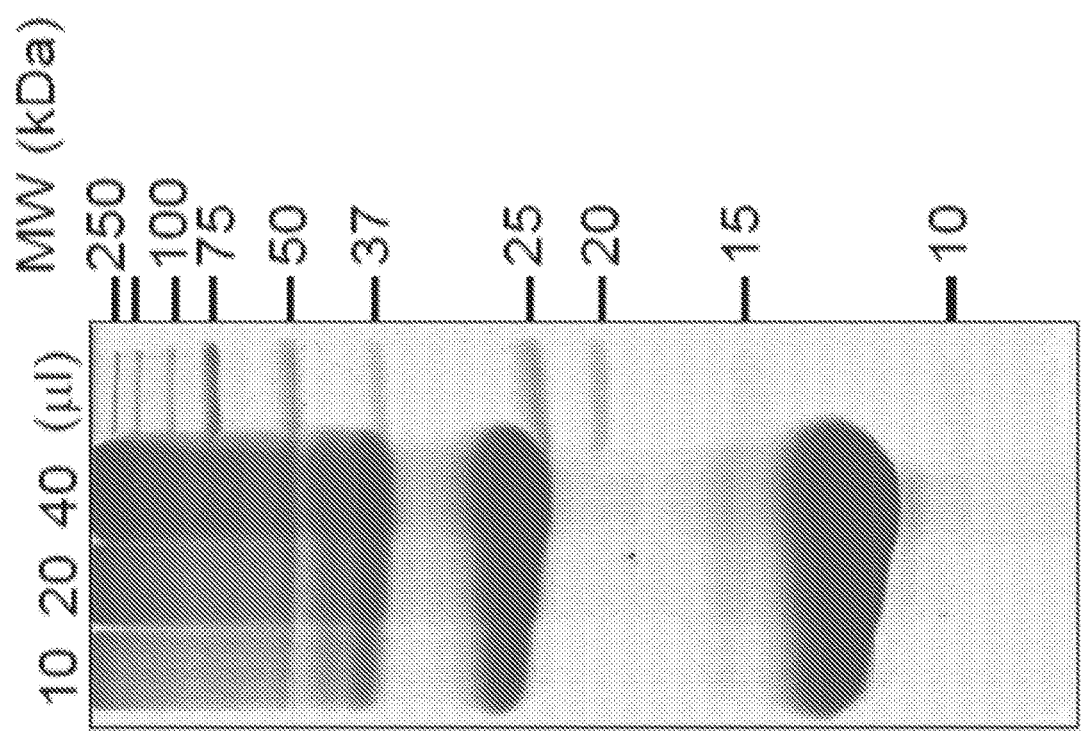
Figure 26B:
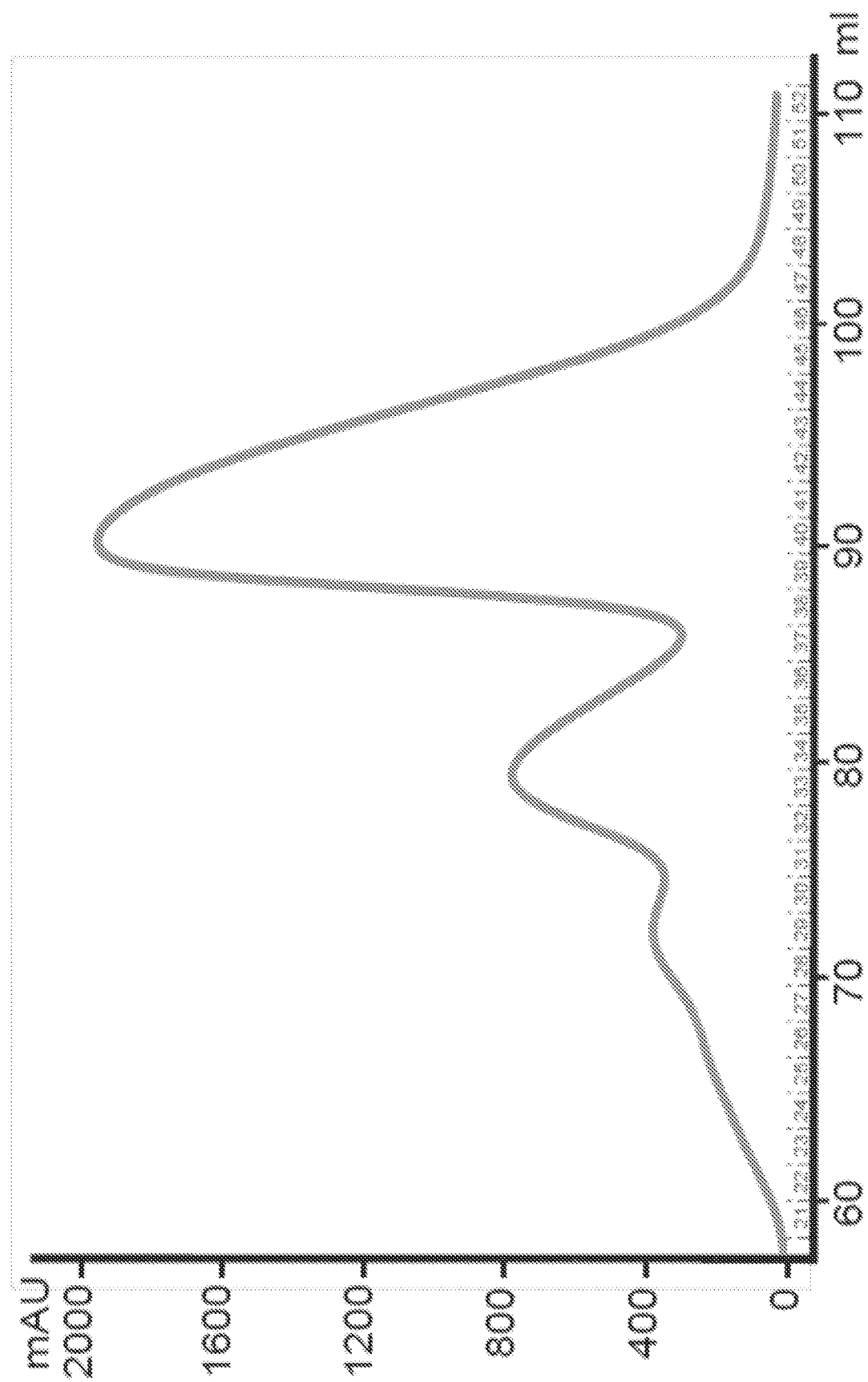
Figure 26C:
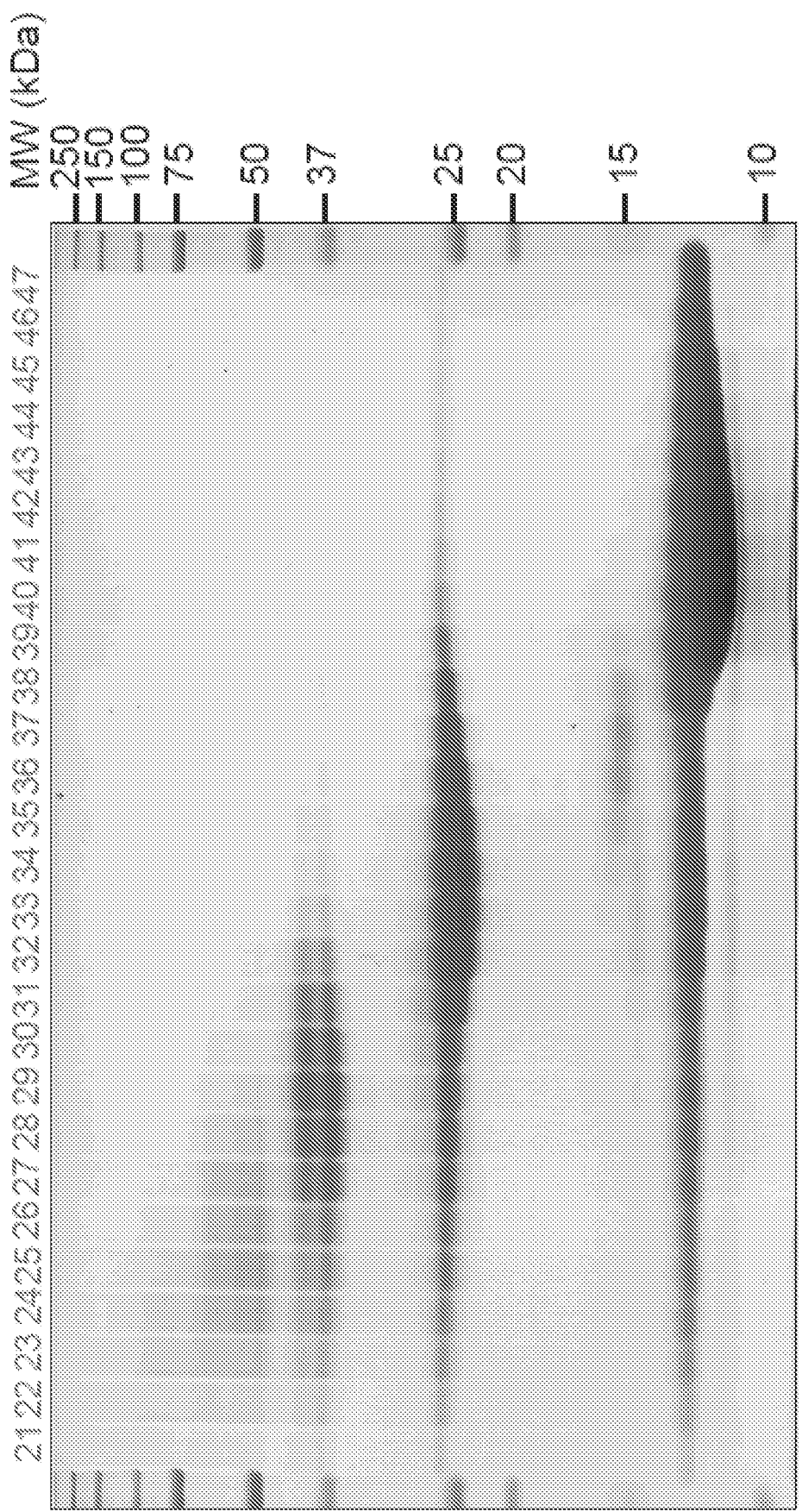

FIGS. 26A-26D illustrate crosslinking and preparation of oligomeric HEL. (FIG. 26A) Hen egg lysozyme (HEL) was crosslinked using glutaraldehyde, quenched by glycine, analyzed by SDS-PAGE, and visualized by Coomassie brilliant blue G-250 staining. (FIGS. 26B-8C) Crosslinked HEL were separated on a Superdex 75 preparation column (FIG. 26B), and fractions were analyzed by SDS-PAGE and visualized by Coomassie blue staining (FIG. 26C). (FIG. 26D) Fractions corresponding to monomers, dimers or oligomers of HEL were pooled, dialyzed against PBS and analyzed by SDS-PAGE followed by Coomassie blue staining. Data in this figure are representative of three independent experiments.

Figure 27A:
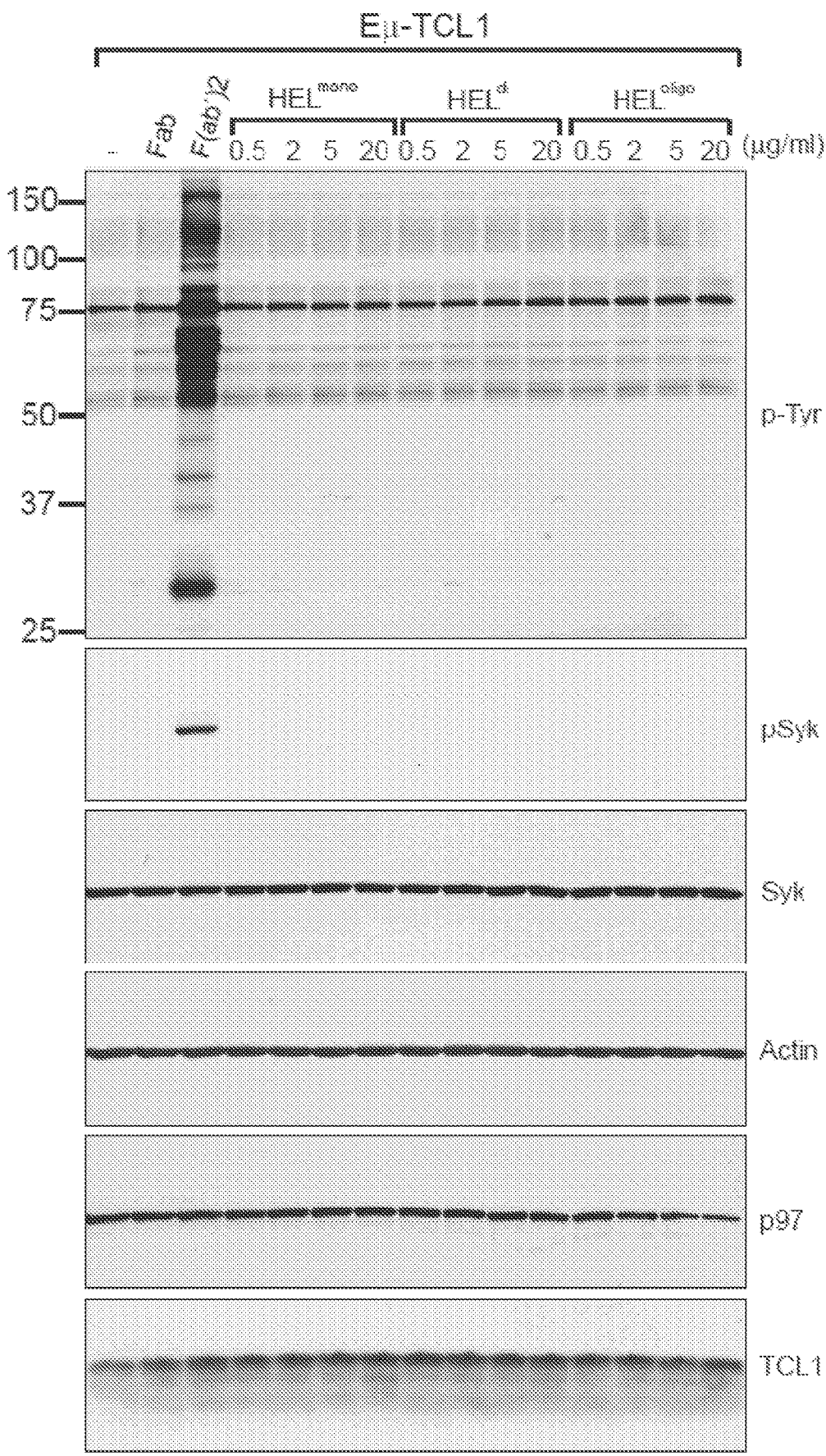
Figure 27B:
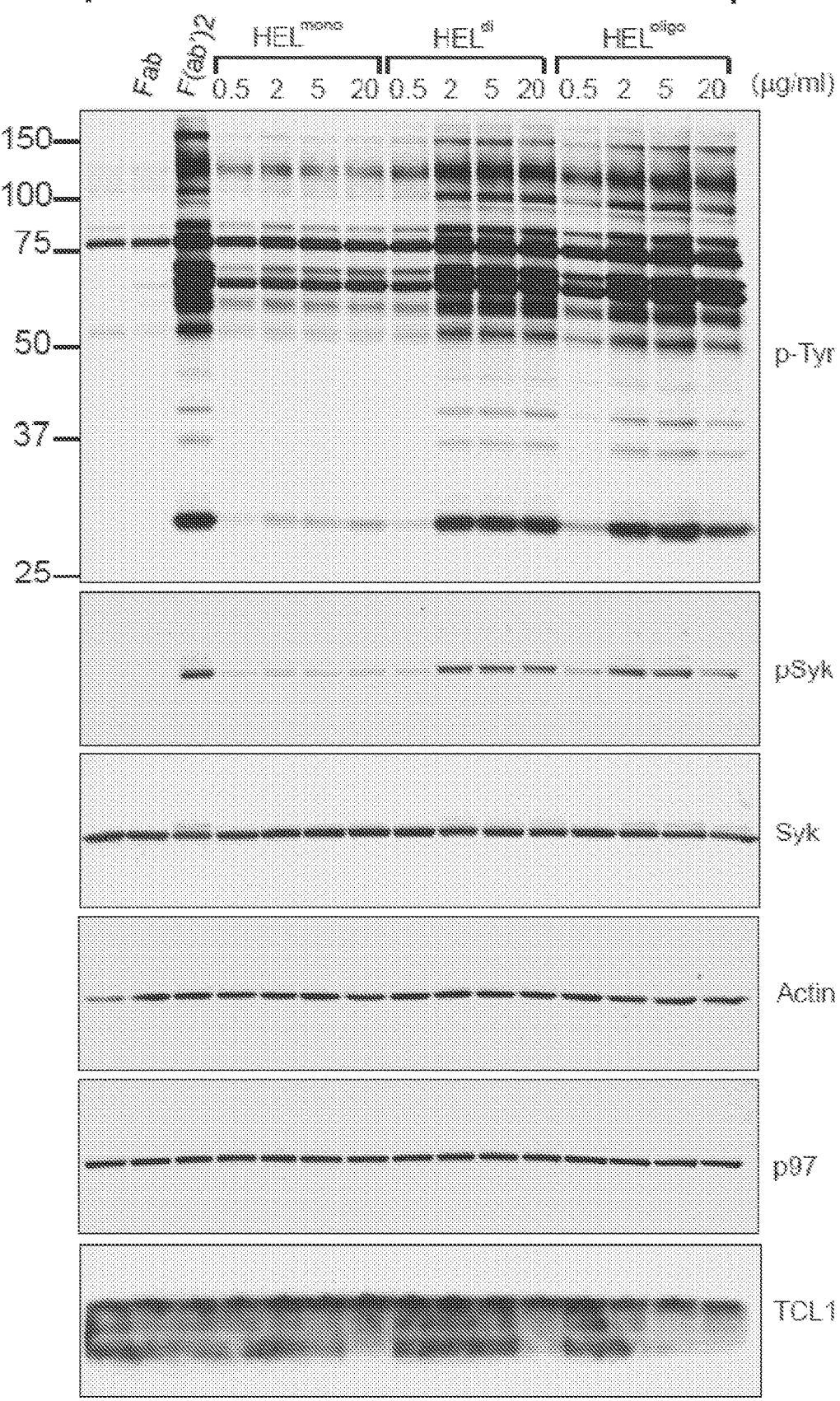

FIGS. 27A-27B illustrate the finding that oligomeric HEL crosslinks the BCR, and induces robust BCR signal transduction in MD4$^{+/-}$/Eμ-TCL1$^{+/+}$ B cells. (FIGS. 27A-27B) B cells purified from Eμ-TCL1$^{+/+}$ (FIG. 27A) or MD4$^{+/-}$/Eμ-TCL1$^{+/+}$ (FIG. 27B) mice were either unstimulated or stimulated with Fab (20 μg/mL), F(ab')2 (20 μg/mL), monomeric HEL, dimeric HEL or oligomeric HEL for 2 min. Cells were lysed immediately and analyzed by immunoblots using indicated antibodies. Data in this figure are representative of three independent experiments.

Figure 28A:
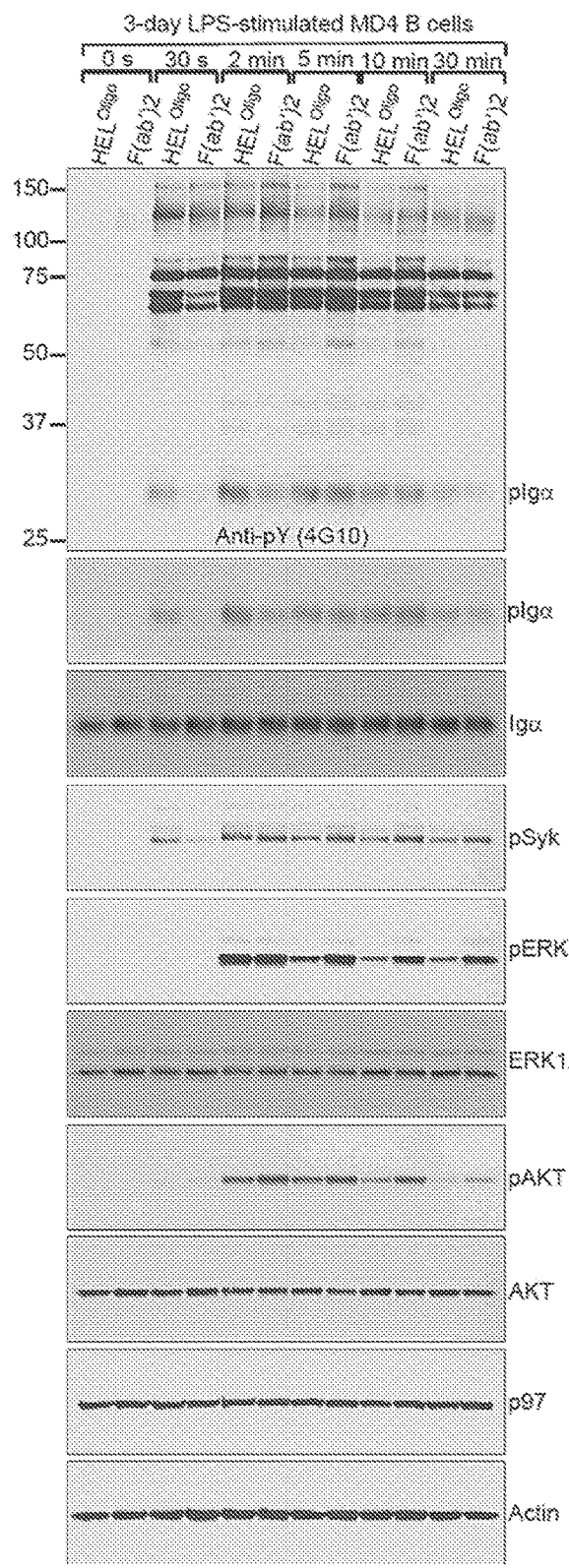
Figure 28B:
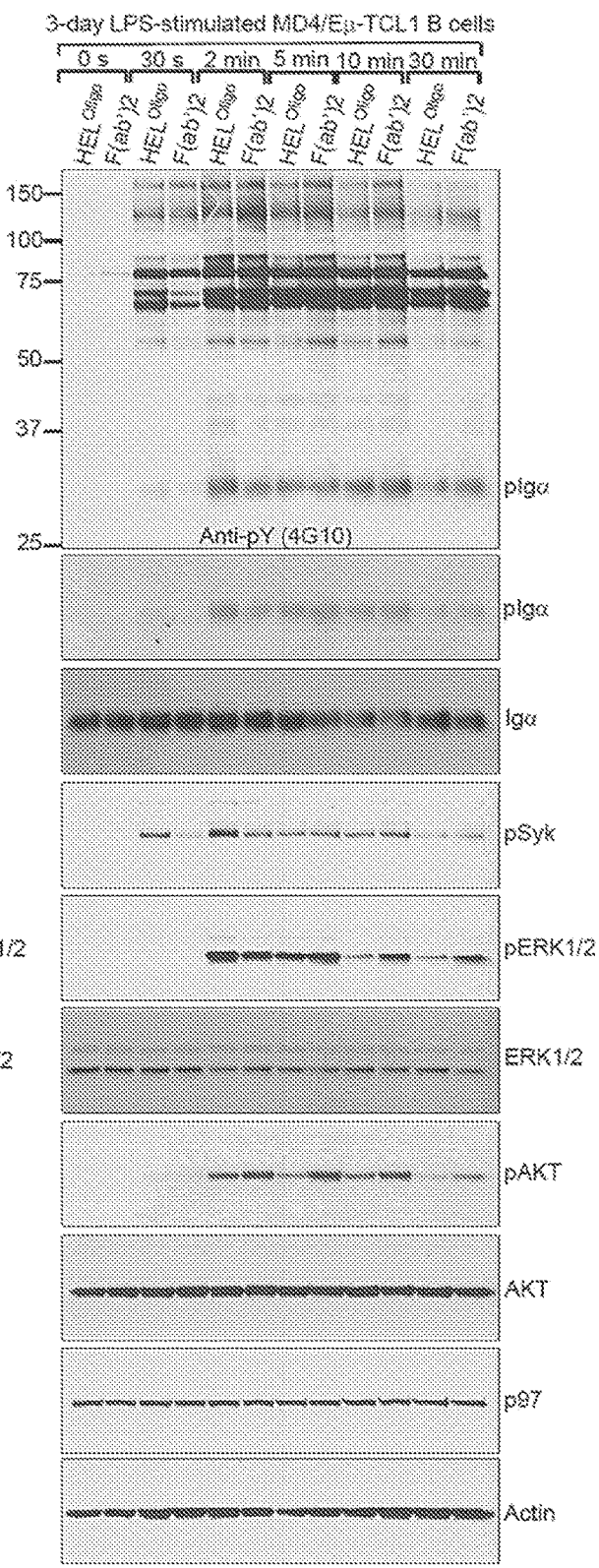

FIGS. 28A-28B illustrate the finding that oligomeric HEL activates a more rapid BCR signaling than F(ab')2 in MD4$^{+/-}$ and MD4$^{+/-}$/Eμ-TCL1$^{+/+}$ B cells. (FIGS. 28A-28B) B cells purified from MD4$^{+/-}$ (FIG. 28A) or MD4$^{+/-}$/Eμ-TCL1$^{+/+}$ (FIG. 28B) mice were cultured in LPS for 3 days, subsequently stimulated with oligomeric HEL (5 μg/mL) or F(ab')2 (20 μg/mL) for indicated times, and lysed immediately. Lysates were immunoblotted for indicated proteins. Data in this figure are representative of three independent experiments.

Figure 29:
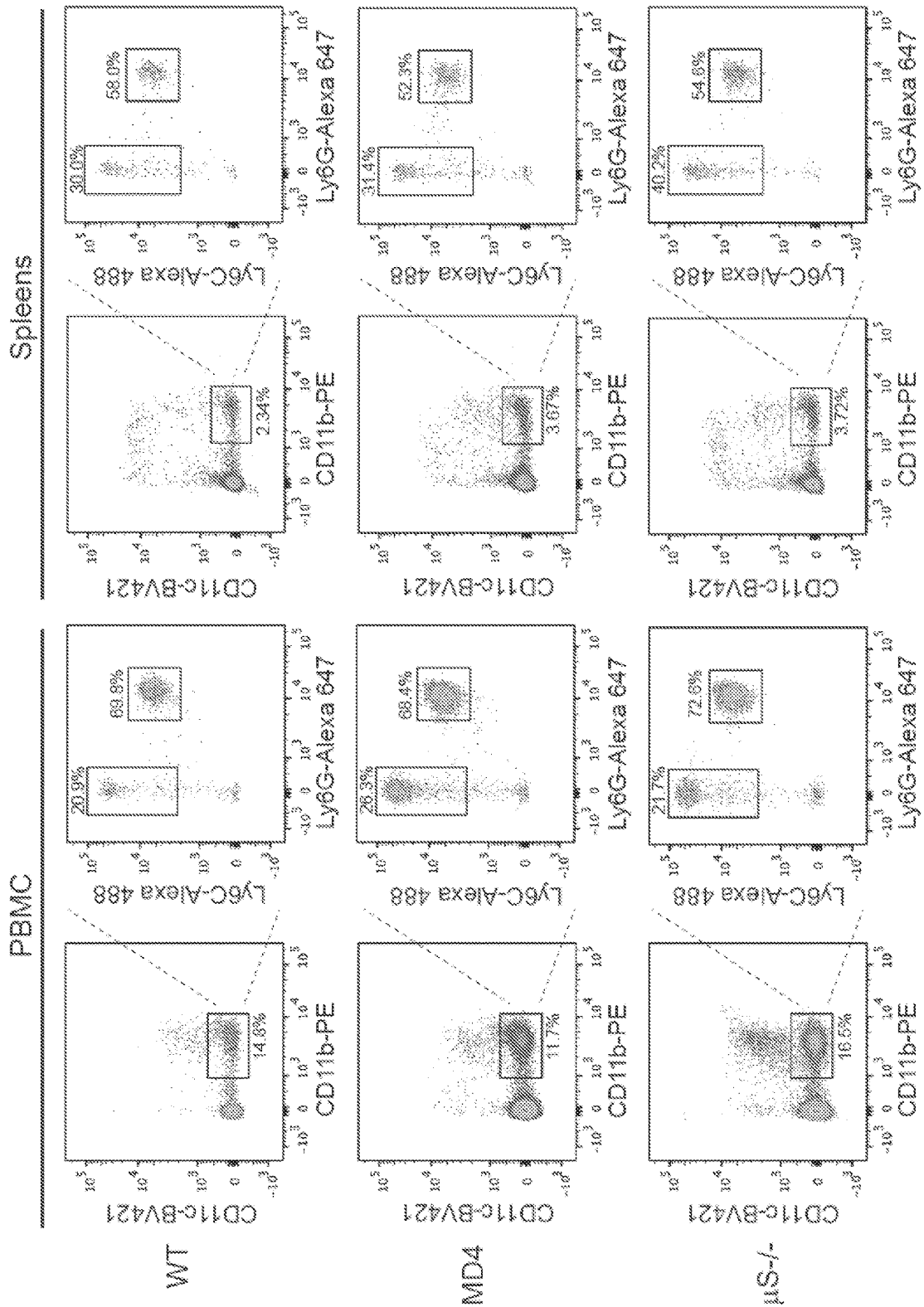

FIG. 29 illustrates the finding that CD11b+/Ly6G+ granulocytic cells or CD11b+/Ly6C+ monocytic cells do not accumulate in the blood and spleens of 6-month-old WT, MD4$^{+/-}$ and μS$^{-/-}$ mice. Blood cells and mashed spleen cells collected from 6-month-old WT, MD4$^{+/-}$ and μS$^{-/-}$ mice were treated with RBC lysis buffer, and stained with CD11c-BV421, CD11b-PE, Ly6C-Alexa 488 and Ly6G-Alexa 647. Gated CD11c–/CD11b+ myeloid populations were analyzed for Ly6C$^{intermediate}$/Ly6G+ granulocytic cells and Ly6C+/Ly6G– monocytic cells.

FIGS. 30A-30E illustrate the finding that B cells and CLL cells from MD4$^{+/-}$/Eμ-TCL1$^{+/+}$ and Eμ-TCL1$^{+/+}$ but not μS$^{-/-}$/Eμ-TCL1$^{+/+}$ mice produce sIgM; human CLL cells also produce and secrete IgM. (FIG. 30A) The levels of anti-HEL IgM in the sera of Eμ-TCL1$^{+/+}$ and MD4$^{+/-}$/Eμ-TCL1$^{+/+}$ mice were determined by ELISA. (FIG. 30B) CD5–/B220+ WT and Eμ-TCL1$^{+/+}$ B cells and CD5+/B220+Eμ-TCL1$^{+/+}$ CLL cells were stimulated with LPS (20 μg/mL) for a course of 3 days, and lysed for analysis of indicated proteins by immunoblots. (FIGS. 30C-30D) Human CLL samples freshly isolated from patients #1 and #2 were immediately radiolabeled for 15 min, chased for indicated time and lysed. Intracellular and extracellular IgM were immunoprecipitated from lysates (FIG. 30C) and culture media (FIG. 30D), respectively, using an anti-human Igμ chain antibody. Immunoprecipitates were analyzed on an SDS-PAGE gel and visualized by autoradiography. (FIG. 30E) CD5–/B220+ B cells purified from Eμ-TCL1$^{+/+}$, μS$^{-/-}$/Eμ-TCL1$^{+/+}$, and μS$^{-/-}$ mice were stimulated with LPS (20 μg/mL) for a course of 3 days, and lysed for analysis of indicated proteins by immunoblots. Data in FIGS. 30B-30E are representative of three independent experiments.

FIGS. 31A-31H illustrate the finding that decreased percentages of CD11b+/Ly6G+ granulocytic cells in spleens of 6-week-old μS$^{-/-}$/Eμ-TCL1$^{+/+}$ mice; decreased percentages of CD11b+/Ly6G+ granulocytic cells and CD11b+/Ly6C+ monocytic cells in the bone marrow of 6-month-old μS$^{-/-}$/Eμ-TCL1$^{+/+}$ mice; increased percentages of CD11b+/Ly6G+ granulocytic cells and CD11b+/Ly6C+ monocytic cells in the bone marrow of 6-week-old MD4$^{+/-}$/Eμ-TCL1$^{+/+}$ mice; and increased percentages of CD11b+/Ly6G+ granulocytic cells in the bone marrow of 6-month-old MD4$^{+/-}$/Eμ-TCL1$^{+/+}$ mice. (FIGS. 31A-13B) Splenocytes from age-matched 6-week-old Eμ-TCL1$^{+/+}$, MD4$^{+/-}$/Eμ-TCL1$^{+/+}$, and μS$^{-/-}$/Eμ-TCL1$^{+/+}$ mice were stained with CD11c-BV421, CD11b-PE, Ly6C-Alexa 488 and Ly6G-Alexa 647. Gated CD11c–/CD11b+ populations were analyzed for Ly6C intermediate/Ly6G+ granulocytic cells and Ly6C+/Ly6G– monocytic cells. Percentages of Ly6C intermediate/Ly6G+ granulocytic cells (FIG. 31A) and Ly6C+/Ly6G– monocytic cells (FIG. 31B) in the spleens were plotted as mean±SEM. (FIG. 31C) Bone marrow cells from age-matched 6-month-old Eμ-TCL1$^{+/+}$, MD4$^{+/-}$/Eμ-TCL1$^{+/+}$, and μS$^{-/-}$/Eμ-TCL1$^{+/+}$ mice were stained with CD11c-BV421, CD11b-PE, Ly6C-Alexa 488 and Ly6G-Alexa 647. Gated CD11c–/CD11b+ myeloid populations were analyzed for Ly6C$^{intermediate}$/Ly6G+ granulocytic cells and Ly6C+/Ly6G– monocytic cells. (FIG. 31D) Percentages of CD11b+ myeloid cells in the bone marrow of age-matched 6-month-old Eμ-TCL1$^{+/+}$, MD4$^{+/-}$/Eμ-TCL1$^{+/+}$ and μS$^{-/-}$/Eμ-TCL1$^{+/+}$ mice were plotted as mean±SEM. (FIG. 31E) Percentages of CD11b+/Ly6C$^{intermediate}$/Ly6G+ granulocytic cells in the bone marrow of age-matched 6-month-old Eμ-TCL1$^{+/+}$, MD4$^{+/-}$/Eμ-TCL1$^{+/+}$ and μS$^{-/-}$/Eμ-TCL1$^{+/+}$ mice were plotted as mean±SEM. (FIG. 31F) Percentages of CD11b+/Ly6C+/Ly6G– monocytic cells in the bone marrow of age-matched 6-month-old Eμ-TCL1$^{+/+}$, MD4$^{+/-}$/Eμ-TCL1$^{+/+}$ and μS$^{-/-}$/Eμ-TCL1$^{+/+}$ mice were plotted as mean±SEM. (FIGS. 31G-31H) Bone marrow cells from age-matched 6-week-old Eμ-TCL1$^{+/+}$, MD4$^{+/-}$/Eμ-TCL1$^{+/+}$, and μS$^{-/-}$/Eμ-TCL1$^{+/+}$ mice were stained with CD11c-BV421, CD11 b-PE, Ly6C-Alexa 488 and Ly6G-Alexa 647. Gated CD11c–/CD11b+ populations were analyzed for Ly6C$^{intermediate}$/Ly6G+ granulocytic cells and Ly6C+/Ly6G– monocytic cells. Percentages of Ly6C$^{intermediate}$/Ly6G+ granulocytic cells (FIG. 31G) and Ly6C+/Ly6G– monocytic cells (FIG. 31H) in the bone marrow were plotted as mean±SEM.

Figure 32A:
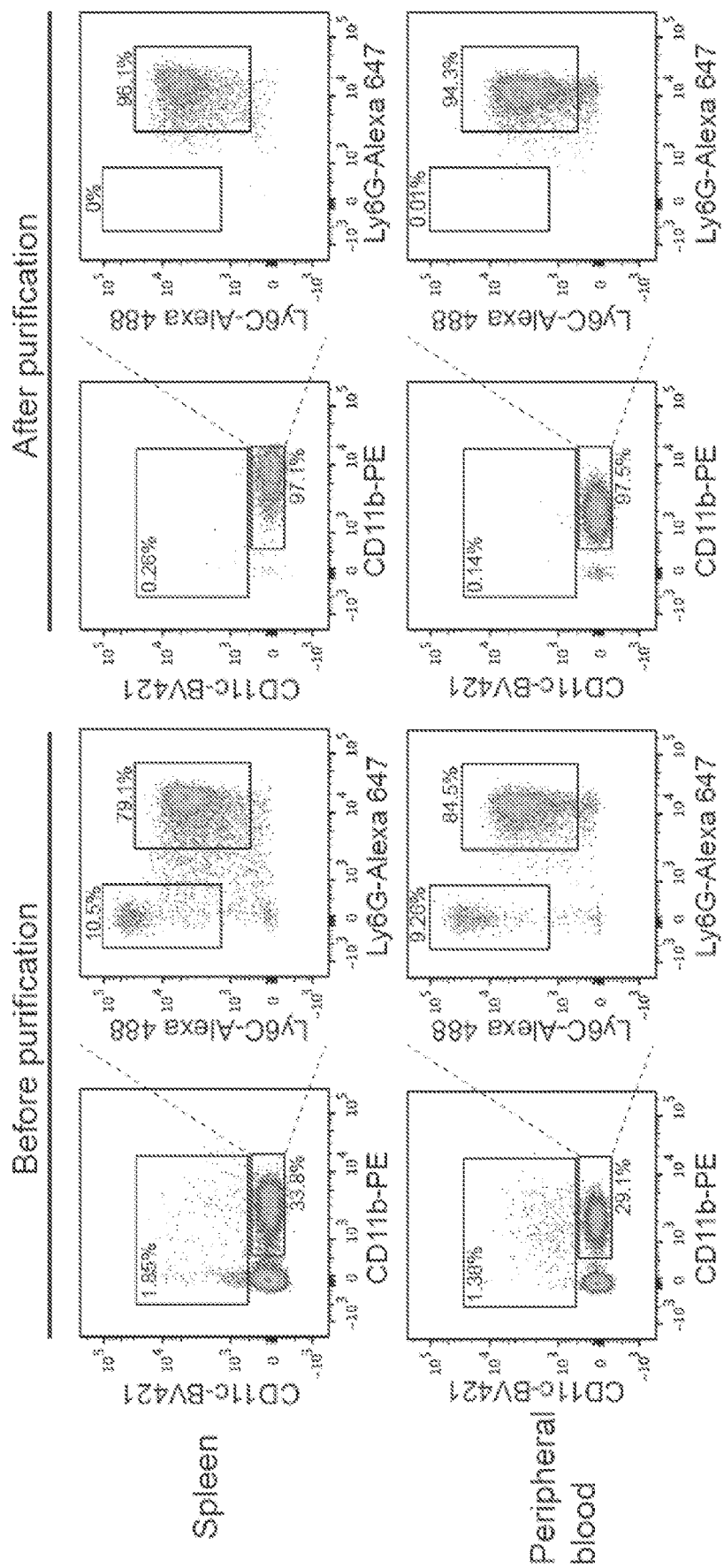
Figure 32C:
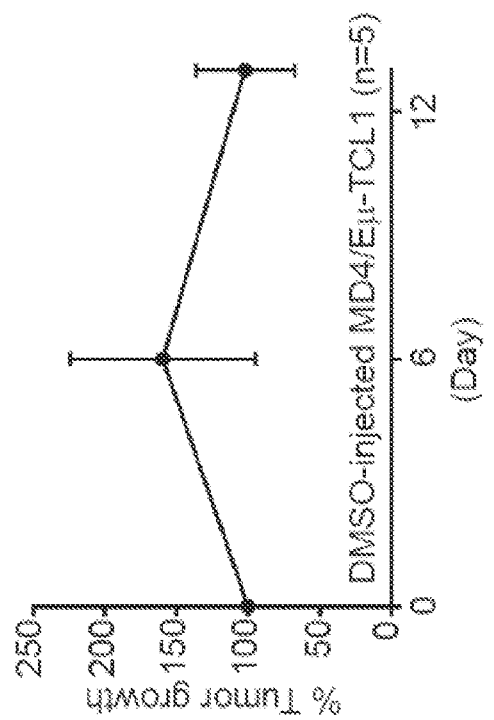
Figure 32B:
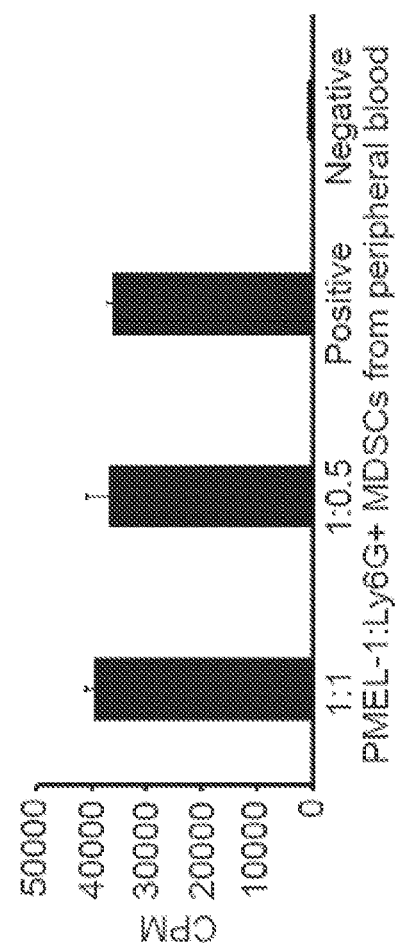

FIGS. 32A-32C illustrate the finding that CD11b+/Ly6G+ granulocytic cells can be purified from the spleens and peripheral blood of MD4$^{+/-}$/Eμ-TCL1$^{+/+}$ mice. (FIG. 32A) Splenocytes and blood cells from MD4$^{+/-}$/Eμ-TCL1$^{+/+}$ mice were treated with RBC lysis buffer. Some cells were subjected to purification of CD11b+/Ly6G+ granulocytic cells using MDSC isolation kit (Miltenyi Biotech). Cells before and after purification were stained with CD11c-BV421, CD11b-PE, Ly6C-Alexa 488 and Ly6G-Alexa 647. Gated CD11c–/CD11b+ myeloid populations were analyzed for Ly6C$^{intermediate}$/Ly6G+ granulocytic MDSCs and Ly6C+/Ly6G– monocytic MDSCs. Data are representative of three independent experiments. (FIG. 32B) Splenocytes from PMEL-1 mice were mixed with splenocytes from naïve mice at the 1:4 ratio. In each well, 1×10$^5$ mixed splenocytes were incubated with 0.5 or 1×10$^5$ CD11b+/Ly6C$^{intermediate}$/Ly6G+ granulocytic cells purified from peripheral blood of MD4$^{+/-}$/Eμ-TCL1$^{+/+}$ mice, in the absence or presence of the gp100 peptide (0.1 μg/mL). After incubation for 48 h, cells were radiolabeled with $^3$H-thymidine for additional 6 h. The $^3$H-thymidine uptake was measured and plotted as mean±SD. (FIG. 32C) MD4$^{+/-}$/Eμ-TCL1$^{+/+}$ mice with high percentage of CLL cells in the peripheral blood were identified and injected intraperitoneally with DMSO (3 mL/kg; n=5) on days 1~5 and days 8~12. The percentage of CLL cells in PBMCs for each mouse was determined by flow cytofluorometry on day 6 and day 13, and compared with the CLL burden data of the mouse on day 0 (100%). Data derived from 5 mice receiving exactly the same DMSO treatment were plotted as mean±SEM.

FIGS. 33A-33D illustrate the finding that CD11b+/Ly6G+ granulocytic cells purified from the spleens or bone marrow of LLC-grafted WT and μS$^{-/-}$ mice have small or little effect in suppressing T cell proliferation. (FIG. 33A) Eight-week-old WT and μS$^{-/-}$ mice were subcutaneously injected with LLC cells on day 0. On day 24, mouse blood samples were collected, and the levels of sIgM in the sera of LLC-grafted WT and μS$^{-/-}$ mice were determined by ELISA. Data were plotted as mean±SEM. (FIG. 33B) Tumors dissected from WT and μS$^{-/-}$ mice on day 24 were cut into pieces, digested with the mouse tumor dissociation kit, and stained with CD45-PE, CD19-APC-Cy7 and B220-FITC. Gated CD45+ hematopoietic cells were further analyzed for CD19+/B220+ B cell populations. Percentages of infiltrating B cells were plotted as mean±SEM. (FIG. 33C) Splenocytes from PMEL-1 mice were mixed with splenocytes from naïve mice at the 1:4 ratio. 1×10$^5$ mixed splenocytes were incubated with 0.25, 0.5 or 1×10$^5$ CD11b+/Ly6C$^{intermediate}$/Ly6G+ granulocytic MDSCs purified from the spleens of LLC-grafted WT and μS$^{-/-}$ mice, in the presence of the gp100 peptide (0.1 μg/mL). After incubation for 48 h, cells were radiolabeled with $^3$H-thymidine for additional 6 h. The $^3$H-thymidine uptake was measured, and the percentages of proliferation were calculated by comparing to the positive control and plotted as mean±SEM. (FIG. 33D) Similar to (FIG. 33C), 1×10$^5$ mixed splenocytes were incubated with 0.25, 0.5 or 1×10$^5$ CD11b+/Ly6C$^{intermediate}$/Ly6G+ granulocytic MDSCs purified from the bone marrow of LLC-grafted WT and μS$^{-/-}$ mice, in the presence of the gp100 peptide. After incubation for 48 h, cells were radiolabeled with $^3$H-thymidine for additional 6 h. The $^3$H-thymidine uptake was measured, and the percentages of proliferation were calculated by comparing to the positive control and plotted as mean±SEM.

DETAILED DESCRIPTION OF THE INVENTION

The invention relates, in certain aspects, to the discovery that certain substituted chromenones are useful to inhibit the IRE1/XBP-1 pathway. In certain embodiments, the compounds of the invention inhibit or hamper IRE1's RNase activity. In other embodiments, the compound of the invention are useful to treat or prevent a cancer that involves activation of the ER stress response.

High-throughput screening of large chemical libraries has led to the discovery of various salicylaldehydes as potent in vitro inhibitors against the RNase activity of IRE-1. The aldehyde moiety of each of these inhibitors is believed to be critical for inhibition of RNase function, allowing the formation of an unusual but highly specific Schiff base with Lys907 in the RNase domain of IRE-1. Although IRE-1 contains 25 lysine residues in its cytosolic domain, only covalent modification at Lys907 (and in some cases K599) is observed in vivo after treatment with salicylaldehyde-based inhibitors. Specific perturbation of the Lys907 ε-amino group pKa in the IRE-1 RNase domain results in enhanced Lys nucleophilicity, slower inhibitor off-rate, and desired phenotypic response. Non-specific lysine modification by salicylaldehydes is generally short-lived (rapid off-rate), resulting in minimal off-target effects.

As described herein, a family of potent tricyclic chromenone-based IRE-1 inhibitors was generated via a Duff formylation that is attended by an unusual cyclization reaction. To improve the in vivo efficacy of these aldehyde inhibitors, a prodrug, B-I09 was developed, in which the reactive aldehyde was protected as a 1,3-dioxane acetal. Such a protecting group can be slowly hydrolyzed under physiological conditions to generate the reactive aldehyde in cells, restoring IRE-1 RNase inhibitory activity. B-I09 is effective in suppressing the growth of CLL and Myc-overexpressing Burkitt's lymphoma in vivo and in preventing the development of the graft-versus-host disease in mice. Additionally, the ability of B cells to produce secretory IgM is potently inhibited by B-I09, leading to significantly decreased immunosuppressive functions of myeloid-derived suppressor cells and reactivation of anti-tumor CD8+ T cell functions in CLL and lung cancer mouse models.

As disclosed herein, a fluorescent tricyclic chromenone inhibitor, D-F07, was developed, in which a 9-methoxy group is incorporated onto the chromenone core to enhance its potency and the aldehyde is masked to achieve long-term efficacy. Protection of the aldehyde as a 1,3-dioxane acetal leads to restoration of strong fluorescence emitted by the coumarin chromophore, enabling D-F07 to be tracked in cultured cells and in vivo. In certain non-limiting embodiments, chemical modifications of the hydroxy group adjacent to the aldehyde can significantly stabilize the 1,3-dioxane acetal, allowing precise control of inhibitory activity. Such protecting group can be slowly hydrolyzed under physiological conditions to generate the reactive aldehyde in cells, restoring IRE-1 RNase inhibitory activity.

Photo-labile, ROS-sensitive, and thiol-reactive structural cage groups were incorporated onto D-F07 to impart stimuli-responsive biological activities and stabilize the 1,3-dioxane acetal prodrug moiety through perturbing chromenone electron density. D-F07 can be generated from these caged derivatives by exposure to UV irradiation, hydrogen peroxide or glutathione, respectively, to emit fluorescence and inhibit IRE-1. In certain non-limiting embodiments, the compounds of the invention allow spatiotemporal control of salicylaldehyde-based IRE-1 inhibitors.

The invention relates, in certain aspects, to the unexpected discovery that secretory IgM (sIgM) can orchestrate an immunosuppressive microenvironment by recruiting myeloid-derived suppressor cells (MDSCs) into different tumor models, such as but not limited to solid tumors (such as lung cancer) and tumors that have high levels of secreted IgM. In certain embodiments, sIgM produced by B cells or CLL cells can contribute to the accumulation of MDSCs in a tumor. In other embodiments, inhibition of the IRE1/XBP-1 pathway can ablate, minimize, or reduce MDSC levels in a tumor.

As demonstrated herein, a HEL-specific MD4/Eμ-TCL1 CLL mouse model was generated and characterized. These mice survive shorter periods of time than Eμ-TCL1 mice. While B cells developed in MD4/Eμ-TCL1 mice recognize HEL, CLL cells developed in these mice fail to recognize HEL. Nevertheless, MD4/Eμ-TCL1 CLL cells reactivate a parental Ig gene allele to produce BCR and secretory IgM (sIgM). MD4/Eμ-TCL1 mice also generate significantly increased myeloid-derived suppressor cells (MDSCs), accounting for significantly decreased numbers of T cells. Because mouse and human CLL cells can produce sIgM, it was tested whether sIgM can contribute to the accumulation of MDSCs by crossing μS$^{-/-}$ mice, which cannot produce sIgM, with Eμ-TCL1 mice. The μS$^{-/-}$/Eμ-TCL1 mice develop decreased numbers of MDSCs, which are less capable of suppressing proliferation of T cells, and were found to survive longer than Eμ-TCL1 mice.

In this study, sIgM showed potent immunosuppressive activity by inducing the accumulations and upregulating the functions of MDSCs in tumor-bearing mice. Further, it was shown that targeting the synthesis and/or secretion of sIgM in tumor-bearing mice can be useful in slowing down tumor progression. Tumor-associated monocytic and granulocytic MDSCs from LLC-grafted μS$^{-/-}$ mice lose their capabilities in suppressing T cell proliferation (FIGS. 25G-25H). Such data suggest that sIgM may directly act on MDSCs to promote their suppressive activities.

Figure 33A:
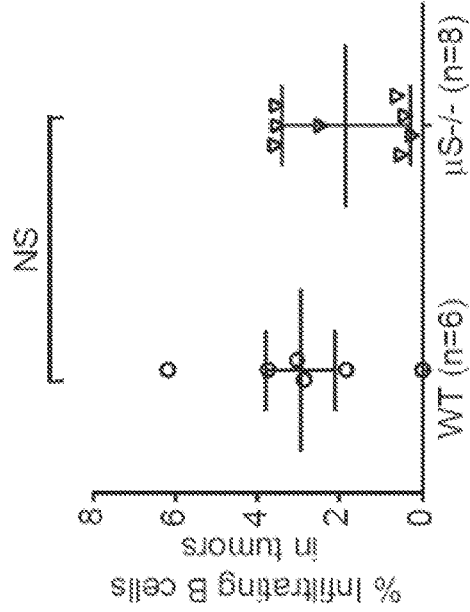
Figure 33B:
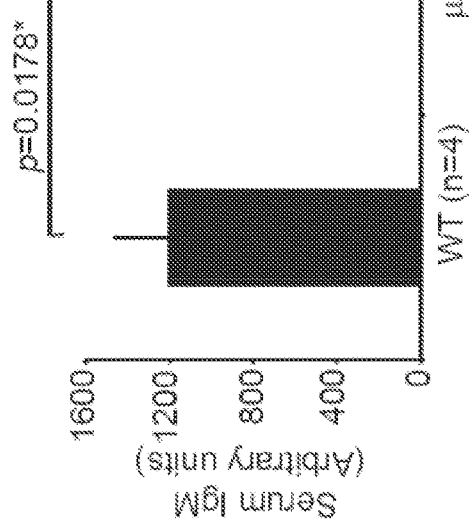
Figure 33C:
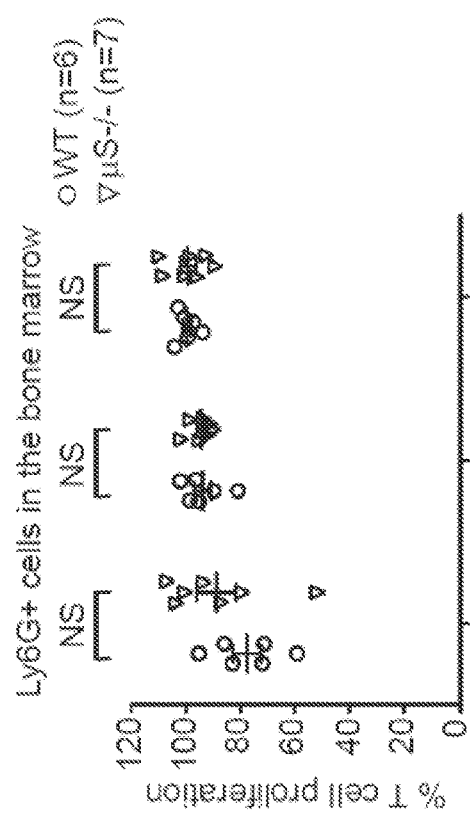
Figure 33D:
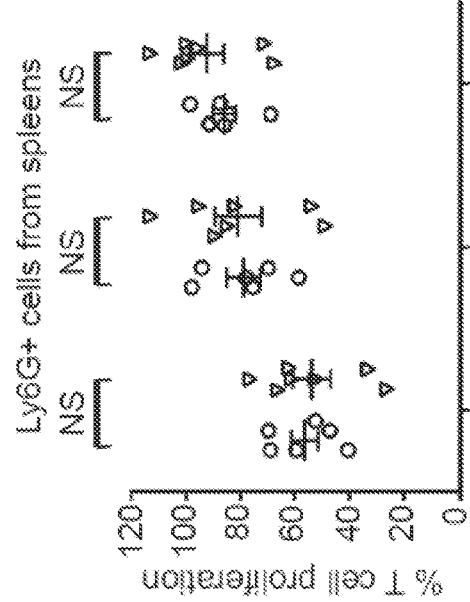

CD11b+/Ly6G+ granulocytic MDSCs isolated from the spleens, where CLL develop, but not from peripheral blood of CLL-bearing MD4$^{+/-}$/Eμ-TCL1$^{+/+}$ mice can suppress the proliferation of T cells (FIGS. 23E-23F, 24G, 24J, 32B). In addition, CD11b+/Ly6G+ granulocytic MDSCs purified from tumors of LLC-grafted mice are much more potent in suppressing T cell proliferation than those purified from the spleens and bone marrow of the same mice (FIGS. 25H and 33C-33D).

Synthesis of sIgM was targeted by deleting the function of XBP-1, because the synthesis of sIgM is tightly regulated by a mechanism called regulated IRE1-dependent decay (RIDD), which is hyperactivated in B cells as a response to XBP-1 deficiency. Targeting XBP-1 genetically or pharmacologically can indeed lead to decreased levels of sIgM, accompanied by decreased numbers and reduced functions of MDSCs in MD4/Eμ-TCL1 mice. Additionally, μS$^{-/-}$ mice grafted with Lewis lung carcinoma exhibit reduced functions of MDSCs in suppressing T cells, resulting in slower tumor growth. These results clearly demonstrate that sIgM produced by B cells can upregulate the functions of MDSCs in tumor-bearing mice to aggravate cancer progression.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —CH$_2$—CH=CH$_2$.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is (C$_1$-C$_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., C$_1$-C$_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is (C$_1$-C$_6$) alkyl, such as, but not limited to, ethyl, methyl, isopropyl, isobutyl, n-pentyl, n-hexyl and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C≡CH. The term "homopropargylic" refers to a group exemplified by —CH$_2$CH$_2$—C≡CH.

As used herein, the term "aromatic" refers to a carbocycle or heterocycle with one or more polyunsaturated rings and having aromatic character, i.e., having (4n+2) delocalized π (pi) electrons, where 'n' is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl and naphthyl. Aryl groups also include, for example, phenyl or naphthyl rings fused with one or more saturated or partially saturated carbon rings (e.g., bicyclo[4.2.0]octa-1,3,5-trienyl, or indanyl), which can be substituted at one or more carbon atoms of the aromatic and/or saturated or partially saturated rings.

As used herein, the term "aryl-(C$_1$-C$_6$)alkyl" refers to a functional group wherein a one to six carbon alkylene chain is attached to an aryl group, e.g., —CH$_2$CH$_2$-phenyl or —CH$_2$— phenyl (or benzyl). Specific examples are aryl-CH$_2$— and aryl-CH(CH$_3$)—. The term "substituted aryl-(C$_1$-C$_6$)alkyl" refers to an aryl-(C$_1$-C$_6$)alkyl functional group in which the aryl group is substituted. A specific example is substituted aryl(CH$_2$)—. Similarly, the term "heteroaryl-(C$_1$-C$_6$)alkyl" refers to a functional group wherein a one to three carbon alkylene chain is attached to a heteroaryl group, e.g., —CH$_2$CH$_2$-pyridyl. A specific example is heteroaryl-(CH$_2$)—. The term "substituted heteroaryl-(C$_1$-C$_6$)alkyl" refers to a heteroaryl-(C$_1$-C$_6$)alkyl functional group in which the heteroaryl group is substituted. A specific example is substituted heteroaryl-(CH$_2$)—.

As used herein, the term "B-I09" refers to 7-(1,3-dioxan-2-yl)-8-hydroxy-1,2,3,4-tetrahydro-5H-chromeno[3,4-c]pyridin-5-one, or a salt or solvate thereof:

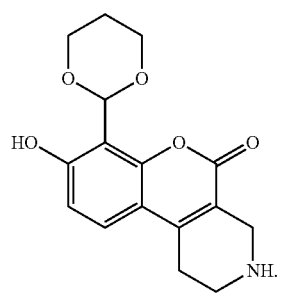 [SMILES: O=c1oc2c(C3OCCCO3)c(O)ccc2c2c1CNCC2]

As used herein, the term "biomarker" refers to a marker (e.g., an expressed gene, including mRNA and/or protein)

that allows detection of a disorder and/or disease in an individual. Biomarkers, as used herein, include nucleic acid and/or protein markers as set forth in the present disclosure. In specific embodiments, the expression level of a biomarker as determined by mRNA and/or protein levels in tissue or biological sample from an individual to be tested is compared with respective levels in normal tissue or biological sample from the same individual or another healthy individual. In other non-limiting embodiments, the presence of a biomarker as determined by mRNA and/or protein levels in a tissue or biological sample from an individual to be tested is compared with the respective presence or absence in normal tissue or biological sample from the same individual or another healthy individual. In certain non-limiting embodiments, a biomarker is a released and/or secreted protein that can be detected in a biological sample of a subject.

As used herein, the term "biological sample" refers to a sample of biological material obtained from a subject, preferably a human subject, including tissue, a tissue sample, a cell sample, a tumor sample, a stool sample and a biological fluid, e.g., blood, urine, lymphatic fluid, ascites, pancreatic cyst fluid and a nipple aspirate. In one non-limiting embodiment, the presence of one or more biomarkers is determined in a peripheral blood sample obtained from a subject. In another non-limiting embodiment, the presence of one or more biomarkers is detected in a stool sample obtained from a subject.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—$CH_3$, —CH═CH—$CH_2$—OH, —$CH_2$—CH═N—$OCH_3$, —CH═CH—N($CH_3$)—$CH_3$, and —$CH_2$—CH═CH—$CH_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —$OCH_2CH_2CH_3$, —$CH_2CH_2CH_2OH$, —$CH_2CH_2NHCH_3$, —$CH_2SCH_2CH_3$, and —$CH_2CH_2S$(═O)$CH_3$. Up to two heteroatoms may be consecutive, such as, for example, —$CH_2NH$—$OCH_3$, or —$CH_2CH_2SSCH_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that comprises carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, a "pharmaceutically effective amount," "therapeutically effective amount" or "effective amount" of a compound is that amount of compound that is sufficient to provide a beneficial effect to the subject to which the compound is administered.

The term "prevent," "preventing" or "prevention" as used herein means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds" as used herein is meant that a first molecule preferentially binds to a second molecule (e.g., a particular receptor or enzyme), but does not necessarily bind only to that second molecule.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In certain embodiments, the subject is human.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl or alkynyl, as defined elsewhere herein, substituted by one, two or three substituents independently selected from the group consisting of halogen, —OH, alkoxy, tetrahydro-2-H-pyranyl, —NH$_2$, —NH(C$_1$-C$_6$ alkyl), —N(C$_1$-C$_6$ alkyl)$_2$, pyridin-2-yl, pyridin-3-yl, pyridin-4-yl, —C(=O)OH, —C(=O)O(C$_1$-C$_6$)alkyl, trifluoromethyl, —C(=O)NH$_2$, —C(=O)NH(C$_1$-C$_6$) alkyl, —C(=O)N((C$_1$-C$_6$)alkyl)$_2$, —SO$_2$NH$_2$, —SO$_2$NH (C$_1$-C$_6$ alkyl), —SO$_2$N(C$_1$-C$_6$ alkyl)$_2$, —C(=NH)NH$_2$, and —NO$_2$, in certain embodiments containing one or two substituents independently selected from halogen, —OH, alkoxy, —NH$_2$, trifluoromethyl, —N(CH$_3$)$_2$, and —C(=O) OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic.

In certain embodiments, each occurrence of alkyl or cycloalkyl is independently optionally substituted with at least one substituent selected from the group consisting of $C_1$-$C_6$ alkyl, halo, —OR, phenyl (thus yielding, in non-limiting examples, optionally substituted phenyl-($C_1$-$C_3$ alkyl), such as, but not limited to, benzyl or substituted benzyl) and —N(R)(R), wherein each occurrence of R is independently H, $C_1$-$C_6$ alkyl or $C_3$-$C_8$ cycloalkyl. In other embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —N(R)(R), —NO$_2$, —S(=O)$_2$N(R)(R), acyl, and $C_1$-$C_6$ alkoxycarbonyl, wherein each occurrence of R is independently H, $C_1$-$C_6$ alkyl or $C_3$-$C_8$ cycloalkyl. In yet other embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —N(R)(R), and $C_1$-$C_6$ alkoxycarbonyl, wherein each occurrence of R is independently H, $C_1$-$C_6$ alkyl or $C_3$-$C_8$ cycloalkyl.

Unless otherwise noted, when two substituents are taken together to form a ring having a specified number of ring atoms (e.g., $R^2$ and $R^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The terms "treat," "treating" and "treatment," as used herein, means reducing the frequency or severity with which symptoms of a disease or condition are experienced by a subject by virtue of administering an agent or compound to the subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Compounds

Compounds useful within the invention include any compound that inhibits IRE1's signaling and/or IRE1's RNase activity in a cell. Such compounds include the following compounds, or a salt, solvate, prodrug, stereoisomer (such as, in a non-limiting example, an enantiomer or diastereoisomer, and any mixtures thereof, such as, in a non-limiting example, mixtures in any proportion of enantiomers and/or diastereoisomers thereof), tautomer, and/or geometric isomer, and any mixtures thereof. It should be noted that the absolute stereochemistry of the chiral center(s) represented in any structure depicted herein and/or compound named herein is merely illustrative and non-limiting.

The invention include a compound of formula (I), or a salt, solvate, prodrug, stereoisomer (such as, in a non-limiting example, an enantiomer or diastereoisomer, and any mixtures thereof, such as, in a non-limiting example, mixtures in any proportion of enantiomers and/or diastereoisomers thereof), tautomer, and/or geometric isomer, and any mixtures thereof. It should be noted that the absolute stereochemistry of the chiral center(s) represented in any structure depicted herein and/or compound named herein is merely illustrative and non-limiting.

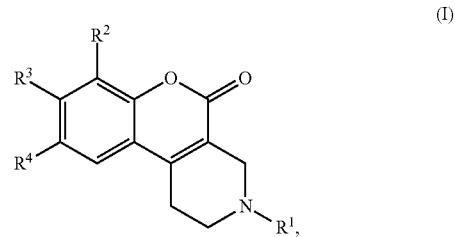

(I)

In certain embodiments, the compound of formula (I) is: wherein:
  $R^1$ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, ($C_3$-$C_8$ cycloalkyl)-C(=O)—, ($C_1$-$C_6$ alkyl)-OC(=O)—, ($C_2$-$C_6$ alkenyl)-OC(=O)—, ($C_2$-$C_6$ alkynyl)-OC(=O)—, and ($C_3$-$C_8$ cycloalkyl)-OC(=O)—, wherein the alkyl, alkenyl, alkynyl, or cycloalkyl are independently optionally substituted;
  $R^2$ is selected from the group consisting of optionally substituted 1,3-dioxolan-2-yl, optionally substituted 1,3-dioxan-2-yl, —CH=N—OR$^5$, and —CH=N—NR$^5$R$^6$, wherein:
    $R^5$ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, and ($C_3$-$C_8$ cycloalkyl)-C(=O)—, wherein the alkyl, alkenyl, alkynyl, or cycloalkyl are independently optionally substituted, $R^6$ is selected from the group consisting of H and $C_1$-$C_6$ alkyl, wherein the alkyl is optionally substituted, or $R^5$ and $R^6$ combine with the N atom to which they are bound to form an optionally substituted heterocyclyl or heteroaryl;

$R^3$ is —OH or a group that can be deprotected in vitro or in vivo to —OH; and $R^4$ is selected from the group consisting of H, —OH, $C_1$-$C_6$ alkoxy, $C_2$-$C_6$ alkenyloxy, $C_2$-$C_6$ alkynyloxy, $C_3$-$C_8$ cycloalkoxy, HC(=O)O—, ($C_1$-$C_6$ alkyl)-C(=O)O—, ($C_2$-$C_6$ alkenyl)-C(=O)O—, ($C_2$-$C_6$ alkynyl)-C(=O)O—, and ($C_3$-$C_8$ cycloalkyl)-C(=O)O—, wherein the alkyl, alkenyl, alkynyl, or cycloalkyl are independently optionally substituted.

In certain embodiments, the heterocyclyl is selected from the group consisting of imidazolyl, dihydroimidazolyl, piperidinyl, piperazinyl, morpholinyl, pyrrolidinyl, and tetrahydropyrimidinyl.

In certain embodiments, the heteroaryl is selected from the group consisting of pyridinyl, pyrimidinyl, pyrrolyl, oxazolyl, isoxazolyl, oxadiazolyl, imidazolyl, pyrazolyl, and triazolyl.

In certain embodiments, each occurrence of alkyl, alkenyl, alkynyl, or cycloalkyl is independently optionally substituted with at least one substituent selected from the group consisting of $C_1$-$C_6$ alkyl, halo, —CN, —OR, phenyl (thus yielding, in non-limiting examples, optionally substituted phenyl-($C_1$-$C_3$ alkyl), such as, but not limited to, benzyl or substituted benzyl), and —N(R)(R), wherein each occurrence of R is independently H, $C_1$-$C_6$ alkyl, or $C_3$-$C_8$ cycloalkyl.

In certain embodiments, each occurrence of phenyl, heterocyclyl, or heteroaryl is independently optionally substituted with at least one substituent selected from the group consisting of $C_1$-$C_6$ alkyl, $C_1$-$C_6$ haloalkyl, $C_1$-$C_6$ alkoxy, $C_1$-$C_6$ haloalkoxy, halo, —CN, —C(=O)OR, —OR, —N(R)(R), —NO$_2$, —S(=O)$_2$N(R)(R), acyl, and $C_1$-$C_6$ alkoxycarbonyl, wherein each occurrence of R is independently H, $C_1$-$C_6$ alkyl, or $C_3$-$C_8$ cycloalkyl.

In certain embodiments, $R^2$ is optionally substituted 1,3-dioxolan-2-yl. In other embodiments, $R^2$ is optionally substituted 1,3-dioxan-2-yl, such as but not limited to 5-methyl-1,3-dioxan-2-yl, or 5,5-dimethyl-1,3-dioxan-2-yl. In yet other embodiments, $R^2$ is —CH=N—OR$^5$. In yet other embodiments, $R^2$ is —CH=N—NR$^5$R$^6$.

In certain embodiments, $R^2$ is not optionally substituted 1,3-dioxolan-2-yl. In other embodiments, $R^2$ is not optionally substituted 1,3-dioxan-2-yl. In yet other embodiments, $R^2$ is not —CH=N—OR$^5$. In yet other embodiments, $R^2$ is not —CH=N—NR$^5$R$^6$.

In certain embodiments, $R^2$ is selected from the group consisting of:

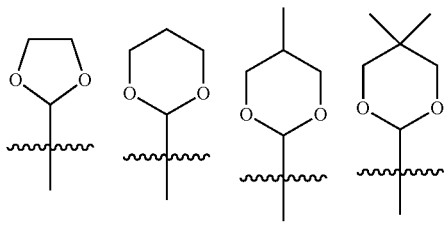

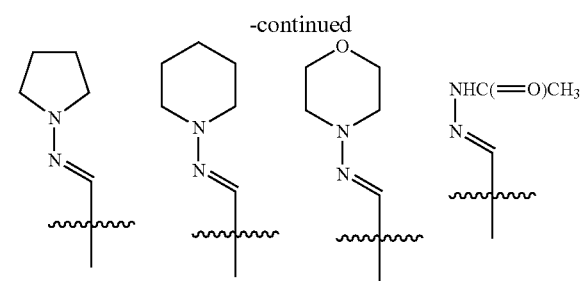

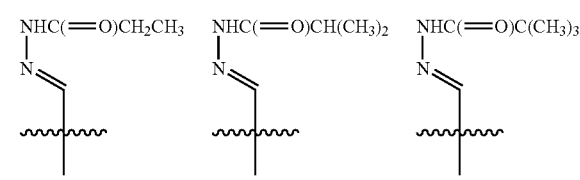

In certain embodiments, $R^3$ is —OH. In other embodiments, $R^3$ is not —OH. In other embodiments, $R^3$ is a group that can be deprotected in vitro or in vivo to —OH.

Non-limiting examples of such deprotectable $R^3$ groups include optionally substituted o-nitrobenzyloxy groups (which can be removed with UV light, for example). Examples of such optionally substituted o-nitrobenzyloxy groups include alpha-R*-ortho-nitrobenzyloxy, 2,6-dinitrobenzyloxy, 2-nitro-4,5-dimethoxybenzyloxy,

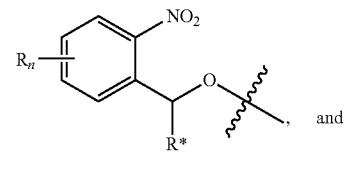, and

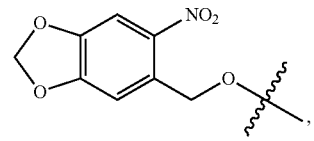, wherein: each occurrence of R* is independently H or not H (such as for example $C_1$-$C_6$ alkyl); each occurrence of n is independently 0, 1, 2, or 3; each occurrence of R is independently selected from the group consisting of H, $C_1$-$C_6$ alkyl, $C_1$-$C_6$ haloalkyl, $C_1$-$C_6$ alkoxy, $C_1$-$C_6$ haloalkoxy, halo, —CN, —C(=O)OR', —OR', —N(R')(R'), —NO$_2$, —S(=O)$_2$N(R')(R'), acyl, and $C_1$-$C_6$ alkoxycarbonyl; each occurrence of R' is independently selected from the group consisting of H, optionally substituted $C_1$-$C_6$ alkyl (such as for example —CH$_2$CH$_2$TMS or any analogue thereof), and optionally substituted $C_3$-$C_8$ cycloalkyl, or two R' groups bound to the same atom can combine to form a 3- to 8-membered ring.

Additional non-limiting examples of such deprotectable $R^3$ groups include optionally substituted benzoin derivatives, such as but not limited to:

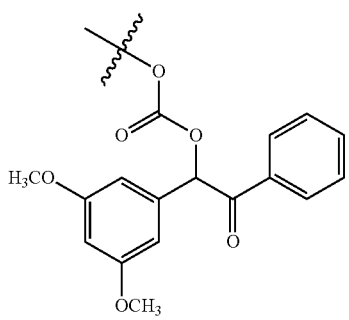 [SMILES: *OC(=O)OC(C(=O)c1ccccc1)c1cc(OC)cc(OC)c1]

(which can be removed with UV light, for example).

Additional non-limiting examples of such deprotectable $R^3$ groups include $(OH)_2B$— and any ether derivatives thereof (such as dimethyl ether, diethyl ether, diisopropyl ether, and 1,1,2,2-tetramethylethylene ether), and/or optionally substituted boronobenzyl groups, such as

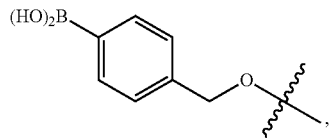 [SMILES: *OCc1ccc(B(O)O)cc1]

and any ether derivatives thereof (such as dimethyl ether, diethyl ether, diisopropyl ether, and 1,1,2,2-tetramethylethylene ether). Such groups can be deprotected under oxidative conditions, in the presence of hydrogen peroxide for example.

Additional non-limiting examples of such deprotectable $R^3$ groups include optionally substituted aryl-$S(=O)_2O$— or heteroaryl-$S(=O)_2O$— groups (such as mono-nitro-substituted-phenyl-$S(=O)_2O$— groups or di-nitro-substituted-phenyl-$S(=O)_2O$— groups). Such groups can be deprotected in the presence of thiol, such as glutathione for example.

Additional non-limiting examples of such deprotectable $R^3$ groups include optionally substituted acyloxy or aroyloxy (such as for example optionally substituted benzoyloxy), which can be deprotected under basic conditions.

In certain embodiments, $R^4$ is H. In other embodiments, $R^4$ is —OH. In yet other embodiments, $R^4$ is optionally substituted $C_1$-$C_6$ alkoxy. In yet other embodiments, $R^4$ is optionally substituted $C_2$-$C_6$ alkenyloxy. In yet other embodiments, $R^4$ is optionally substituted $C_2$-$C_6$ alkynyloxy. In yet other embodiments, $R^4$ is optionally substituted $C_3$-$C_8$ cycloalkoxy. In yet other embodiments, $R^4$ is $HC(=O)O$—. In yet other embodiments, $R^4$ is optionally substituted ($C_1$-$C_6$ alkyl)-$C(=O)O$—. In yet other embodiments, $R^4$ is optionally substituted ($C_2$-$C_6$ alkenyl)-$C(=O)O$—. In yet other embodiments, $R^4$ is optionally substituted ($C_2$-$C_6$ alkynyl)-$C(=O)O$—. In yet other embodiments, $R^4$ is optionally substituted ($C_3$-$C_8$ cycloalkyl)-$C(=O)O$—.

In certain embodiments, $R^4$ is not H. In other embodiments, $R^4$ is not —OH. In yet other embodiments, $R^4$ is not optionally substituted $C_1$-$C_6$ alkoxy. In yet other embodiments, $R^4$ is not optionally substituted $C_2$-$C_6$ alkenyloxy. In yet other embodiments, $R^4$ is not optionally substituted $C_2$-$C_6$ alkynyloxy. In yet other embodiments, $R^4$ is not optionally substituted $C_3$-$C_8$ cycloalkoxy. In yet other embodiments, $R^4$ is not $HC(=O)O$—. In yet other embodiments, $R^4$ is not optionally substituted ($C_1$-$C_6$ alkyl)-$C(=O)$ O—. In yet other embodiments, $R^4$ is not optionally substituted ($C_2$-$C_6$ alkenyl)-$C(=O)O$—. In yet other embodiments, $R^4$ is not optionally substituted ($C_2$-$C_6$ alkynyl)-$C(=O)O$—. In yet other embodiments, $R^4$ is not optionally substituted ($C_3$-$C_8$ cycloalkyl)-$C(=O)O$—.

In certain embodiments, the compound of formula (I) is selected from the group consisting of:

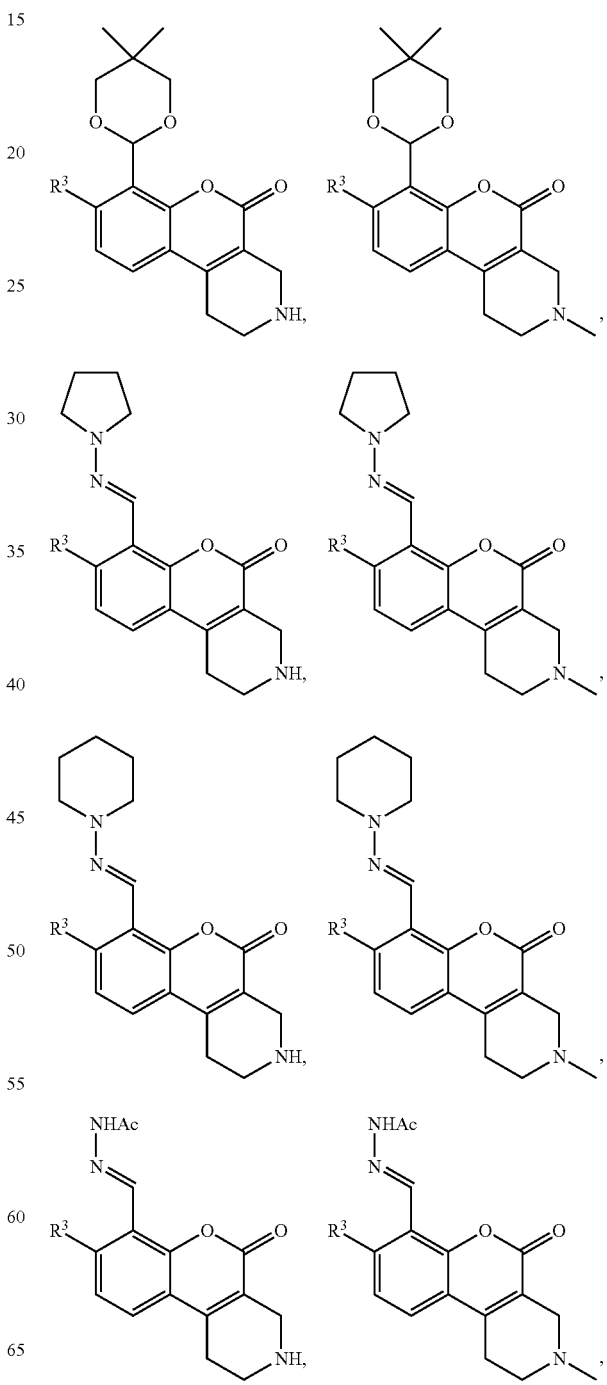

27
-continued
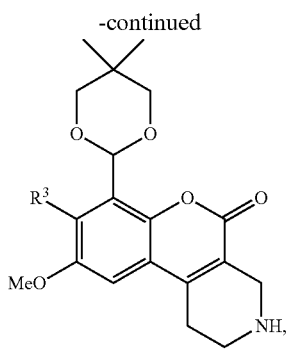
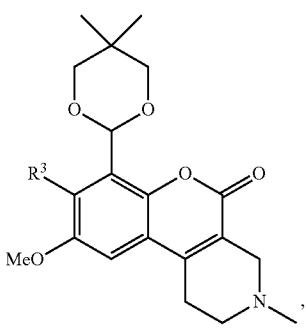
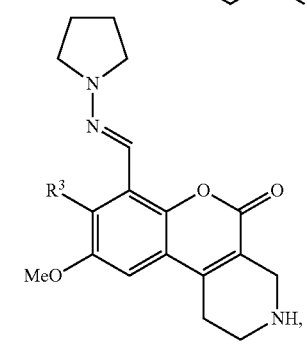
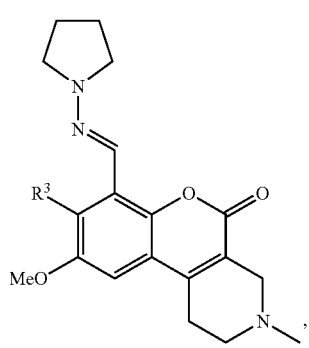
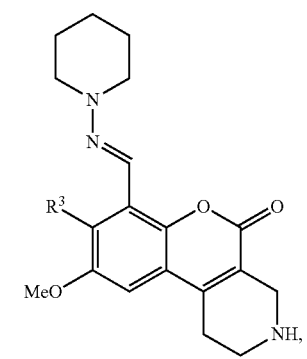
28
-continued
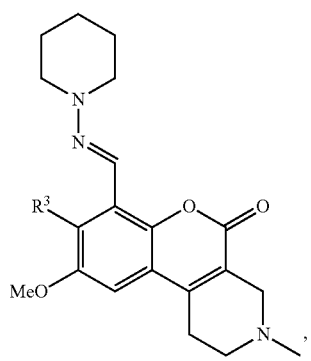
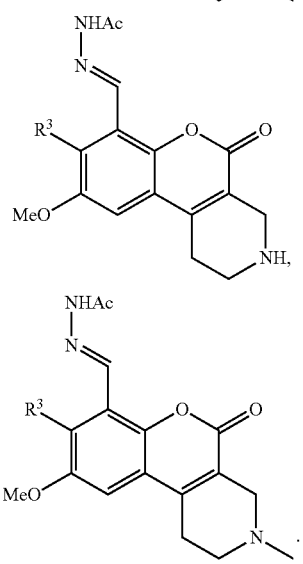
In certain embodiments, the compound of formula (I) is selected from the group consisting of:
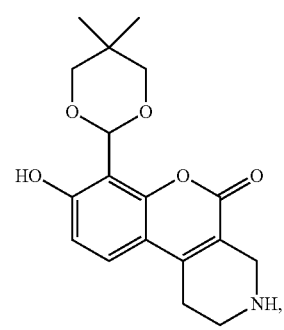
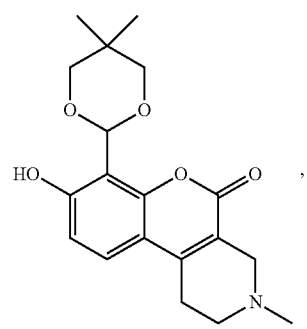

29
-continued
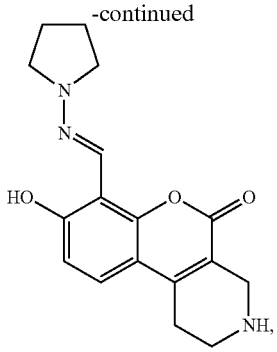
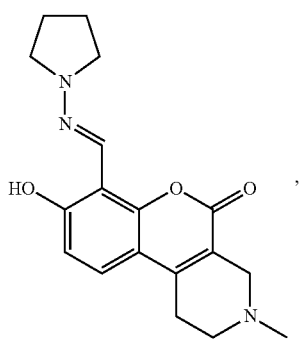,
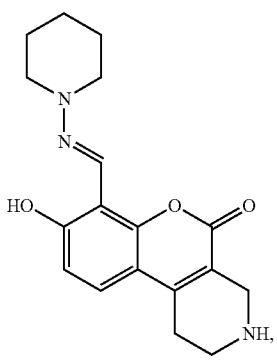,
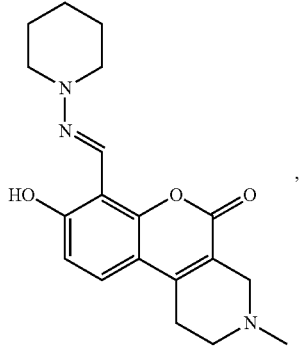,
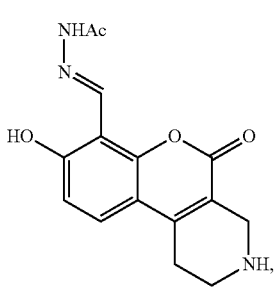,
30
-continued
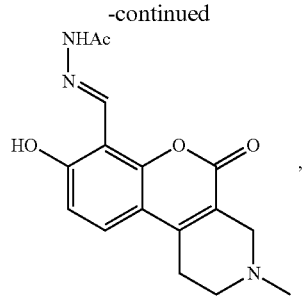,
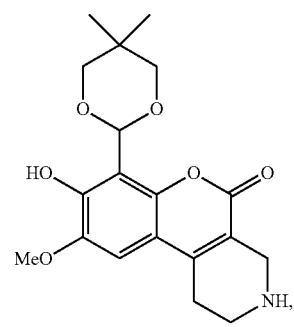,
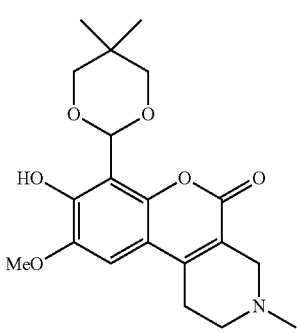,
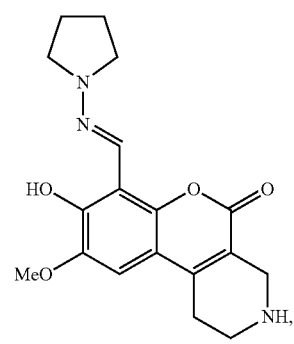,
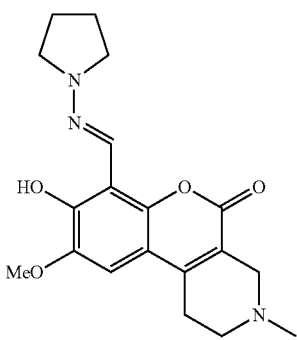, -continued

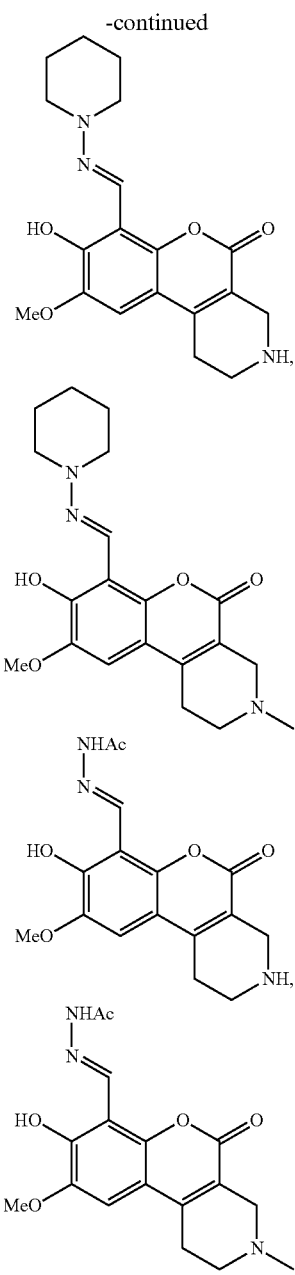

In certain embodiments, the compound is any of the compounds recited in U.S. Patent Application Publication No. US 2016/0083361, which is incorporated herein in its entirety by reference. In other embodiments, the compound is of formula (II):

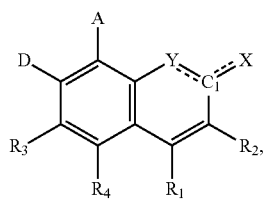

wherein:
the dotted lines between Y and $C_1$ and between $C_1$ and X represent single or double bonds;

A is a chalcogen containing moiety;
D is selected from the group consisting of hydrogen, hydroxyl, carbonyl, alkoxy, halogen, thiol, thioalkyl, aryl, alkylaryl, and alkyl;
$R^3$ and $R^4$ in the compound of formula (II) are independently selected from the group consisting of hydrogen, halogen, hydroxy, amino, alkyl, alkenyl, alkynyl, haloalkyl, cycloalkyl, heterocycloalkyl, alkylaryl, aryl, alkylheteroaryl, or heteroaryl, any of which is optionally substituted with carbonyl, alkyl, amino, amido, —$NR^6R^7$, —$C(O)NR^6R^7$, alkoxy, alkylhydroxyl, cycloalkyl, heterocycloalkyl, aryl, heteroaryl, carbonyl, halo, hydroxy, thiol, cyano, and nitro;
Y is selected from the group consisting of S, N, O, and C, wherein, when Y is C, the dotted line between Y and $C_1$ in the ring represents a double bond and the dotted line between $C_1$ and X is a single bond; and
wherein, when Y is S, N, or O, the dotted line between Y and $C_1$ in the ring represents a single bond and the dotted line between $C_1$ and X represents a double bond;
X is selected from the group consisting of hydrogen, oxygen, halogen, hydroxy, amino, thiol, thioalkyl, alkyl, alkenyl, alkynyl, haloalkyl, cycloalkyl, heterocycloalkyl, alkylaryl, aryl, alkylheteroaryl, or heteroaryl, any of which is optionally substituted with acetyl, alkyl, amino, amido, —$NR^6R^7$, —$C(O)NR^6R^7$, alkoxy, alkylhydroxyl, cycloalkyl, heterocycloalkyl, aryl, heteroaryl, carbonyl, halo, hydroxy, thiol, cyano, and nitro;
$R^1$ and $R^2$ in the compound of formula (II) are independently selected from the group consisting of hydrogen, benzoate, alkyl, heteroalkyl, alkenyl, heteroalkenyl, alkynyl, haloalkyl, cycloalkyl, heterocycloalkyl, alkylaryl, aryl, alkylheteroaryl, or heteroaryl, any of which is optionally substituted with acetyl, alkyl, amino, amido, —$NR^6R^7$, —$C(O)NR^6R^7$, alkoxy, alkylhydroxyl, cycloalkyl, heterocycloalkyl, aryl, heteroaryl, carbonyl, halo, hydroxy, thiol, cyano, and nitro; or
$R^1$ and $R^2$ in the compound of formula (II) together with the atoms to which they are attached form a 5-7 membered cyclic moiety wherein any of the additional atoms are optionally heteroatoms and the 5 to 7-membered ring is, optionally, a heterocyclic structure that is optionally substituted; and
$R^6$ and $R^7$ in the compound of formula (II) are independently H or alkyl; or
$R^6$ and $R^7$ in the compound of formula (II) together with the atoms to which they are attached form a 3-7 membered cyclic moiety wherein any of the additional atoms are optionally heteroatoms and the 3 to 7-membered ring is, optionally, a heterocyclic structure that is optionally substituted; or a pharmaceutically acceptable salt thereof.

The chalcogen containing moiety (A) can include aldehyde, protected aldehyde (e.g., dioxane and dithiane), reduced aldehyde, benzoate, ester, ketone, carbonyl, ether, carboxylic acid, alcohol, or alkoxyl groups. Also, chalcogen containing moieties can include amine, amide, sulfonamide, sulfonyl, sulfinyl, halogenated alkyl, CH=CH—$CO_2R^9$, CH=CH$SO_2R^9$; where $R^9$ is H, OH, or alkyl. Suitable benzoate groups include alkyl benzoates such as methyl or ethyl benzoate. The chalcogen containing moiety also includes sulfur and selenium analogs of any of the foregoing oxygen-containing chalcogen moieties, where a sulfur or selenium atom replaces one or more of the oxygen atoms.

In certain embodiments, the compound is B-I09, or a salt or solvate thereof.

In certain embodiments, the compound is 1-[4-(8-amino-3-tert-butylimidazo[1,5-a]pyrazin-1-yl)naphthalen-1-yl]-3-[3-(trifluoromethyl)phenyl]urea, or a salt or solvate thereof, or any other IRE1 signaling inhibitor compound recited in US 20160024094A1, which is incorporated herein in its entirety by reference.

In certain embodiments, the compound is toyomycin (4-Aminopyrrolo[2,3-d]pyrimidine-5-carbonitrile 7-(β-D-ribofuranoside), 7-Deaza-7-cyanoadenosine), or a salt or solvate thereof.

In certain embodiments, the compound is 4μ8C (7-hydroxy-4-methyl-2-oxo-2H-1-benzopyran-8-carboxaldehyde), or a salt or solvate thereof. See Cross et al., 2012, PNAS USA 109:E869E878, which is incorporated herein in its entirety by reference.

In certain embodiments, the compound is STF-083010 (N-[(2-Hydroxynaphthalen-1-yl)methylidene]thiophene-2-sulfonamide, N-[(2-Hydroxy-1-naphthyl)methylene]-2-thiophenesulfonamide), or a salt or solvate thereof.

In certain embodiments, the compound is any IRE1 signaling inhibitor compound recited in WO 2017152117A1, which is incorporated herein in its entirety by reference.

In certain embodiments, the compound is any salicylaldehyde that acts as a IRE1-signaling inhibitor (Volkmann, et al., 2011, J. Biol. Chem. 286:12743-12755), such as 3-ethoxy-5,6-dibromosalicylaldehyde, or a salt or solvate thereof. See also Sanches et al., 2014, Nature Comm. 5:4202.

In certain embodiments, the compound is MKC-3946 (2-hydroxy-6-(5-(4-methylpiperazine-1-carbonyl)thiophen-2-yl)-1-naphthaldehyde), or a salt or solvate thereof.

In certain embodiments, the compound is any IRE1 signaling inhibitor compound recited in U.S. Pat. No. 9,359,299, which is incorporated herein in its entirety by reference.

The compounds of the invention may possess one or more stereocenters, and each stereocenter may exist independently in either the (R) or (S) configuration. In certain embodiments, compounds described herein are present in optically active or racemic forms.

The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}F$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, (3-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Combination Therapies

In one aspect, the compounds of the invention are useful within the methods of the invention in combination with one or more additional agents useful for treating diseases or disorders contemplated herein. These additional agents may comprise compounds or compositions identified herein, or compounds (e.g., commercially available compounds)

known to treat, prevent, or reduce the symptoms of diseases or disorders contemplated herein.

In certain embodiments, the additional agent is a BTK inhibitor, such as, but not limited to ibrutinib.

In certain embodiments, the additional agent is a proteasome inhibitor, such as but not limited to bortezomib, carfilzomib, ixazomib, lactacystin, disulfiram, epigallocatechin-3-gallate, marizomib, oprozomib (ONX-0912), delanzomib (CEP-18770), epoxomicin, or beta-hydroxy beta-methylbutyrate.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Synthesis

The present invention further provides methods of preparing the compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Methods

The invention provides a method of inhibiting IRE1's signaling in a cell. The invention further provides a method of inhibiting IRE1's RNase activity in a cell. The invention further provides a method of inhibiting IRE1's RNase activity in a subject.

The invention further provides a method of treating or preventing cancer in a subject. In certain embodiments, the cancer is at least one selected from the group consisting of CLL, Burkitt's lymphoma, mantle cell lymphoma, breast cancer, and multiple myeloma. In other embodiments, the cancer is c-myc positive and/or c-myc overexpressing. In yet other embodiments, the cancer is c-myc overexpressing Burkitt's lymphoma. In yet other embodiments, the cancer is myc-driven breast cancer. In yet other embodiments, the subject is further administered a BTK inhibitor, such as but not limited to ibrutinib (1-[(3R)-3-[4-Amino-3-(4-phenoxyphenyl)-1H-pyrazolo[3,4-d]pyrimidin-1-yl]piperidin-1-yl]prop-2-en-1-one) or a salt or solvate thereof.

The teachings of Tang, et al., 2014, J. Clin. Invest. 124(6):2585-2598; Xie, et al., 2018, J Clin Invest. doi dot org/10 dot 1172/JCI95864; and Zhao, et al., 2018, J Clin Invest. doi dot org/10 dot 1172/JCI95873 are incorporated herein in their entireties by reference.

The invention further provides a method of treating or preventing guest-versus-host disease (GVHD) in a subject. The teachings of Schutt, et al., 2018, Blood Advances 2:414-427 are incorporated herein in their entireties by reference.

The invention further provides a method of minimizing or abrogating thapsigargin (THG) inducible upregulation of LOX-1 and T cells suppression in human normal polymorphonuclear cells (PMN) from healthy donors. The teachings of U.S. Application Publication No. US20180059115 A1 are incorporated herein in their entireties by reference.

The invention further provides a method of enhancing efficacy of cancer immunotherapy. In certain embodiments, administration of the compound of the invention overcomes the immunosuppressive effect of UPR in tumors. In other embodiments, administration of the compound of the invention reprograms function of tumor-infiltrating myeloid cells. The teachings of Cubillos-Ruiz, et al., 2017, J. ImmunoTher. Cancer 5:5 are incorporated herein in their entireties by reference.

The invention provides a method of reducing or minimizing production of secretory IgM (sIgM) in a cell. The invention provides a method of reducing or minimizing production of sIgM in a subject suffering from cancer. The invention further provides a method of minimizing or reducing number and/or activity of MDSC in a subject suffering from cancer. The invention further provides a method of treating or preventing a sIgM-assisted or -driven cancer in a subject. The invention further provides a method of stimulating or increasing proliferation of anti-tumor T cells in a subject suffering from a sIgM-assisted or -driven cancer.

In certain embodiments, the method comprises contacting a cell with at least one compound of the invention. In other embodiments, the method comprises administering to the subject in need thereof a therapeutically effective amount of at least one compound of the invention. In yet other embodiments, the compound of the invention is the only anticancer agent administered to the subject. In yet other embodiments, the at least one compound is administered to the subject in a pharmaceutically acceptable composition. In yet other embodiments, the subject is further administered at least one additional agent useful for treating the cancer. In yet other embodiments, the subject is co-administered the at least one compound and the at least one additional agent. In yet other embodiments, the at least one compound and the at least one additional agent are coformulated.

In certain embodiments, the subject is a mammal. In other embodiments, the mammal is a human.

Biomarker Detection

A biomarker used in the methods of the disclosure can be identified in a biological sample using any method known in the art. Determining the presence of a biomarker, protein or degradation product thereof, the presence of mRNA or pre-mRNA, or the presence of any biological molecule or product that is indicative of biomarker expression, or degradation product thereof, can be carried out for use in the methods of the disclosure by any method described herein or known in the art.

Protein Detection Techniques:

Methods for the detection of protein biomarkers are well known to those skilled in the art, and include but are not limited to mass spectrometry techniques, 1-D or 2-D gel-based analysis systems, chromatography, enzyme linked immunosorbent assays (ELISAs), radioimmunoassays (RIA), enzyme immunoassays (EIA), Western Blotting, immunoprecipitation and immunohistochemistry. These methods use antibodies, or antibody equivalents, to detect protein. Antibody arrays or protein chips can also be employed, see for example U.S. Patent Application Nos: 20030013208A1; 20020155493A1, 20030017515 and U.S. Pat. Nos. 6,329,209 and 6,365,418, herein incorporated by reference in their entireties.

ELISA and RIA procedures can be conducted such that a biomarker standard is labeled (with a radioisotope such as $^{125}$I or $^{35}$S, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker in the sample is allowed to react with the corresponding immobilized antibody, radioisotope or enzyme-labeled anti-biomarker antibody is allowed to react with the system, and radioactivity or the enzyme assayed (ELISA-sandwich assay). Other conventional methods can also be employed as suitable.

The above techniques can be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods can also be employed as suitable.

In one embodiment, a method for measuring biomarker expression includes the steps of: contacting a biological sample, e.g., blood, with an antibody or variant (e.g., fragment) thereof which selectively binds the biomarker, and detecting whether the antibody or variant thereof is bound to the sample. A method can further include contacting the sample with a second antibody, e.g., a labeled antibody. The method can further include one or more steps of washing, e.g., to remove one or more reagents.

It can be desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene can provide a suitable support.

Enzymes employable for labeling are not particularly limited, but can be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase can be assayed by measuring the concentration of hydrogen peroxide formed after reaction of the enzyme-labeled antibody with the substrate under controlled conditions well-known in the art.

Other techniques can be used to detect a biomarker according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection can also be used.

Immunohistochemistry can be used to detect the expression and/presence of a biomarker, e.g., in a biopsy sample. A suitable antibody is brought into contact with, for example, a thin layer of cells, followed by washing to remove unbound antibody, and then contacted with a second, labeled, antibody. Labeling can be by fluorescent markers, enzymes, such as peroxidase, avidin or radiolabeling. The assay is scored visually, using microscopy and the results can be quantitated.

Other machine or autoimaging systems can also be used to measure immunostaining results for the biomarker. As used herein, "quantitative" immunohistochemistry refers to an automated method of scanning and scoring samples that have undergone immunohistochemistry, to identify and quantitate the presence of a specified biomarker, such as an antigen or other protein. The score given to the sample is a numerical representation of the intensity of the immunohistochemical staining of the sample, and represents the amount of target biomarker present in the sample. As used herein, Optical Density (OD) is a numerical score that represents intensity of staining. As used herein, semi-quantitative immunohistochemistry refers to scoring of immunohistochemical results by human eye, where a trained operator ranks results numerically (e.g., as 1, 2 or 3).

Various automated sample processing, scanning and analysis systems suitable for use with immunohistochemistry are available in the art. Such systems can include automated staining (see, e.g., the Benchmark system, Ventana Medical Systems, Inc.) and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.).

Another method that can be used for detecting and quantitating biomarker protein levels is Western blotting. Cells can be frozen and homogenized in lysis buffer. Immunodetection can be performed with antibody to a biomarker using the enhanced chemiluminescence system (e.g., from PerkinElmer Life Sciences, Boston, Mass.). The membrane can then be stripped and re-blotted with a control antibody, e.g., anti-actin (A-2066) polyclonal antibody from Sigma (St. Louis, Mo.).

Antibodies against biomarkers can also be used for imaging purposes, for example, to detect the presence of a biomarker in cells of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99m}$Tc), fluorescent labels, such as fluorescein and rhodamine and biotin. Immunoenzymatic interactions can be visualized using different enzymes such as peroxidase, alkaline phosphatase, or different chromogens such as DAB, AEC or Fast Red.

For in vivo imaging purposes, antibodies are not detectable, as such, from outside the body, and so must be labeled, or otherwise modified, to permit detection. Markers for this purpose can be any that do not substantially interfere with the antibody binding, but which allow external detection. Suitable markers can include those that can be detected by X-radiography, NMR or MRI. For X-radiographic techniques, suitable markers include any radioisotope that emits detectable radiation but that is not overtly harmful to the subject, such as barium or caesium, for example. Suitable markers for NMR and MRI generally include those with a detectable characteristic spin, such as deuterium, which can be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99 m.

The labeled antibody or antibody fragment will then preferentially accumulate at the location of cells which contain a biomarker. The labeled antibody or variant thereof, e.g., antibody fragment, can then be detected using known techniques. Antibodies include any antibody, whether natural or synthetic, full length or a fragment thereof, monoclonal or polyclonal, that binds sufficiently strongly and specifically to the biomarker to be detected. An antibody can have a Kd of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant.

Antibodies and derivatives thereof that can be used encompasses polyclonal or monoclonal antibodies, chimeric, human, humanized, primatized (CDR-grafted), veneered or single-chain antibodies, phase produced antibodies (e.g., from phage display libraries), as well as functional binding fragments, of antibodies. For example, antibody fragments capable of binding to a biomarker, or portions thereof, including, but not limited to Fv, Fab, Fab' and F(ab')2 fragments can be used. Such fragments can be produced by enzymatic cleavage or by recombinant techniques. For example, papain or pepsin cleavage can generate Fab or F(ab')2 fragments, respectively. Other proteases with the requisite substrate specificity can also be used to generate Fab or F(ab')2 fragments. Antibodies can also be produced in a variety of truncated forms using antibody genes in which one or more stop codons have been introduced upstream of the natural stop site. For example, a chimeric gene encoding a F(ab')2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies.

In some embodiments, agents that specifically bind to a polypeptide other than antibodies are used, such as peptides. Peptides that specifically bind can be identified by any means known in the art, e.g., peptide phage display libraries. Generally, an agent that is capable of detecting a biomarker polypeptide, such that the presence of a biomarker is detected and/or quantitated, can be used. As defined herein, an "agent" refers to a substance that is capable of identifying or detecting a biomarker in a biological sample (e.g., identifies or detects the mRNA of a biomarker, the DNA of a biomarker, the protein of a biomarker). In one embodiment, the agent is a labeled or labelable antibody which specifically binds to a biomarker polypeptide.

In addition, a biomarker can be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait).

For additional information regarding mass spectrometers, see, e.g., Principles of Instrumental Analysis, 3rd edition. Skoog, Saunders College Publishing, Philadelphia, 1985; and Kirk-Othmer Encyclopedia of Chemical Technology, 4th ed. Vol. 15 (John Wiley & Sons, New York 1995), pp. 1071-1094.

Detection of the presence of a marker or other substances will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of a particular biomarker. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer (e.g., desorption source, mass analyzer, detect, etc.) and varied sample preparations can be combined with other suitable components or preparations described herein, or to those known in the art. For example, in some embodiments a control sample can contain heavy atoms (e.g., $^{13}C$) thereby permitting the test sample to be mixed with the known control sample in the same mass spectrometry run.

In one preferred embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to better quantify the amount of the biomolecule present in the first sample. In certain embodiments, the identity of the biomolecules in the first and second sample can also be determined.

RNA Detection Techniques:

Any method for qualitatively or quantitatively detecting a nucleic acid biomarker can be used. Detection of RNA transcripts can be achieved, for example, by Northern blotting, wherein a preparation of RNA is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography.

Detection of RNA transcripts can further be accomplished using amplification methods. For example, it is within the scope of the present disclosure to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by Marshall, et al., PCR Methods and Applications 4: 80-84 (1994).

In one embodiment, quantitative real-time polymerase chain reaction (qRT-PCR) is used to evaluate mRNA levels of biomarker. The levels of a biomarker and a control mRNA can be quantitated in cancer tissue or cells and adjacent benign tissues. In one specific embodiment, the levels of one or more biomarkers can be quantitated in a biological sample.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in Walker et al., Clin. Chem. 42: 9-13 (1996) and European Patent Application No. 684315; and target mediated amplification, as described by PCT Publication WO9322461.

In situ hybridization visualization can also be employed, wherein a radioactively labeled antisense RNA probe is hybridized with a thin section of a biopsy sample, washed, cleaved with RNase and exposed to a sensitive emulsion for autoradiography. The samples can be stained with haematoxylin to demonstrate the histological composition of the sample, and dark field imaging with a suitable light filter shows the developed emulsion. Non-radioactive labels such as digoxigenin can also be used.

Another method for evaluation of biomarker expression is to detect mRNA levels of a biomarker by fluorescent in situ hybridization (FISH). FISH is a technique that can directly identify a specific region of DNA or RNA in a cell and therefore enables to visual determination of the biomarker expression in tissue samples. The FISH method has the advantages of a more objective scoring system and the presence of a built-in internal control consisting of the biomarker gene signals present in all non-neoplastic cells in the same sample. Fluorescence in situ hybridization is a direct in situ technique that is relatively rapid and sensitive. FISH test also can be automated. Immunohistochemistry can be combined with a FISH method when the expression level of the biomarker is difficult to determine by immunohistochemistry alone.

Alternatively, mRNA expression can be detected on a DNA array, chip or a microarray. Oligonucleotides corresponding to the biomarker(s) are immobilized on a chip which is then hybridized with labeled nucleic acids of a test sample obtained from a subject. Positive hybridization signal is obtained with the sample containing biomarker transcripts. Methods of preparing DNA arrays and their use are well known in the art. (See, for example, U.S. Pat. Nos. 6,618,6796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug Discovery Today 5: 59-65, which are herein incorporated by reference in their entirety). Serial Analysis of Gene Expression (SAGE) can also be performed (See for example U.S. Pat. Appl. Doc. 20030215858).

To monitor mRNA levels, for example, mRNA can be extracted from the biological sample to be tested, reverse transcribed and fluorescent-labeled cDNA probes are generated. The microarrays capable of hybridizing to a biomarker, cDNA can then probed with the labeled cDNA probes, the slides scanned and fluorescence intensity measured. This intensity correlates with the hybridization intensity and expression levels.

Types of probes for detection of RNA include cDNA, riboprobes, synthetic oligonucleotides and genomic probes. The type of probe used will generally be dictated by the particular situation, such as riboprobes for in situ hybridization, and cDNA for Northern blotting, for example. Most preferably, the probe is directed to nucleotide regions unique to the particular biomarker RNA. The probes can be as short as is required to differentially recognize the particular biomarker mRNA transcripts, and can be as short as, for example, 15 bases; however, probes of at least 17 bases, more preferably 18 bases and still more preferably 20 bases are preferred. Preferably, the primers and probes hybridize specifically under stringent conditions to a nucleic acid fragment having the nucleotide sequence corresponding to the target gene. As herein used, the term "stringent conditions" means hybridization will occur only if there is at least 95% and preferably at least 97% identity between the sequences.

The form of labeling of the probes can be any that is appropriate, such as the use of radioisotopes, for example, $^{32}P$ and $^{35}S$. Labeling with radioisotopes can be achieved, whether the probe is synthesized chemically or biologically, by the use of suitably labeled bases.

Kits

In non-limiting embodiments, the present disclosure provides for a kit for determining whether a subject has sIgM-driven cancer comprising a means for detecting levels of sIgM in the subject's cancer sample. The disclosure further provides for kits for determining the efficacy of a therapy for preventing or treating cancer in a subject.

Types of kits include, but are not limited to, packaged probe and primer sets (e.g. TaqMan probe/primer sets), arrays/microarrays, biomarker-specific antibodies and beads, which further contain one or more probes, primers or other detection reagents for detecting one or more biomarkers of the present disclosure.

In a specific, non-limiting embodiment, a kit can comprise a pair of oligonucleotide primers suitable for polymerase chain reaction (PCR) or nucleic acid sequencing, for detecting one or more biomarker(s) to be identified. A pair of primers can comprise nucleotide sequences complementary to biomarker sIgM, and be of sufficient length to selectively hybridize with said biomarker. Alternatively, the complementary nucleotides can selectively hybridize to a specific region in close enough proximity 5' and/or 3' to the biomarker position to perform PCR and/or sequencing. Multiple biomarker-specific primers can be included in the kit to simultaneously assay large number of biomarkers. The kit can also comprise one or more polymerases, reverse transcriptase and nucleotide bases, wherein the nucleotide bases can be further detectably labeled.

In non-limiting embodiments, a primer can be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length.

In a further non-limiting embodiment, the oligonucleotide primers can be immobilized on a solid surface or support, for example, on a nucleic acid microarray, wherein the position of each oligonucleotide primer bound to the solid surface or support is known and identifiable.

In a specific, non-limiting embodiment, a kit can comprise at least one nucleic acid probe, suitable for in situ hybridization or fluorescent in situ hybridization, for detecting the biomarker(s) to be identified. Such kits will generally comprise one or more oligonucleotide probes that have specificity for various biomarkers.

In other non-limiting embodiments, a kit can comprise at least one antibody for immunodetection of the biomarker(s) to be identified. Antibodies, both polyclonal and monoclonal, specific for a biomarker, can be prepared using conventional immunization techniques, as will be generally known to those of skill in the art. The immunodetection reagents of the kit can include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels ($^{3}H$, $^{35}S$, $^{32}P$, $^{14}C$, $^{131}I$) or enzymes (alkaline phosphatase, horseradish peroxidase).

In other non-limiting embodiments, a kit can comprise a primer for detection of a biomarker by primer extension.

In a further non-limiting embodiment, the biomarker-specific antibody can be provided bound to a solid support, such as a column matrix, an array, or well of a microtiter plate. Alternatively, the support can be provided as a separate element of the kit.

In certain non-limiting embodiments, a kit can comprise one or more primers, probes, microarrays, or antibodies suitable for biomarker sIgM.

In certain non-limiting embodiments, a biomarker detection kit can comprise one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction to detect a biomarker. A kit can also include additional components or reagents necessary for the detection of a biomarker, such as secondary antibodies for use in immunohistochemistry. A kit can further include one or more other biomarkers or reagents for evaluating other prognostic factors, e.g., tumor stage.

A kit can further contain means for comparing the biomarker with a standard, and can include instructions for using the kit to detect the biomarker of interest. Specifically, the instructions describes that the presence of a biomarker, set forth herein, is indicative that the subject has or will develop cancer.

Reports, Programmed Computers, and Systems

The results of a test (e.g., an individual's risk for cancer), or an individual's predicted drug responsiveness (e.g., response to chemotherapy), based on assaying one or more biomarkers of the invention, and/or any other information pertaining to a test, can be referred to herein as a "report". A tangible report can optionally be generated as part of a testing process (which can be interchangeably referred to herein as "reporting," or as "providing" a report, "producing" a report, or "generating" a report).

Examples of tangible reports can include, but are not limited to, reports in paper (such as computer-generated printouts of test results) or equivalent formats and reports stored on computer readable medium (such as a CD, USB flash drive or other removable storage device, computer hard drive, or computer network server, etc.). Reports, particularly those stored on computer readable medium, can be part of a database, which can optionally be accessible via the internet (such as a database of patient records or genetic information stored on a computer network server, which can be a "secure database" that has security features that limit access to the report, such as to allow only the patient and the patient's medical practitioners to view the report while preventing other unauthorized individuals from viewing the report, for example). In addition to, or as an alternative to, generating a tangible report, reports can also be displayed on a computer screen (or the display of another electronic device or instrument).

A report can include, for example, an individual's risk for cancer, or can just include presence, absence or levels of one or more biomarkers of the invention (for example, a report on computer readable medium such as a network server can include hyperlink(s) to one or more journal publications or websites that describe the medical/biological implications, such as increased or decreased disease risk, for individuals having certain biomarkers or levels of certain biomarkers). Thus, for example, the report can include disease risk or other medical/biological significance (e.g., drug responsiveness, suggested prophylactic treatment, etc.) as well as optionally also including the biomarker information, or the report can just include biomarker information without including disease risk or other medical/biological significance (such that an individual viewing the report can use the biomarker information to determine the associated disease risk or other medical/biological significance from a source outside of the report itself, such as from a medical practitioner, publication, website, etc., which can optionally be linked to the report such as by a hyperlink).

A report can further be "transmitted" or "communicated" (these terms can be used herein interchangeably), such as to the individual who was tested, a medical practitioner (e.g., a doctor, nurse, clinical laboratory practitioner, genetic counselor, etc.), a healthcare organization, a clinical laboratory, and/or any other party or requester intended to view or possess the report. The act of "transmitting" or "communicating" a report can be by any means known in the art, based on the format of the report. Furthermore, "transmitting" or "communicating" a report can include delivering a report ("pushing") and/or retrieving ("pulling") a report. For example, reports can be transmitted/communicated by various means, including being physically transferred between parties (such as for reports in paper format) such as by being physically delivered from one party to another, or by being transmitted electronically or in signal form (e.g., via e-mail or over the internet, by facsimile, and/or by any wired or wireless communication methods known in the art) such as by being retrieved from a database stored on a computer network server, etc.

In certain exemplary embodiments, the disclosed subject matter provides computers (or other apparatus/devices such as biomedical devices or laboratory instrumentation) programmed to carry out the methods described herein. For example, in certain embodiments, the disclosed subject matter provides a computer programmed to receive (i.e., as input) the identity of the one or more biomarkers disclosed herein, alone or in combination with other biomarkers, and provide (i.e., as output) the disease risk (e.g., risk of cancer) or other result (e.g., disease diagnosis or prognosis, drug responsiveness, etc.) based on the level or identity of the biomarker(s). Such output (e.g., communication of disease risk, disease diagnosis or prognosis, drug responsiveness, etc.) can be, for example, in the form of a report on computer readable medium, printed in paper form, and/or displayed on a computer screen or other display.

Certain further embodiments of the disclosed subject matter provide a system for determining an individual's cancer risk, or whether an individual will benefit from chemotherapy treatment (or other therapy), or prophylactic treatment. Certain exemplary systems include an integrated "loop" in which an individual (or their medical practitioner) requests a determination of such individual's cancer risk (or drug response), this determination is carried out by testing a sample from the individual, and then the results of this determination are provided back to the requester. For example, in certain systems, a sample (e.g., stool, blood, etc.) is obtained from an individual for testing (the sample can be obtained by the individual or, for example, by a medical practitioner), the sample is submitted to a laboratory (or other facility) for testing (e.g., determining the biomarker(s) disclosed herein, alone or in combination with one or more other biomarkers), and then the results of the testing are sent to the patient (which optionally can be done by first sending the results to an intermediary, such as a medical practitioner, who then provides or otherwise conveys the results to the individual and/or acts on the results), thereby forming an integrated loop system for determining an individual's cancer risk (or drug response, etc.). The portions of the system in which the results are transmitted (e.g., between any of a testing facility, a medical practitioner, and/or the individual) can be carried out by way of electronic or signal transmission (e.g., by computer such as via e-mail or the internet, by providing the results on a website or computer network server which can optionally be a secure database, by phone or fax, or by any other wired or wireless transmission methods known in the art).

In exemplary embodiments, the system is controlled by the individual and/or their medical practitioner in that the individual and/or their medical practitioner requests the test, receives the test results back, and (optionally) acts on the test results to reduce the individual's disease risk, such as by implementing a disease management system.

The various methods described herein, such as correlating the presence or absence or level of a biomarker with an altered (e.g., increased or decreased) risk (or no altered risk) for cancer can be carried out by automated methods such as by using a computer (or other apparatus/devices such as biomedical devices, laboratory instrumentation, or other apparatus/devices having a computer processor) programmed to carry out any of the methods described herein. For example, computer software (which can be interchangeably referred to herein as a computer program) can perform correlating the presence or absence of a biomarker in an individual with an altered (e.g., increased or decreased) risk (or no altered risk) for cancer for the individual. Accordingly, certain embodiments of the disclosed subject matter provide a computer (or other apparatus/device) programmed to carry out any of the methods described herein.

Pharmaceutical Compositions and Formulations

The invention provides pharmaceutical compositions comprising at least one compound of the invention or a salt or solvate thereof, which are useful to practice methods of the invention. Such a pharmaceutical composition may consist of at least one compound of the invention or a salt or solvate thereof, in a form suitable for administration to a subject, or the pharmaceutical composition may comprise at least one compound of the invention or a salt or solvate thereof, and one or more pharmaceutically acceptable carriers, one or more additional ingredients, or some combination of these. At least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the invention are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 µg to about 7,500 mg, and any and all whole or partial increments thereof. In some embodiments, the dose of a compound of the invention is from about 0.5 µg and about 5,000 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the compositions and/or formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods
Chemical Synthesis:

Unless stated otherwise, reactions were performed in flame-dried glassware under a positive pressure of argon or nitrogen gas using dry solvents. Commercial grade reagents and solvents were used without further purification except where noted. Diethyl ether, toluene, dimethylformamide dichloromethane, and tetrahydrofuran were purified by a Glass Contour column-based solvent purification system. Other anhydrous solvents were purchased directly from chemical suppliers.

Thin-layer chromatography (TLC) was performed using silica gel 60 F254 pre-coated plates (0.25 mm). Flash chromatography was performed using silica gel (60 μm particle size). The purity of all compounds was judged by TLC analysis (single spot/two solvent systems) using a UV lamp, CAM (ceric ammonium molybdate), ninhydrin, or basic $KMnO_4$ stain(s) for detection purposes. NMR spectra were recorded on a 400 MHz spectrometer. $^1H$ and $^{13}C$ NMR chemical shifts are reported as δ using residual solvent as an internal standard. Analytical (4×150 mm column, 1 mL/min flow rate) RP-HPLC was performed on a $C_{18}$ column with acetonitrile/water (0.1% formic acid) as eluent.

General Methods:

UV-vis and fluorescence spectra were carried out on a BioTek SYNERGY™ NEO2 instrument (96 well plate). Confocal laser scanning microscope (CLSM) images were taken on an inverted fluorescence microscope (Leica TCS SP5). The photo-cleavage of PC-D-F07 was achieved by irradiation using a portable UV lamp (0.55 W/cm$^2$). LPS was purchased from Sigma-Aldrich.

Antibodies and Reagents:

Antibodies against XBP-1s (Cell Signaling), p97 (Fitzgerald), and actin (Sigma-Aldrich) were obtained commercially. LPS, cysteine, methionine, glycine, GSH and catalase were purchased from Sigma-Aldrich.

Cell Culture:

5TGM1 mouse multiple myeloma cells, primary mouse B cells, primary mouse Eμ-TCL1 CLL cells, and human CLL cell lines (MEC2 and WaC3) were cultured at 37° C. in a 5% $CO_2$ incubator using RPMI 1640 media (Gibco) supplemented with 10% heat-inactivated FBS, 2 mM L-glutamine, 100 U/mL penicillin G sodium, 1 mM sodium pyruvate, 0.1 mM non-essential amino acids, 100 μg/mL streptomycin sulfate and 0.1 mM β-mercaptoethanol (β-ME).

Purified mouse B cells or CLL cells were cultured in the RPMI 1640 media (Corning) supplemented with 10% heat-inactivated fetal bovine serum (FBS, Sigma), 2 mM L-glutamine, 100 U/ml penicillin G sodium, 100 μg/ml streptomycin sulfate, 1 mM sodium pyruvate, 0.1 mM non-essential amino acids, and 0.1 mM β-mercaptoethanol (β-ME). Lewis lung carcinoma (LLC) cells were obtained from ATCC, cultured in DMEM (Corning Incorporated) supplemented with 10% FBS, and regularly tested negative for mycoplasma. Cells were incubated in a 37° C. and 5% CO2 incubator. 70-80% confluent cells were harvested using 0.25% Trypsin (Thermo Fisher Scientific Inc.) and passaged or used for experiments.

Protein Isolation and Immunoblotting:

Cells were lysed using RIPA buffer (10 mM Tris-HCl, pH 7.4, 150 mM NaCl, 1% NP-40, 0.5% sodium deoxycholate, 0.1% SDS, and 1 mM EDTA) supplemented with protease inhibitors (Roche). Protein concentrations were determined by BCA assays (Pierce).

Samples were boiled in SDS-PAGE sample buffer (62.5 mM Tris-HCl, pH 6.8, 2% SDS, 10% glycerol, 0.1% bromophenol blue) with β-ME and analyzed by SDS-PAGE. Proteins were transferred to nitrocellulose membranes, blocked in 5% nonfat milk (wt/vol in PBS), and immuno-blotted with indicated primary antibodies and appropriate horseradish peroxidase-conjugated secondary antibodies. Immunoblots were developed using Western Lighting Chemiluminescence Reagent (PerkinElmer).

Surface Plasmon Resonance

Surface plasmon resonance measurement was performed using a Biacore T200 system (GE Healthcare). A total of 9700 resonance units of human IRE-1 (59.2 kD polyhistidine-tagged puritin-hIRE-1 fusion protein; Tang, et al., 2014, J. Clin. Invest. 124:2585-2598) was immobilized through amine coupling (EDC/NHS) in the flow well of a CM5 sensor chip (GE Healthcare) at a speed of 5 μL/minute, and a control well was similarly treated with buffer only (PBS, pH 7.4, containing 2% DMSO). Inhibitors of various concentrations were injected at a speed of 40 μL/minute in PBS, pH 7.4, containing 2% DMSO. Chip surface was regenerated by injecting 10 μL solution of 50 mM aq. NaOH at a speed of 5 μL/minute. Resonance differences between the wells containing protein and the control wells were plotted against inhibitor concentrations. Determination of $K_d$ was performed through asymptotic 1 fitting of the curve to steady-state one site binding model (OriginPro 8.5).

Cell Proliferation XTT Assays:

5TGM1 cells were suspended in phenol red-free RPMI media, seeded in 96-well cell culture plates, and treated with indicated IRE1 inhibitors (20 μM, unless indicated otherwise). At indicated time points, cells were spun down and cell proliferation was assessed by XTT assays (Roche) according to the manufacturer's instructions. Briefly, 50 μl XTT labeling reagent, 1 μl electron-coupling reagent, and 100 μl phenol red-free RPMI media were combined and applied to each well of the 96-well plates. Cells were incubated for 4 h in a $CO_2$ incubator to allow for the yellow tetrazolium salt XTT to be cleaved by mitochondrial dehydrogenases of metabolically active cells to form the orange formazan dye, which can be quantified at 492 nm using a BioTek SYNERGY™ NEO2 Multimode Reader.

Confocal Microscopy:

5TGM1 cells were plated onto the 24-well plate for 12 h before treatment. Live cells were treated with 10 μM of PC-D-F07 for 4 h, washed with PBS for 3 times, fixed in 4% paraformaldehyde solution at room temperature for 15 min, washed with PBS again, resuspended with 100 μL PBS, seeded onto a clean cover glass, and air-dried. Cells were rehydrated with PBS, mounted on a glass slide, and observed using a Leica TCS SP5 II confocal microscope. Photo-activation of PC-D-F07 was conducted using the DAPI filtered diode laser (50 mW). D-F07, resulted from PC-D-F07, were excited at 488 nm, observed at the emission wavelength from 498 to 650 nm, and expressed as green.

Compound Degradation HPLC Assay

A 20 mM DMSO stock solution of analyte compounds (7, 8, D-F07, PC-D-F07 and TC-D-F07) were diluted to 400 µM with PBS, pH 7.4, or to 800 µM with RMPI plus 10% FBS culture media (experiments with TC-D-F07 were performed using RPMI without FBS). After incubation at 37° C., aliquots at various time points were injected onto an analytical HPLC instrument and the peaks integrated (UV monitored at 220 nm). Intact compound relative to t=0 was plotted as a function of time.

Hydrogen Peroxide Detection

Levels of $H_2O_2$ were determined using the Amplex Red reagent in the presence of HRP. Briefly, 100,000 cells in 1 mL phenol red-free RPMI media were incubated with or without catalase (500 U/mL) in a 5% $CO_2$ incubator for 3 h, and seeded in 96-well cell culture plates (150 µL each well). Fifty µL Amplex Red reagent (containing 4 U/mL of HRP and 200 µM Amplex Red) was added into each well. After 1-h incubation in a $CO_2$ incubator, cells were spun down and the supernatant was transferred into 96-well black plates to measure the fluorescence intensity (Ex/Em: 571/578 nm) using a BioTek SYNERGY™ NEO2 Multimode Reader. Each fluorescent reading value was adjusted by subtracting the background measured from phenol red-free RPMI media. The rate of $H_2O_2$ production was calculated by fitting individual data points in a linear standard equation, y=bx+c. The $H_2O_2$ standard curve was created by combining 50 µL Amplex Red reagent with 150 µL phenol red-free RPMI media containing serially diluted $H_2O_2$ concentrations, incubating in a $CO_2$ incubator for 1 h, and measuring the fluorescence intensity (Ex/Em: 571/578 nm) using a BioTek SYNERGY™ NEO2 Multimode Reader. Each data point derived from four independent groups receiving the same treatment was plotted as means±SD. Results are representative of three independent experiments.

Pharmacokinetics

In vivo pharmacokinetics studies were carried out by intraperitoneally injecting 58 mg/kg D-F07 (347.36 Daltons) or 96 mg/kg TC-D-F07 (577.52 Daltons) into each Eµ-TCL1 mouse to achieve equivalent molar concentrations in the sera. Blood was collected via submandibular bleeding into an Eppendorf tube at 0.25-, 0.5-, 1-, and 1.5-h time points after a single injection. Blood samples were stored at room temperature for 5 min, placed on wet ice for 5 min, and centrifuged at 15,000 rpm/min for 5 min to obtain sera. D-F07 in sera was quantified by measuring the fluorescence intensity using a BioTek SYNERGY™ NEO2 Multimode Reader (Ex/Em: 350/456 nm). Each fluorescent reading value was adjusted by subtracting the background from serum samples without D-F07. D-F07 concentrations were calculated by fitting individual data points in a linear standard equation, y=bx+c. The D-F07 standard curve was created by measuring the fluorescence intensity in serum samples containing serially diluted D-F07. Data derived from three mice receiving the same treatment were plotted as means±SEM.

Mice:

Eµ-TCL1$^{+/+}$, MD4$^{+/-}$, MD4$^{+/-}$/Eµ-TCL1$^{+/+}$, µS$^{-/-}$, µS$^{-/-}$/Eµ-TCL1$^{+/+}$, XBP-1$^{f/f}$/MD4$^{+/-}$/Eµ-TCL1$^{+/+}$, and CD19Cre/XBP-1$^{f/f}$/MD4$^{+/-}$/Eµ-TCL1$^{+/+}$ mice were maintained at the animal facility strictly following standard animal care guidelines. All strains had been extensively and continuously backcrossed to the B6C3 background.

Flow Cytometric Analysis:

Single cell suspensions from spleens, bone marrow or peripheral lymph nodes were blocked for 30 minutes using FBS. Cell surface staining was achieved by incubating cells at 4° C. for 30 minutes with the following anti-mouse antibodies: CD3-APC-Cy7 (145-2C11; Biolegend); IgM-PE-Cy7 (RMM-1; Biolegend); B220-FITC (RA3-6B2; Biolegend); CD5-APC (53-7.3; e-Bioscience); CD11c-BV421 (N418; Biolegend); CD11b-PE (M1/70; Biolegend); Ly6C-Alexa 488 (HK1.4; Biolegend); Ly6G-Alexa 647 (1A8; Biolegend); CD4-BV605 (RM4-5; Biolegend); CD8α-PE-Cy7 (53-6.7; Biolegend); CD45-PE (30-F11; BD Biosciences); CD11b-BV605 (M1/70; Biolegend); and Arg-1-PE (pAB; R&D). Viability staining was accomplished using DAPI exclusion during acquisition. Acquisition of cell populations was performed on a LSRII cytometer (BD Biosciences). Cytometry data was analyzed using FlowJo software version 7.6.1 (Tree Star Inc.).

Antibodies and Reagents:

Polyclonal antibodies against Igα, Derlin-1, Derlin-2, BiP, and PDI were generated in rabbits. Antibodies against TCL1 (Cell Signaling), IRE1 (Cell Signaling), XBP-1 (Cell Signaling), Syk (Cell Signaling), phospho-Syk (Tyr525/526) (Cell Signaling), AKT (Cell Signaling), phospho-AKT (Ser473) (Invitrogen), ERK1/2 (Cell Signaling), phospho-ERK1/2 (Thr202/Tyr204) (Cell Signaling), GRP94 (Stressgen), p97 (Fitzgerald), actin (Sigma), phospho-Igα (Tyr182) (Cell Signaling), mouse µ (SouthernBiotech), human µ (SouthernBiotech), and phosphotyrosine (4G10; Millipore) were obtained commercially. Anti-µ Fab and F(ab')2 were purchased from SouthernBiotech. LPS (Sigma), CpG-1826 oligodeoxynucleotides (TIB-Molbiol), CFSE (Biolegend), Ultra-LEAF™ purified anti-mouse CD3ε antibody (145-2C11), and Ultra-LEAF™ purified anti-mouse CD28 antibody (37.51) were also obtained commercially.

Crosslinking of Hen Egg Lysozyme (HEL) and Purification of Oligomeric HEL:

Hen egg lysozyme (Sigma) was dissolved in PBS (pH 7.4), cross-linked with glutaraldehyde (Fisher) for 30 min at room temperature, and quenched with 1 M glycine. The insoluble precipitates were removed by centrifugation. Soluble proteins in the supernatant were precipitated by the addition of ammonium sulfate, and the precipitate was dissolved in a buffer containing 50 mM Tris-HCl (pH 7.4) and 8 M urea. The HEL monomers, dimers and oligomers were then separated on a Superdex 75 preparation column (GE Healthcare) equilibrated with 50 mM Tris-HCl (pH 7.4), 5 M urea and 300 mM NaCl. Monomeric, dimeric, and oligomeric HEL conjugates were pooled, dialyzed against PBS, and analyzed by SDS-PAGE followed by Coomassie blue staining.

Purification of Mouse B Cells, CLL Cells and MDSCs:

Splenocytes were obtained from mice by mashing the spleens through cell strainers followed by RBC lysis (Sigma). Mouse B cells and CLL cells were purified from mouse spleens by negative selection using CD43 (Ly48) or Pan-B magnetic beads (Miltenyi Biotech), respectively. MDSCs were purified from spleens, bone marrow or LLC tumors (digested with the mouse tumor dissociation kit purchased from Miltenyi Biotech) by positive selection using myeloid-derived suppressor cell isolation kit (Miltenyi Biotech).

BCR Activation:

Wild-type mouse MD4$^{+/-}$, MD4$^{+/-}$/Eμ-TCL1$^{+/+}$, and Eμ-TCL1$^{+/+}$ B cells were suspended in RPMI serum-free media supplemented with 25 mM Hepes; stimulated with Fab or F(ab')$_2$ fragments of the goat anti-mouse IgM antibody (20 μg/mL) (SouthernBiotech) or with monomeric, dimeric or oligomeric HEL (5 μg/mL) for indicated times; and lysed immediately by adding ice-cold lysis buffer (50 mM Tris-HCl, pH 8.0; 150 mM NaCl; 1% Triton X-100; 1 mM EDTA) supplemented with protease inhibitor cocktail (Roche), 4 mM sodium pyrophosphate, 2 mM sodium vanadate and 10 mM sodium fluoride. The lysates were analyzed by SDS-PAGE and immunoblotted for molecules of interest using specific antibodies.

Protein Isolation and Immunoblotting:

Cells were lysed in RIPA buffer (10 mM Tris-HCl, pH 7.4; 150 mM NaCl; 1% NP-40; 0.5% sodium deoxycholate; 0.1% SDS; 1 mM EDTA) supplemented with protease inhibitors (Roche) and phosphatase inhibitors. Protein concentrations were determined by BCA assays (Pierce). Proteins were boiled in SDS-PAGE sample buffer (62.5 mM Tris-HCl, pH 6.8; 2% SDS; 10% glycerol; 0.1% bromophenol blue) with n-ME, analyzed by SDS-PAGE, and transferred to nitrocellulose membranes, which were subsequently blocked in 5% non-fat milk (wt/vol in PBS), and immunoblotted with indicated primary antibodies and appropriate horseradish peroxidase-conjugated secondary antibodies. Immunoblots were developed using Western Lighting Chemiluminescence Reagent (Perkin-Elmer).

Tumor Bearing Mice and Treatment:

LLC cells were harvested and suspended in DPBS (Corning) as 200 μL containing 5×10$^5$ cells, and injected subcutaneously into wild-type and μS$^{-/-}$ mice. The in vivo anti-mouse CD8α monoclonal antibody (53-6.7, Rat IgG2a) and isotype control monoclonal antibody (2A3, Rat IgG2a) were procured from BioXCell.

Patient Samples:

Primary human CLL cells were obtained from patients at the Abramson Cancer Center of the University of Pennsylvania.

Pulse Chase Experiments and Immunoprecipitation:

Human CLL cells were starved in methionine- and cysteine-free media containing dialyzed fetal bovine serum for 1 h, and pulse-labeled with 250 μCi/ml [$^{35}$S]-methionine and [$^{35}$S]-cysteine (Perkin-Elmer) for indicated times. After labeling, cells were incubated in the chase medium containing unlabeled methionine (2.5 mM) and cysteine (0.5 mM). At the end of each chase interval, cells were lysed in RIPA buffer containing protease inhibitors. Pre-cleared lysates were incubated with an anti-human Igμ heavy chain antibody (SouthernBiotech), together with Protein G-sepharose beads. Immunoprecipitates were boiled in SDS-PAGE sample buffer (62.5 mM Tris-HCl, pH 6.8; 2% SDS; 10% glycerol; 0.1% bromophenol blue) with β-ME, analyzed by SDS-PAGE and visualized by autoradiography.

Enzyme-Linked Immunosorbent Assay (ELISA):

ELISA analyses of IgM (captured by goat anti-mouse μ chain IgG) or α-HEL IgM (captured by HEL) in mouse sera were achieved using an HRP-conjugated α-mouse IgM antibody (SouthernBiotech) and 3,3',5,5'-Tetramethylbenzidine (TMB) liquid substrate system (Sigma).

MDSC-Mediated T Cell Suppression Assay:

MDSCs were purified from the spleens, bone marrow, or tumors. The purity of cell populations was >95%. The PMEL-1 and OT-I responder mice have CD8+ T cells which recognize gp100-derived and OVA-derived peptides, respectively. Splenocytes from PMEL-1 or OT-I mice were mixed with splenocytes from nave mice at the 1:4 ratio in the complete RPMI media, and plated into 96-well U-bottom plates at 10$^5$ cells per well. CD11b+/Ly6G+ or CD11b+/Ly6C+ MDSCs were added to the wells at 0.25, 0.5 or 1×10$^5$ cells per well. The murine gp100 peptide (amino acids 25~33), EGSRNQDWL (AnaSpec), or OVA peptide (amino acids 257~264), SIINFEKL (AnaSpec) was dissolved in pure water, diluted with the RPMI complete media, and added into the wells at the final concentration of 0.1 μg/mL. After incubation for 48 h, cells were radiolabeled with $^3$H-thymidine (1 μCi per well; GE Healthcare) for 6 h. The uptake of $^3$H-thymidine was counted as CPM using a liquid scintillation counter. The percentage of proliferation in comparison to positive controls (the wells with responder cells and the corresponding peptide) was calculated.

Statistics:

The Kaplan-Meier analysis was used to evaluate mouse survival data. For comparison of percentages of cell populations among experimental groups, data were graphed as mean±SEM and analyzed by unpaired two-tailed Student's t test. A p value of <0.05 was considered significant.

Example 1: Tricyclic Chromenone Compounds with NH and N—CH$_3$ are More Potent IRE1 Inhibitors To develop inhibitors with improved potency to target the IRE1/XBP-1 pathway, tricyclic chromenone-based IRE1 RNase inhibitors with different amine group (R$^1$) were synthesized and compared: allyloxycarbonyl (alloc) in B-H09 (1), —H in C-B06 (2), and —CH$_3$ in C-D06 (3) (FIG. 1A). 5TGM1 multiple myeloma cells were chosen to evaluate inhibitory effects of these inhibitors because they have constitutively activated IRE1/XBP-1 pathways.

Figure 1B:
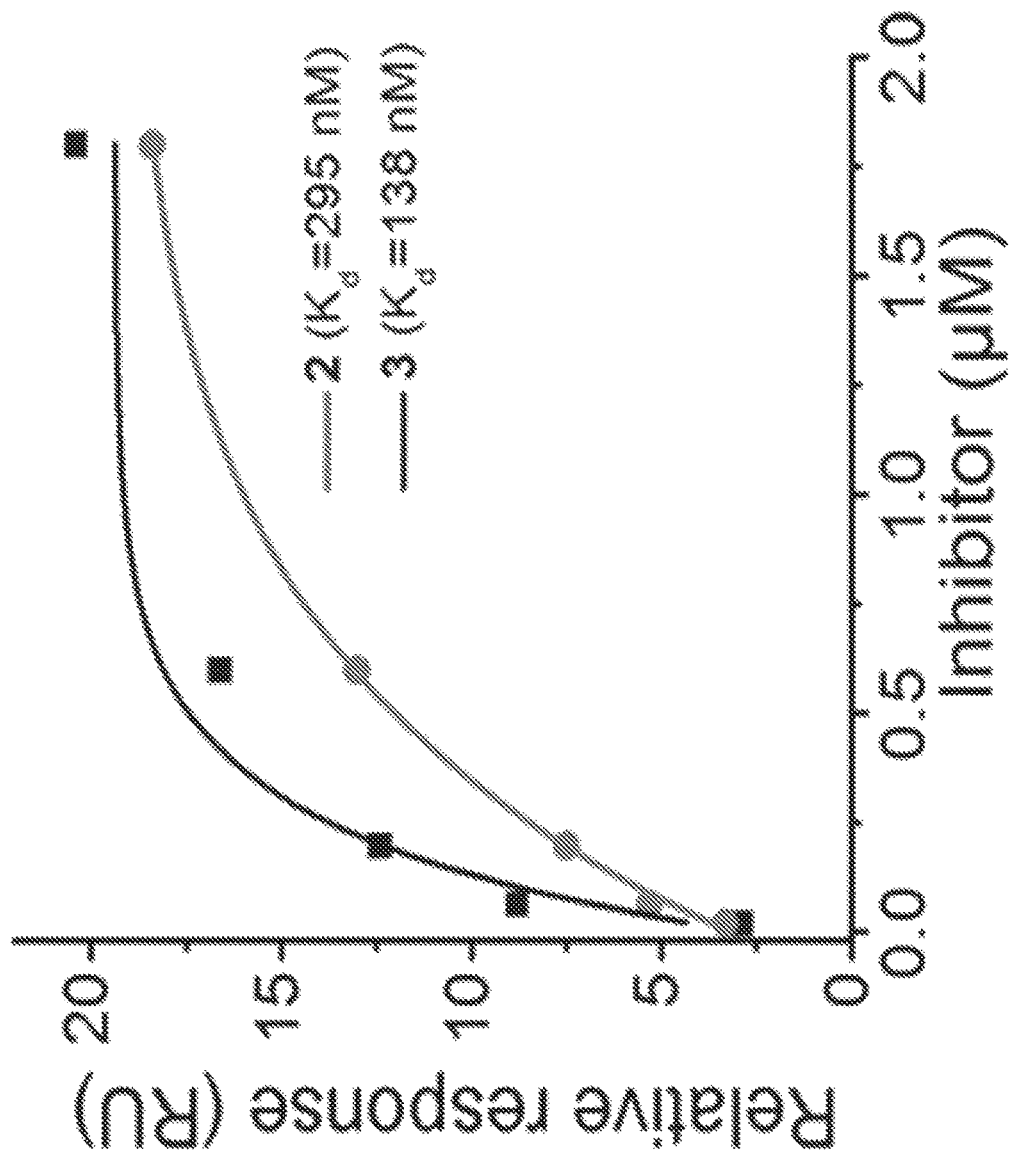

A biotin-tagged derivative of 1 can pull down endogenously expressed IRE-1 in B cells, while the reduced derivative B-I07 (aldehyde replaced by alcohol) fails to do so. The direct interaction of 2 and 3 with IRE-1 was confirmed using surface plasmon resonance (SPR), and a Kd value of 295 nM for 2 and a Kd value of 138 nM for 3 were determined (FIG. 1B). These compounds also exhibited slow off-rates ($k_d$=~1×10$^{-5}$ s$^{-1}$) indicating formation of a relatively stable but reversible adduct with IRE-1.

Figure 1C:
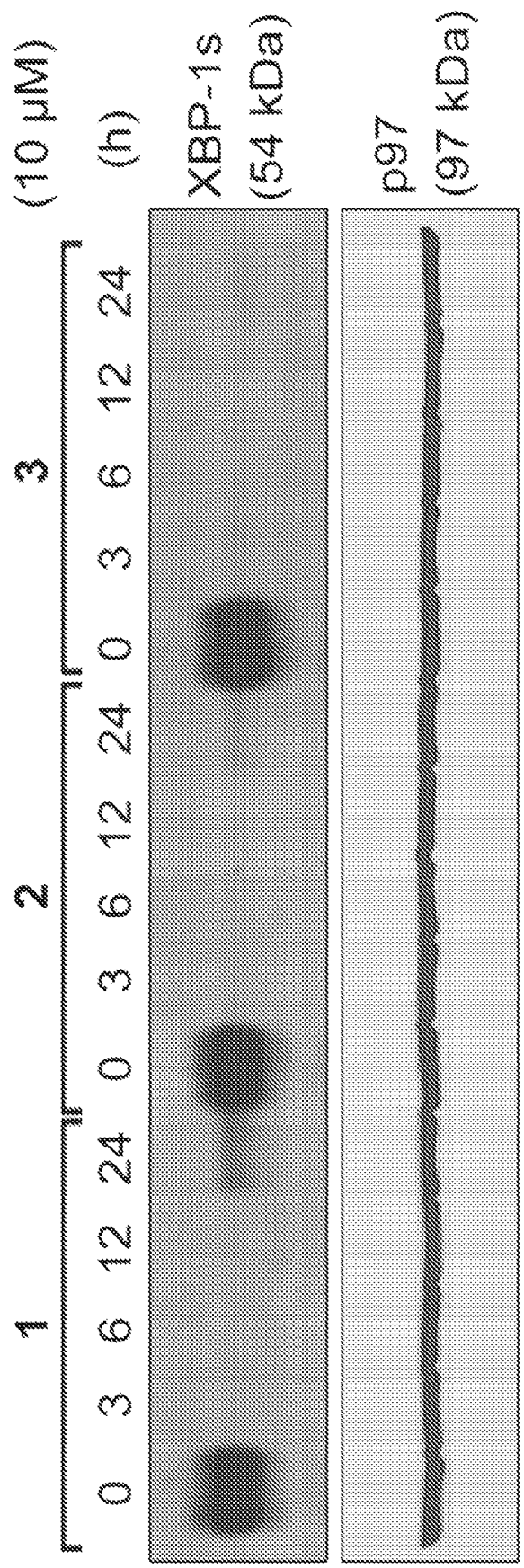

5TGM1 cells were treated with 10 μM 1, 2, or 3 for 0, 3, 6, 12, or 24 h, and levels of XBP-1s were analyzed. While 1, 2, and 3 rapidly inhibited the expression of XBP-1s, 1, 2, and 3 showed much better long-term inhibitory activities than 1 (FIG. 1C).

Figure 1D:
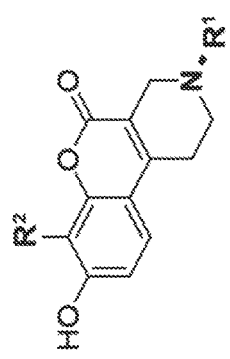
Figure 7:
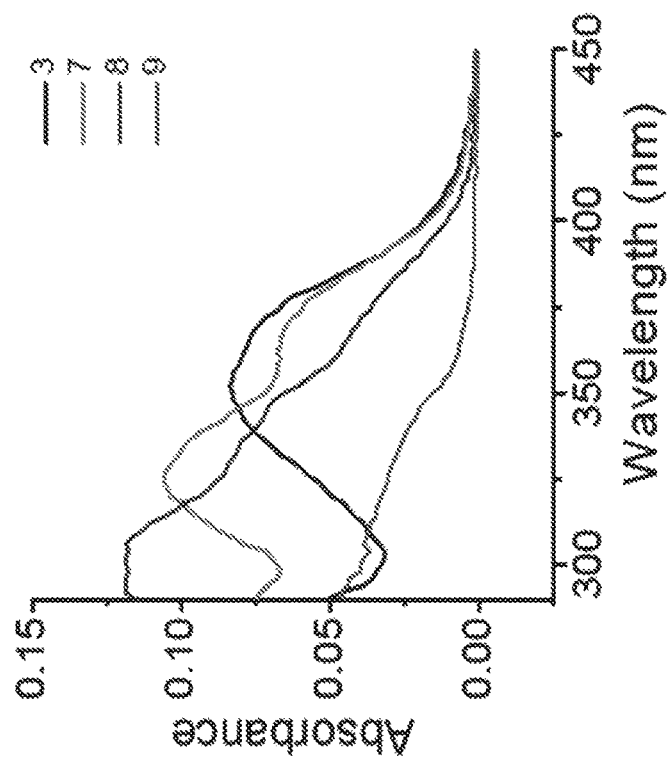
FIG. 7 illustrates absorbance curves of derivatives of 2 and 3 (10 µM) in the DMSO/PBS (v/v=1:99) solution.
Figure 7:
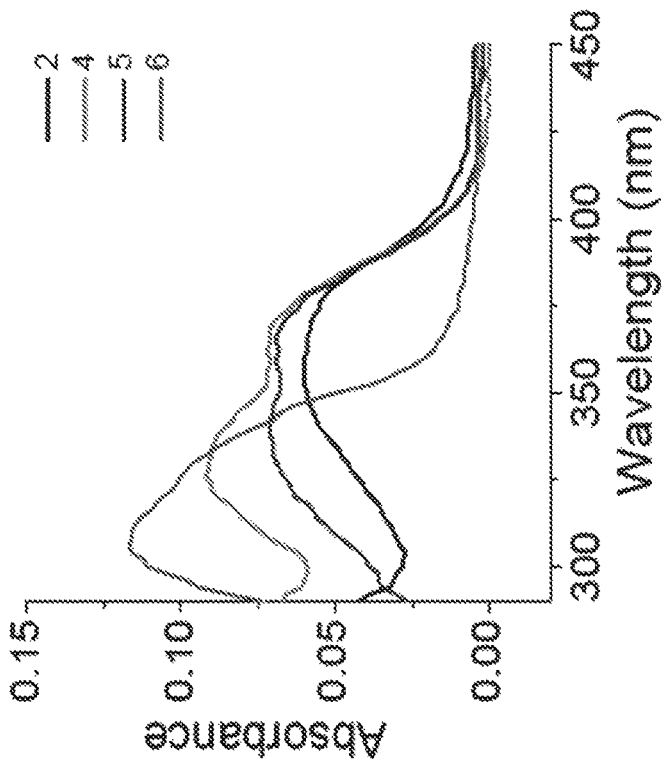

Example 2: Tricyclic Chromenone Compounds with the 1,3-dioxane Protective Groups Emit Strong Fluorescence It was then explored whether using different group (R$^2$) would protect the active aldehyde of tricyclic chromenone compound (FIG. 1D). Some of the protective groups considered are dioxane acetal groups, as in B-I09 (4), 5, and 7. Another protection was achieved by hydrazone-based coupling via the reaction of carbonyl with hydrazine, as in 6, 8 and 9. Installation of the 1,3-dioxane type of protective groups allowed 4, 5, and 7 to emit strong fluorescence at around 452 nm with an approximately 45- to 72-fold increased intensity when compared with their aldehyde counterparts, C-B06 and C-D06, respectively (FIGS. 1E-1F and 7). As the aldehyde is strongly electron withdrawing, its conversion to the acetal dramatically alters the electronic character of the aromatic substituent at R$^2$, leading to the fluorescence recovery of the coumarin chromophore.

Nevertheless, when the 1,3-dioxane acetal was replaced with hydrazone derivatives, 6, 8 and 9, weak or no fluorescence could be observed (FIG. 1F). This is because the C=N donor system in the hydrazone group can quench the fluorescence by photo-induced electron transfer (PET). Fluorescence brightness of 2 and 3 derivatives in aqueous solution could also be visualized by fluorescence imaging under 365 nm illumination (FIG. 1G).

Figure 2A:
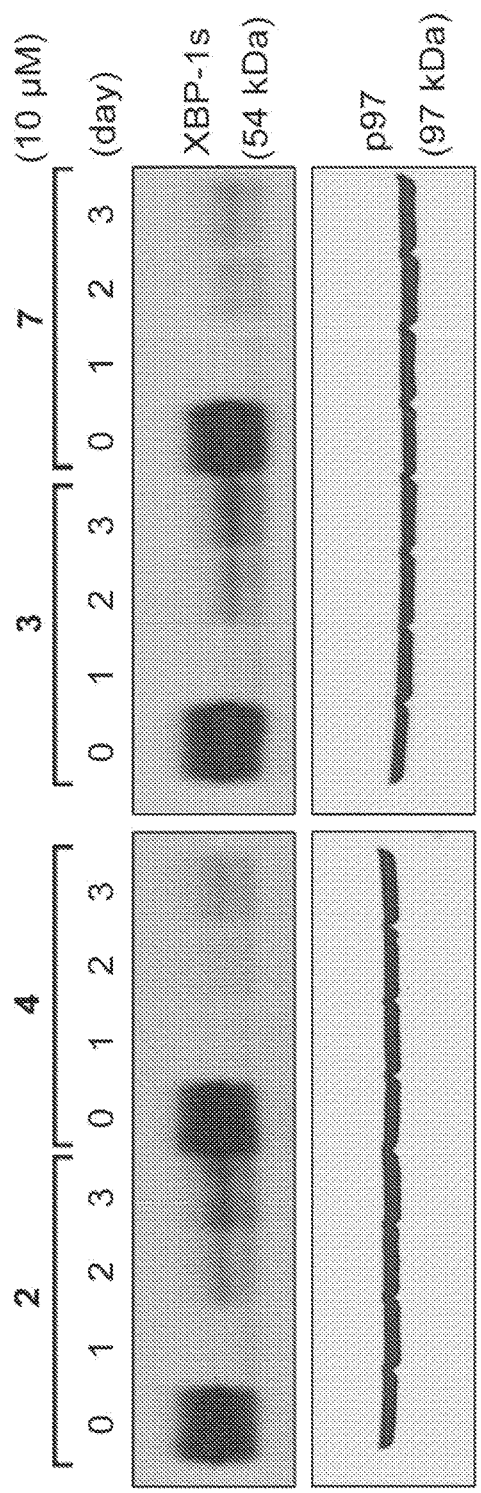
FIGS. 2A-2G illustrate the finding that tricyclic chromenone inhibitors with an N-acetohydrazone protective group can rapidly inhibit the expression of XBP-1s in cancerous B cells.

Example 3: Installation of the 1,3-dioxane Protective Group Increases the Potency of Tricyclic Chromenone Compounds in Inhibiting the Expression of XBP-1s 5TGM1 cells were treated with 2 or 3 at the concentration of 10 μM for a course of 3 days. The expression levels of XBP-1s recovered significantly in cells treated for 2 days (FIG. 2A). Without wishing to be limited by any theory, this happens possibly due to the reaction of the exposed aldehyde with proteins in culture media resulting in significantly lower drug uptake at later time points. However, when 5TGM1 cells were treated with prodrugs, 4 or 7, at 10 μM, the levels of XBP-1s were continuously suppressed even after 3-day treatment (FIG. 2A), highlighting that the slow hydrolysis of the 1,3-dioxane group allowed for the gradual release of the active compounds to achieve long-term efficacy.

Figure 2B:
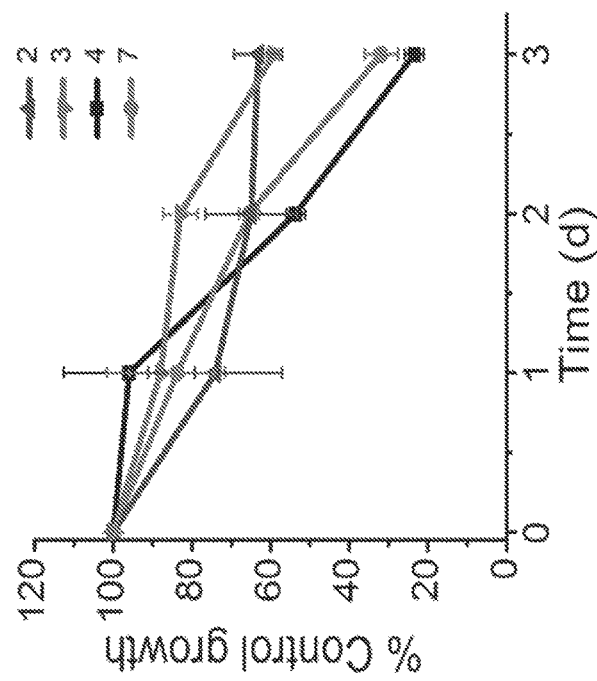

To evaluate cytotoxicity of these compounds, 5TGM1 cells were treated with indicated inhibitors at 20 μM for a course of 3 days, and XTT assays were performed. 4 and 7 were more potent than their respective aldehyde counterparts, 2 and 3, in inhibiting the growth of 5TGM1 cells (FIG. 2B). 5TGM1 cells were further treated with 4 and 5 for 24 h, and 4 was more potent than 5 in suppressing the expression of XBP-1s at the concentration of 5 μM (FIG. 2C). 4 effectively blocked the expression of XBP-1s in 5TGM1 cells at 5 μM, while 7 required a higher concentration (10 μM) to achieve the similar inhibition. Without wishing to be limited by any theory, this is likely due to the enhanced stability of 2,2-dimethyl-1,3-dioxane acetals toward hydrolysis relative to their unsubstituted counterparts.

Figure 2D:
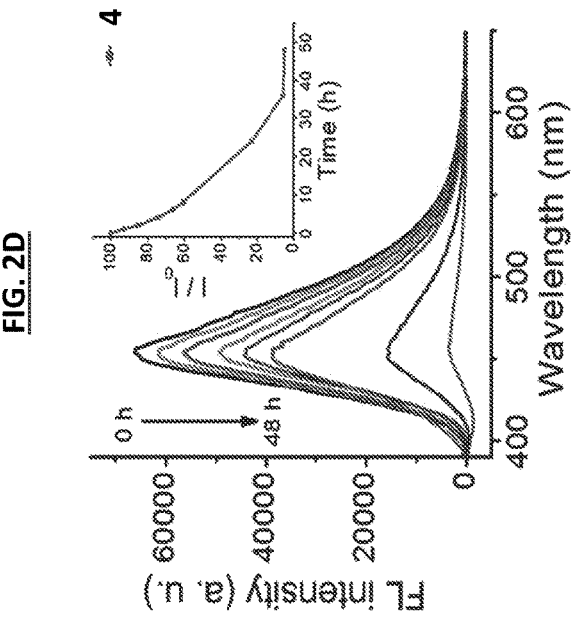
Figure 2C:
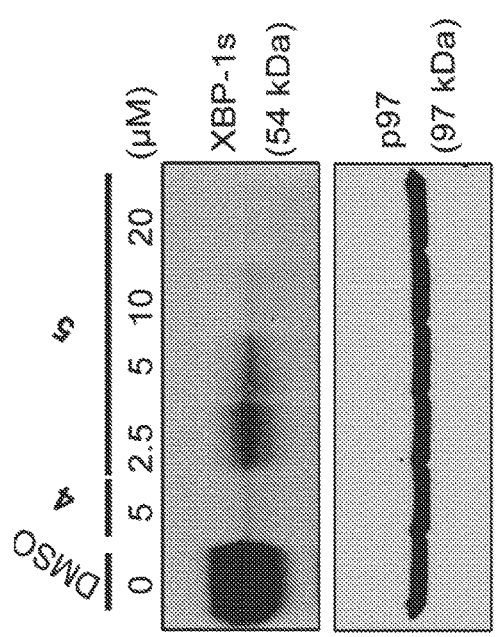
Figure 2E:
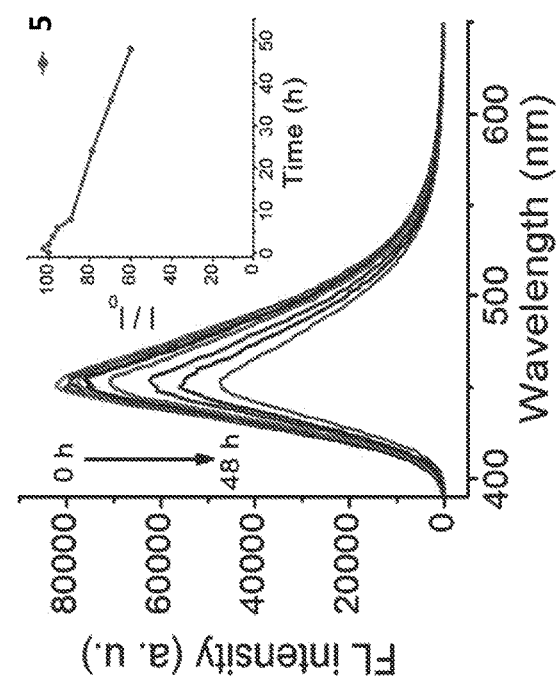

The decomposition rate of 4 and 5 in PBS solution (containing 1% DMSO) was evaluated by measuring fluorescence intensity. After incubation at 37° C. for 48 h, the fluorescence intensity of 4 declined from 100% to 5.1% (FIG. 2D). Under the same conditions, fluorescence intensity of 5 declined to approximately 60% (FIG. 2E).

Figure 2F:
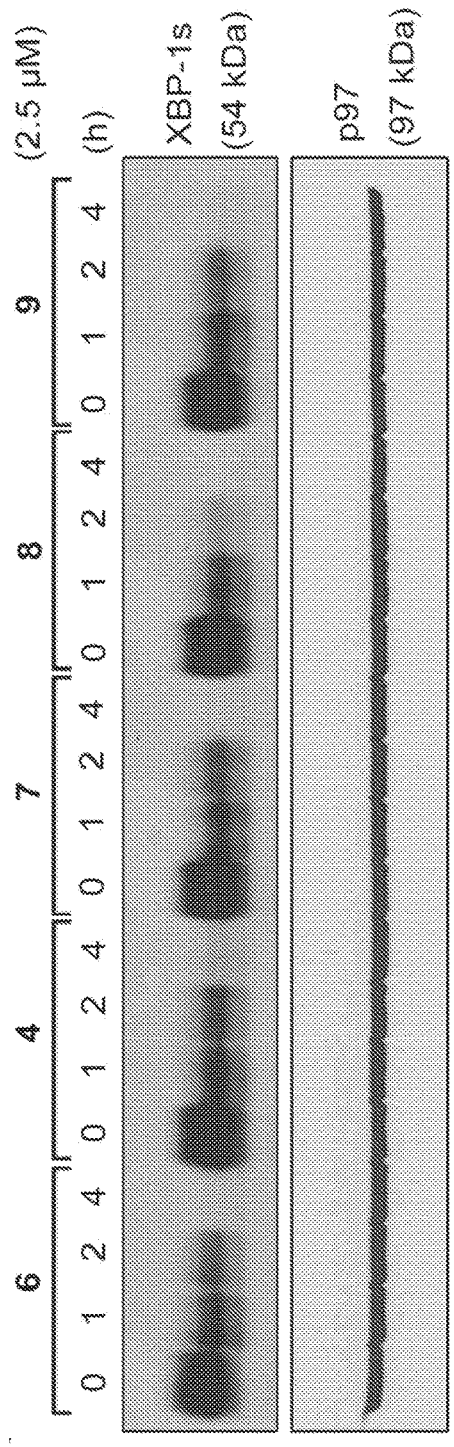

Example 4: Tricyclic Chromenone Compounds with the N-acetohydrazone Protective Group Rapidly Inhibit the Expression of XBP-1s 5TGM1 cells were treated with 6, 4, 7, 8 and 9 at the concentration of 2.5 μM for 1, 2, or 4 h. 8 (with the N-acetohydrazone group) rapidly inhibited XBP-1s (FIG. 2F).

Figure 2G:
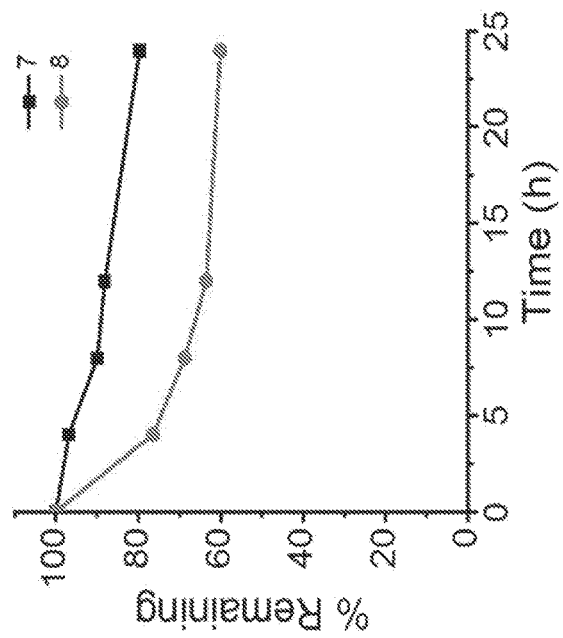
Figure 8:
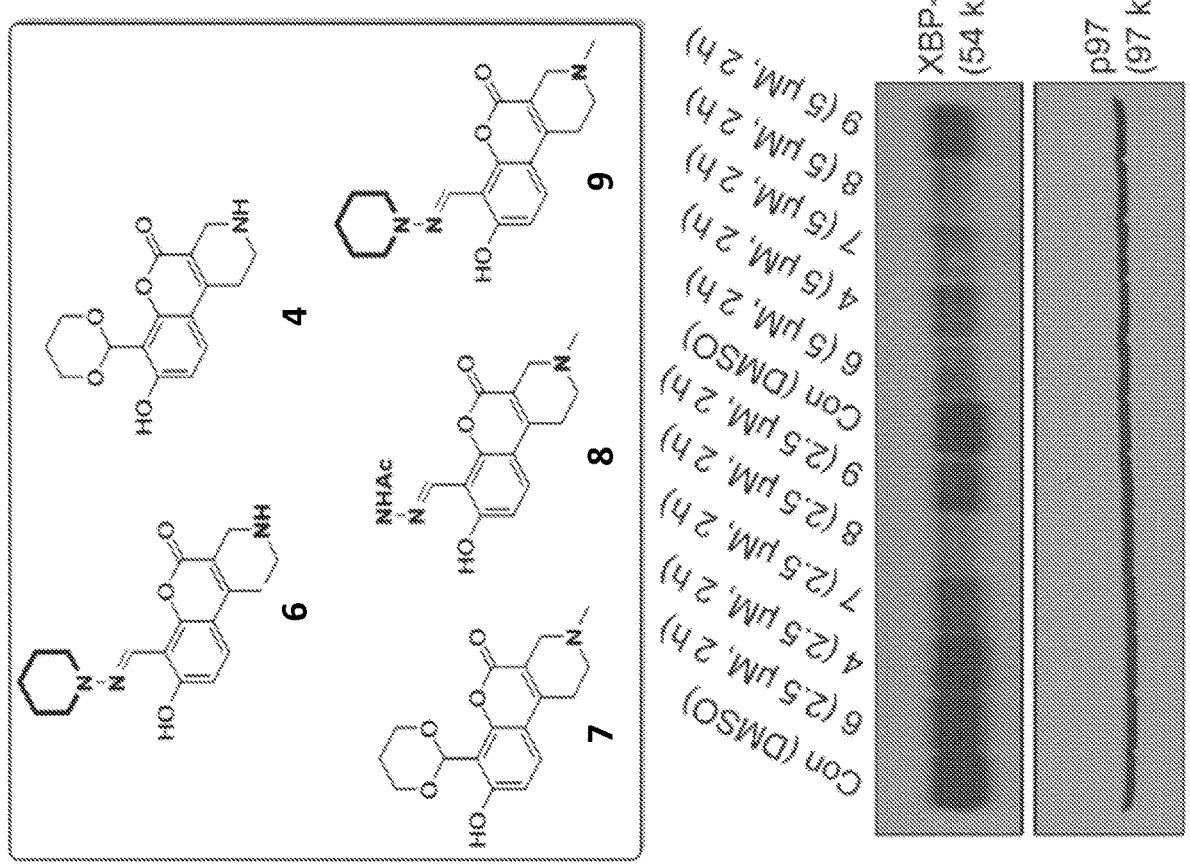
FIG. 8 illustrates chemical structures of 6, 4, 7, 8, and 9. Primary B cells purified from spleens of wild-type mice were stimulated with LPS for 72 h, subsequently treated with indicated inhibitors at 2.5 or 5 µM for 2 h, lysed, and analyzed for the expression of indicated proteins by immunoblots.

LPS-stimulated primary mouse B cells were similarly treated with the same inhibitors at 2.5 or 5 μM for 2 h. 8 also rapidly suppressed the expression of XBP-1s in mouse B cells (FIG. 8). In certain non-limiting embodiments, the electron-withdrawing nature of the acetyl moiety in the N-acetylhydrazone in 8 results in faster hydrolysis relative to 7. HPLC degradation experiments confirmed that this was indeed the case (FIG. 2G).

Figure 3A:
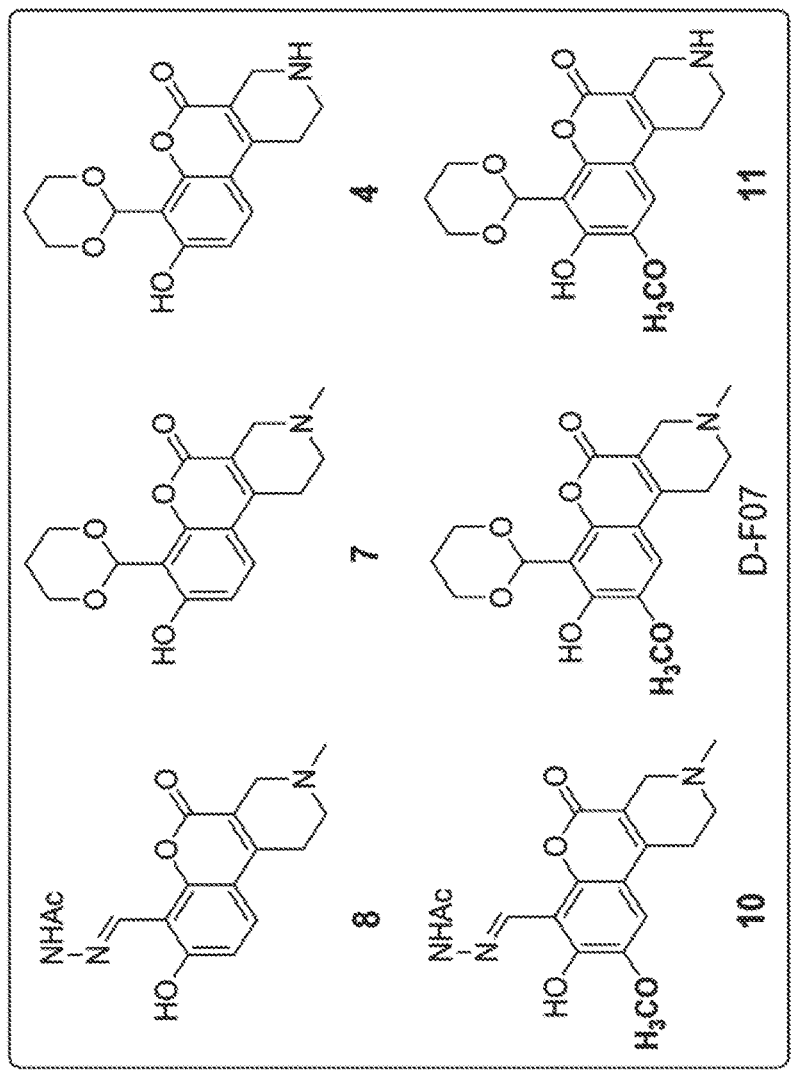
FIGS. 3A-3G illustrate the finding that installation of the methoxy group to tricyclic chromenone inhibitors of IRE1 enhances their activities in suppressing the expression of XBP-1s.
Figure 3A:
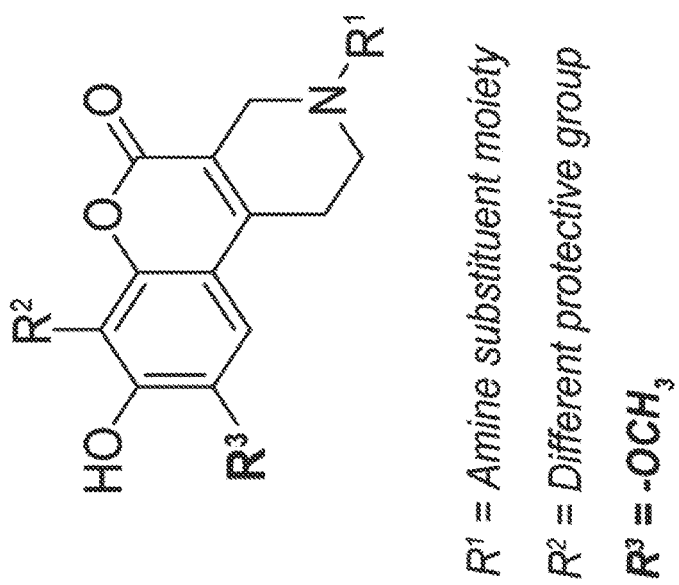
Figure 3C:
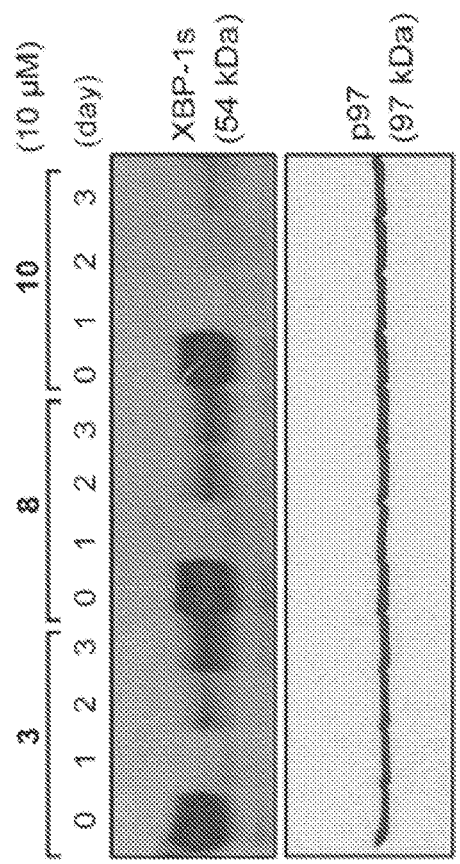
Figure 3B:
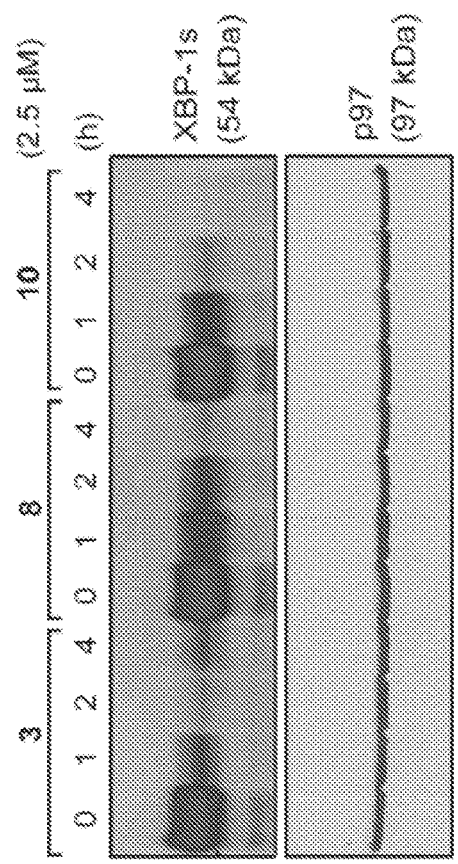

Example 5: Installation of a Methoxy Group Increases the Inhibitory Potency of Tricyclic Chromenone Compounds Unlike 3 (a tricyclic chromenone compound with an exposed aldehyde, which began to lose its inhibitory effect within 4 h), the installation of the N-acetohydrazone protective group allowed the resultant 8 to effectively inhibit the expression of XBP-1s for longer than 4 h (FIGS. 2F, 3A, and 3B). Despite its use at a higher concentration (10 μM), 8 still lost its inhibitory effect after treatment for 2 days (FIG. 3C).

Figure 3D:
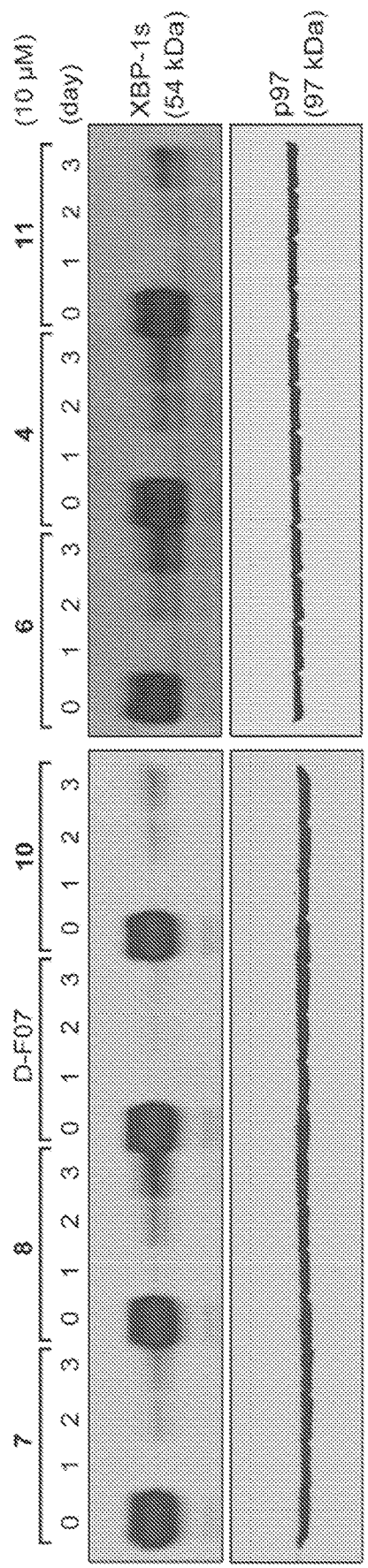
Figure 9:
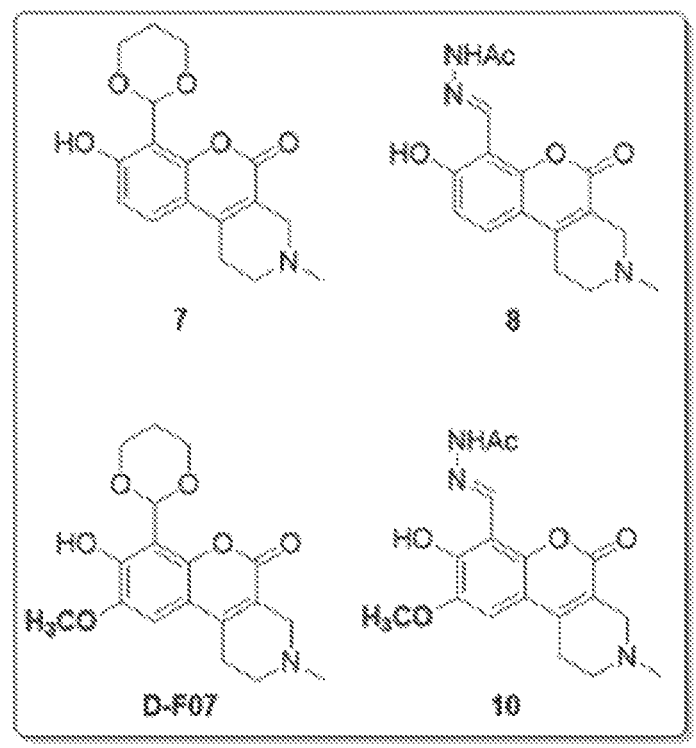
FIG. 9 illustrates chemical structures of 7, 8, D-F07, and 10. 5TGM1 cells were treated with indicated inhibitors at 2.5 µM for 0, 1, 2, or 4 h, lysed, and analyzed for the expression of indicated proteins by immunoblots.
Figure 9:
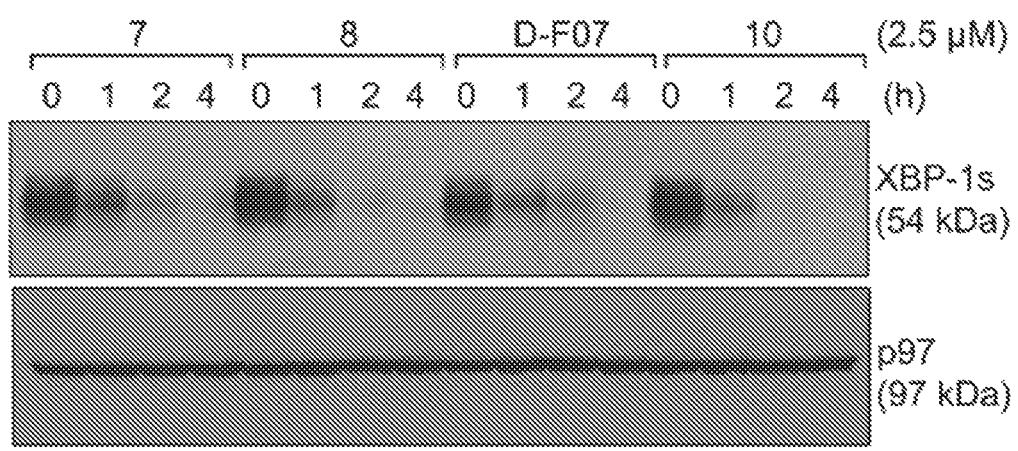

To develop an inhibitor that could suppress the expression of XBP-1s for an extended period of time, the inhibitory effect was first improved by incorporating a methoxy moiety with which the inhibitors could form stable hydrogen bonds with IRE1 via the highly electronegative oxygen (FIG. 3A). When 5TGM1 cells were treated with 8 and its methoxy derivative, 10, at 2.5 μM for 1, 2, or 4 h, or at 10 μM for a course of 3 days, 10 not only suppressed the expression of XBP-1s more rapidly than 8 (FIG. 3B), but also exhibited a long-term inhibitory effect (FIG. 3C). Nevertheless, the levels of XBP-1s still slightly recovered in cells treated with 10 for 3 days (FIG. 3C). 8 inhibited the expression of XBP-1s more rapidly than 7 (FIGS. 2F and 9). Without wishing to be limited by any theory, in certain embodiments, a slowly hydrolysable 1,3-dioxane acetal, 7, can be more effective than 8 in suppressing the expression of XBP-1s for a longer term, and it was indeed the case (FIG. 3D).

Figure 3F:
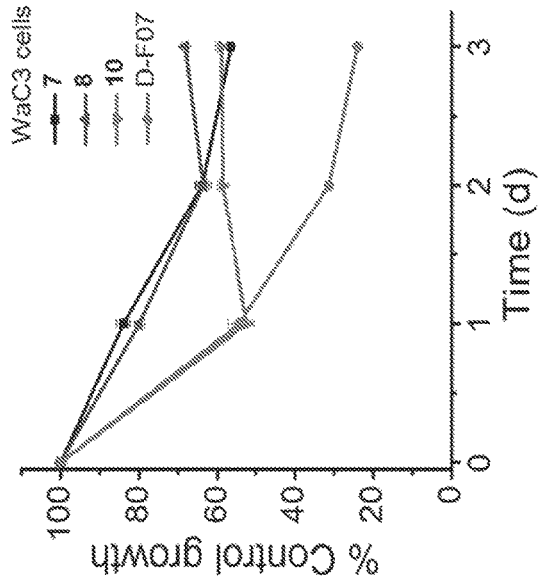
Figure 3E:
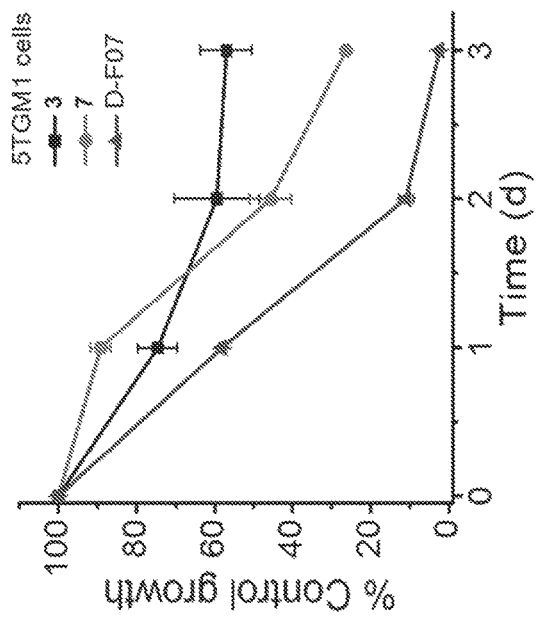
Figure 10:
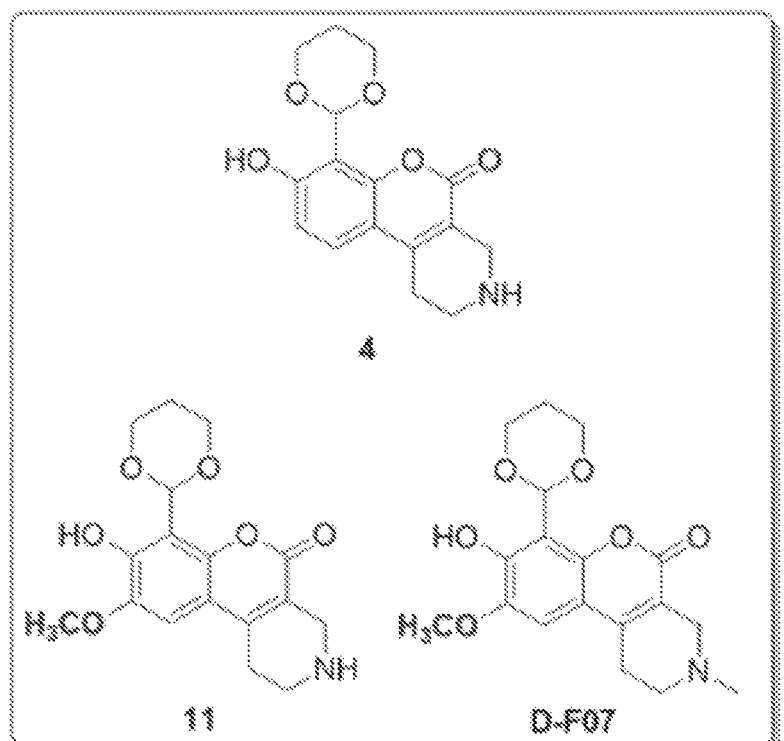
FIG. 10 illustrates chemical structures of 4, 11, and D-F07. 5TGM1 cells were treated with indicated inhibitors at 10 µM for a course of 3 days, lysed, and analyzed for the expression of indicated proteins by immunoblots.
Figure 10:
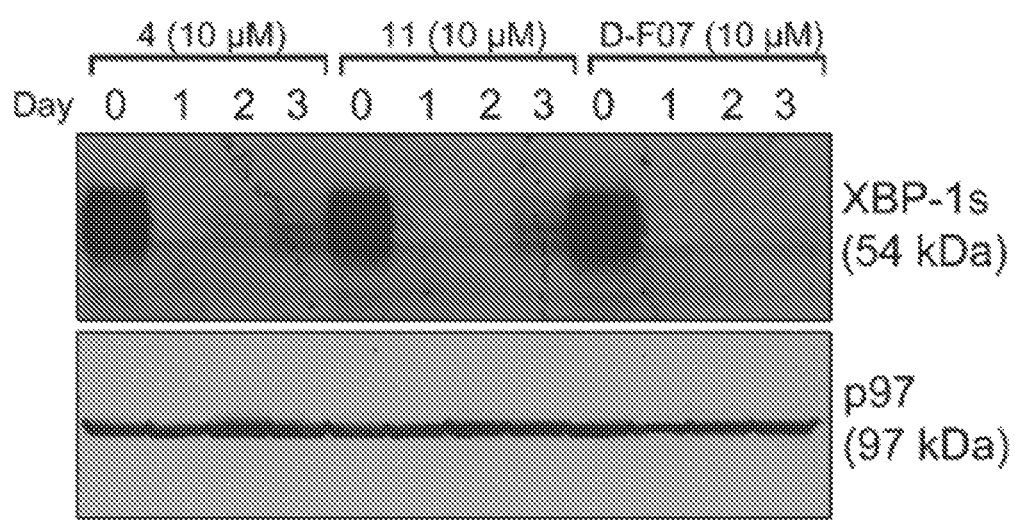

D-F07, the methoxy derivative of 7, was further synthesized and found to have a better long-term efficacy in suppressing the expression of XBP-1s than 7 and 10 (FIG. 3D). 11, the methoxy derivative of 4, was also synthesized (FIG. 3A). 11 was also more potent than 4 in suppressing XBP-1s expression (FIG. 3D); however, 11 was at least 16 times less soluble than 4 when dissolved in organic solvent, such as DMSO, and it was less potent than D-F07 in suppressing the expression of XBP-1s (FIG. 10). To evaluate cytotoxicity induced by these compounds, 5TGM1 cells were treated with 3 carrying the exposed aldehyde, 7 carrying the 1,3-dioxane protecting group, or D-F07 carrying both the 1,3-dioxane protecting group and the C9 methoxy group, at 20 μM for a course of 3 days, and XTT assays were performed. D-F07 exerted higher cytotoxicity than 3 and 7 in 5TGM1 cells (FIG. 3E).

A human chronic lymphocytic leukemia cell line, WaC3, was sensitive to 4 (B-I09 12). WaC3 cells were treated with 7, 8 as well as their respective methoxy derivatives, D-F07 and 10, at 20 μM for a course of 3 days. Both D-F07 and 10 were initially more potent than 7 and 8 in suppressing WaC3 cell growth (FIG. 3F); however, acetylhydrazone 10 was incapable of continuously inhibiting the growth of WaC3 cells. D-F07 carrying the 1,3-dioxane acetal and C9 methoxy group suppressed WaC3 cell growth potently.

Figure 3G:
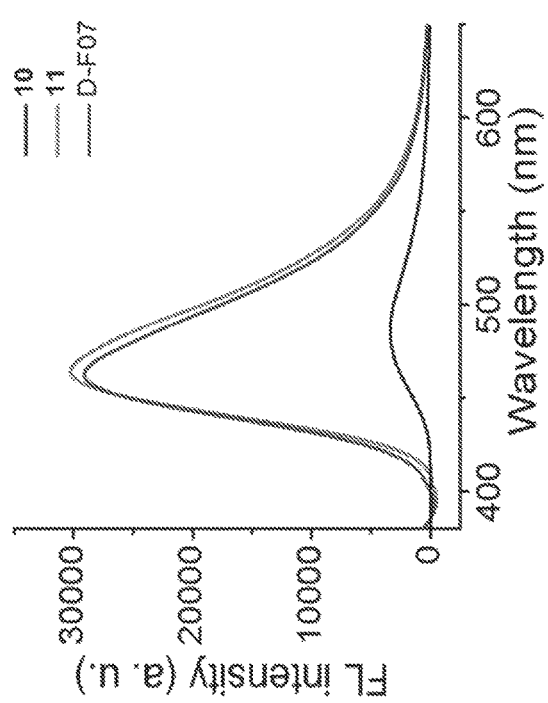
Figure 4A:
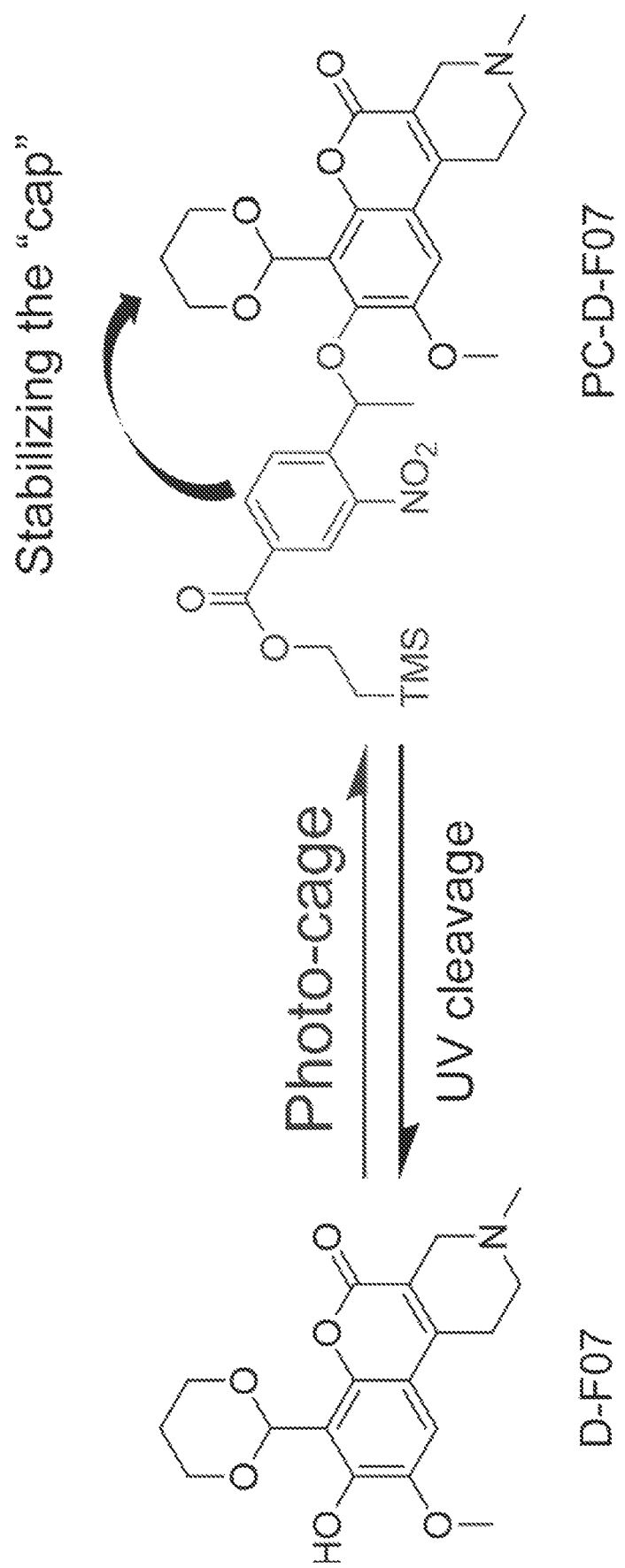
FIGS. 4A-4H illustrate the finding that installation of a photocage on the hydroxyl group stabilizes the 1,3-dioxane acetal protective group of D-F07 to allow for temporal inhibition of XBP-1s mediated by UV irradiation.
Figure 4B:
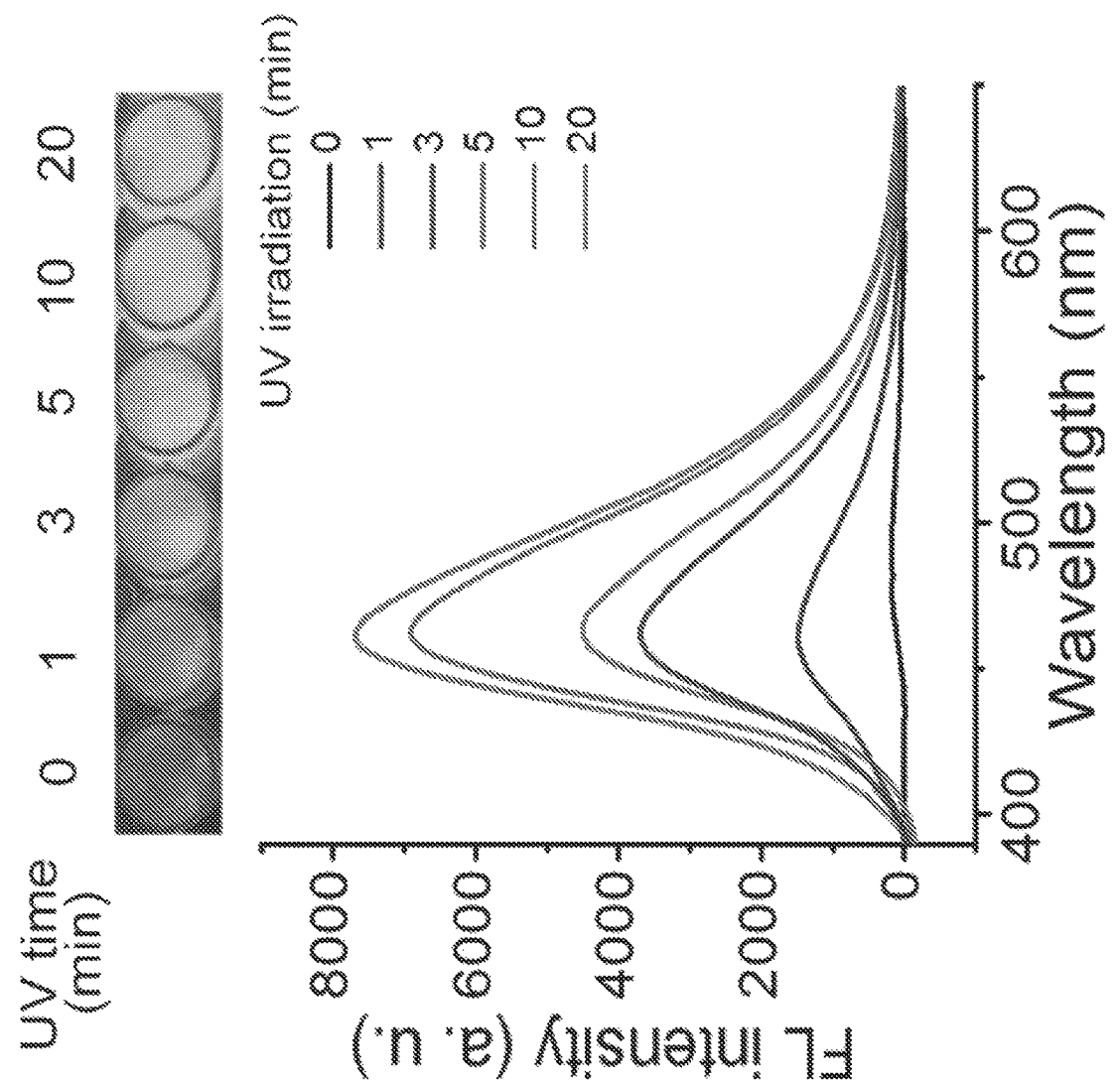
Figure 4C:
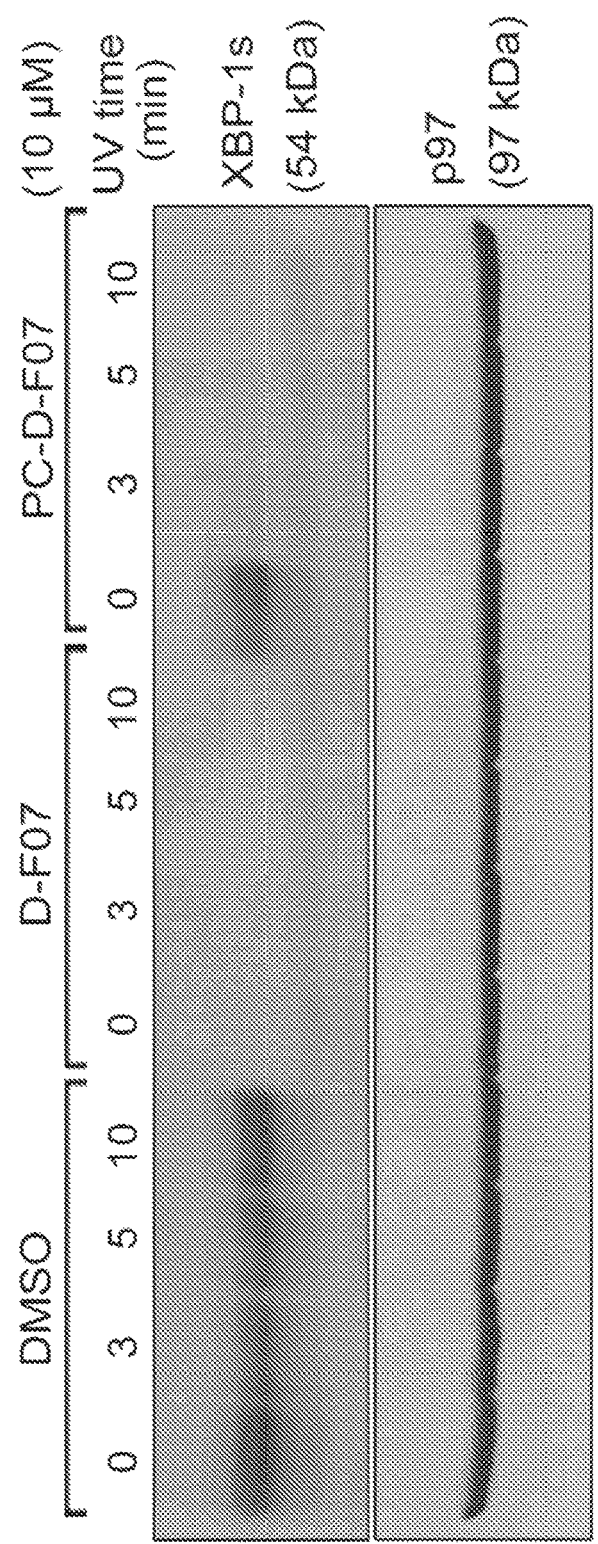
Figure 4D:
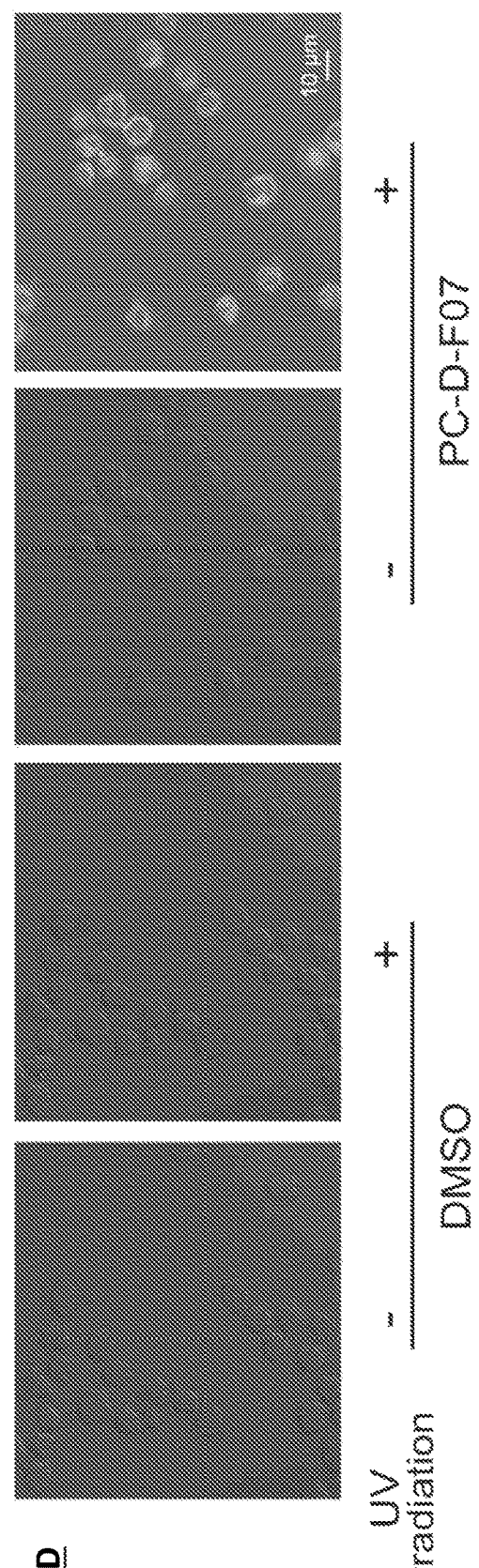
Figure 4E:
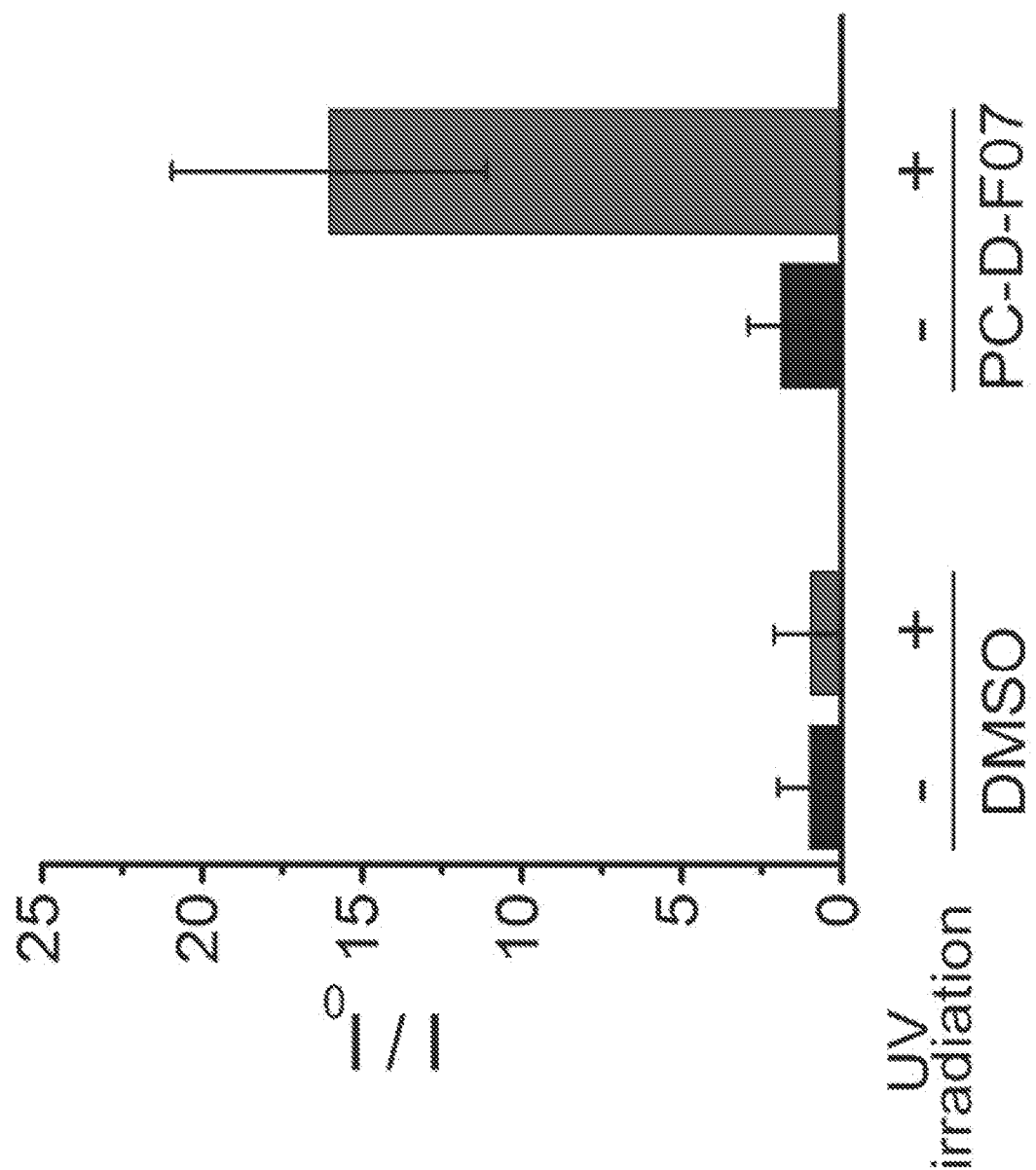
Figure 11:
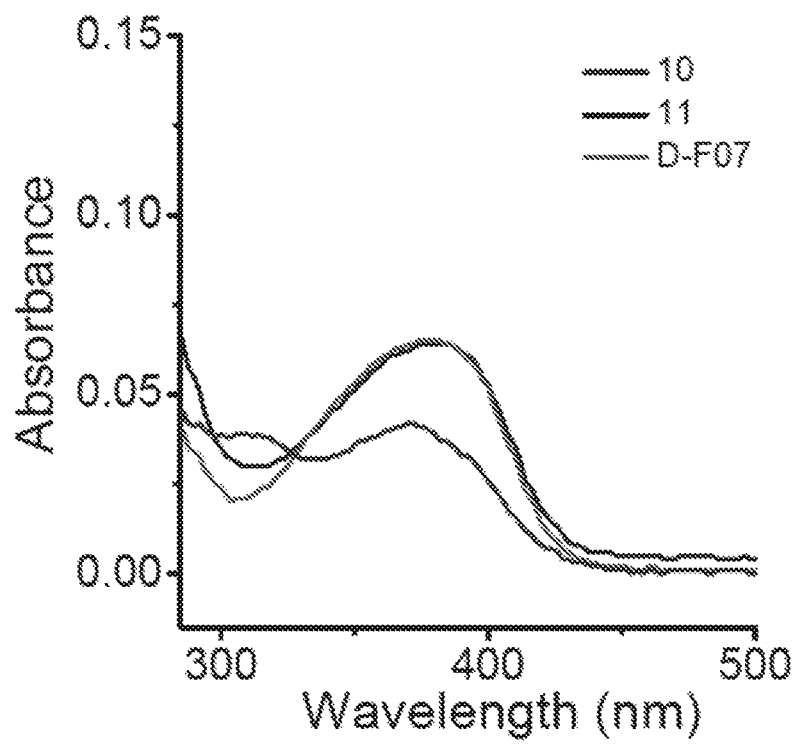
FIG. 11 illustrates absorbance curves of 10, 11, and D-F07 (10 µM) in the DMSO/PBS (v/v=1:99) solution.
Figure 12:
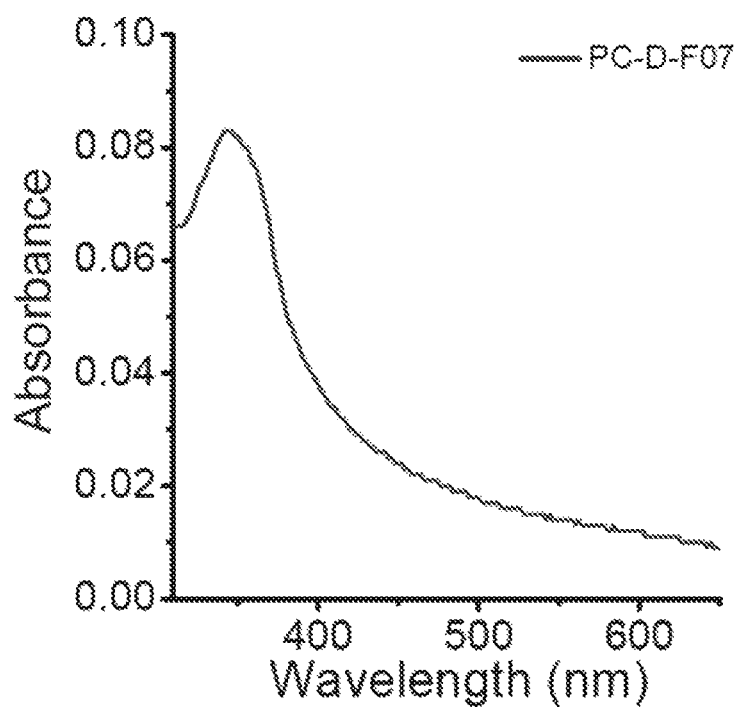
FIG. 12 illustrates the absorbance curve of PC-D-F07 (10 µM) in the DMSO/PBS (v/v=1:99) solution.

Example 6: Installation of a Photocage on the Hydroxyl Group of D-F07 Stabilizes the 1,3-dioxane Acetal Protective Group The fluorescent property of tricyclic chromenone compounds can be used to visualize their subcellular localization and evaluate their pharmacokinetics in cells. The fluorescence of methoxy-containing tricyclic chromenone derivatives was examined, confirming that D-F07 and 11, both harboring the 1,3-dioxane protecting group, emitted bright fluorescence at 460 nm (FIGS. 3G and 11), while 10, bearing the N-acetylhydrazone protecting group, showed weak fluorescence. Since D-F07 could emit strong blue fluorescence and had the most potent effect in inhibiting the expression of XBP-1s in whole cells, the hydroxy group of D-F07 was further modified with a photo-labile moiety, 4-isopropyl-3-nitrobenzoate. Alkylation of the 8-hydroxy group with the photo-labile cage quenched the fluorescence of D-F07. The fluorescence of the photo-caged (PC)-D-F07 could be 'turned on' by UV irradiation (FIG. 4A). Upon UV irradiation, the 4-isopropyl-3-nitrobenzoate moiety was cleaved, converting PC-D-F07 into D-F07 with an approximately 75-fold increase in fluorescence intensity (FIGS. 4B and 12). 5TGM1 cells were treated with D-F07 or PC-D-F07 at 10 µM, and then immediately UV-irradiated for 0, 3, 5 or 10 min, and the cells were cultured for additional 4 h. PC-D-F07 could suppress the expression of XBP-1s only after UV irradiation (FIG. 4C), highlighting the importance of the hydroxy group of tricyclic chromenone compounds in suppressing the expression of XBP-1s. To visualize intracellular photoactivation of the inhibitor, 5TGM1 cells were treated with PC-D-F07 at 10 µM for 4 h and these cells were analyzed by confocal microscopy (FIG. 4D). A rapidly increased fluorescence intensity in the cytoplasm of PC-D-F07-treated 5TGM1 cells was detected after 10-s UV irradiation (FIGS. 4D-4E).

Figure 4G:
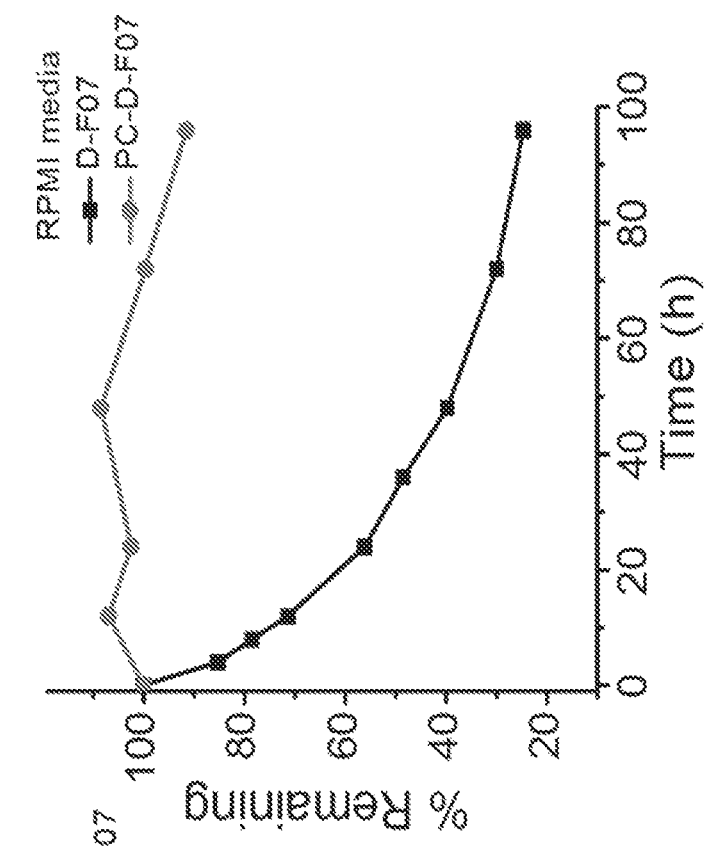
Figure 4F:
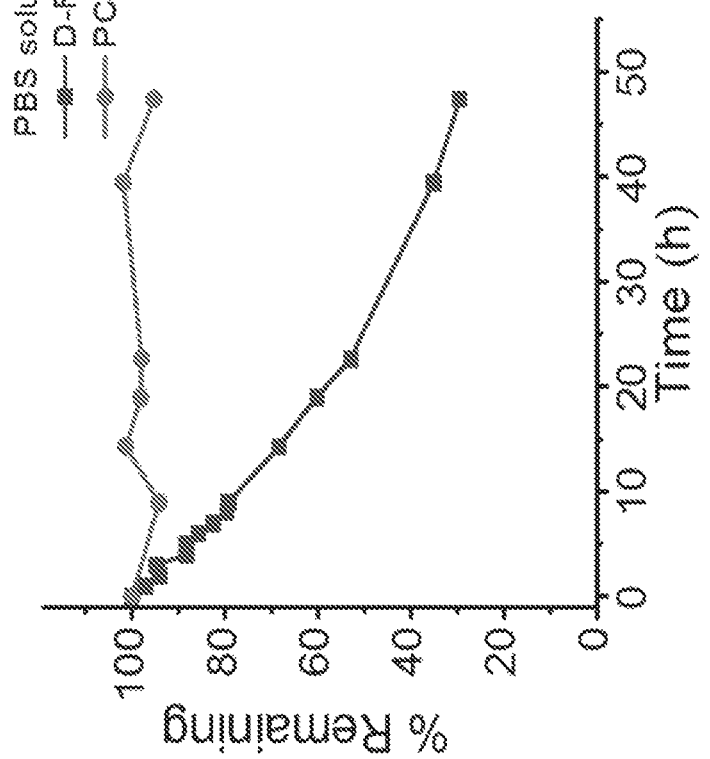
Figure 4H:
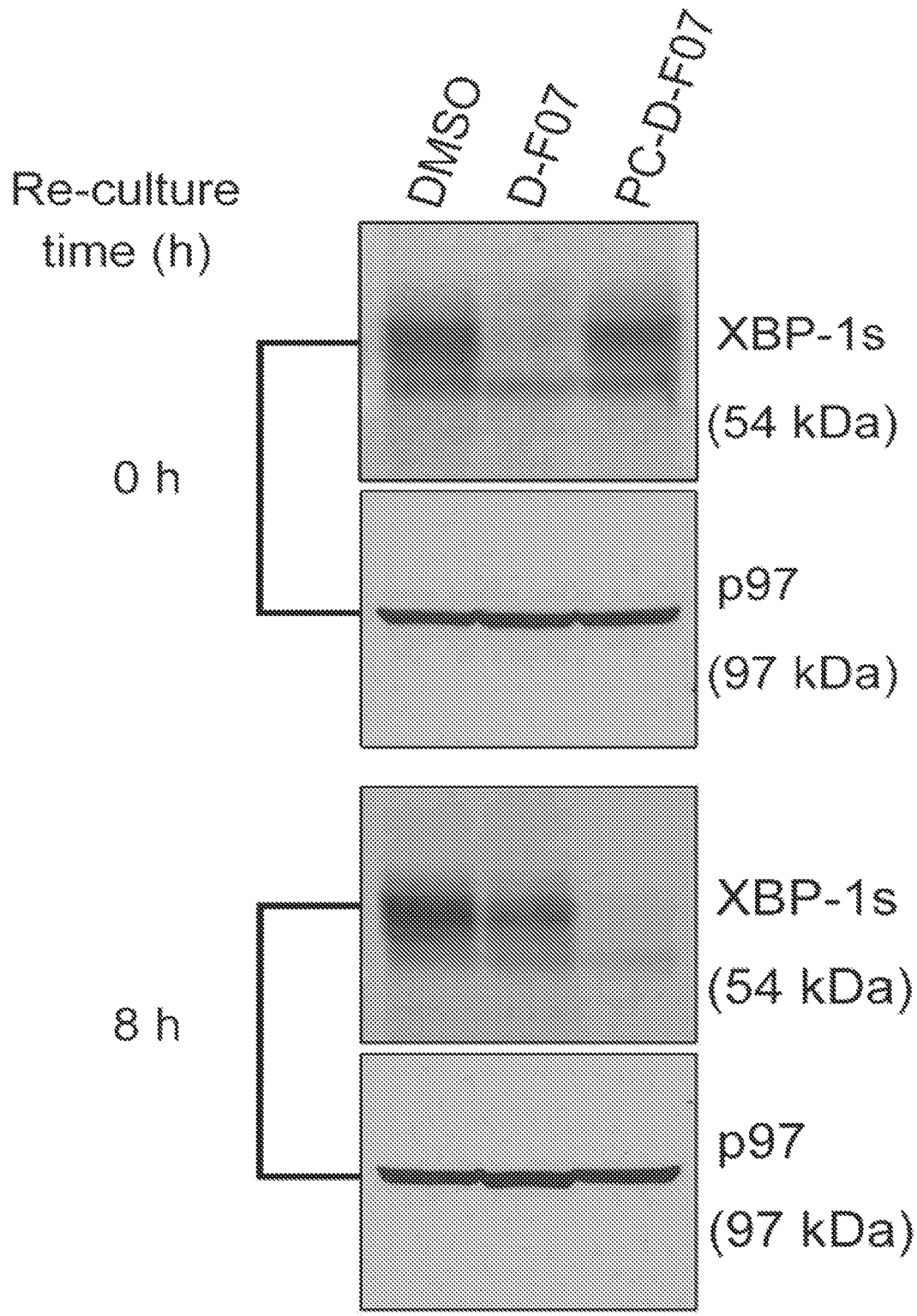

Because PC-D-F07 was incapable of inhibiting the expression of XBP-1s, it is possible that the 1,3-dioxane acetal protecting group could not be hydrolyzed when the neighboring hydroxy group was modified. The rate of 1,3-dioxane acetal hydrolysis for D-F07 and PC-D-F07 (in PBS and RPMI media at 37° C.) was measured by analytical HPLC. Compared with D-F07, PC-D-F07 was completely stable in PBS for 48 h (FIG. 4F) and in RPMI media for 96 h (FIG. 4G). 5TGM1 cells were further treated with D-F07 or PC-D-F07 at 10 µM for 4 h, the compounds removed from culture media by washing cells with PBS for 3 times, cells resuspended in fresh RPMI media, cells UV-irradiated for 10 min, and cells incubated for 8 h (FIG. 4H). After removal of the inhibitor supply from the media, D-F07 failed to suppress XBP-1s continuously. However, PC-D-F07, upon UV irradiation, was converted to D-F07, triggering hydrolysis of the 1,3-dioxane acetal group and revealing the aldehyde group to allow for IRE-1 inhibition and suppression of XBP-1s expression (FIG. 4H). Together, these results indicated that the 1,3-dioxane acetal prodrug moiety could be stabilized by the installation of a photo-labile group on the 8-hydroxy of a coumarin-based compound in aqueous solution; and that UV irradiation-mediated cleavage of the photo-cage from PC-D-F07 could reveal the hydroxy group on D-F07 to trigger the hydrolysis of the acetal prodrug moiety.

Figure 5A:
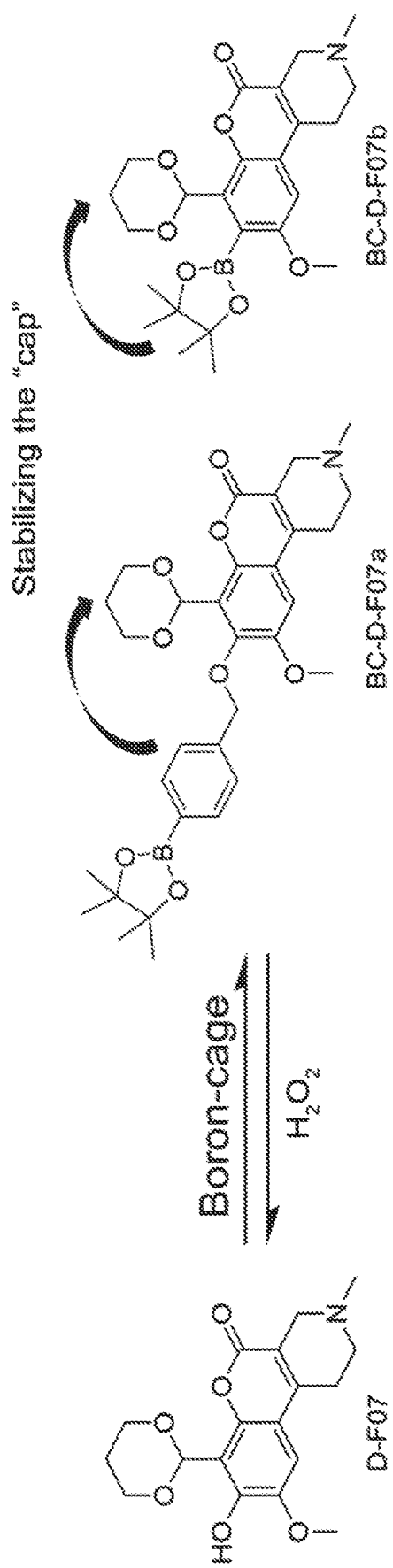
FIGS. 5A-5J illustrate the finding that installation of a boronate cage cleavable by $H_2O_2$ stabilizes the 1,3-dioxane acetal protective group of D-F07 to allow for temporal inhibition of XBP-1s upon contact with $H_2O_2$.

Example 7: Installation of a Reactive Oxygen Species (ROS)-Sensitive Boronate Cage on the Hydroxy Group of D-F07 Stabilizes the 1,3-dioxane Acetal To test whether the 1,3-dioxane acetal could also be stabilized by other 8-hydroxy modifications, ROS-sensitive boronate cages were installed onto D-F07 (FIG. 5A). In certain embodiments, replacement of the C8 hydroxy with boronates can reduce the fluorescence of D-F07 due to the electron withdrawing property of boron. In certain embodiments, boronate cages can be cleaved by hydrogen peroxide and other ROS to allow for liberation of D-F07, which could be detected by measuring increased fluorescence. In certain embodiments, these cages can be cleaved by intracellular hydrogen peroxide, the levels of which were often found to be significantly higher in malignant tumor cells.

Figure 5C:
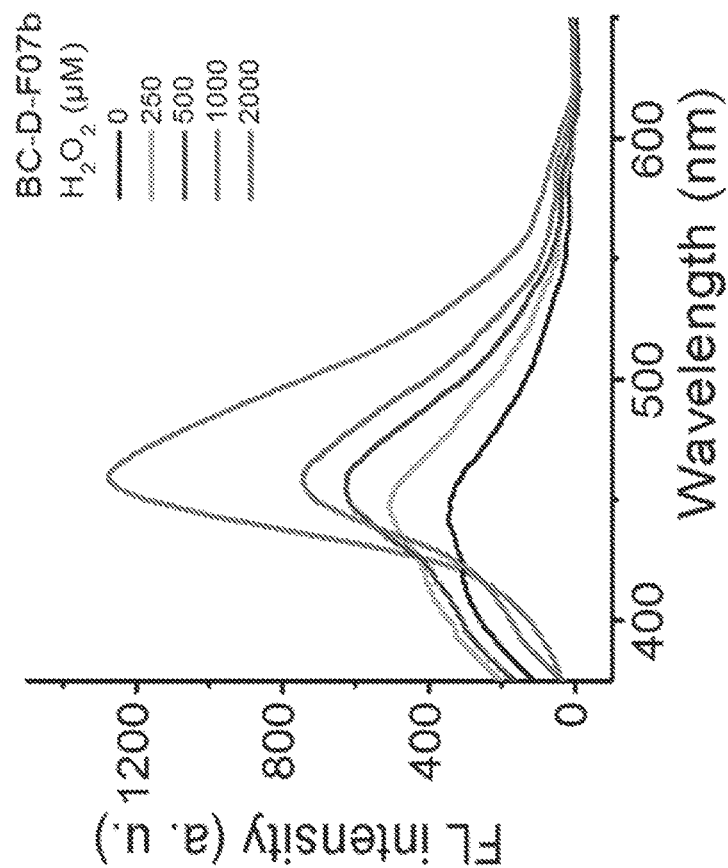
Figure 5B:
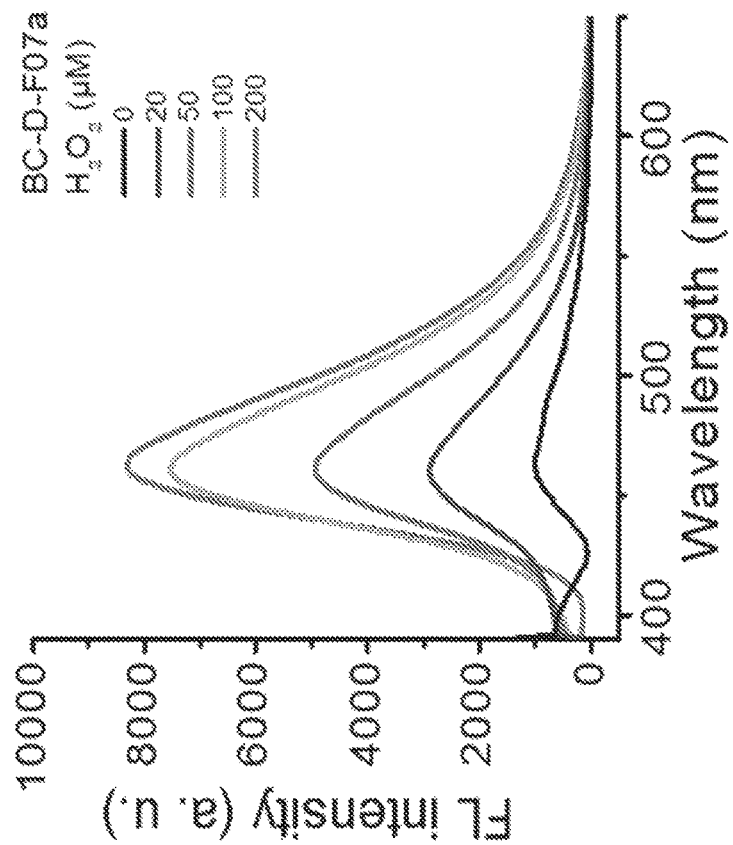
Figure 5E:
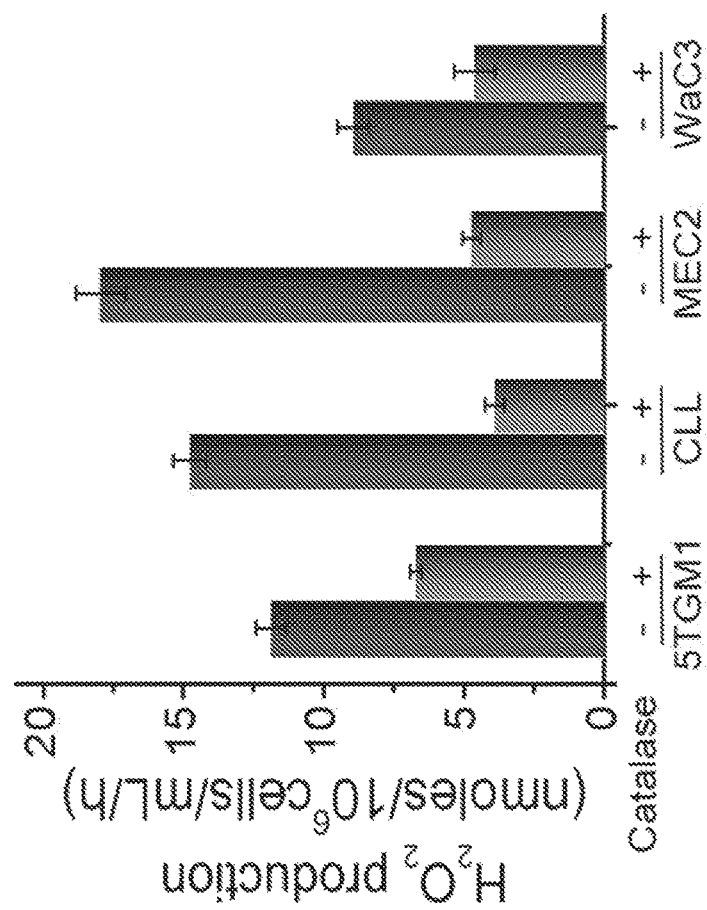
Figure 5D:
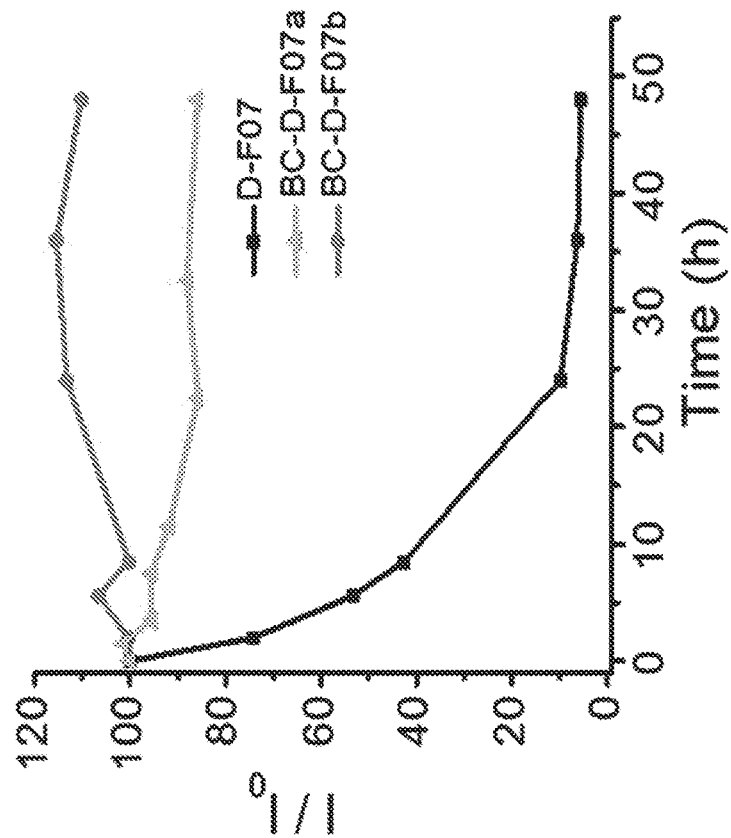
Figure 13:
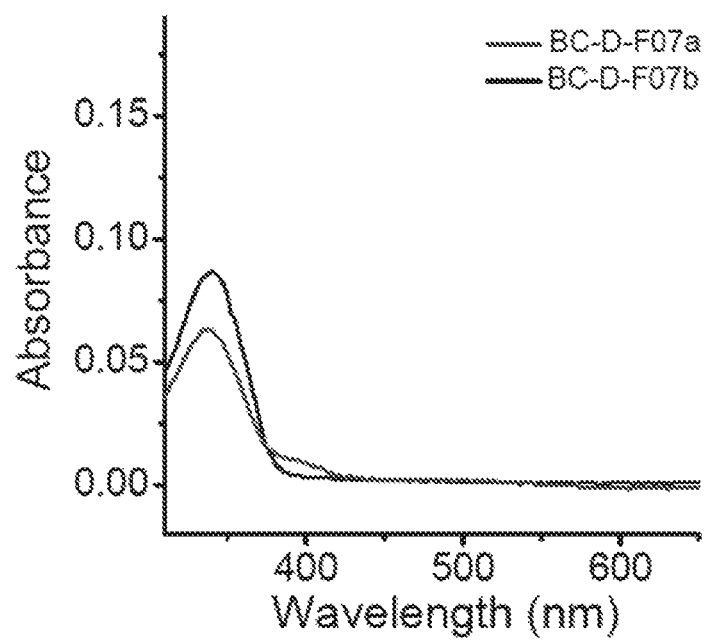
FIG. 13 illustrates absorbance curves of BC-D-F07a and BC-D-F07b (10 µM) in the DMSO/PBS (v/v=1:99) solution.

ROS-sensitive boron-caged (BC)-D-F07a and BC-D-F07b were synthesized, incubated with increasing concentrations of hydrogen peroxide, and increased fluorescence intensity resulting from liberated D-F07 was measured (FIGS. 5A-5C). Initially, both BC-D-F07a and BC-D-F07b emitted weak fluorescence. After incubation with 200 µM hydrogen peroxide for 1 h at room temperature, the fluorescence intensity from BC-D-F07a samples increased approximately 8-fold (FIGS. 5B and 13). Although the similar hydrogen peroxide dose-dependent fluorescence enhancement was observed in BC-D-F07b samples, higher concentrations of hydrogen peroxide and higher incubation temperature (37° C.) were required to oxidize the 1,3-dioxaborolane moiety from BC-D-F07b to generate D-F07 (FIGS. 5C and 13). Fluorescence decay was used to monitor the hydrolysis rate of the 1,3-dioxane acetal group from D-F07, BC-D-F07a, and BC-D-F07b in aqueous solution (FIG. 5D). Installation of the boron-cages stabilized the 1,3-dioxane acetal protecting group on D-F07 (FIG. 5D).

Figures 5F, 5G:
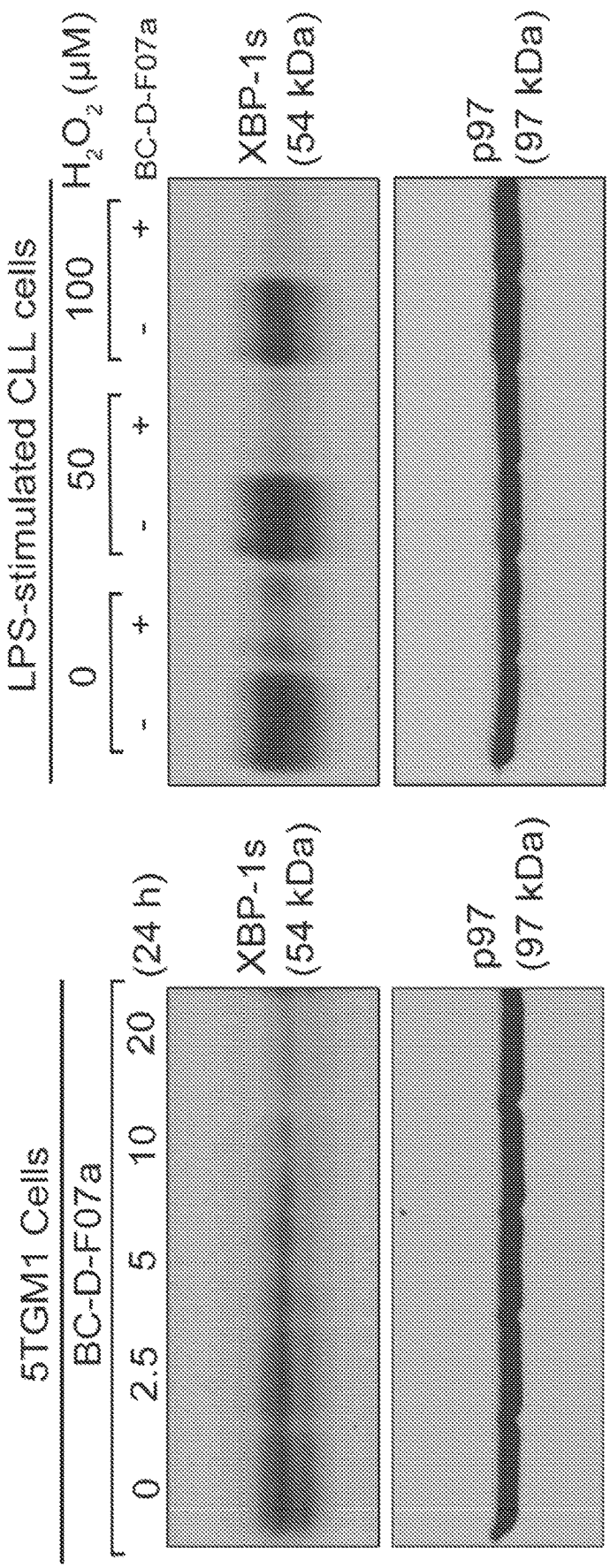
Figure 5H:
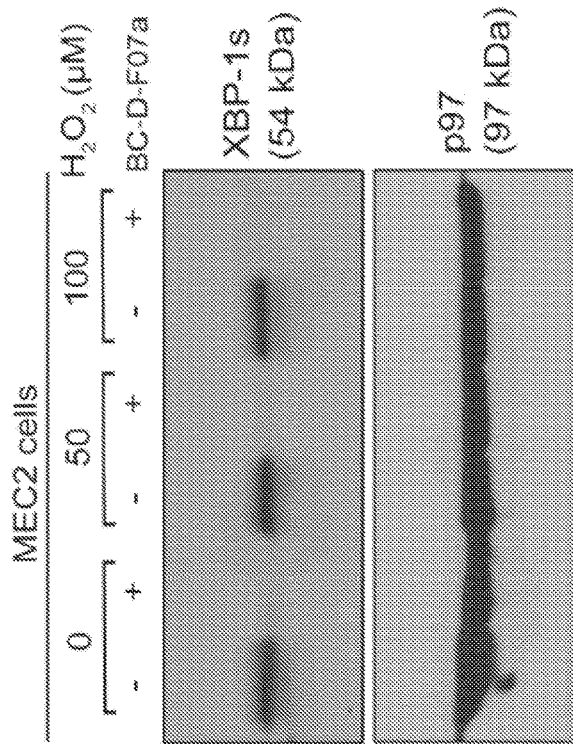
Figure 5J:
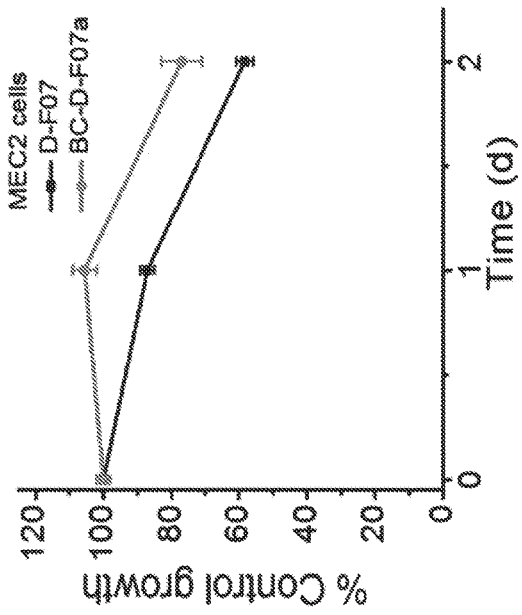
Figure 5I:
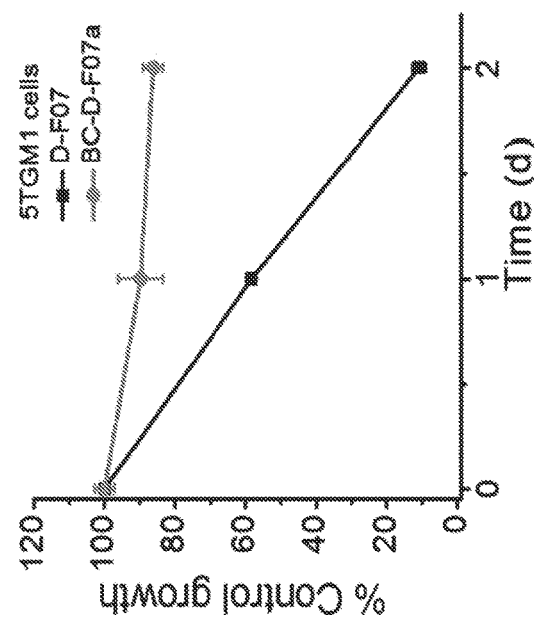
Figure 14A:
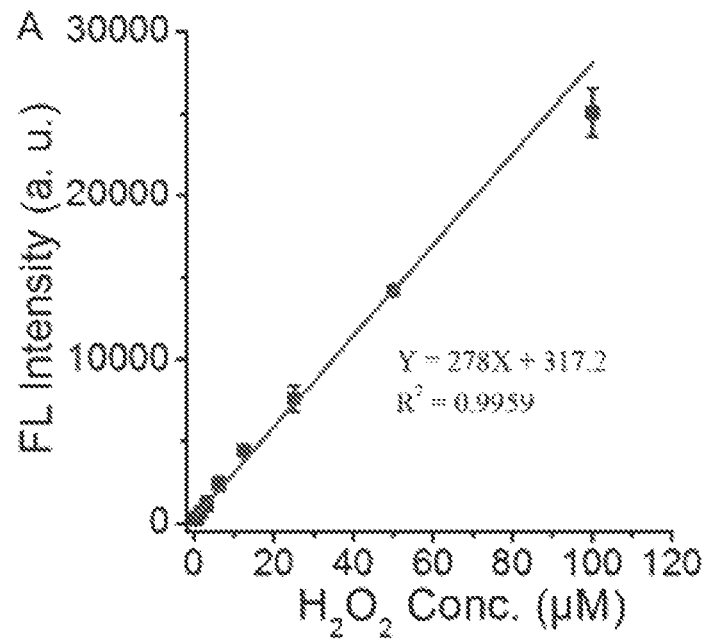
FIG. 14A illustrates a graph of fluorescence intensity plotted as a function of $H_2O_2$ concentrations in the presence of Amplex Red and HRP.
Figure 14B:
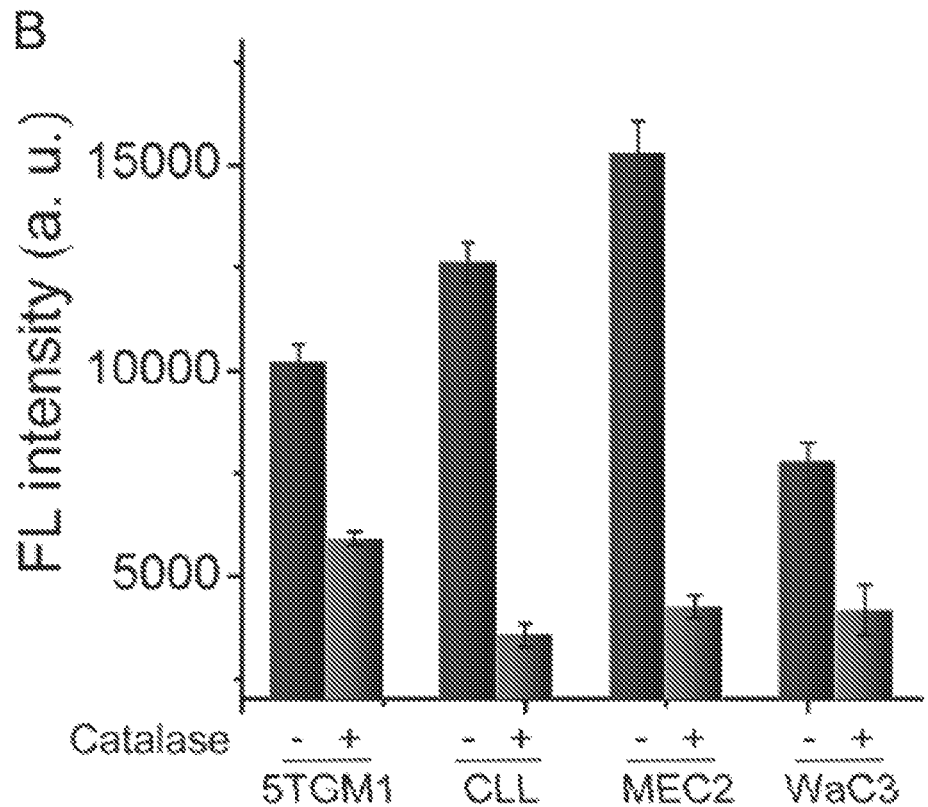
FIG. 14B illustrates fluorescence intensity representing the levels of $H_2O_2$ produced by 5TGM1, 72-h LPS-stimulated primary CLL, MEC2, and WaC3 cells was measured by Amplex Red with or without the addition of extracellular catalase (500 U/mL).

Example 8: BC-D-F07a can be Cleaved by Endogenous Hydrogen Peroxide Produced by Cancerous B Cells Next, the levels of hydrogen peroxide were surveyed in different types of cancerous B cells (FIGS. 5E and 14A). When compared with 5TGM1 cells, LPS-stimulated primary mouse CD5+ CLL cells, and WaC3 cells, human MEC2 CLL cells produced higher levels of hydrogen peroxide (FIG. 5E). As an assay control, treatment of these 4 cell types with 500 U/mL extracellular catalase resulted in reduced levels of hydrogen peroxide (FIGS. 5E and 14B). 5TGM1 cells were treated with increasing concentrations of BC-D-F07a, and the dose-dependent suppression of XBP-1s was observed (FIG. 5F), indicating that the endogenous hydrogen peroxide produced by 5TGM1 cells can oxidize the aryl boronate of BC-D-F07a to generate D-F07. LPS-stimulated primary CLL cells were further treated with BC-D-F07a at 20 µM for 16 h, and exposed to 0, 50 or 100 µM hydrogen peroxide for another 4 h. The endogenous hydrogen peroxide produced by LPS-stimulated primary CLL cells could similarly oxidize BC-D-F07a to generate D-F07 to suppress the expression of XBP-1s. This oxidation can be enhanced by adding exogenous hydrogen peroxide (FIG. 5G). The higher levels of endogenous hydrogen peroxide produced by MEC2 cells corresponded to a more efficient suppression of XBP-1s (FIG. 5H). To evaluate the cytotoxicity of the ROS-sensitive inhibitor, 5TGM1 and MEC2 cells were treated with 20 µM D-F07 or BC-D-F07a for a course of 2 days. The lower levels of hydrogen peroxide produced by 5TGM1 cells could not efficiently oxidize BC-D-F07a, inhibit XBP-1s, or suppress cell growth (FIG. 5I). Although BC-D-F07a could efficiently suppress the expression of XBP-1s in MEC2 cells, it is also less capable than D-F07 in inhibiting growth of MEC2 cells (FIG. 5J).

Figure 6A:
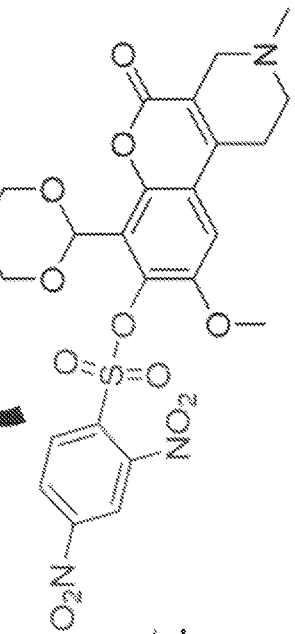
FIGS. 6A-6J illustrate the finding that installation of a thiol-reactive cage on the hydroxy group stabilizes the 1,3-dioxane acetal protecting group of D-F07, and allows for thiol-mediated release of D-F07.
Figure 6B:
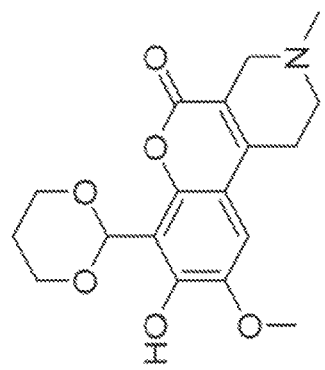
Figure 6B:
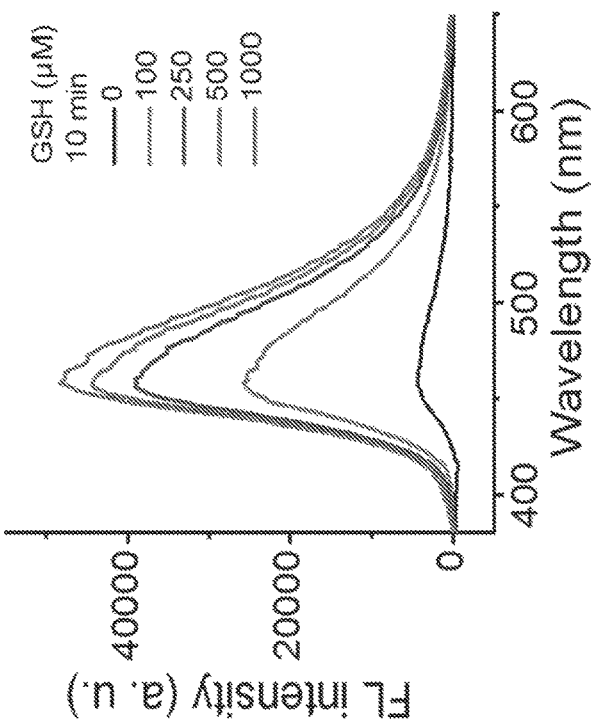
Figure 6D:
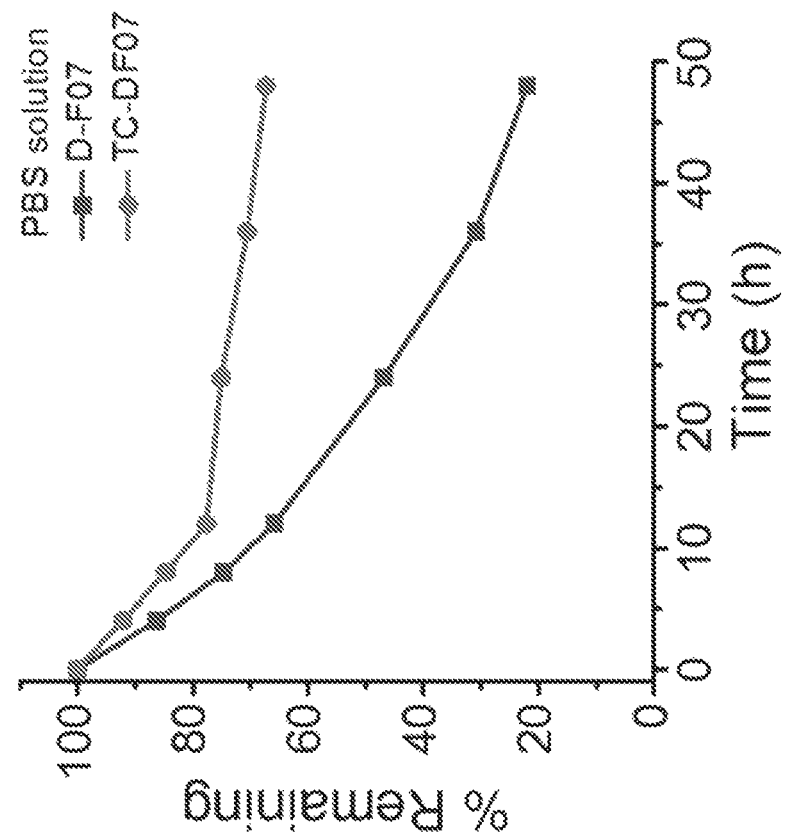
Figure 6C:
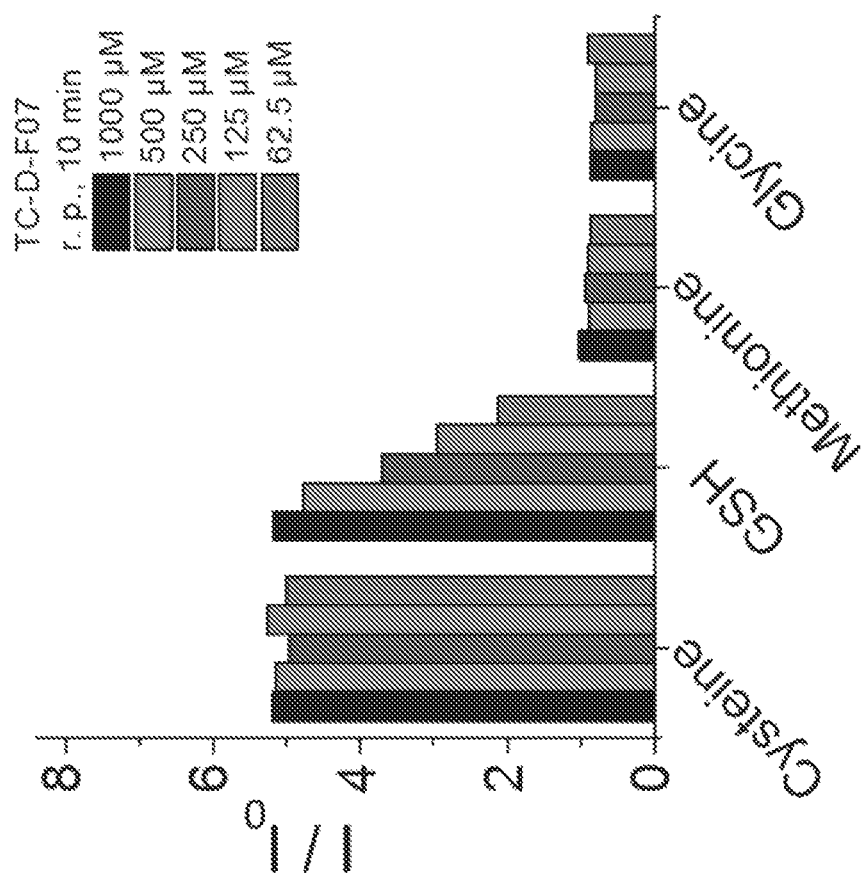
Figure 15:
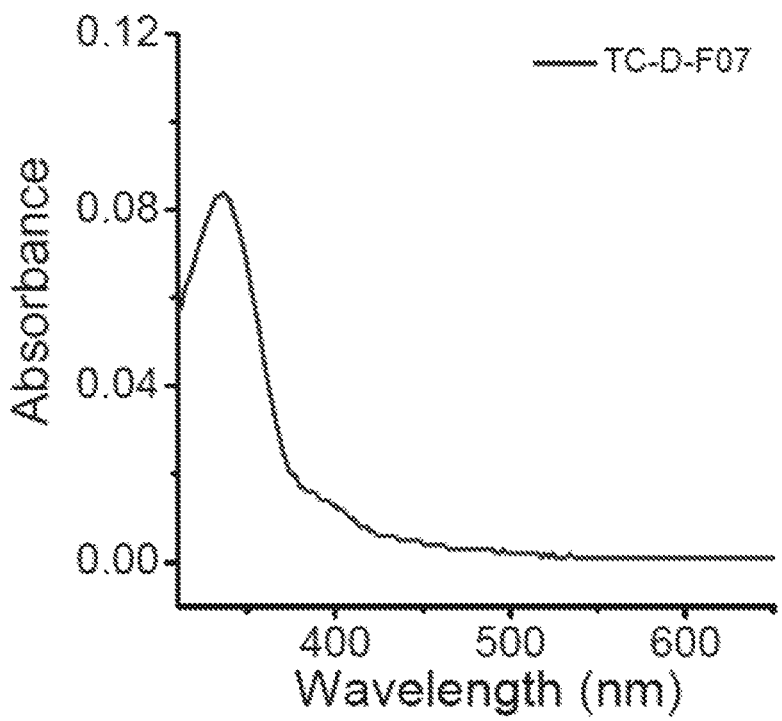
FIG. 15 illustrates the absorbance curve of TC-D-F07 (10 µM) in the DMSO/PBS (v/v=1:99) solution.

Example 9: Installation of a Thiol-Cage on the Hydroxy Group of D-F07 Stabilizes the 1,3-Dioxane Acetal Protecting Group A thiol-reactive group was installed onto the C8 hydroxy of D-F07. In certain embodiments, the thiol-sensitive sulfonate cage (TC) of TC-D-F07 is effectively cleaved in cancer cells because they often express higher levels of glutathione (GSH). The hydroxy group of D-F07 was modified with a thiol-responsive moiety, 2,4-dinitrobenzenesulfonyl group, resulting in quenched fluorescence (FIG. 6A). TC-D-F07 initially emitted weak fluorescence in aqueous solution. Dose-dependent increase of fluorescence was observed upon incubating TC-D-F07 with increasing concentrations of GSH at room temperature for 10 min (FIGS. 6B and 15). As expected, cysteine was very efficient in cleaving the sulfonate of TC-D-F07 via a nucleophilic aromatic substitution to liberate D-F07 (FIG. 6C). No change in fluorescence was observed when TC-D-F07 was incubated with increasing concentrations of methionine or glycine. Similarly, installation of the thiol-reactive group onto the C8 hydroxy group of D-F07 could stabilize the 1,3-dioxane acetal protecting group, as evidenced by the slower decomposition rate of TC-D-F07 detected by HPLC (FIG. 6D). TC-D-F07 missing the 1,3-dioxane acetal was not detected in the decomposed mixtures of TC-D-F07, suggesting that the sulfonate group was cleaved prior to hydrolysis of the 1,3-dioxane acetal.

Example 10: TC-D-F07 Exerted Enhanced Cytotoxicity Towards Cancerous B Cells

Figure 6E:
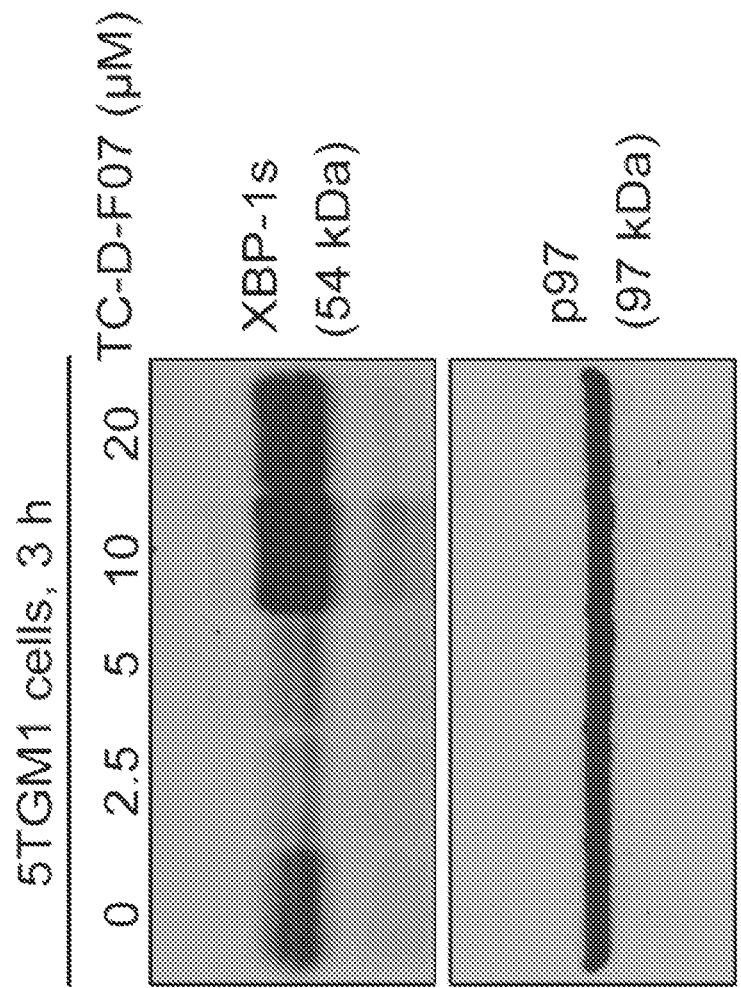

5TGM1 cells were treated with TC-D-F07 at increasing concentrations for 3 h, and TC-D-F07 at 2.5 µM could significantly suppress the expression of XBP-1s, indicating that the high levels of thiols (e.g., GSH) in 5TGM1 cells could rapidly cleave the sulfonate group in TC-D-F07 to liberate D-F07 (FIG. 6E). Unexpectedly, the levels of XBP-1s increased when 5TGM1 cells were treated with TC-D-F07 at 10 and 20 µM for 3 h (FIG. 6E).

Figure 6F:
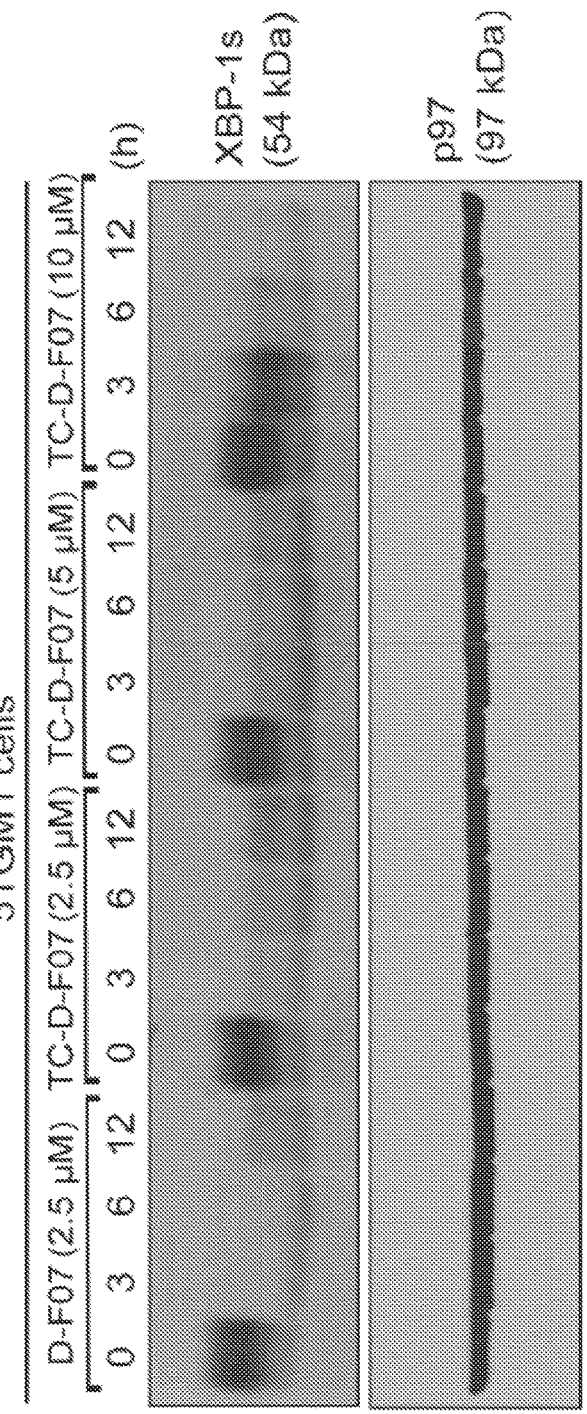
Figure 6G:
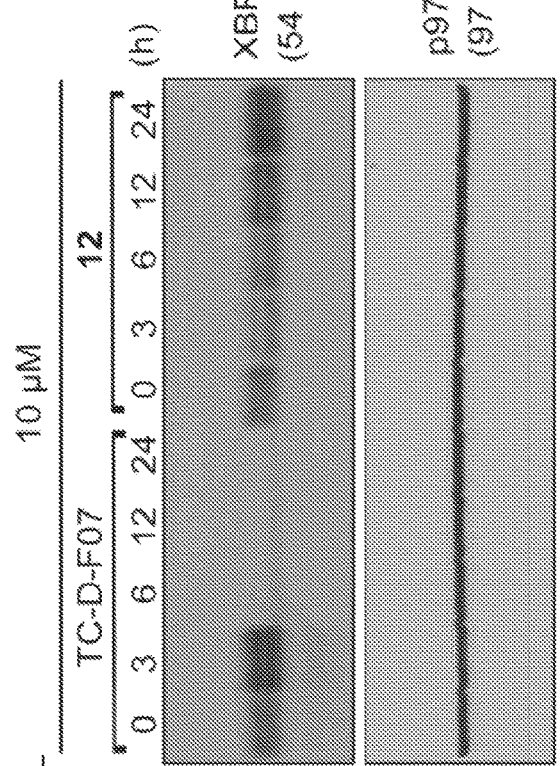
Figure 6I:
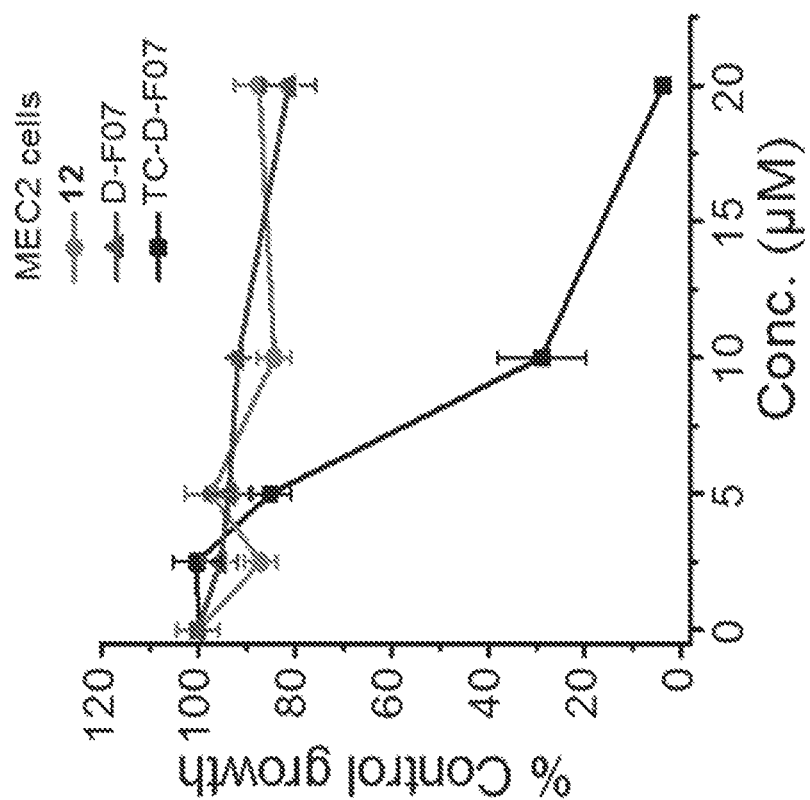
Figure 6H:
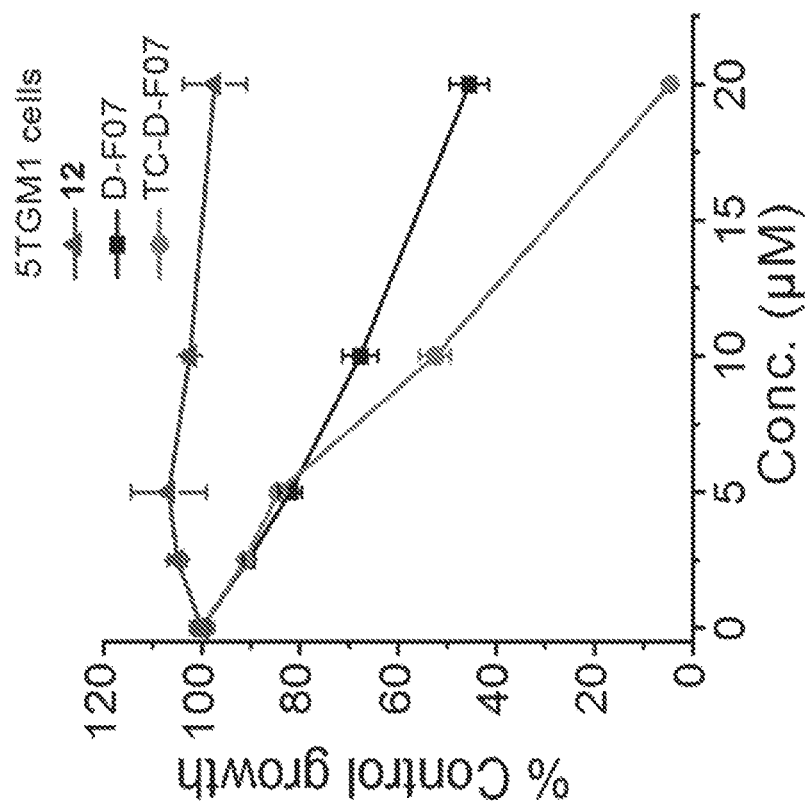
Figure 6J:
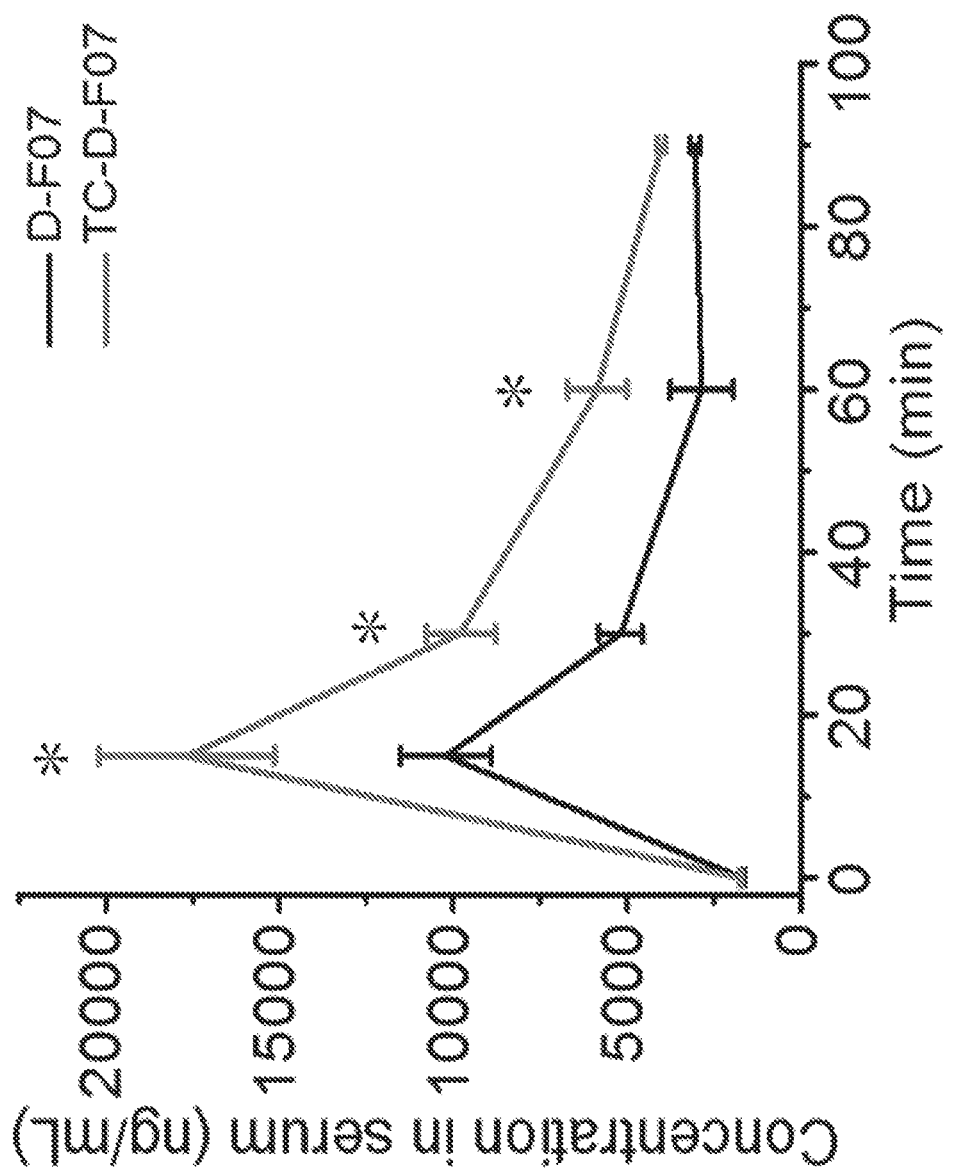
Figure 16:
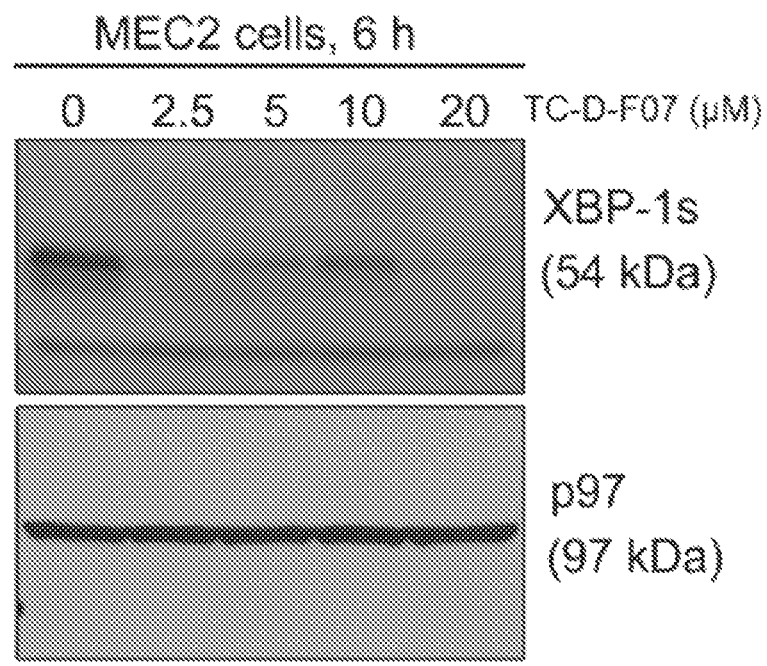
FIG. 16 illustrates an immunoblot obtained by treating MEC2 cells with TC-D-F07 at increasing concentrations for 6 h, lysing the cells, and analyzing them for the expression of indicated proteins.
Figure 17:
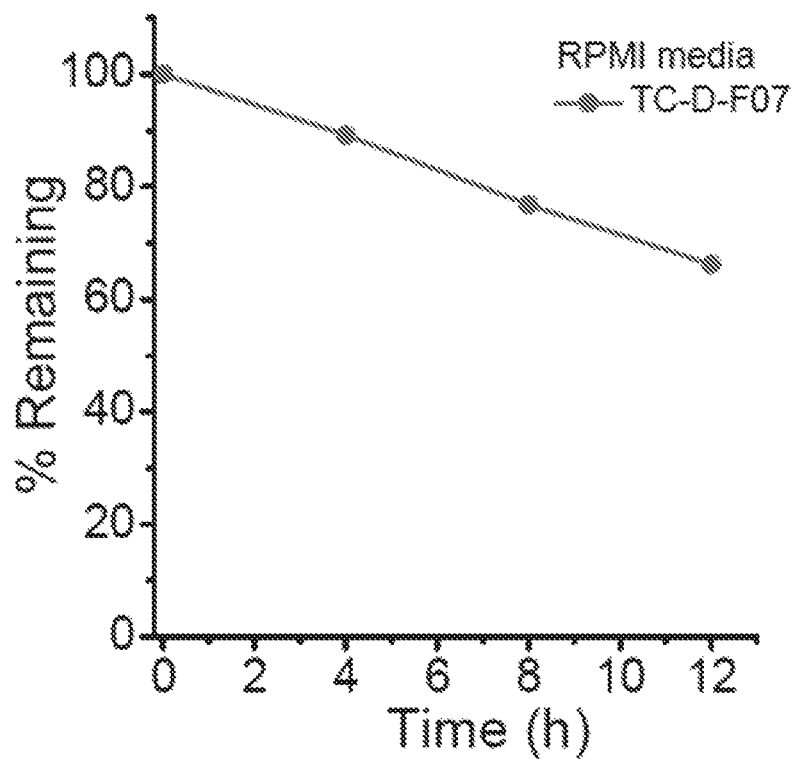
FIG. 17 illustrates a graph of decomposition of TC-D-F07 as a function of time in RPMI media at 37° C. Aliquots were analyzed by HPLC and the peaks integrated.
Figure 18:
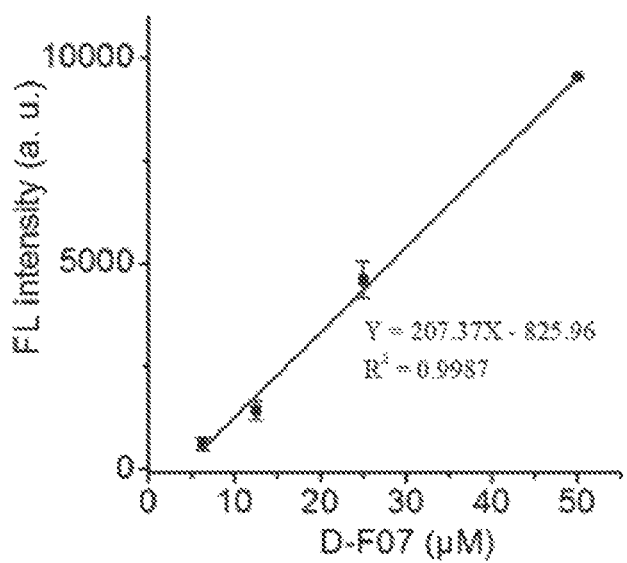
FIG. 18 illustrates fluorescence intensity of 0 to 50 µM D-F07 in mouse sera measured at 460 nm at 37° C. [DMSO/serum mixture (v/v=1:99), $E_x$=360 nm].

Similar results were observed in MEC2 cells treated with TC-D-F07 for 6 h (FIG. 16). Time-course experiments were performed to examine the levels of XBP-1s in 5TGM1 cells treated with TC-D-F07 at 2.5, 5 and 10 µM (FIG. 6F). In 5TGM1 cells treated with TC-D-F07 at 2.5 µM for 12 h, the levels of XBP-1s began to recover similar to those treated with D-F07. This is due to the rapid consumption of D-F07 decomposed from TC-D-F07 used at low concentrations. When 5TGM1 cells were treated with TC-D-F07 at 10 µM, the levels of XBP-1s initially increased after 3-h treatment and subsequently decreased in response to continuous 12-h treatment (FIG. 6F). Since 90% TC-D-F07 was still intact after 4-h incubation in both PBS and RPMI media (FIGS. 6D and 17), in certain non-limiting embodiments TC-D-F07 can induce ER stress in 5TGM1 cells. The 1,3-dinitro moiety on the sulfonate cage was shown to induce ER stress. The cysteine adduct 12 was prepared, and 5TGM1 cells were treated with TC-D-F07 and 12 at 10 µM for 24 h. Indeed 12 could also induce ER stress, as evidenced by the time-dependent increased expression of XBP-1s (FIG. 6G). Such data suggested that TC-D-F07 could initially act as an ER stress inducer, and subsequently decompose to become an IRE-1 inhibitor. To evaluate the cytotoxicity of 12 and TC-D-F07, 5TGM1 cells were treated with TC-D-F07, D-F07 or 12 at 0, 2.5, 5, 10 or 20 µM for 24 h, and TC-D-F07 was more cytotoxic than D-F07 (FIG. 6H). MEC2 CLL cells, which were less sensitive to 4 (B-I09) due to the lack of Myc expression, were treated with TC-D-F07, D-F07 or 12 (FIG. 6I). While D-F07 and 12 were not cytotoxic to MEC2 cells, TC-D-F07 potently inhibited the growth of these cells. Inspired by the thiol-reactive and cytotoxic characteristics of TC-D-F07, in vivo pharmacokinetics of TC-D-F07 and D-F07 were further compared by measuring compound fluorescence in mouse sera. Three CLL-bearing Eµ-TCL1 mice were intraperitoneally injected with an equal dose of TC-D-F07 or D-F07, and D-F07 reached its peak serum concentration at 10203 ng/mL in 15 minutes after a single injection (FIGS. 6J and 18). In mouse sera, TC-D-F07 could be cleaved by thiols to liberate D-F07, allowing for measurement by fluorescence. In mice injected with TC-D-F07, the maximal fluorescence in mouse sera in 15 minutes was similarly observed (FIG. 6J), and this fluorescence readout is equivalent to 17675 ng/mL of D-F07 (FIG. 18), indicating that the installation of the thiol-reactive sulfonate improved the retention of D-F07 in mouse sera.

Example 11

Upon structural modification of a tricyclic chromenone IRE-1 RNase inhibitor with different amine substituents ($R^1$: allyloxycarbonyl in 1, —H in 2, —$CH_3$ in 3, and so forth), 2 and 3 were identified as the most efficient aldehyde compounds in inhibiting IRE-1 in intact cells.

Different groups ($R^2$) were used to protect the reactive aldehyde of the tricyclic chromenone compound. Aldehyde masking was achieved through acid-catalyzed conversion to the corresponding 1,3-dioxane acetals (4, 5 and 7) or by reaction with hydrazines to give the hydrazone derivatives (6, 8 and 9). Installation of the 1,3-dioxane group (4 and 7) allowed for the restoration of blue fluorescence from the coumarin chromophore, and the gradual release of the active compound via slow hydrolysis to achieve a long-term efficacy in whole cells. Compounds with the N-acetylhydrazone protecting group (8) were not fluorescent but could rapidly decompose and inhibit IRE-1.

To increase the binding affinity of the inhibitor to IRE-1, a methoxy group ($R^3$) was incorporated to the C9 position of the tricyclic chromenone, and this compound, D-F07, had the most potent effect in inhibiting the expression of XBP-1s in whole cells.

Here, a unique prodrug strategy is used to enhance the efficacy of salicylaldehyde-based IRE-1 inhibitors, such as 4µ8C, MKC-3946 and MKC-9989. The activities of these inhibitors can also be precisely controlled. One can first protect the reactive aldehyde of these IRE-1 inhibitors as a 1,3-dioxane acetal to allow for enhanced cell uptake and gradual release of the aldehyde to achieve long-term efficacy. Taking advantage of our finding that the 8-hydroxy group renders the 1,3-dioxane acetal at C7 more labile, one can functionalize this hydroxy group through various methods to stabilize the prodrug and enable a 'cascade' mechanism of activation in response to environmental stimuli. The functional groups installed on the hydroxy group can be further linked to targeting antibodies (e.g., anti-CD20 antibodies or nanobodies for B cell cancer therapy) to generate antibody-drug conjugates via sortagging. After bound to tumor cells, the aldehyde-masked IRE-1 inhibitors are more efficiently liberated by endogenous hydrogen peroxide or GSH generated at higher concentrations by tumor cells, or are liberated at a precise time and location by the use of tissue-penetrable photons. Since liberated aldehyde-masked IRE-1 inhibitors are fluorescent, one can monitor the release efficiency of the inhibitors from antibody-drug conjugates. Once liberated, the re-exposed hydroxy group on the IRE-1 inhibitors will trigger the aldehyde-protecting 1,3-dioxane acetal to slowly hydrolyze, allowing inhibition of IRE-1 RNase activity to occur.

Inhibitors of IRE-1 RNase activity and XBP-1s expression have gained attention for the treatment of multiple myeloma (MM), a plasma cell cancer typified by an abundant rough ER and a robust ER stress response. Because IRE-1 RNase inhibitors trigger modest growth inhibition in MM cell lines, preclinical studies utilizing these inhibitors have generally involved the combination with bortezomib (Velcade), which acts to block proteasome activity leading to increased proteotoxic stress and activation of XBP-1s (an undesired effect). Bortezomib targets the ubiquitin-proteasome system, which is a first-line defense engaged by cells experiencing aberrant protein expression. However, subsequent activation of XBP-1s protects cancer cells from treatment with bortezomib, leading to drug resistance. Thus, the combination of an IRE-1 inhibitor with bortezomib can be an effective therapeutic strategy for MM.

TC-D-F07 can be cleaved by cysteine and GSH to generate D-F07 to effectively inhibit IRE-1 RNase activity. The byproduct, 12, while not toxic by itself, can induce the expression of XBP-1s in MM cells. TC-D-F07 indeed exerts much more potent cytotoxic effects than D-F07 or 12 against MM and CLL cells. These results highlight the possibility of designing a prodrug that contains both XBP-1s-inducing and XBP-1s-inhibiting activities for the treatment of MM. Additionally, TC-D-F07, PC-D-F07 and BC-D-F07 can be useful molecular tools to investigate the roles of the IRE-1/XBP-1 pathway in normal and malignant B cells.

Example 12: Synthesis a. Synthesis of 1-4

Compounds 1-4 were prepared according to the previously published procedure (Tang, et al., 2014, J. Clin. Inv. 124:2585; Ranatunga, et al., 2014, J. Med. Chem. 57:4289).

b. Synthesis of 5

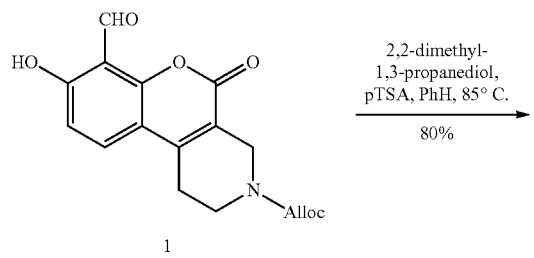

Allyl 7-(5,5-dimethyl-1,3-dioxan-2-yl)-8-hydroxy-5-oxo-4,5-dihydro-1H-chromeno[3,4-c]pyridine-3 (2H)-carboxylate (S1)

A mixture of 1 [Tang, et al., 2014, J. Clin. Inv. 124:2585] (50 mg, 0.15 mmol), 2,2-dimethyl-1,3-propandiol (47 mg, 0.46 mmol) and pTsOH·H2O (1.4 mg, 8.0 µmol) in benzene (5 mL) was heated at 85° C. for 2 h. Triethylamine (3 drops) was added, the reaction was concentrated, and the crude material was diluted with EtOAc. The organic layer was washed with water and brine and dried over anhydrous MgSO$_4$. Purification by silica gel flash chromatography (30% EtOAc/hexanes) gave S1 as a white solid (49 mg, 80%). $^1$H NMR (500 MHz, CDCl$_3$) δ 9.01 (s, 1H), 7.39 (d, J=8.9 Hz, 1H), 6.84 (d, J=8.9 Hz, 1H). 6.20 (s, 1H), 5.93 (ddd, J=16.4, 10.8, 5.4 Hz, 1H), 5.31 (dd, J=17.2, 1.6 Hz, 1H), 5.22 (dd, J=10.4, 1.5 Hz, 1H), 4.63 (dt, J=5.7, 1.5 Hz, 2H), 4.42 (s, 2H), 3.80 (s, 4H), 3.76 (t, J=5.8 Hz, 2H), 2.81 (t, J=5.8 Hz, 2H), 1.31 (s, 3H), 0.83 (s, 3H); HRMS (ESI-TOF) m/z [M+H]+ cald for $C_{22}H_{26}NO_7$ 416.1704. found 416.1706.

7-(5,5-dimethyl-1,3-dioxan-2-yl)-8-hydroxy-3,4-dihydro-1H-chromeno[3,4-c]pyridin-5(2H)-one (5)

Tetrakis(triphenylphosphine)palladium(0) (6.0 mg, 5.2 µmol) was added to a mixture of S1 (43 mg, 0.10 mmol) and phenylsilane (56 mg, 0.52 mmol) in DCM (8 mL) and the reaction was stirred for 1 h at room temperature. The reaction mixture was concentrated and the residue purified by silica gel flash chromatography (0 to 10% MeOH/CHCl$_3$) gave 5 as a pale yellow solid (37 mg, 79%). $^1$H NMR (500 MHz, CDCl$_3$) δ 7.41 (d, J=8.8 Hz, 1H), 6.85 (d, J=8.8 Hz, 1H), 6.23 (s, 1H), 3.82 (s, 6H), 3.17 (d, J=5.7 Hz. 2H), 2.76 (dd, J=5.1, 2.7 Hz, 2H), 2.09 (s, 1H), 1.33 (s, 3H), 0.84 (s, 3H); HRMS (ESI-TOF) m/z [M+Na]+ cald for $C_{18}H_{21}NNaO_5$ 354.1311. found 354.1325.

c. Synthesis of 6

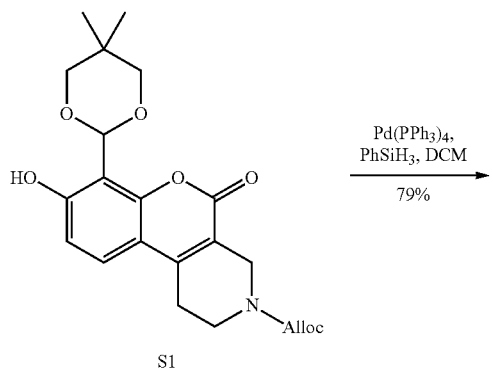

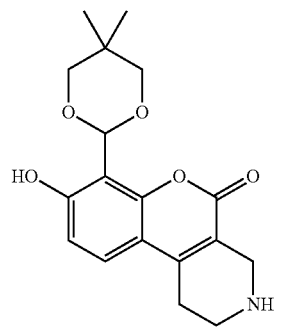

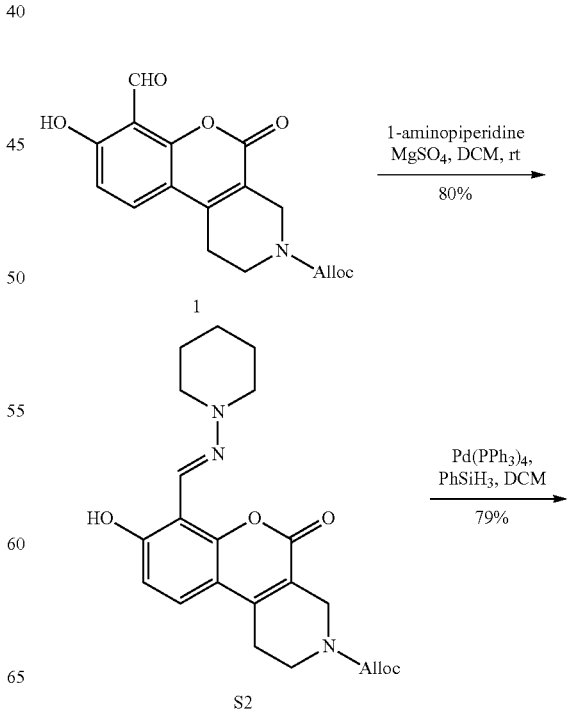

-continued

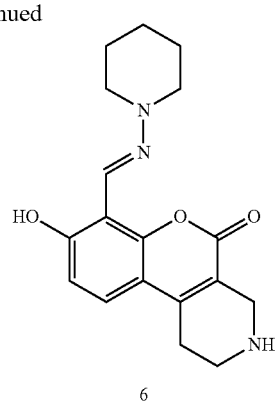

6

Allyl (E)-8-hydroxy-5-oxo-7-((piperidin-1-ylimino)methyl)-1,5-dihydro-2H-chromeno[3,4-c]pyridine-3(4H)-carboxylate (S2)

A mixture of 1 [Tang, et al., 2014, J. Clin. Inv. 124:2585] (50 mg, 0.15 mmol), 1-aminopiperidine (21 mg, 0.21 mmol) and anhydrous magnesium sulfate (60 mg, 0.50 mmol) in DCM (5 mL) was stirred for 3 h at room temperature. The reaction was diluted with DCM and water and the organic layer was washed with brine and dried over anhydrous MgSO$_4$. purification by silica gel flash chromatography (30% EtOAc/hexanes) gave S2 as a pale yellow solid (50 mg, 80%). $^1$H NMR (500 MHz, CDCl$_3$) δ 12.91 (s, 1H), 8.14 (s, 1H), 7.27 (d, J=10.5 Hz, 1H), 6.81 (d, J=8.8 Hz, 1H), 5.94 (ddt, J=16.4, 10.9, 5.6 Hz, 1H), 5.31 (dd, J=17.2, 1.8 Hz, 1H), 5.21 (d, J=10.5 Hz, 1H), 4.63 (d, J=5.7 Hz, 2H), 4.42 (s, 2H), 3.76 (t, J=5.8 Hz, 2H), 3.18 (t, J=5.7 Hz, 4H), 2.82 (s, 2H), 1.77 (t, J=5.9 Hz, 4H), 1.64-1.44 (m, 2H);

HRMS (ESI-TOF) m/z [M+H]+ cald for C$_{22}$H$_{26}$N$_3$O$_5$ 412.1867. found 412.1876.

(E)-8-hydroxy-7-((piperidin-1-ylimino)methyl)-1,2,3,4-tetrahydro-5H-chromeno[3,4-c]pyridin-5-one (6)

Tetrakis(triphenylphosphine)palladium(0) (6.6 mg, 5.7 μmol) was added to a mixture of S2 (47 mg, 0.11 mmol) and phenylsilane (62 mg, 0.57 mmol) in DCM (8 mL) and the reaction was stirred for 1 h at room temperature. The reaction mixture was concentrated and the residue purified by silica gel flash chromatography (0 to 10% MeOH/CHCl$_3$) gave 6 as a pale yellow solid (37 mg, 79%). $^1$H NMR (500 MHz, CDCl$_3$) δ 12.90 (s, 1H), 8.19 (s, 1H), 7.28 (d, J=8.8 Hz, 1H), 6.83 (d, J=8.8 Hz, 1H), 3.81 (s, 2H), 3.43-3.08 (m, 6H), 2.95-2.84 (m, 1H), 2.76 (d, J=5.7 Hz, 2H), 1.82-1.71 (m, 4H), 1.67-1.45 (m, 2H); HRMS (ESI-TOF) m/z [M+Na]+ cald for C$_{18}$H$_{21}$N$_3$NaO$_3$ 350.1475. found 350.1485.

d. Synthesis of 7

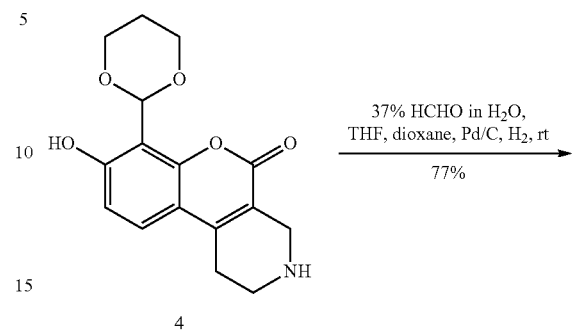

7-(1,3-dioxan-2-yl)-8-hydroxy-3-methyl-1,2,3,4-tetrahydro-5H-chromeno[3,4-c]pyridin-5-one (7)

A mixture of 4 (100 mg, 330 μmol), 37% formaldehyde in H$_2$O (54 mg, 0.66 mmol) and Pd/C (10 wt. %, 80 mg) in 1:1 THF/dioxane (2 mL) was stirred for 6 h under H2 atmosphere at room temperature. The reaction was filtered through celite, rinsed with MeOH and concentrated. Purification by silica gel flash chromatography (0 to 10% MeOH/CHCl$_3$) gave 7 as a pale yellow solid (81 mg, 77%). $^1$H NMR (400 MHz, CDCl$_3$) δ 8.83 (s, 1H), 7.41 (d, J=8.8 Hz, 1H), 6.85 (d, J=8.8 Hz, 1H), 6.33 (s, 1H), 4.31 (dd, J=10.8, 5.1 Hz, 2H), 4.12 (td, J=12.4, 2.4 Hz, 2H), 3.51 (d, J=2.3 Hz, 2H), 3.01-2.92 (m, 2H), 2.87-2.79 (m, 2H), 2.58 (s, 3H), 2.29 (dtt, J=13.9, 12.6, 5.1 Hz, 1H), 1.56 (ddt, J=13.8, 2.6, 1.3 Hz, 1H);

HRMS (ESI-TOF) m/z [2M+H]+ cald for C$_{34}$H$_{39}$N$_2$O$_{10}$ 635.2599. found 635.2630.

e. Synthesis of 8

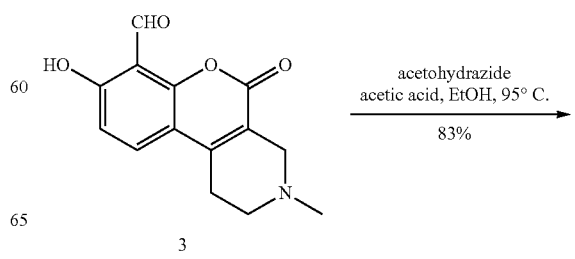

3

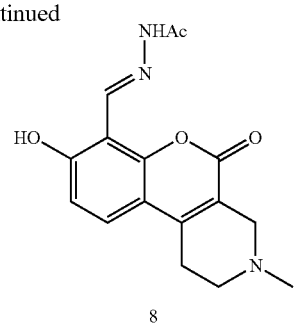

(E)-N'-((8-hydroxy-3-methyl-5-oxo-1,3,4,5-tetrahydro-2H-chromeno[3,4-c]pyridin-7-yl)methylene)acetohydrazide (8)

A mixture of 3 [Ranatunga, et al., 2014, J. Med. Chem. 57:4289] (25 mg, 0.10 mmol), acetohydrazide (11 mg, 0.15 mmol) and acetic acid (1.2 mg, 19 μmol) in ethanol (5 mL) was heated at 95° C. for 3 h. The reaction was cooled to room temperature and concentrated. Purification by silica gel flash chromatography (0 to 10% MeOH/CHCl$_3$) gave 8 as a pale yellow solid (25 mg, 83%). $^1$H NMR (400 MHz, DMSO-d$_6$) δ 12.48 (s, 1H), 11.92 (s, 0.8H), 11.50 (s, 0.2H), 8.76 (s, 0.8H), 8.61 (s, 0.2H), 7.60 (d, J=8.9 Hz, 1H), 6.91 (d, J=8.8 Hz, 1H), 3.20 (s, 2H), 2.84 (t, J=5.7 Hz, 2H), 2.62 (t, J=5.6 Hz, 2H), 2.36 (s, 3H), 2.16 (s, 0.6H), 1.98 (s, 2.4H); HRMS (ESI-TOF) m/z [M+H]+ cald for C$_{16}$H$_{18}$N$_3$O$_4$ 316.1292. found 316.1299.

f. Synthesis of 9

(E)-8-hydroxy-3-methyl-7-((piperidin-1-ylimino)methyl)-1,2,3,4-tetrahydro-5H-chromeno[3,4-c]pyridin-5-one (9)

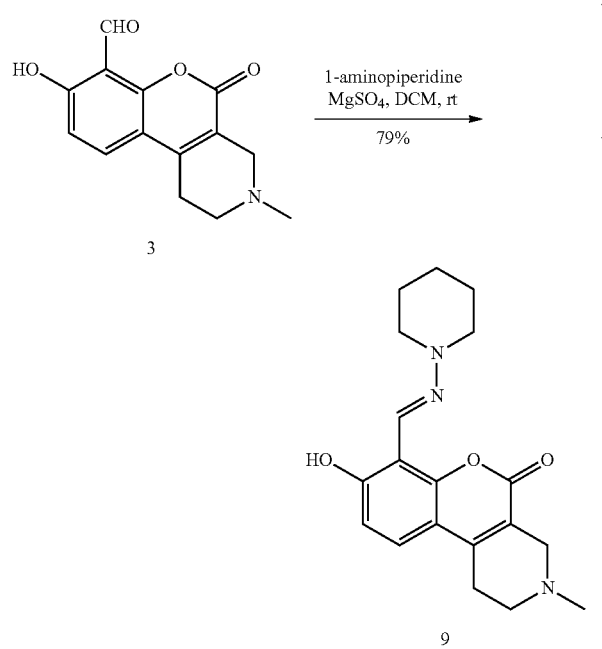

A mixture of 3 [Ranatunga, et al., 2014, J. Med. Chem. 57:4289] (25 mg, 0.10 mmol), 1-aminopiperidine (14 mg, 0.13 mmol) and anhydrous magnesium sulfate (60 mg, 0.50 mmol) in DCM (5 mL) was stirred for 30 min at room temperature. The reaction was diluted with DCM and water and the organic layer was washed with brine and dried over anhydrous MgSO$_4$. Purification by silica gel flash chromatography (0 to 10% MeOH/CHCl$_3$) gave 9 as a pale yellow solid (26 mg, 79%). $^1$H NMR (400 MHz, DMSO-d$_6$) δ 12.73 (s, 1H), 8.07 (s, 1H), 7.49 (d, J=8.8 Hz, 1H), 6.85 (d, J=8.8 Hz, 1H), 3.20 (s, 2H), 3.17 (t, J=5.7 Hz, 4H), 2.85 (t, J=5.8 Hz, 2H), 2.63 (t, J=5.7 Hz, 2H), 2.36 (s, 3H), 1.69 (p, J=5.6 Hz, 4H), 1.51 (td J=6.5 3.5 Hz, 2H); HRMS (ESI-TOF) m/z [M+H]+ cald for C$_{19}$H$_{24}$N$_3$O$_3$ 342.1822. found 342.1813.

g. Synthesis of D-F07

Allyl (2-(7-hydroxy-6-methoxy-2-oxo-2H-chromen-4-yl)ethyl)carbamate (S3)

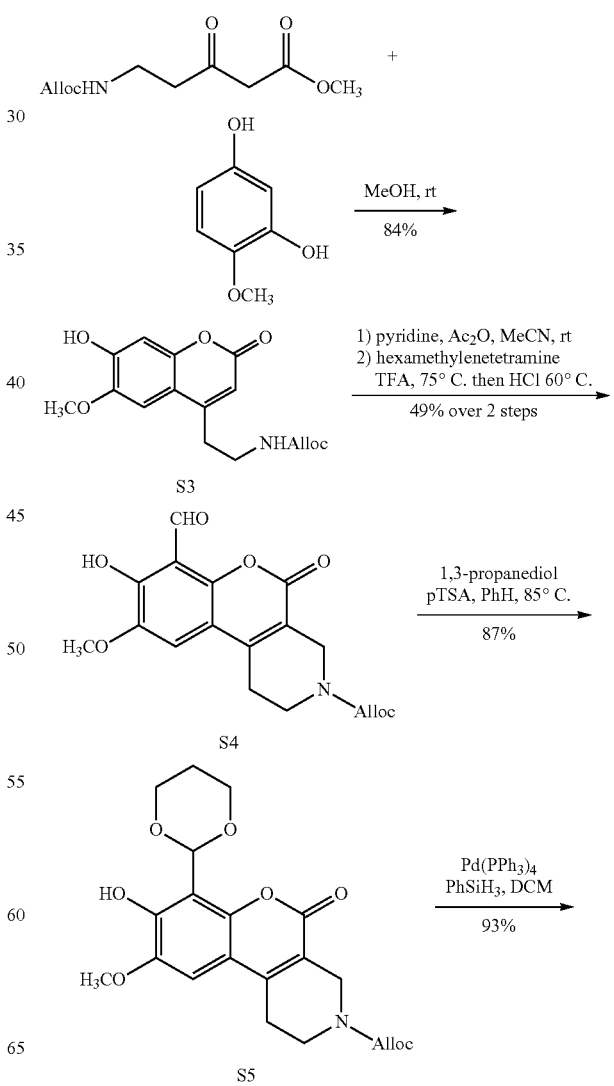

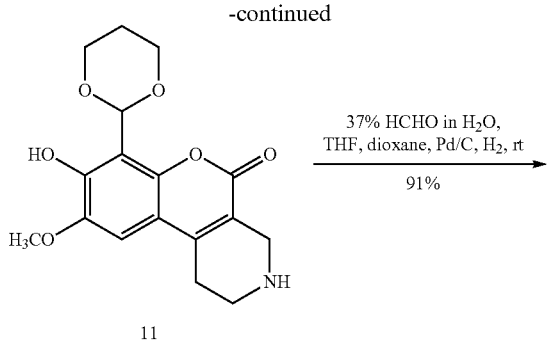

A mixture of methyl 5-(((allyloxy)carbonyl)amino)-3-oxopentanoate (327 mg, 1.43 mmol) and 4-methoxybenzene-1,3-diol (200 mg, 1.43 mmol) in methanesulfonic acid (10 mL) was stirred for 1 h at room temperature. Ice was added to the reaction slowly to quench the reaction and diluted with EtOAc. After removing the aqueous layer, the organic later was washed with sat. aq. $NaHCO_3$ and concentrated. The resulting solid was washed with EtOAc to give pure S3 as a yellow solid (382 mg, 84%). $^1$H NMR (500 MHz, $CD_3OD$) δ 7.31 (s, 1H), 6.75 (s, 1H), 6.11 (s, 1H), 5.89 (ddt, J=15.8, 10.6, 5.4 Hz, 1H), 5.26 (dd, J=17.2, 1.7 Hz, 1H), 5.16 (dd, J=10.6, 1.7 Hz, 1H), 4.51 (d, J=5.4 Hz, 2H), 3.95 (s, 3H), 3.42 (t, J=7.2 Hz, 2H), 2.97 (t, J=7.1 Hz, 2H); HRMS (ESI-TOF) m/z [M+H]+ cald for $C_{16}H_{18}NO_6$ 320.1129. found 320.1132.

Allyl 7-formyl-8-hydroxy-9-methoxy-5-oxo-1,5-dihydro-2H-chromeno[3,4-c]pyridine-3(4H)-carboxylate (S4)

Acetic anhydride (1.12 g, 10.9 mol) was added to a mixture of S3 (700 mg, 2.19 mmol) and pyridine (87 mg, 1.1 mmol) in acetonitrile (70 mL) and the reaction was stirred for 18 h at room temperature. The reaction was diluted with EtOAc, washed with brine and concentrated. The resulting crude material was dissolved in TFA (25 mL), treated with hexamethylenetetramine (768 mg, 5.48 mmol) and stirred for 18 h at 75° C. The reaction was concentrated, dissolved in THF (50 mL) and aq. 1M HCl (50 mL) and stirred for 2 h at 60° C. The reaction was diluted with EtOAc and the organic layer washed with brine. Purification by silica gel flash chromatography (0 to 10% MeOH/$CHCl_3$) gave S4 as a yellow solid (383 mg, 49% over 2 steps). $^1$H NMR (400 MHz, $CDCl_3$) δ 12.44 (s, 1H), 10.59 (s, 1H), 7.10 (s, 1H), 5.95 (ddt, J=16.4, 10.9, 5.6 Hz, 1H), 5.33 (dd, J=17.2, 1.6 Hz, 1H), 5.24 (dd, J=10.4, 1.5 Hz, 1H), 4.64 (d, J=5.7 Hz, 2H), 4.47 (s, 2H), 3.95 (s, 3H), 3.82 (t, J=5.7 Hz, 2H), 2.86 (t, J=5.8 Hz, 2H); HRMS (ESI-TOF) m/z [M+H]+ cald for $C_{18}H_{18}NO_7$ 360.1078. found 360.1076.

Allyl 7-(1,3-dioxan-2-yl)-8-hydroxy-9-methoxy-5-oxo-1,5-dihydro-2H-chromeno[3,4-c]pyridine-3(4H)-carboxylate (S5)

A mixture of S4 (721 mg, 2.00 mmol), 1,3-propandiol (458 mg, 6.02 mmol) and pTsOH·$H_2O$ (19 mg, 0.1 mmol) in toluene (70 mL) was refluxed with Dean-Stark apparatus at 150° C. for 4 h. Triethylamine (10 drops) was added and the reaction was concentrated. The crude material was then diluted with EtOAc. The organic layer was washed with water and brine and dried over anhydrous $MgSO_4$. Purification by silica gel flash chromatography (0 to 5% MeOH/$CHCl_3$) gave S5 as a pale yellow solid (776 mg, 93%). $^1$H NMR (400 MHz, $CDCl_3$) δ 8.86 (s, 1H), 6.77 (s, 1H), 6.24 (s, 1H), 5.89 (ddt, J=16.0, 10.9, 5.6 Hz, 1H), 5.26 (dd, J=17.2, 1.6 Hz, 1H), 5.17 (dd, J=10.4, 1.4 Hz, 1H), 4.58 (d, J=5.7 Hz, 2H), 4.36 (s, 2H), 4.25 (dd, J=10.8, 5.1 Hz, 2H), 4.06 (td, J=12.4, 2.3 Hz, 2H), 3.82 (s, 3H), 3.76 (t, J=5.8 Hz, 2H), 2.75 (t, J=5.8 Hz, 2H), 2.33-2.16 (m, 1H), 1.50 (d, J=14.4 Hz, 1H); HRMS (ESI-TOF) m/z [M+H]+ cald for $C_{21}H_{24}NO_8$ 418.1496. found 418.1496.

7-(1,3-dioxan-2-yl)-8-hydroxy-9-methoxy-1,2,3,4-tetrahydro-5H-chromeno[3,4-c]pyridin-5-one (11)

Tetrakis(triphenylphosphine)palladium(0) (3.6 mg, 3.1 μmol) was added to a mixture of 7 (26 mg, 62 μmol) and phenylsilane (34 mg, 0.31 mmol) in DCM (2 mL) and the reaction was stirred for 1 h at room temperature. The reaction mixture was concentrated and purification by silica gel flash chromatography (0 to 10% MeOH/$CHCl_3$) gave 11 as an orange solid (19 mg, 93%). $^1$H NMR (500 MHz, DMSO-$d_6$) δ 8.33 (s, 1H), 7.13 (s, 1H), 6.11 (s, 1H), 4.15 (dd, J=11.4, 4.7 Hz, 2H), 3.93 (t, J=11.6 Hz, 2H), 3.87 (s, 3H), 3.75 (s, 2H), 3.21 (s, 2H), 2.93 (s, 2H), 2.11 (tt, J=12.6, 7.5 Hz, 1H), 1.43 (d, J=13.4 Hz, 1H); HRMS (ESI-TOF) m/z [M+H]+ cald for $C_{17}H_{20}NO_6$ 334.1285. found 334.1286.

7-(1,3-dioxan-2-yl)-8-hydroxy-9-methoxy-3-methyl-1,2,3,4-tetrahydro-5H-chromeno[3,4-c]pyridin-5-one (D-F07)

A mixture of 11 (272 mg, 820 μmol), 37% formaldehyde in $H_2O$ (133 mg, 660 μmol) and Pd/C (10 wt. %, 200 mg) in 1:1 THF/dioxane (30 mL) was stirred for 5 h under $H_2$ atmosphere at room temperature. The reaction was filtered through celite, rinsed with MeOH and concentrated. Purification by silica gel flash chromatography (0 to 7% MeOH/$CHCl_3$) gave D-F07 as an orange solid (258 mg, 91%). $^1$H NMR (400 MHz, DMSO-$d_6$) δ 9.43 (s, 1H), 7.11 (s, 1H), 6.11 (s, 1H), 4.15 (dd, J=11.5, 4.7 Hz, 2H), 3.93 (t, J=11.8 Hz, 2H), 3.85 (s, 3H), 3.20 (s, 2H), 2.88 (s, 1H), 2.64 (t, J=5.7 Hz, 2H), 2.49 (s, 3H), 2.37 (s, 2H), 2.11 (qt, J=12.1, 4.8 Hz, 1H), 1.43 (d, J=13.3 Hz, 1H); HRMS (ESI-TOF) m/z [M+K]+ cald for $C_{18}H_{21}KNO_6$ 386.1000. found 386.1005.

h. Synthesis of 10

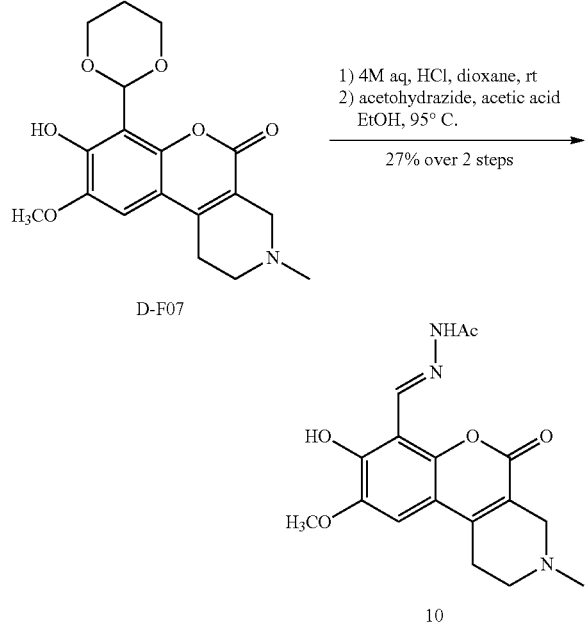

(E)-N'-((8-hydroxy-9-methoxy-3-methyl-5-oxo-1,3,4,5-tetrahydro-2H-chromeno[3,4-c]pyridin-7-yl)methylene)acetohydrazide (10)

4M aq. HCl (4 mL) was added to a solution of D-F07 (40 mg, 0.12 mmol) in 1,4-dioxane (1 mL) and the reaction was stirred for 1 h at room temperature. The reaction was neutralized with 4M aq. NaOH, poured to silica gel (3 g) and concentrated to silica gel powder. Purification by solid load silica gel flash chromatography (0 to 10% MeOH/CHCl$_3$) gave aldehyde compound. A mixture of the aldehyde compound above, acetohydrazide (13 mg, 0.17 mmol) and acetic acid (1.4 mg, 23 μmol) in ethanol (10 mL) was heated at 95° C. for 3 h. The reaction was cooled to room temperature and concentrated. Purification by silica gel flash chromatography (0 to 20% MeOH/CHCl$_3$) gave 10 as a orange solid (11 mg, 27% over 2 steps). $^1$H NMR (400 MHz, DMSO-d$_6$) δ 12.63 (s, 1H), 11.91 (s, 0.8H), 11.50 (s, 0.2H), 8.74 (s, 0.8H), 8.60 (s, 0.2H), 7.12 (s, 1H), 3.83 (s, 3H), 3.18 (s, 2H), 2.86 (t, J=5.8 Hz, 2H), 2.61 (t, J=5.7 Hz, 2H), 2.34 (s, 3H), 2.14 (s, 0.6H), 1.96 (s, 2.4H); HRMS (ESI-TOF) m/z [M+H]+ calcd for C$_{17}$H$_{20}$N$_3$O$_5$ 346.1398. found 346.1394.

i. Synthesis of PC-D-F07

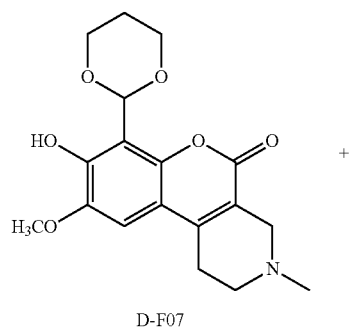

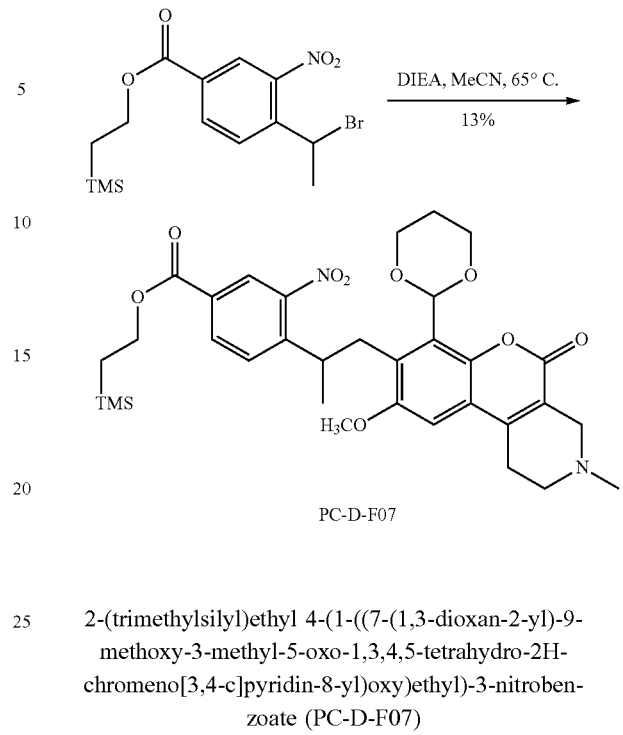

2-(trimethylsilyl)ethyl 4-(1-(((7-(1,3-dioxan-2-yl)-9-methoxy-3-methyl-5-oxo-1,3,4,5-tetrahydro-2H-chromeno[3,4-c]pyridin-8-yl)oxy)ethyl)-3-nitrobenzoate (PC-D-F07)

A mixture of D-F07 (100 mg, 290 μmol), 2-(trimethylsilyl)ethyl 4-(1-bromoethyl)-3-nitrobenzoate (162 mg, 430 μmol) and N,N-diisopropylethylamine (74 mg, 0.58 mmol) in acetonitrile (5 mL) was stirred for 24 h at 65° C. The reaction and diluted with EtOAc, washed with water and brine and dried over anhydrous MgSO$_4$. Purification by silica gel flash chromatography (0 to 5% MeOH/CHCl$_3$) gave PC-D-F07 as an orange solid (24 mg, 13%). $^1$H NMR (400 MHz, CDCl$_3$) δ 8.48 (s, 1H), 8.22 (s, 2H), 6.79 (s, 1H), 6.27 (s, 1H), 6.11 (q, J=6.3 Hz, 1H), 4.46-4.36 (m, 2H), 4.30-4.16 (m, 2H), 4.04-3.91 (m, 2H), 3.59 (s, 3H), 3.37 (s, 2H), 2.78 (t, J=5.8 Hz, 2H), 2.67 (t, J=5.4 Hz, 2H), 2.45 (s, 3H), 2.36-2.19 (m, 1H), 1.71 (d, J=6.3 Hz, 3H), 1.41 (d, J=13.4 Hz, 1H), 1.18-1.03 (m, 2H), 0.05 (s, 9H); HRMS (ESI-TOF) m/z [M+H]+ calcd for C$_{32}$H$_{41}$N$_2$O$_{10}$Si 641.2516. found 641.2538.

j. Synthesis of BC-D-F07a

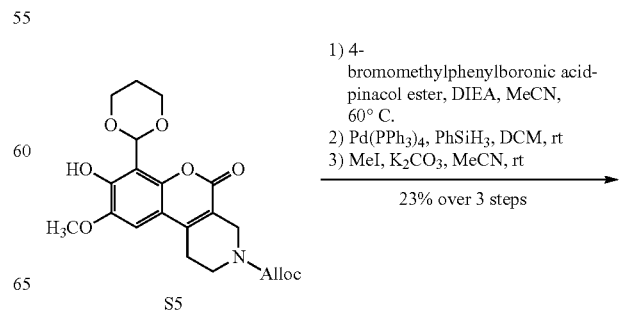

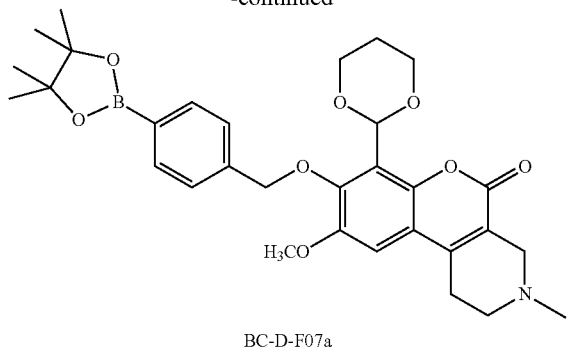

BC-D-F07a

7-(1,3-dioxan-2-yl)-9-methoxy-3-methyl-8-((4-(4,4,5,5-tetramethyl-1,3,2-dioxaborolan-2-yl)benzyl)oxy)-1,2,3,4-tetrahydro-5H-chromeno[3,4-c]pyridin-5-one (BC-D-F07a)

A mixture of S5 (48 mg, 0.11 mmol), 4-bromomethylphenylboronic acid pinacol ester (68 mg, 0.23 mmol) and N,N-diisopropylethylamine (88 ng, 0.68 mmol) in acetonitrile (3 mL) was stirred for 3 days at 60° C. The reaction and diluted with EtOAc, washed with water and brine and dried over anhydrous MgSO₄. Purification by silica gel flash chromatography (30 to 80% EtOac/hexanes) gave boronic compound (68 mg, 94%). Tetrakis(triphenylphosphine) palladium(0) (6.2 mg, 5.4 µmol) was added to a mixture of the boronic compound above (68 mg, 0.11 mmol) and phenylsilane (58 mg, 0.54 mmol) in DCM (mL) and the reaction was stirred for 1 h at room temperature. The reaction mixture was concentrated and purification by silica gel flash chromatography (0 to 5% MeOH/CHCl₃) gave alloc deprotected compound (40 mg, 68%). Iodomethane (7.8 mg, 55 µmol) was added to a mixture of the alloc deprotected compound above (40 mg, 73 µmol) and potassium carbonate (30 mg, 0.22 mmol) in acetonitrile (5 mL) and the reaction was stirred for 4 h at room temperature. The reaction and diluted with EtOAc, washed with water and brine and dried over anhydrous MgSO₄. Purification by silica gel flash chromatography (0 to 5% MeOH/CHCl₃) gave BC-D-F07a as an orange solid (15 mg, 23% over 3 steps). ¹H NMR (400 MHz, CDCl₃) δ 7.82 (d, J=7.7 Hz, 2H), 7.52 (d, J=7.6 Hz, 2H), 6.95 (s, 1H), 6.21 (s, 1H), 5.13 (s, 2H), 4.15 (dd, J=11.3, 4.7 Hz, 2H), 3.95-3.82 (m, 2H), 3.87 (s, 3H), 3.42 (s, 2H), 2.87 (t, J=5.8 Hz, 2H), 2.73 (t, J=5.6 Hz, 2H), 2.49 (s, 3H), 2.26-2.09 (m, 1H), 1.34 (s, 12H), 1.28 (d, J=2.9 Hz, 1H); HRMS (ESI-TOF) m/z [M+Na]+ cald for C₃₁H₃₈BNNaO₈ 586.2588. found 586.2593.

k. Synthesis of BC-D-F07b

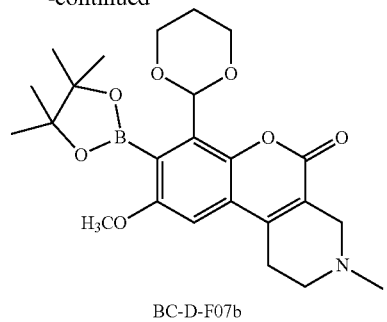

BC-D-F07b

7-(1,3-dioxan-2-yl)-9-methoxy-3-methyl-8-(4,4,5,5-tetramethyl-1,3,2-dioxaborolan-2-yl)-3,4-dihydro-1H-chromeno[3,4-c]pyridin-5(2H)-one (BC-D-F07b)

A solution of D-F07 (87 µmol, 30 mg) and N-phenyl-bis(trifluoromethanesulfonimide) (173 µmol, 62.0 mg) in DMF (1.3 mL) was treated with Na₂CO₃ (432 µmol, 46.0 mg) and stirred for 16 h. The solvent was removed under vacuum and the residue dissolved in EtOAc. The solution was washed with aq. HCl, the layers separated, and the aqueous layer extracted with EtOAc. The organic layers were combined and dried over Na₂SO₄. The crude material was purified using silica gel flash chromatography (0 to 20% CHCl₃/MeOH) to provide the aryl triflate as an orange solid (279 mg, 72%). The aryl triflate above (0.2 mmol, 96 mg) was dissolved in dioxane (3.3 mL) and the solution purged with argon for 15 min. This solution was then cannulated into a sealed vessel containing Pd(ddpf)Cl2·DCM (4.0 µmol, 3.0 mg), (Bpin)₂ (0.3 mmol, 66 mg), and KOAc (6.0 mmol, 59 mg). The mixture was stirred at 100° C. for 16 h. Upon completion, the solvent was removed under vacuum and the residue dissolved in DCM. The solution was washed with water, the layers separated, and the aqueous layer extracted with DCM. The organic layers were combined and dried over Na₂SO₄. The crude material was purified by RP-HPLC (C12 preparative column, 5-95% MeCN/H₂O with 0.1% formic acid, linear gradient) to give a BC-D-F07b yellow powder after lyophilization (31 mg, 25% over two steps). ¹H NMR (400 MHz, CDCl₃) δ 6.83 (s, 1H), 6.15 (s, 1H), 4.27 (dd, 2H), 4.09 (m, 2H), 3.82 (s, 3H), 3.45 (s, 2H), 2.91 (m, 2H), 2.76 (m, 2H), 2.51 (s, 3H), 2.17 (m, 1H), 1.41 (s, 13H); HRMS (ESI-TOF) m/z [M+H]+ cald for C₂₄H₃₃BNO₇ 458.2345. found 458.2362.

l. Synthesis of TC-D-F07

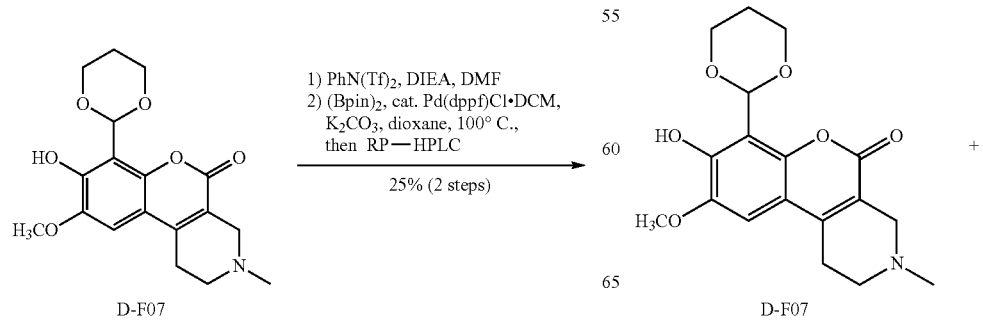

D-F07 → D-F07

1) PhN(Tf)₂, DIEA, DMF
2) (Bpin)₂, cat. Pd(dppf)Cl·DCM, K₂CO₃, dioxane, 100° C., then RP—HPLC 25% (2 steps)

+

-continued

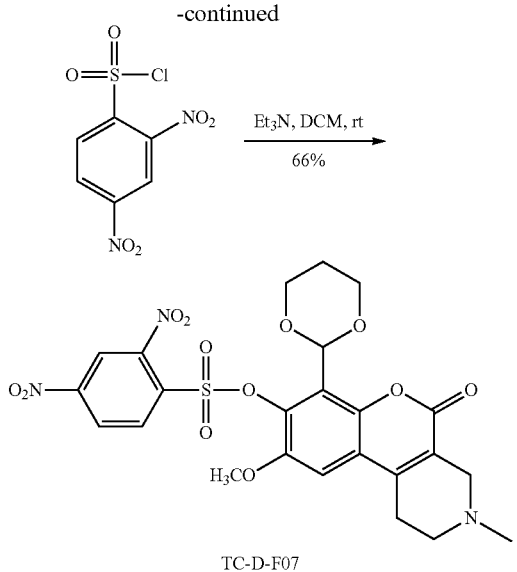

TC-D-F07

7-(1,3-dioxan-2-yl)-9-methoxy-3-methyl-5-oxo-1,3,4,5-tetrahydro-2H-chromeno[3,4-c]pyridin-8-yl 2,4-dinitrobenzenesulfonate (TC-D-F07)

2,4-dinitrobenzenesulfonyl chloride (77 mg, 0.29 mmol) was added to a mixture of D-F07 (50 mg, 0.14 mmol) and triethylamine (29 mg, 0.29 mmol) in DCM (5 mL) and the reaction was stirred for 5 h at room temperature. The reaction and diluted with DCM, washed with water and brine and dried over anhydrous $MgSO_4$. Purification by silica gel flash chromatography (0 to 5% $MeOH/CHCl_3$) gave TC-D-F07 as an orange solid (55 mg, 66%).

$^1$H NMR (400 MHz, $CDCl_3$) δ 8.70 (d, J=2.2 Hz, 1H), 8.55 (dd, J=8.7, 2.3 Hz, 1H), 8.37 (d, J=8.7 Hz, 1H), 6.92 (s, 1H), 6.30 (s, 1H), 4.11 (dd, J=11.3, 4.6 Hz, 2H), 3.98-3.83 (m, 2H), 3.52 (s, 3H), 3.41 (s, 2H), 2.83 (dt, J=5.5, 3.2 Hz, 2H), 2.73 (t, J=5.5 Hz, 2H), 2.48 (s, 3H), 2.26-2.09 (m, 1H), 1.32 (d, J=13.4 Hz, 1H); HRMS (ESI-TOF) m/z [M+H]+ cald for $C_{24}H_{24}N_3O_{12}S$ 578.1075. found 578.1084.

m. Synthesis of 12

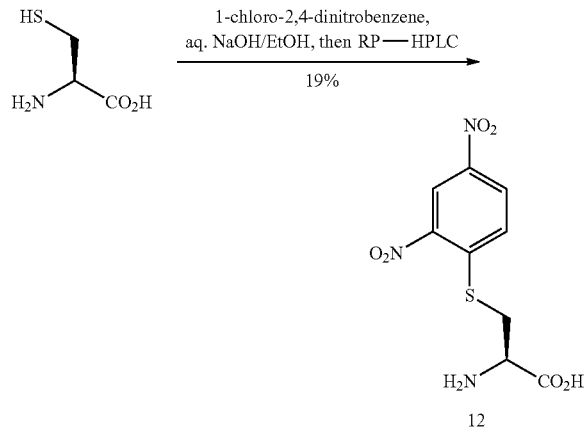

(S-2,4-Dinitrophenyl)cysteine (12)

1-Chloro-2,4-dinitrobenzene (130 mg, 0.63 mmol) and L-cysteine (925 mg, 764 μmol) were dissolved in a mixture of 2M aq. NaOH (0.5 mL) and ethanol (0.42 mL). After stirring for 24 h, the solution was neutralized with 1M aq. HCl, to provide a yellow precipitate that was filtered and washed with water. The crude material was dissolved in a 1:1 mixture of MeCN/aq. PBS buffer and purified by RP-HPLC (C12 preparative column, 5-95% $MeCN/H_2O$ with 0.1% formic acid, linear gradient) to give 12 as a yellow powder (26 mg, 19%). $^1$H NMR (400 MHz, $CD_3CN$) δ 9.12 (s, 1H), 8.99 (s, 1H), 8.26 (d, 1H), 7.05 (d, 1H), 4.84 (s, 1H), 3.15 (dd 2H); HRMS (ESI-TOF) m/z [M+H]+ cald for $C_9H_{10}N_3O_6S$, 288.0285. found 288.0282.

Figure 19A:
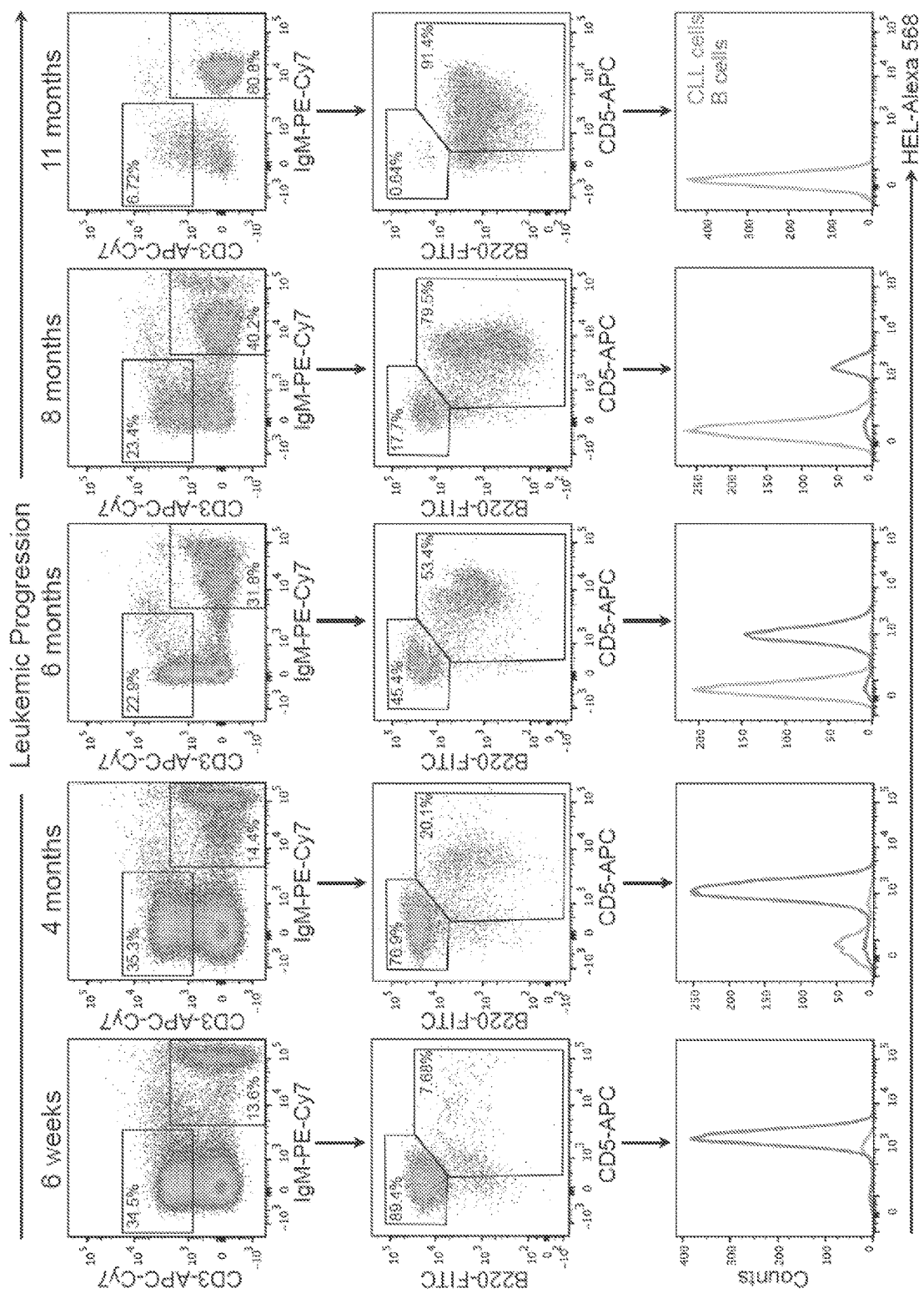
FIGS. 19A-19B illustrate the finding CLL cells developed in MD4$^{+/-}$/Eµ-TCL1$^{+/+}$ mice fail to recognize hen egg lysozyme (HEL).
Figure 19B:
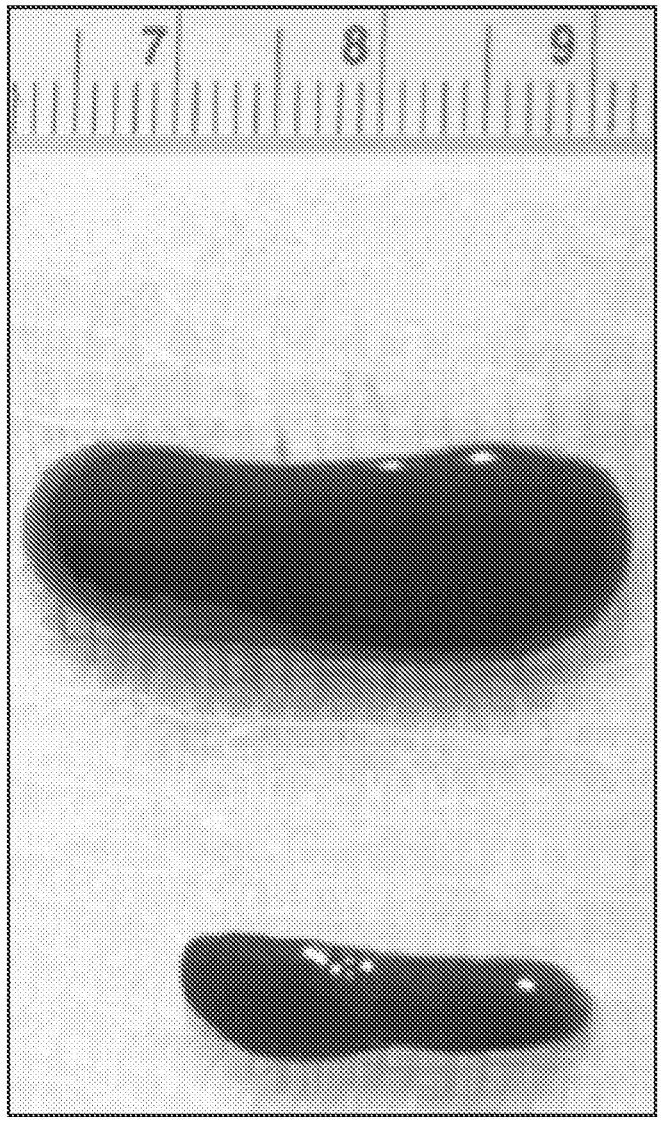

Example 13: CLL Cells Developed in MD4$^{+/-}$/Eμ-TCL1$^{+/+}$ Mice Fail to Recognize HEL To investigate the role of a monoclonal B cell receptor (BCR) in the progression of CLL in mice, the MD4/Eμ-TCL1 mouse model was generated by crossing Eμ-TCL1$^{+/+}$ mice, which spontaneously develop CLL, with MD4$^{+/-}$ transgenic mice, which produce a monoclonal BCR against HEL. To maintain consistent numbers of the BCR and equal dose of the TCL1 transgene, MD4$^{+/-}$/Eμ-TCL1$^{+/+}$ were routinely crossed with Eμ-TCL1$^{+/+}$ mice since the establishment of this colony. To enumerate HEL-positive B or CLL cells, HEL was conjugated with Alexa 568 for cell surface staining. Splenocytes harvested from MD4$^{+/-}$/Eμ-TCL1$^{+/+}$ mice of different age groups were stained with CD3-APC-Cy7, IgM-PE-Cy7, B220-FITC, CD5-APC and HEL-Alexa-568. The IgM+ cells were gated to analyze for B220$^{hi}$/CD5− precancerous B cells and B220$^{lo}$/CD5+ CLL cells (FIG. 19A). MD4$^{+/-}$/Eμ-TCL1$^{+/+}$ mice developed CLL with enlarged spleens (FIGS. 19A-19B), and all IgM+/B220$^{lo}$/CD5+ CLL cells developed in older MD4$^{+/-}$/Eμ-TCL1$^{+/+}$ mice failed to recognize HEL (FIG. 19A).

Figure 26D:
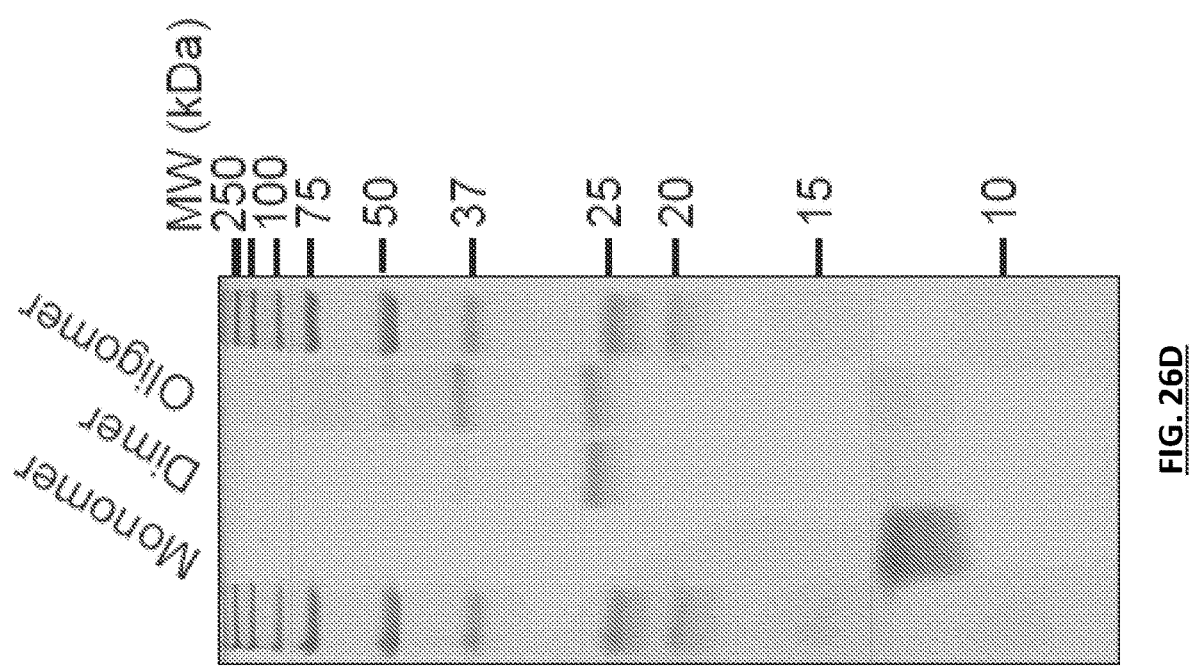

Example 14: Precancerous B Cells and CLL Cells Purified from MD4$^{+/-}$/Eμ-TCL1$^{+/+}$ Mice Respond to BCR Crosslinking by Activating Robust BCR Signaling To activate the BCR via antigen-binding sites instead of constant regions, dimeric and oligomeric HEL were generated by chemically crosslinking HEL using glutaraldehyde (FIG. 26A) and monomeric, dimeric and oligomeric HEL separated by size exclusion column chromatography (FIGS. 26B-26D). When Eμ-TCL1$^{+/+}$ and MD4$^{+/-}$/Eμ-TCL1$^{+/+}$ B cells were exposed to goat Fab or F(ab')2 anti-mouse IgM (used as negative or positive controls, respectively), monomeric, dimeric or oligomeric HEL for 2 min, only MD4$^{+/-}$/Eμ-TCL1$^{+/+}$ B cells responded to HEL by activating BCR signaling, as evidenced by increased tyrosine phosphorylation of BCR signaling molecules, such as Syk (FIGS. 27A-27B). Dimeric or oligomeric HEL was more effective than monomeric HEL in activating BCR signaling in MD4$^{+/-}$/Eμ-TCL1$^{+/+}$ B cells (FIG. 27B). MD4$^{+/-}$ and MD4$^{+/-}$/Eμ-TCL1$^{+/+}$ B cells responded to oligomeric HEL within 30 sec, reached the maximal response at 2 min, and began to downregulate the BCR signaling at 5 min and thereafter (FIGS. 28A-28B). Activating the same cells via crosslinking the constant regions of the BCR using goat anti-mouse IgM F(ab')2 resulted in delayed yet more persistent BCR signaling, as shown by phosphorylated Igα, Syk, AKT and ERK (FIGS. 28A-28B). These data highlighted the different response between activation of the BCR via antigen-binding sites and constant regions.

Figure 20A:
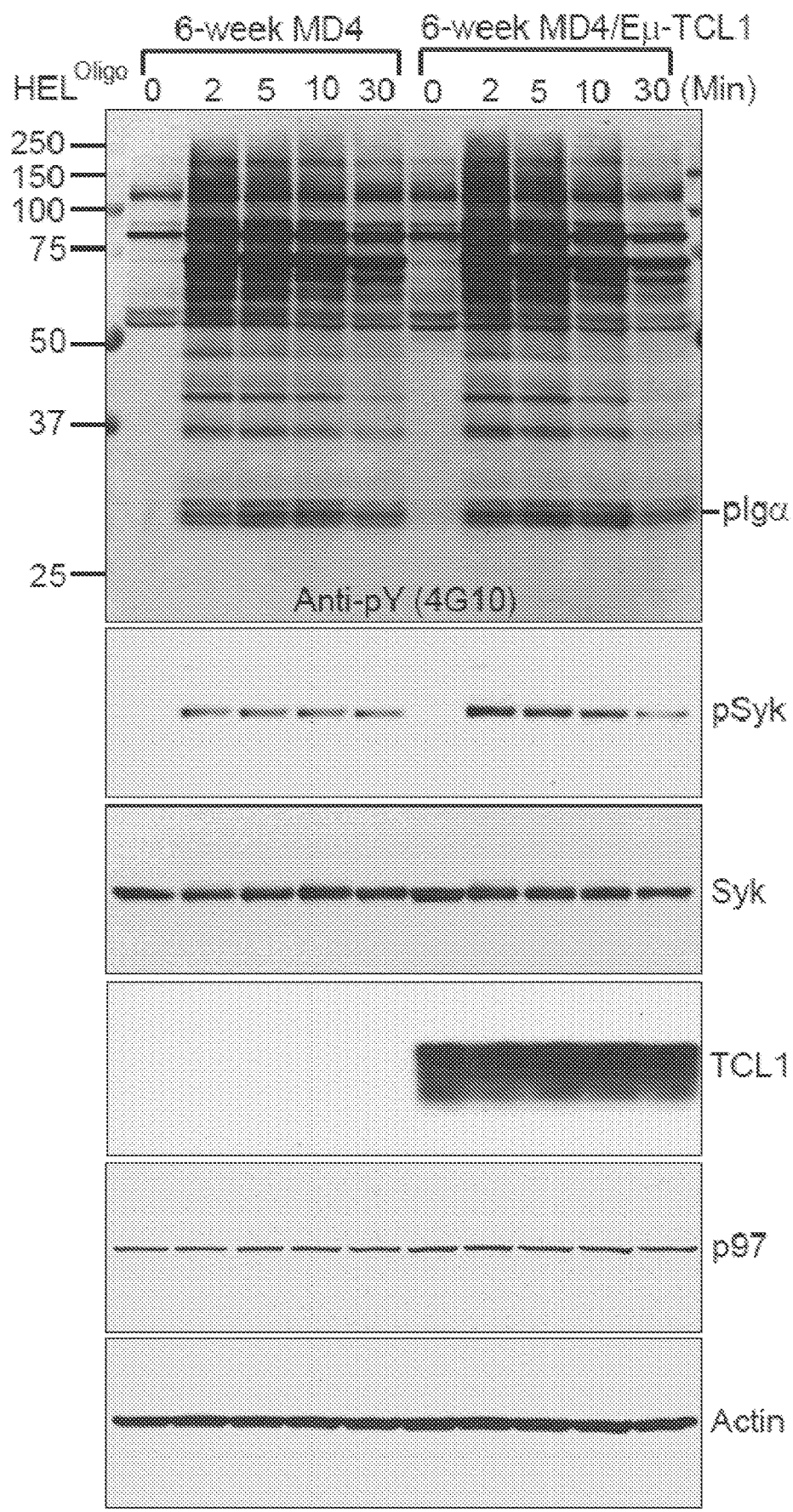
Figure 20B:
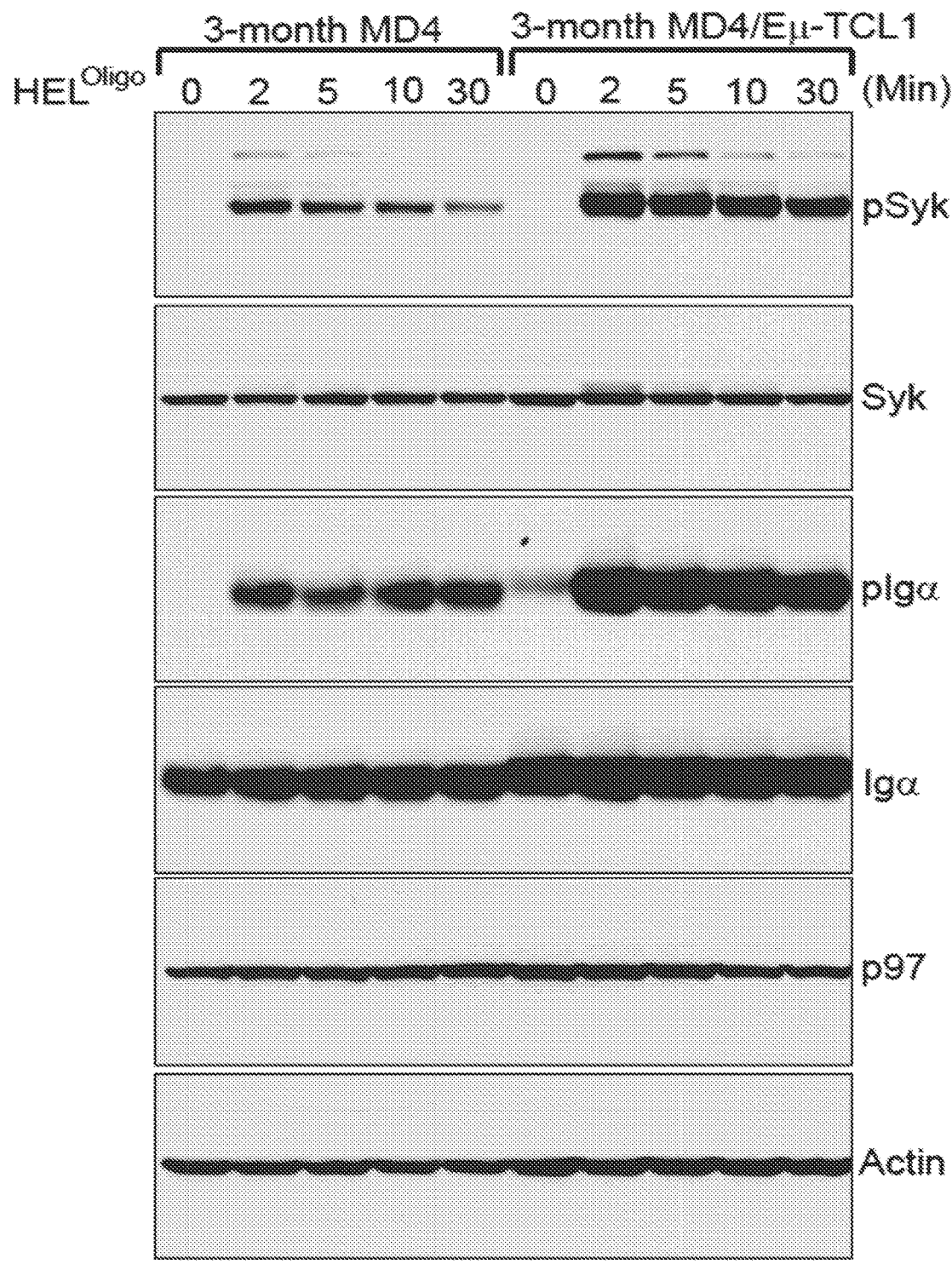
Figure 20C:
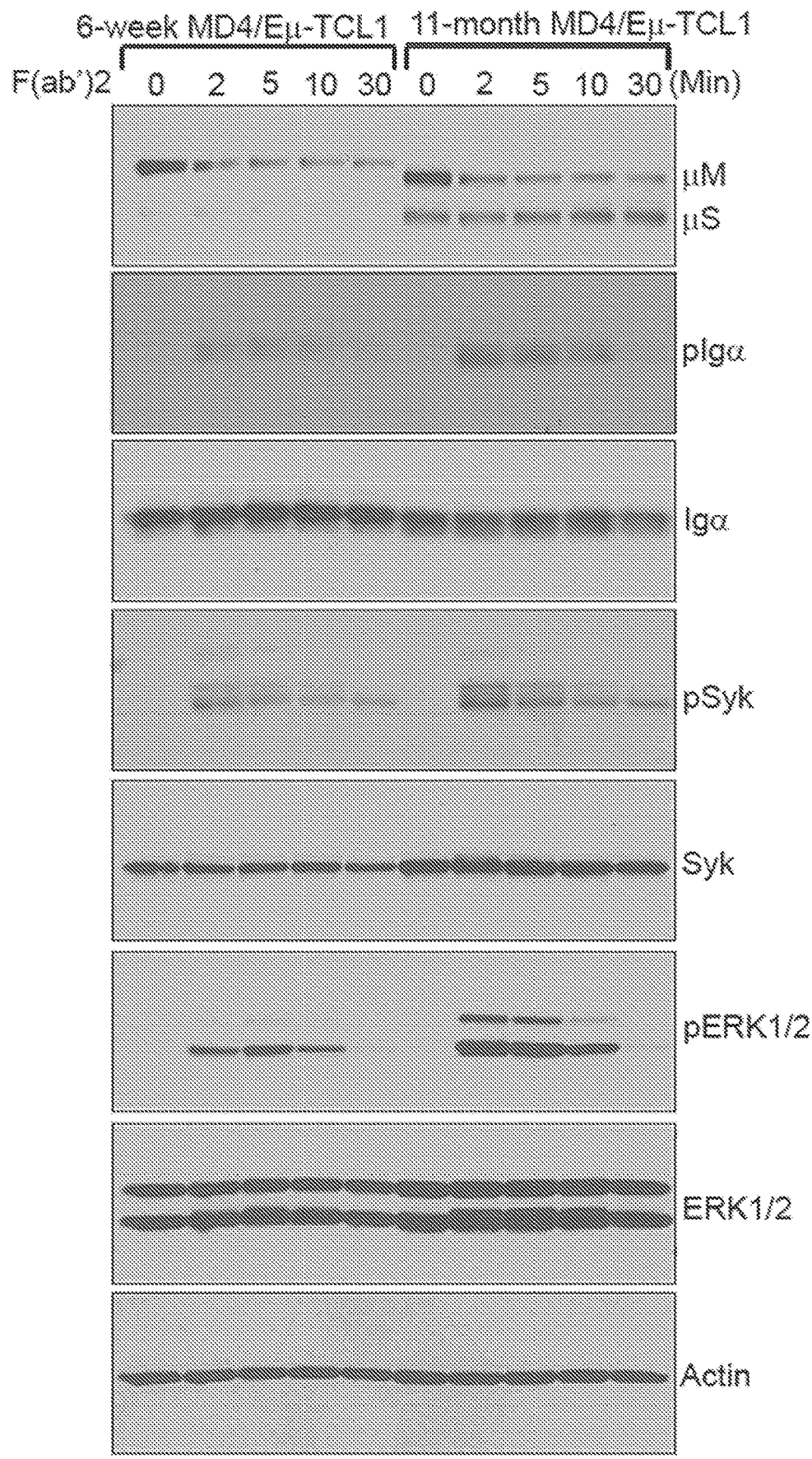
Figure 20D:
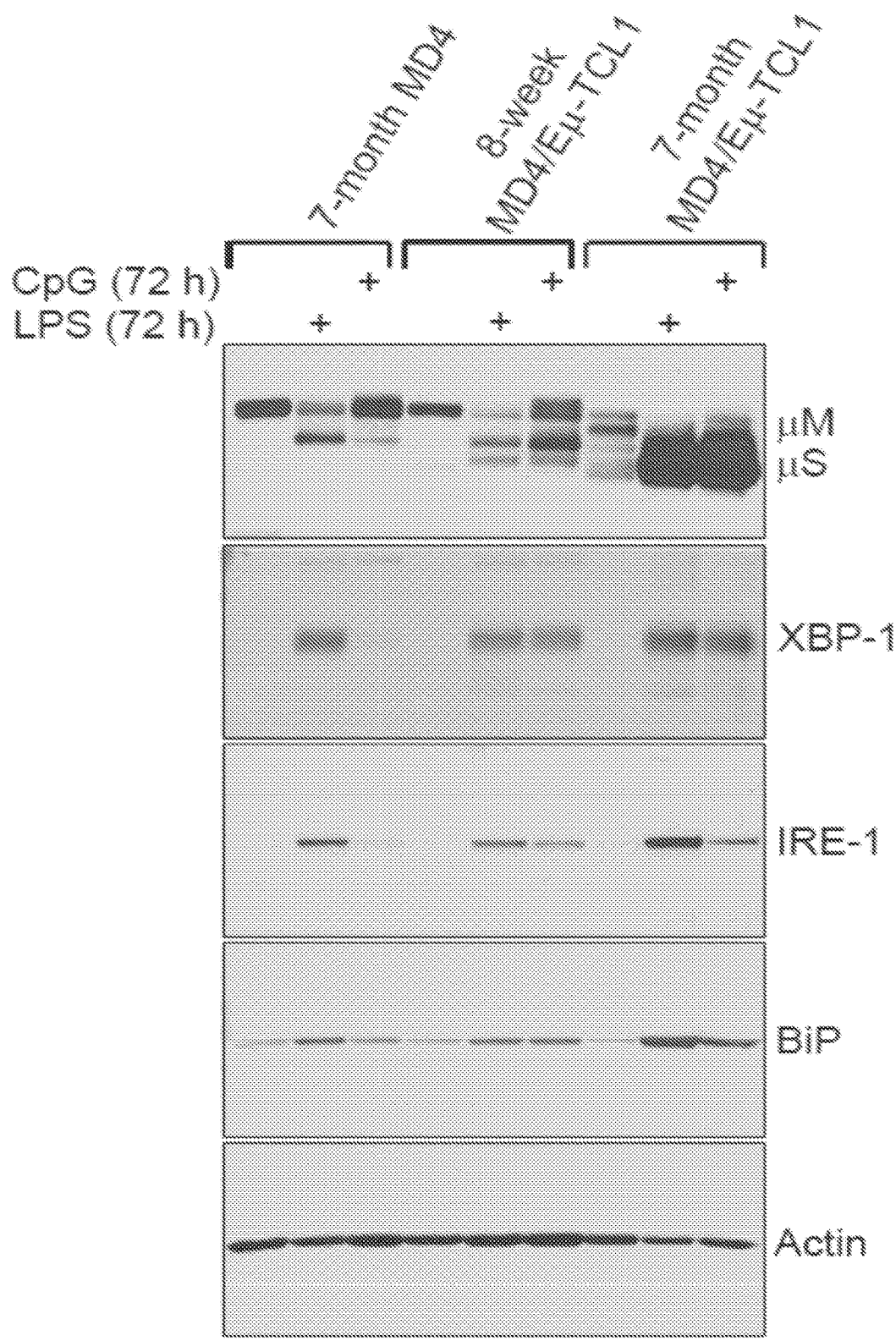

BCR signaling is critical for CLL survival. To evaluate BCR signaling in precancerous B cells developed in MD4$^{+/-}$/Eµ-TCL1$^{+/+}$ mice, IgM+/B220$^{hi}$/CD5− B cells isolated from the spleens of 6-week-old and 3-month-old MD4$^{+/-}$ and MD4$^{+/-}$/Eµ-TCL1$^{+/+}$ mice were stimulated with oligomeric HEL for a course of 30 min, and precancerous B cells from MD4$^{+/-}$/Eµ-TCL1$^{+/+}$ mice were much more responsive to oligomeric HEL stimulations than B cells from their age-matched MD4$^{+/-}$ counterparts (FIGS. 20A-20B). Since IgM+/B220$^{lo}$/CD5+ CLL cells developed in MD4$^{+/-}$/Eµ-TCL1$^{+/+}$ mice did not recognize HEL (FIG. 19A), it was examined whether these CLL cells still expressed the anti-HEL IgM encoded by the MD4 transgene. IgM+/B220$^{lo}$/CD5+ CLL cells in MD4$^{+/-}$/Eµ-TCL1$^{+/+}$ consistently shut down the expression of the MD4 transgene and reactivated the non-MD4 Ig gene allele to express both membrane-bound and secretory IgM. When these CLL cells were stimulated with goat anti-mouse IgM F(ab'2), they responded by eliciting stronger phosphorylation of Igα, Syk and ERK1/2 than precancerous B cells isolated from 6-week-old MD4$^{+/-}$/Eµ-TCL1$^{+/+}$ mice (FIG. 20C). In addition, when IgM+/B220$^{lo}$/CD5+ CLL cells isolated from MD4$^{+/-}$/Eµ-TCL1$^{+/+}$ mice were stimulated with lipopolysaccharide (LPS, a TLR4 ligand) or CpG-1826 (a TLR9 ligand), they began to produce large quantities of secretory IgM (sIgM) encoded from the non-MD4 Ig gene allele. Reactivation of the non-MD4 transgene Ig allele did not occur in B cell isolated from MD4$^{+4}$ mice at any age group or in precancerous B cells isolated from young MD4$^{+/-}$/Eµ-TCL1$^{+/+}$ mice (FIG. 20D). The abundant production of sIgM was accompanied by the enhanced endoplasmic reticulum (ER) stress response, as evidenced by activation of the IRE1/XBP-1 pathway and increased expression levels of BiP (FIG. 20D).

Figure 21A:
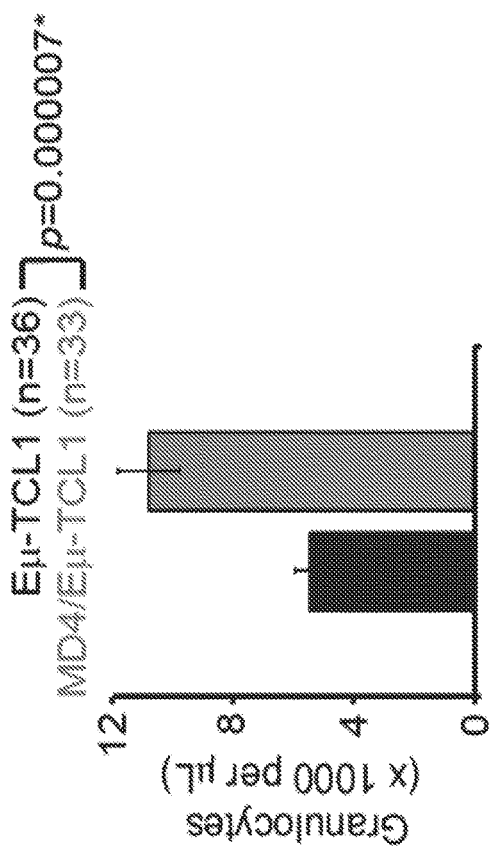
Figure 21B:
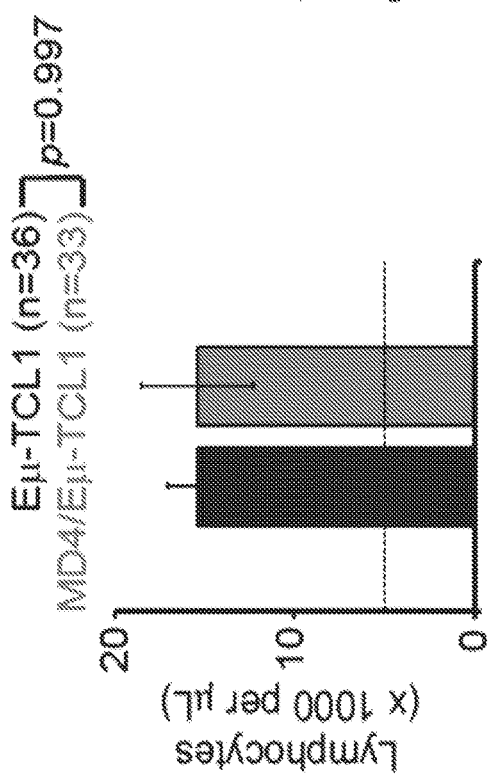
Figure 21C:
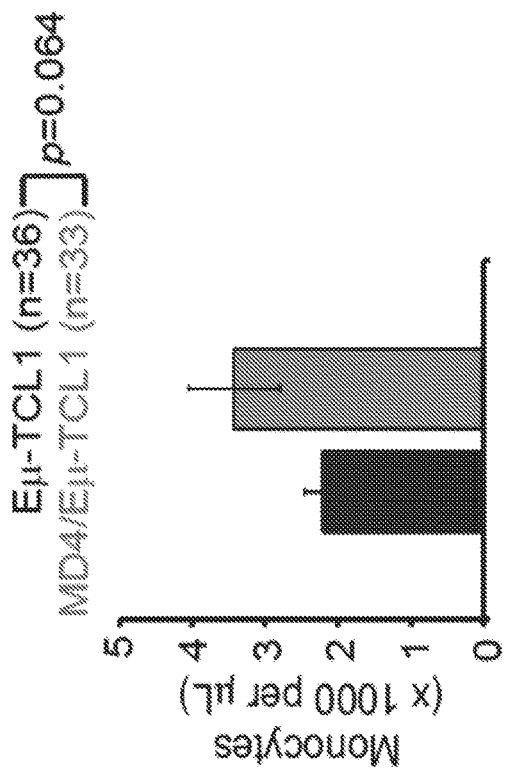
Figure 21D:
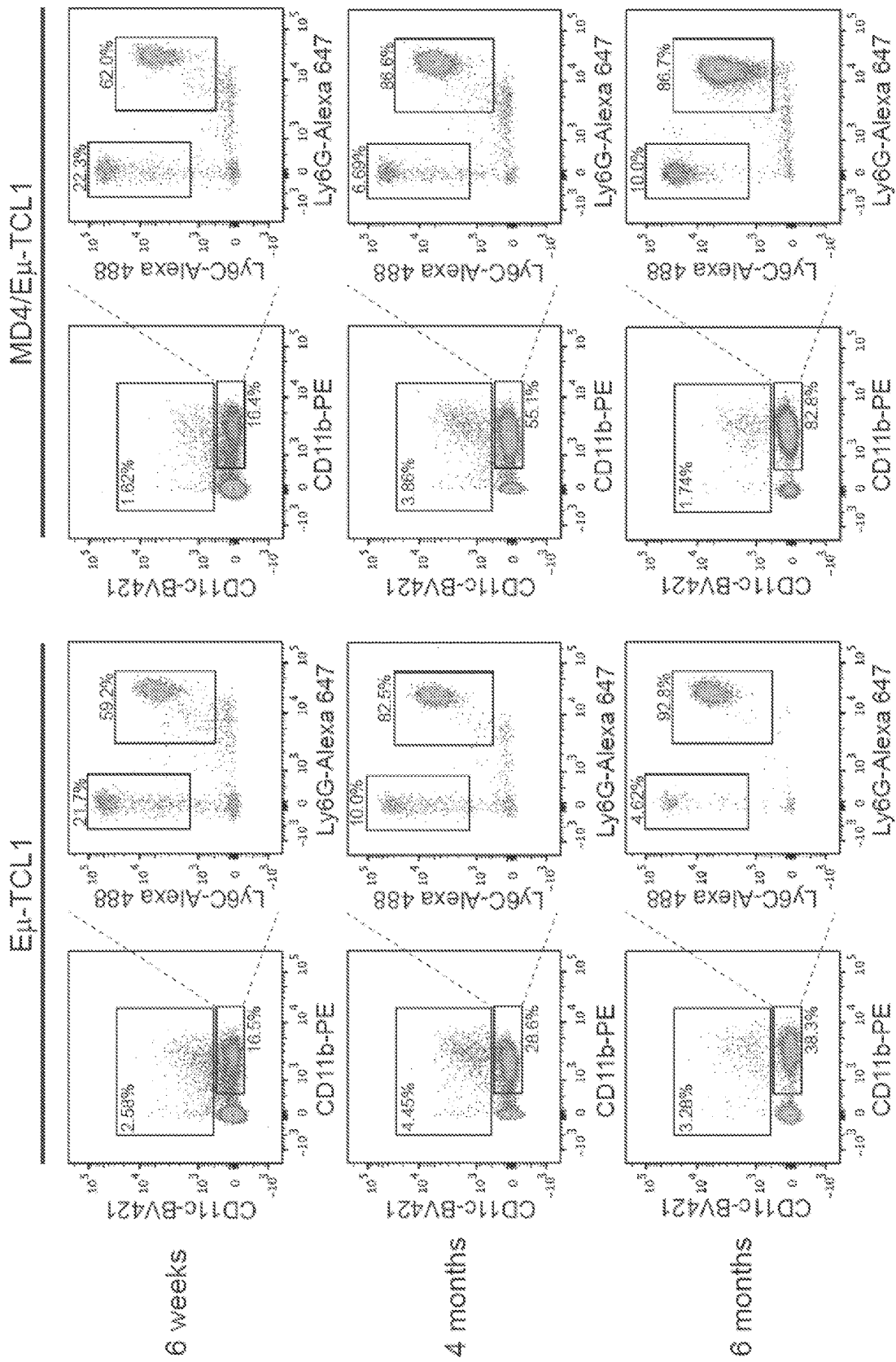

Example 15: Accumulation of CD11b+/Ly6G+ Granulocytic Cells in Eµ-TCL1$^{+/+}$ and MD4$^{+/-}$/Eµ-TCL1$^{+/+}$ Mice The routine complete blood count analyses of approximately 6-month old MD4$^{+/-}$/Eµ-TCL1$^{+/+}$ and Eµ-TCL1$^{+/+}$ mice showed that CLL (>5000 lymphocytes per µL blood) developed in both mouse models (FIG. 21A). Significantly increased numbers of granulocytic cell populations were observed in the blood of MD4$^{+/-}$/Eµ-TCL1$^{+/+}$ mice (FIG. 21B). Although there was an increase in the mean of monocytic cell populations in MD4$^{+/+}$/Eµ-TCL1$^{+/+}$ mice, the data were not statistically significant due to large variations (FIG. 21C). Next peripheral blood cells from age-matched Eµ-TCL1$^{+/+}$ and MD4$^{+/-}$/Eµ-TCL1$^{+/+}$ mice were stained with CD11c-BV421, CD11b-PE, Ly6C-Alexa 488 and Ly6G-Alexa 647, and CD11b+ myeloid populations were gated to analyze for Ly6C+ monocytic and Ly6G+ granulocytic populations (FIG. 21D). Significantly higher percentages of CD11b+ myeloid populations and CD11b+/Ly6G+ granulocytic cells were discovered in the peripheral blood of MD4$^{+/-}$/Eµ-TCL1$^{+/+}$ mice than those in Eµ-TCL1$^{+/+}$ mice in age-matched 4 month-old (FIG. 21D), 6 month-old (FIGS. 21D-21G) and 8 month-old (FIGS. 21H-21J) groups. These CD11b+/Ly6G+ granulocytic cells reached the highest percentages in the blood of MD4$^{+/-}$/Eµ-TCL1$^{+/+}$ mice at the age of approximately 6 months (FIGS. 21D-21G).

Figure 30A:
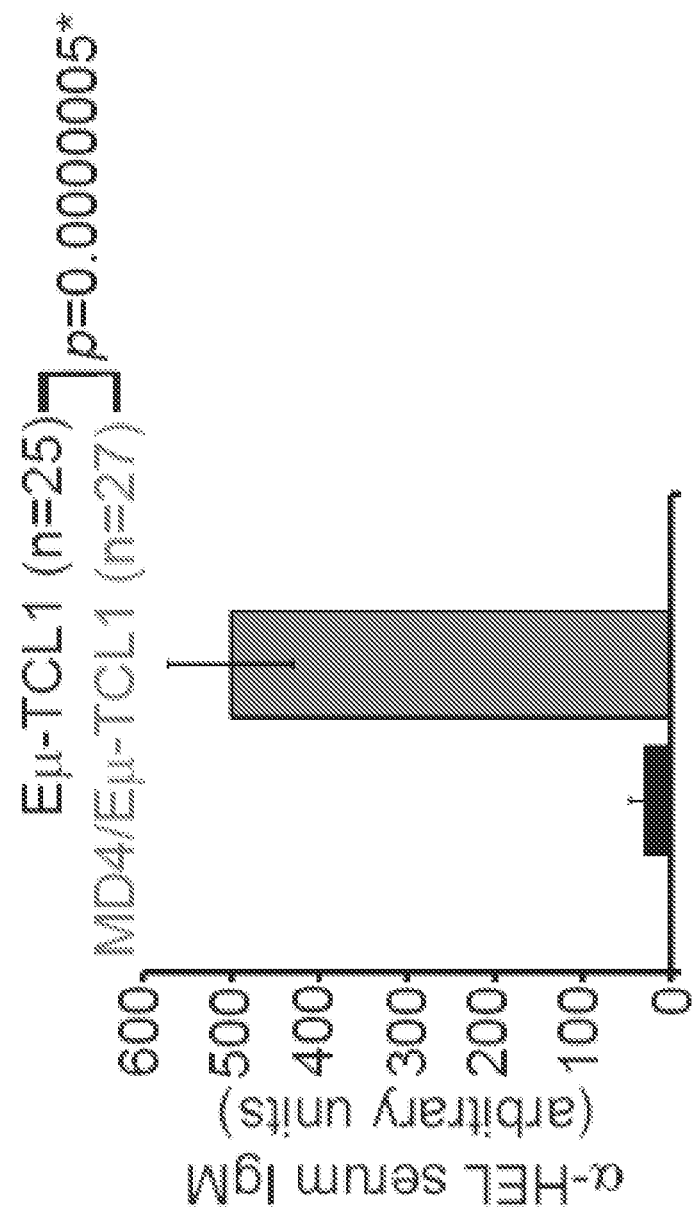
Figure 30B:
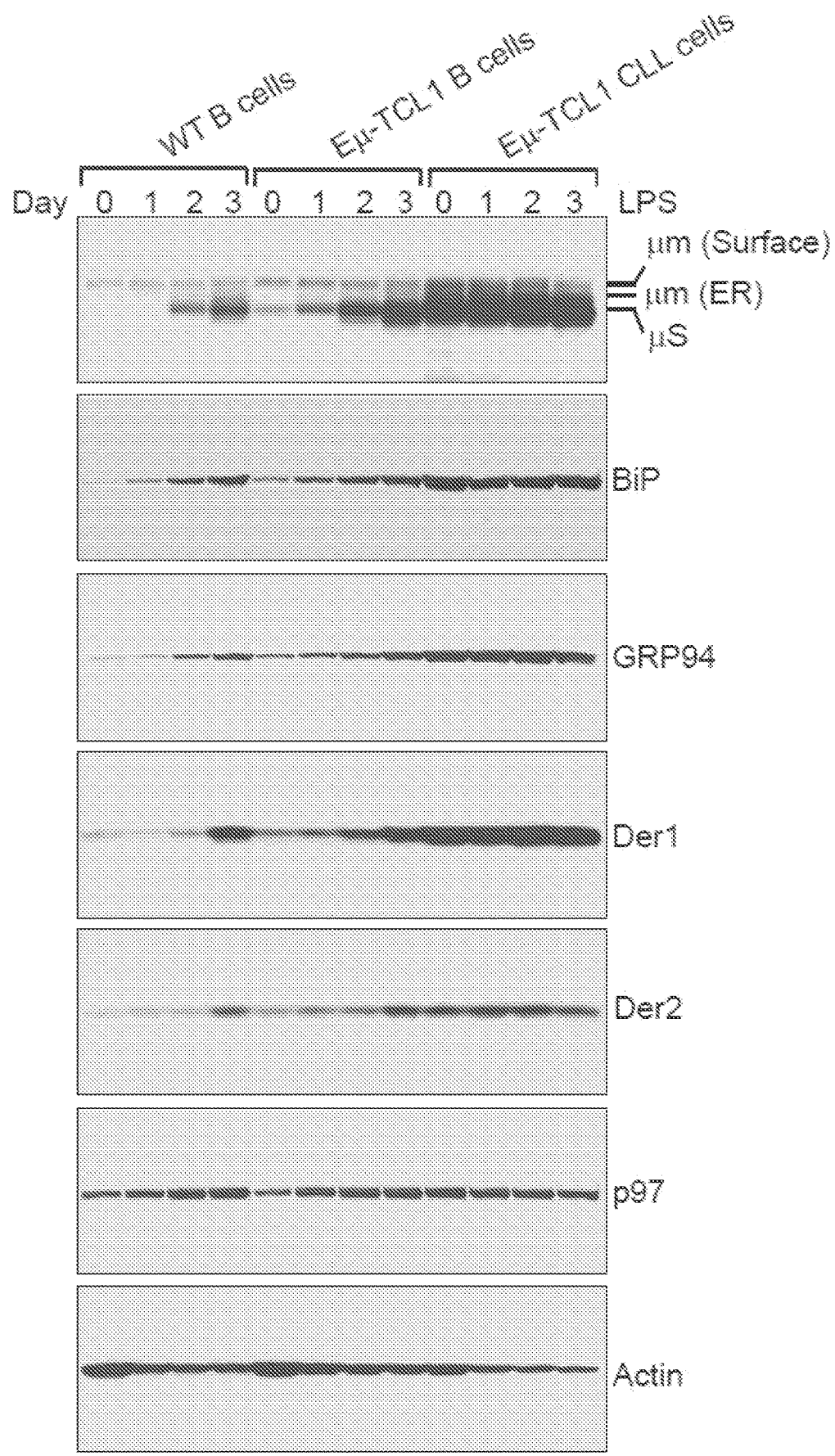
Figure 30C:
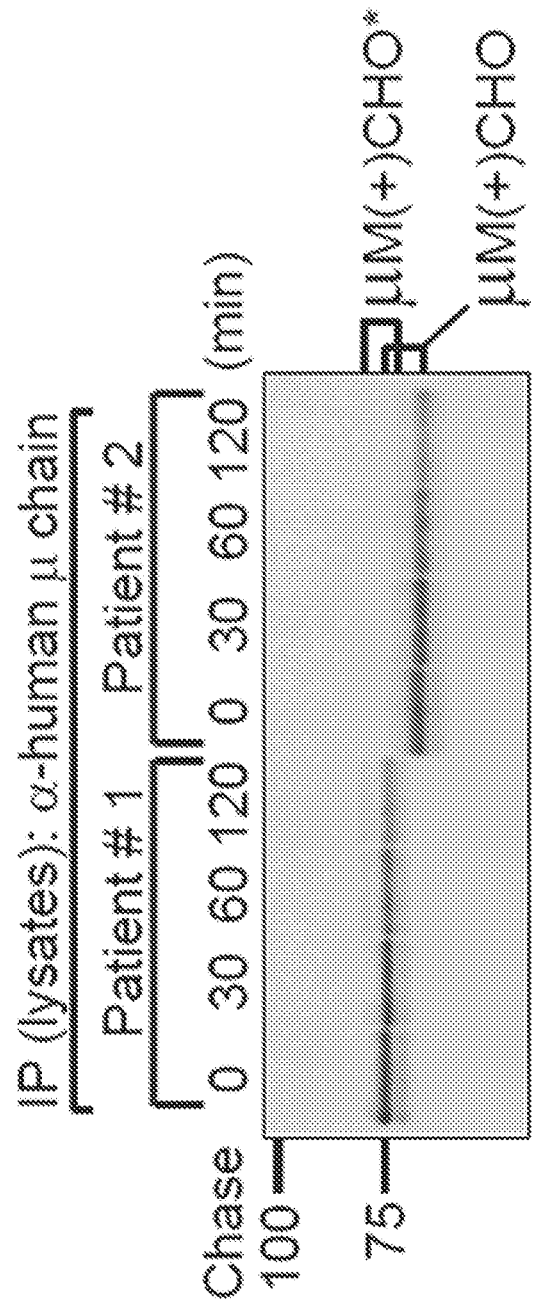
Figure 30D:
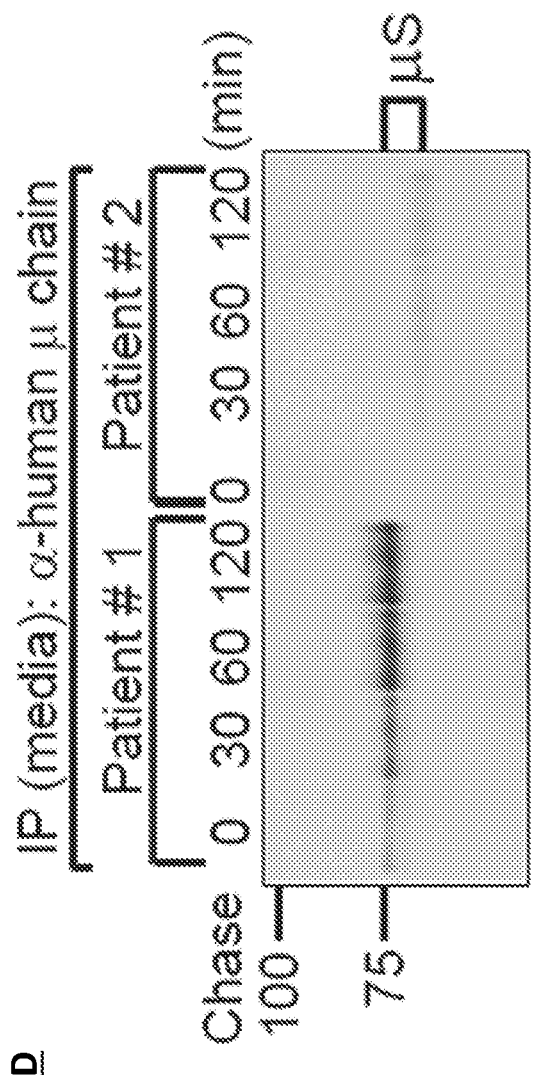

Since 6-month-old wild-type and MD4$^{+/-}$ mice did not accumulate CD11b+/Ly6G+ granulocytic cells in the peripheral blood (FIG. 29), it was hypothesized that such phenotypes found in Eµ-TCL1$^{+/+}$ and MD4$^{+/-}$/Eµ-TCL1$^{+/+}$ mice were associated with CLL progression driven by the 14-kDa TCL1 proto-oncoprotein. The introduction of the MD4 transgene in Eµ-TCL1$^{+/+}$ mice forced precancerous B cells in MD4$^{+/-}$/Eµ-TCL1$^{+/+}$ mice to produce not only HEL-reactive BCR on B cell surface (FIGS. 19A, 20A, 20B, 27B and 28B) but also sIgM against HEL in mouse sera (FIG. 30A). Although CLL cells developed in MD4$^{+/-}$/Eµ-TCL1$^{+/+}$ mice were no longer HEL-reactive (FIGS. 19A, 20C-20D), they still produced large quantities of sIgM (FIG. 20D). Together with the data showing that CLL cells from Eµ-TCL1$^{+/+}$ mice also produced large quantities of sIgM and increased levels of ER chaperones and ER-associated misfolded protein degradation machineries (FIG. 30B), in certain embodiments, sIgM can play a role in inducing CD11b+/Ly6G+ granulocytic cells to accumulate in Eµ-TCL1$^{+/+}$ and MD4$^{+/-}$/Eµ-TCL1$^{+/+}$ mice. To establish the relevance of sIgM in human CLL, pulse-chase experiments were performed using fresh CLL cells from human patients, and immunoprecipitated IgM from the cell lysates and culture media using an anti-human Igµ chain antibody. Human CLL cells from patients could secrete IgM (FIGS. 30C-30D).

Figure 22B:
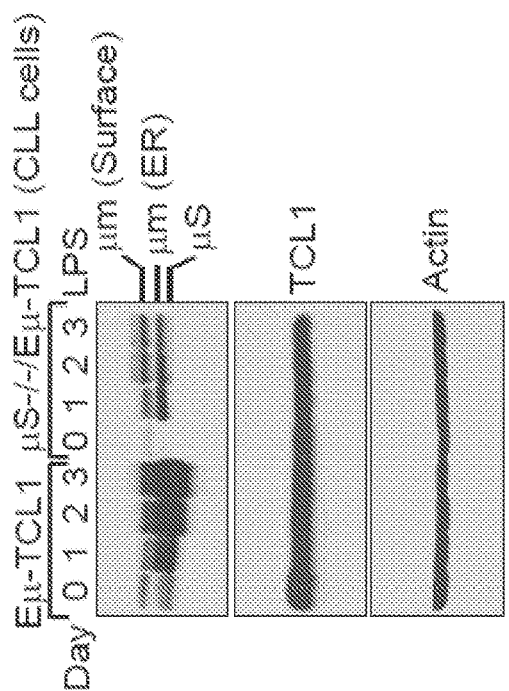
Figure 22A:
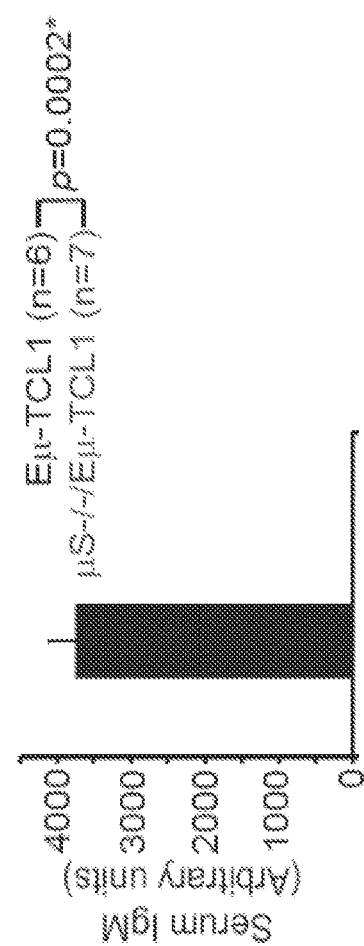
Figure 22C:
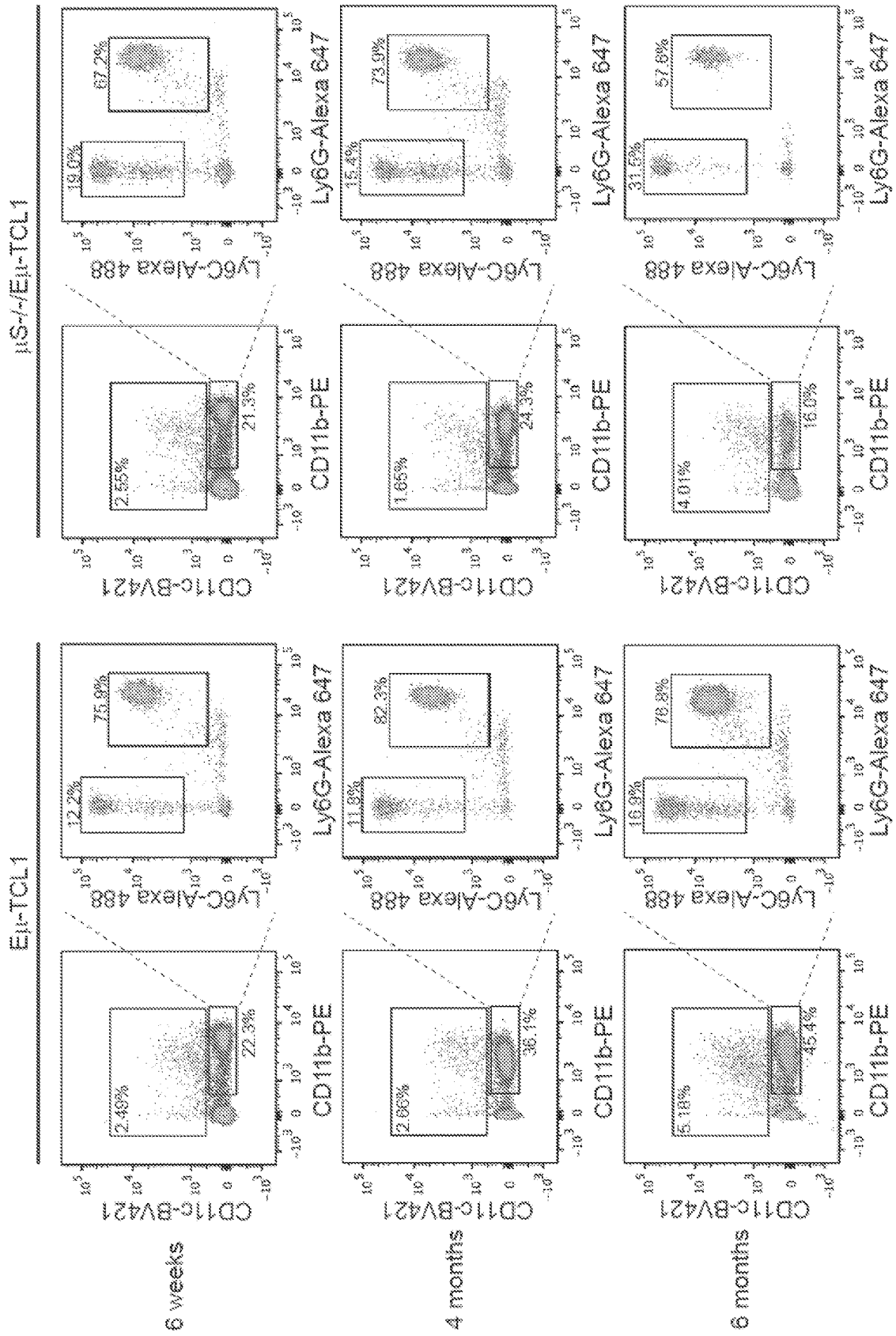
Figure 23B:
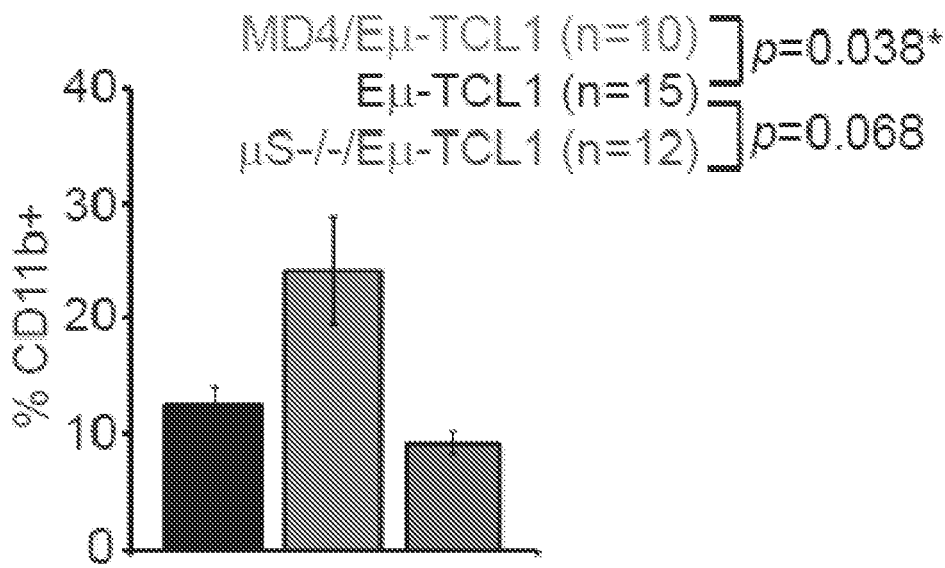
Figure 23C:
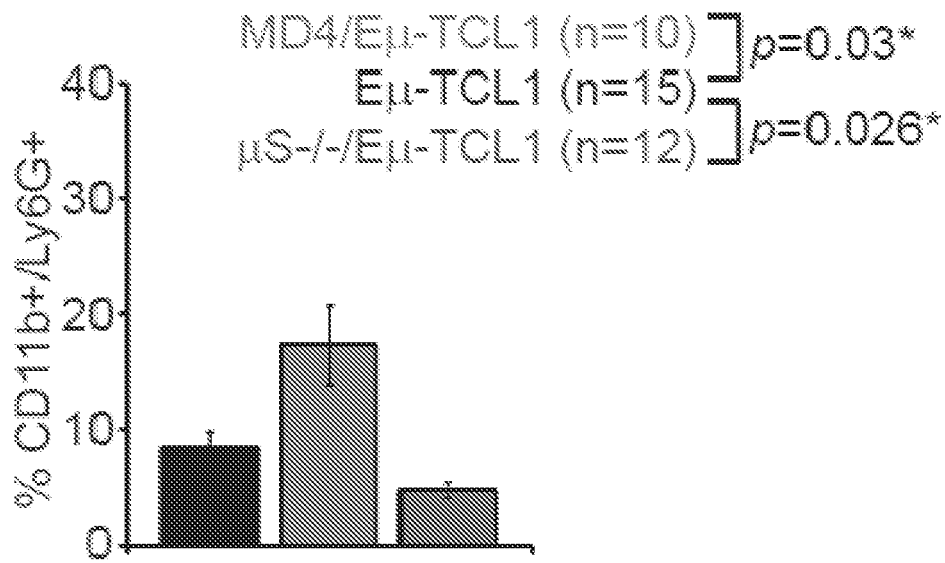
Figure 23D:
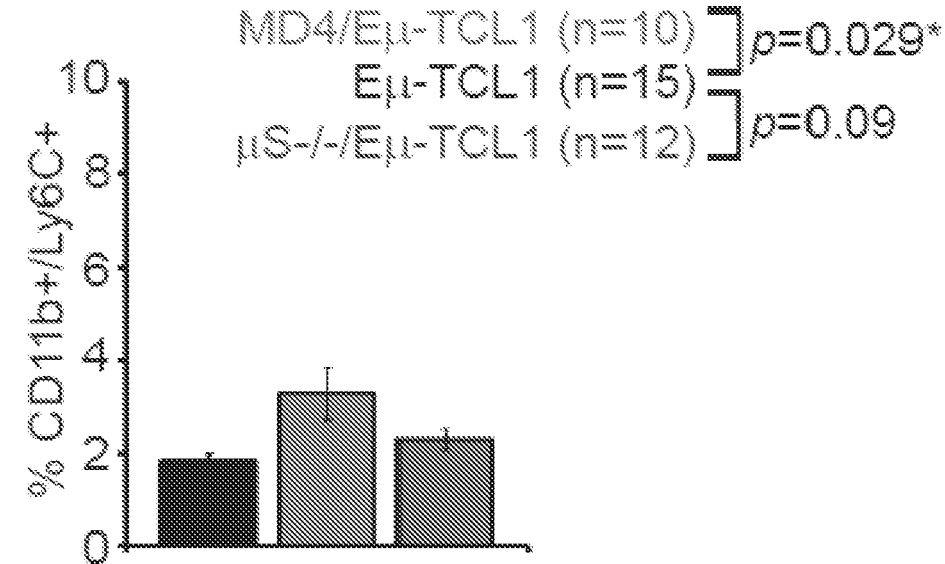
Figure 30E:
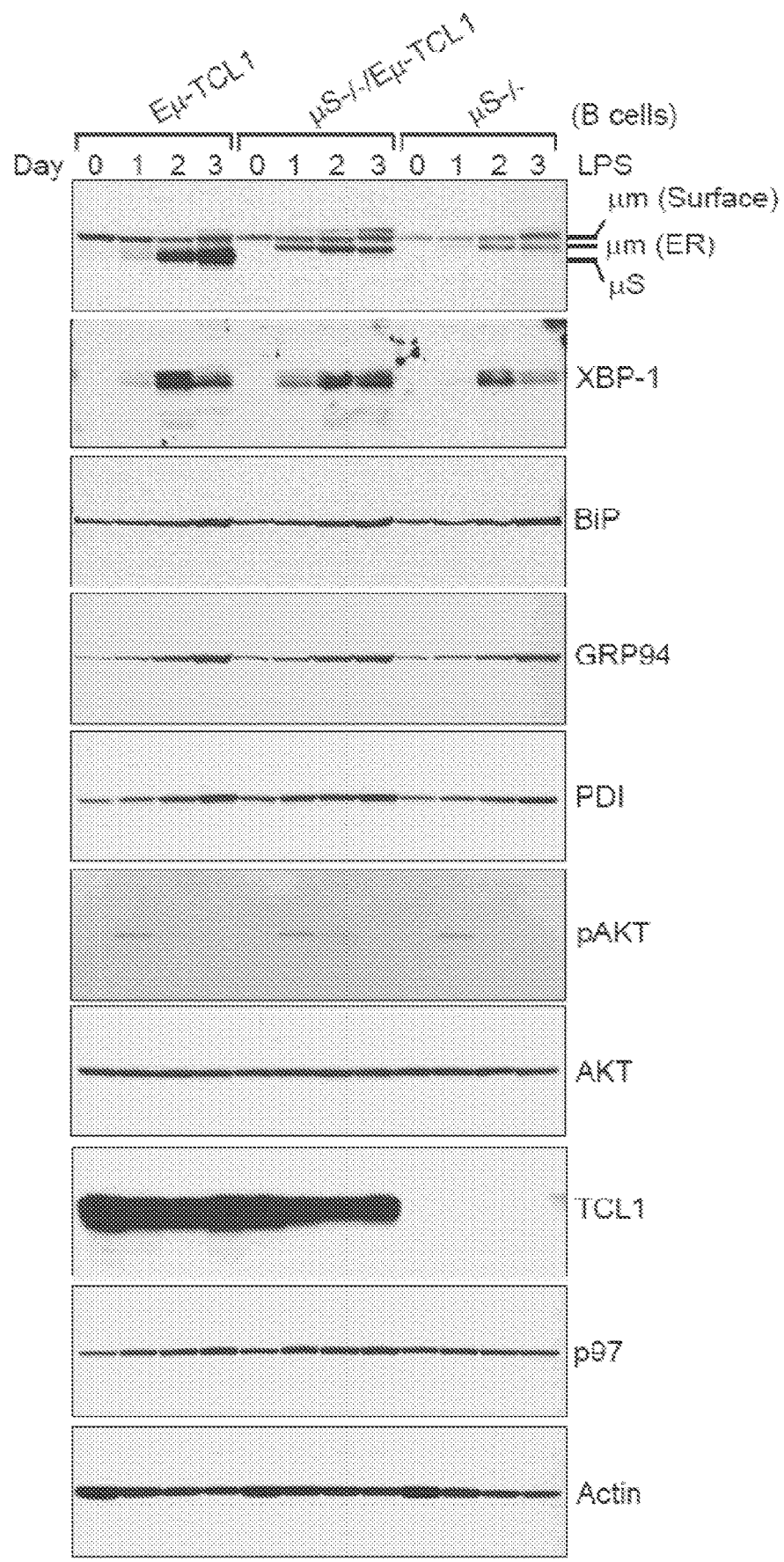

Example 16: Secretory IgM is Responsible for the Accumulation of CD11b+/Ly6G+ Granulocytic Cells in Eµ-TCL1$^{+/+}$ Mice To examine the role of sIgM in inducing the accumulation of CD11b+/Ly6G+ granulocytic cells in Eµ-TCL1$^{+/+}$ mice, Eµ-TCL1$^{+4}$ were crossed with µS$^{-/-}$ mice, in which the Igµ chain gene allele was genetically manipulated to allow for the expression of membrane-bound IgM but not sIgM. When B cells purified from 6-week-old µS$^{-/-}$, µS$^{-/-}$/Eµ-TCL1$^{+/+}$, and Eµ-TCL1$^{+/+}$ mice were stimulated with LPS, those from µS$^{-/-}$ and µS$^{-/-}$/Eµ-TCL1$^{+/+}$ did not produce sIgM (FIG. 30E). In addition, µS$^{-/-}$/Eµ-TCL1$^{+/+}$ B cells produced higher levels of membrane-bound IgM and ER chaperones than µS$^{-/-}$ B cells (FIG. 30E). Compared with Eµ-TCL1$^{+/+}$ mice, µS$^{-/-}$/Eµ-TCL1$^{+/+}$ mice did not produce sIgM in the sera (FIG. 22A). IgM+/CD5+ CLL cells purified from µS$^{-/-}$/Eµ-TCL1$^{+4}$ also did not respond to LPS by producing sIgM (FIG. 22B). When compared with age-matched 4-month-old and 6-month-old Eµ-TCL1$^{+/+}$ mice, these µS$^{-/-}$/Eµ-TCL1$^{+/+}$ mice indeed produced significantly decreased CD11b+ myeloid populations and CD11b+/Ly6G+ granulocytic cells but not CD11b+/Ly6C+ monocytic cells in the peripheral blood (FIGS. 22C-22F). The µS$^{-/-}$/Eµ-TCL1$^{+/+}$ mice survived longer than Eµ-TCL1$^{+/+}$ mice, while MD4$^{+/-}$/Eµ-TCL1$^{+/+}$ mice survived significantly shorter than Eµ-TCL1$^{+/+}$ mice (FIG. 22G). Such differences in survival were observed in both sexes (FIGS. 22H-22I).

Figure 31B:
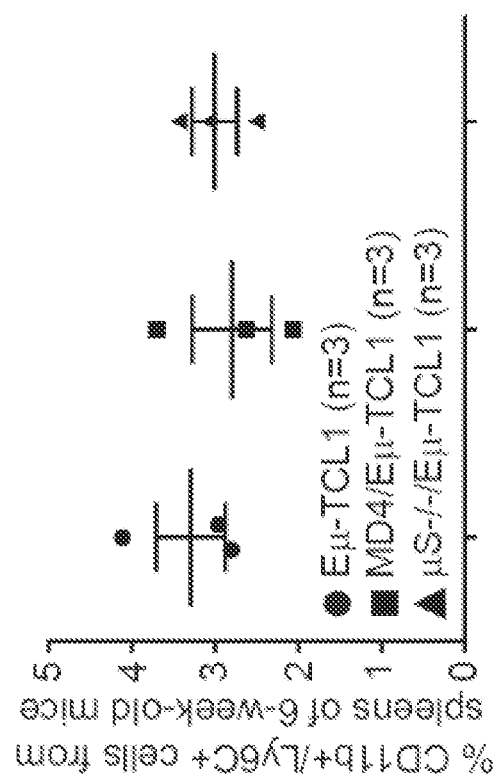
Figure 31A:
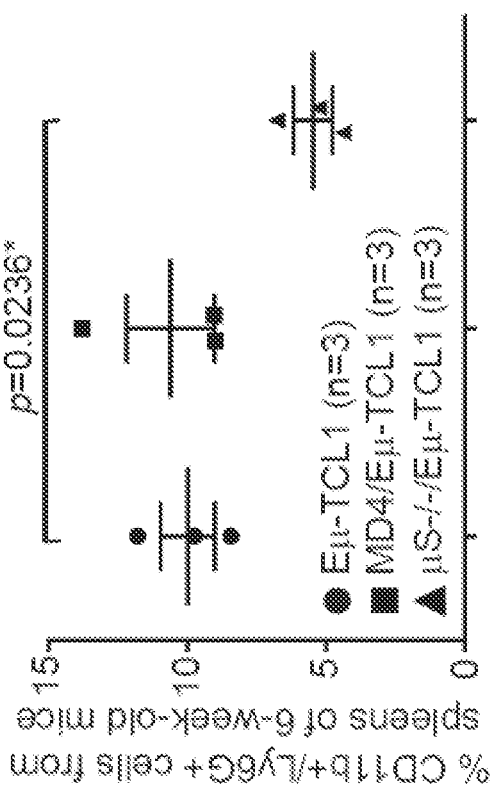
Figure 31C:
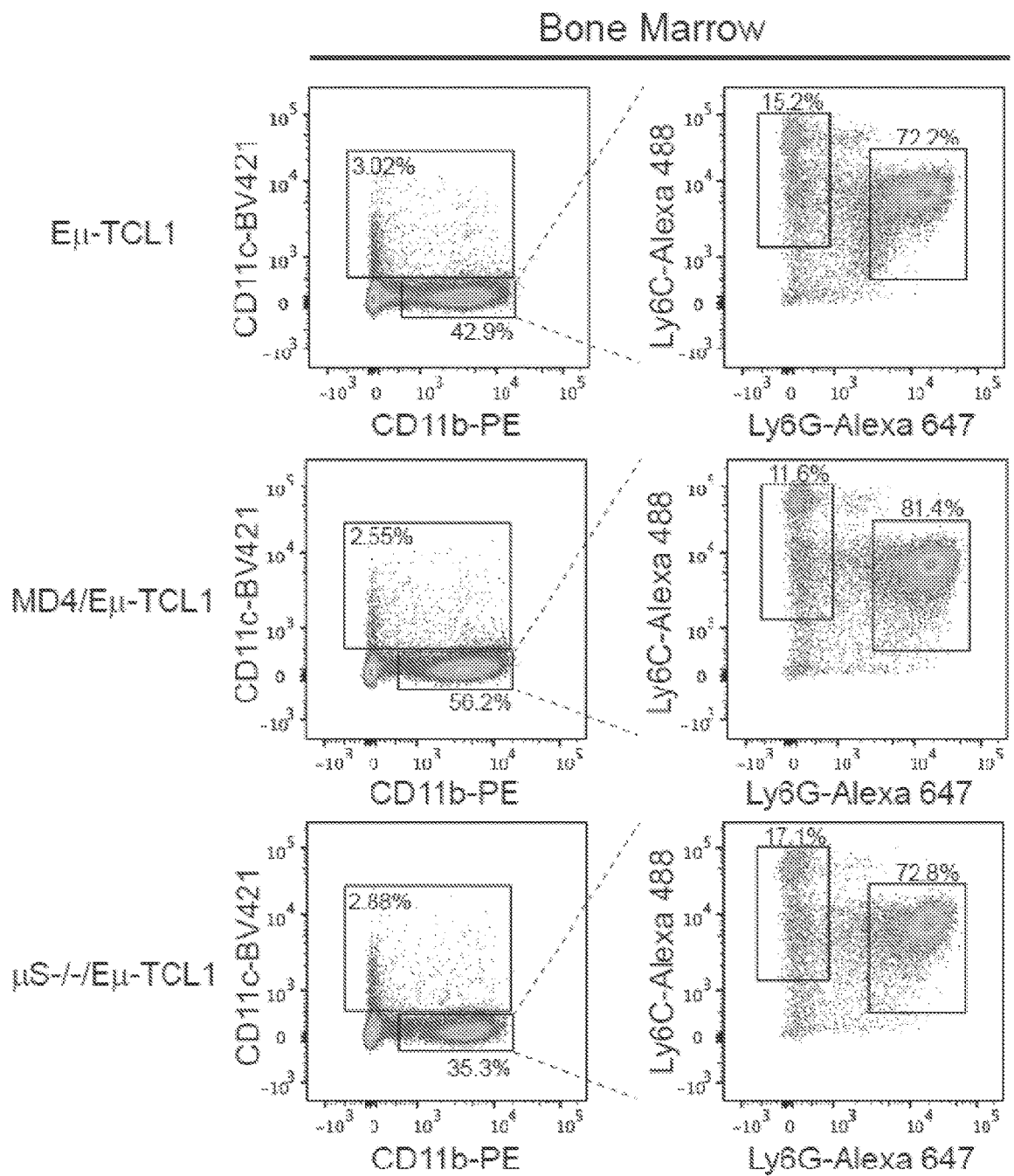
Figure 31D:
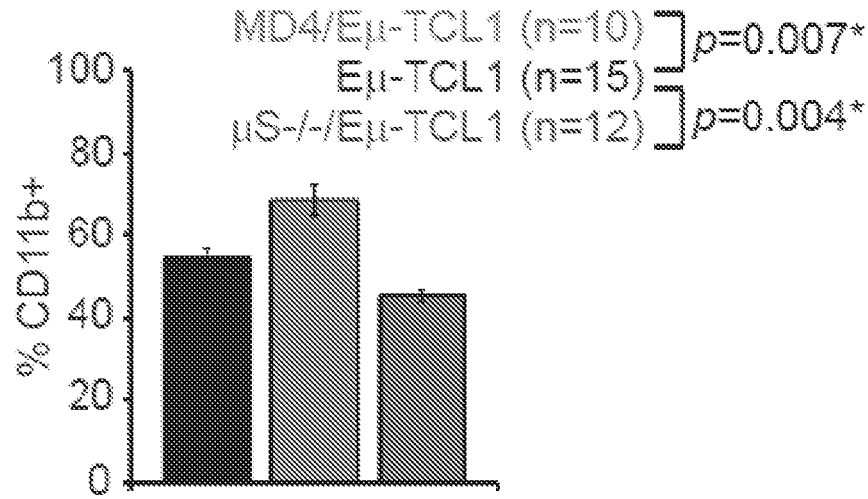
Figure 31E:
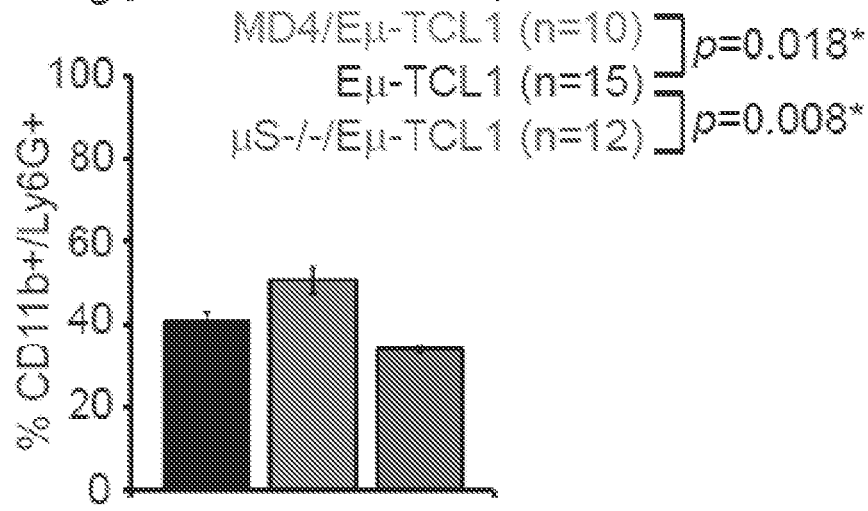
Figure 31F:
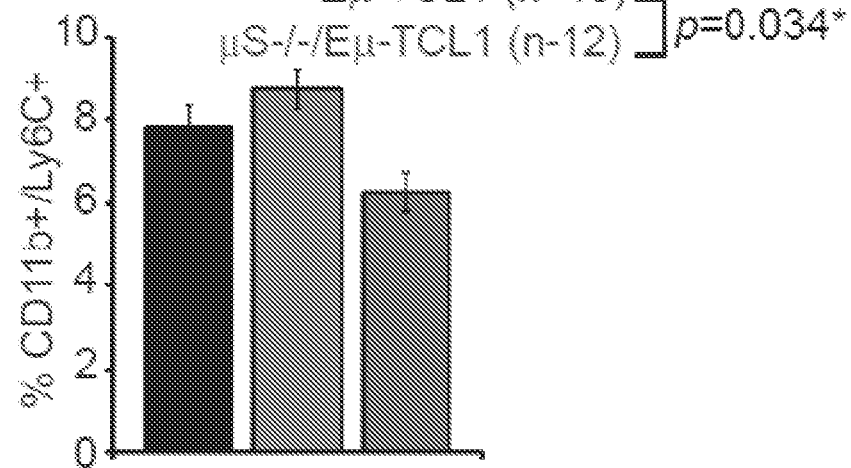
Figure 31G:
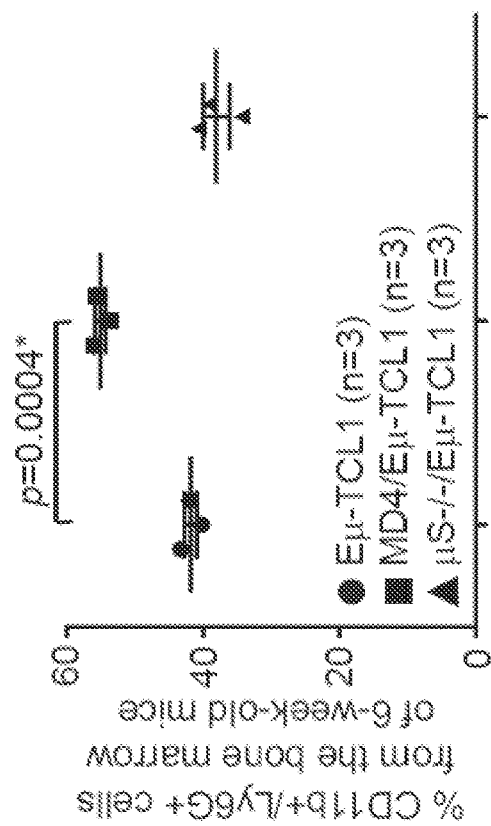
Figure 31H:
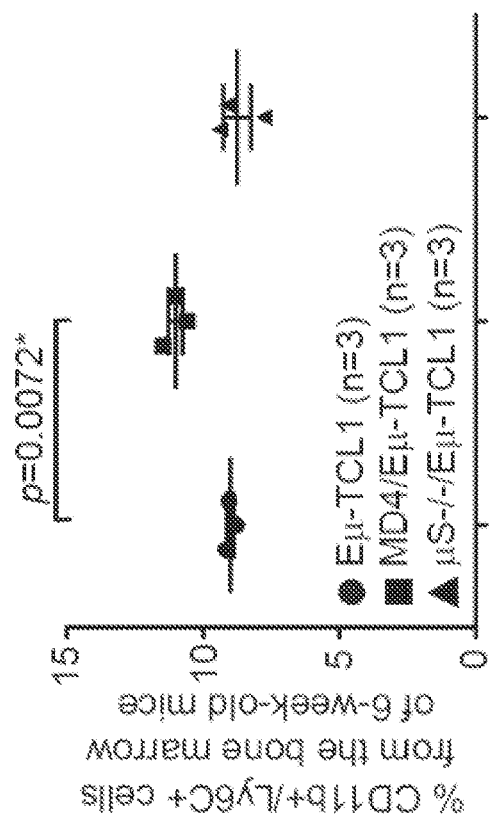

Example 17: CD11b+/Ly6G+ Granulocytic Cells Purified from Spleens of MD4$^{+/-}$/Eµ-TCL1$^{+/+}$ Mice can Suppress CD3/CD28-Stimulated and gp100-Stimulated T Cell Proliferation CLL cells proliferate and survive via interactions with other types of immune cells in the secondary lymphoid organs. In certain embodiments, accumulations of CD11b+/Ly6G+ granulocytic cells in the spleens of MD4$^{+/-}$/Eµ-TCL1$^{+/+}$ mice plays a role in suppressing the anti-tumor T cell function, leading to the decreased numbers of CD3+ T cells in the spleens of CLL-bearing MD4$^{+/-}$/Eµ-TCL1$^{+/+}$ mice (FIG. 19A). The spleens of 6-month-old wild-type, MD4$^{+/-}$ and μS$^{-/-}$ mice contained only low percentages of CD11b+/Ly6G+ granulocytic cells and CD11b+/Ly6C+ monocytic cells (FIG. 29). When the granulocytic cells and monocytic cells in the spleens of 6-month-old MD4$^{+/-}$/Eμ-TCL1$^{+/+}$ mice were examined, significantly higher percentages of these cells were found in MD4$^{+/-}$/Eμ-TCL1$^{+/+}$ mice than in age-matched MD4$^{+/-}$ (FIG. 29) and Eμ-TCL1$^{+/+}$ mice (FIGS. 23A-23D). Deleting the capability of B cells in producing sIgM in Eμ-TCL1$^{+/+}$ mice led to significantly decreased granulocytic cells but not monocytic cells in the spleens of 6-month-old μS$^{-/-}$/Eμ-TCL1$^{+/+}$ mice (FIGS. 23A-23D), and such a difference could also be observed in the spleens of 6-week-old μS$^{-/-}$/Eμ-TCL1$^{+/+}$ mice (FIGS. 31A-31B). In the bone marrow, significantly higher percentages of granulocytic cells were found in 6-month-old MD4$^{+/-}$/Eμ-TCL1$^{+/+}$ mice than those in age-matched Eμ-TCL1$^{+/+}$ mice, and significantly lower percentages of both granulocytic and monocytic cells in 6-month-old μS$^{-/-}$/Eμ-TCL1$^{+/+}$ mice than those in age-matched Eμ-TCL1$^{+/+}$ mice (FIGS. 31C-31F). Although there was no percentage difference of granulocytic and monocytic cells in the bone marrow between 6-week-old μS$^{-/-}$/Eμ-TCL1$^{+/+}$ mice and Eμ-TCL1$^{+/+}$ mice, both populations increased significantly in the bone marrow of 6-week-old MD4$^{+/-}$/Eμ-TCL1$^{+/+}$ mice (FIGS. 31G-31H).

It was next tested whether CD11b+/Ly6G+ granulocytic cells could suppress proliferation of T cells, thus functionally qualifying these cells as MDSCs. MDSCs that associate with tumor cells are capable of inhibiting T cell function. CLL cells proliferate in the spleens and circulate in the peripheral blood. CD11b+/Ly6G+ granulocytic cells were thus purified from spleens and peripheral blood of MD4$^{+/-}$/Eμ-TCL1$^{+/+}$ mice (FIG. 32A). CD11b+/Ly6G+ granulocytic cells purified from peripheral blood of MD4$^{+/-}$/Eμ-TCL1$^{+/+}$ mice did not suppress gp100-loaded class I MHC-mediated proliferation of CD8+ T cells from PMEL-1 mice (FIG. 32B). CD11b+/Ly6G+ granulocytic cells purified from spleens of MD4$^{+/-}$/Eμ-TCL1$^{+/+}$ mice could suppress CD3/CD28-stimulated proliferation of CFSE-stained CD8+ T lymphocytes (FIG. 23E). Both CD11b+/Ly6G+ granulocytic cells and CD11b+/Ly6C+ monocytic cells purified from spleens of MD4$^{+/-}$/Eμ-TCL1$^{+/+}$ mice could suppress gp100-loaded class I MHC-mediated proliferation of CD8+ T cells from PMEL-1 mice (FIGS. 30F-30G). In addition, when compared with CD11b+/Ly6G+ granulocytic cells purified from spleens of 8-month-old Eμ-TCL1$^{+/+}$ mice, those cells from spleens of age-matched μS$^{-/-}$/Eμ-TCL1$^{+/+}$ mice were less capable of suppressing proliferation of CD8+ T cells (FIG. 23H), suggesting that sIgM can mediate immunosuppressive functions of MDSCs.

Figure 24A:
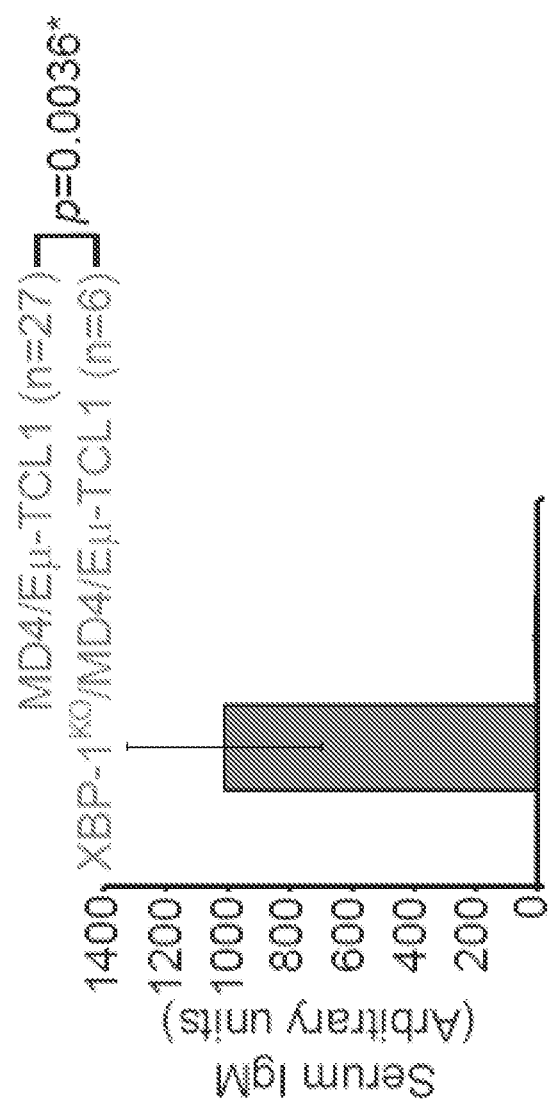
Figure 24E:
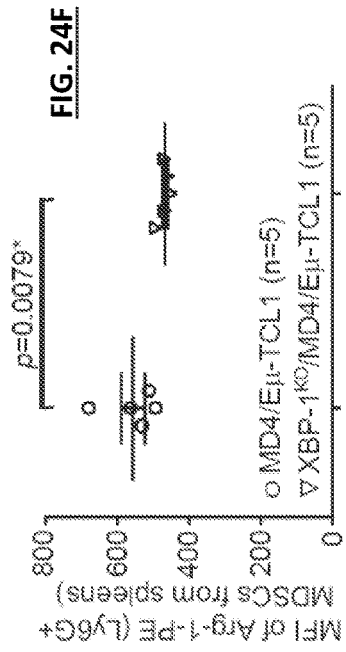
Figure 24G:
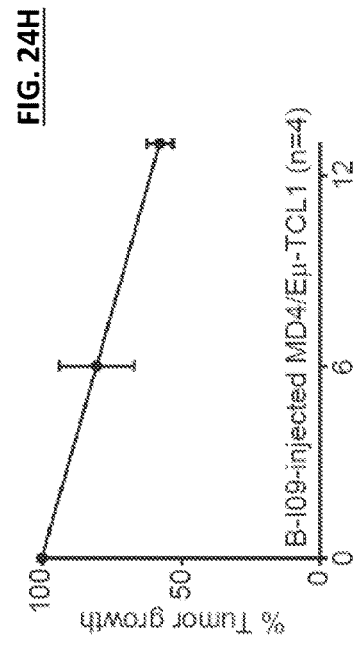
Figure 24F:
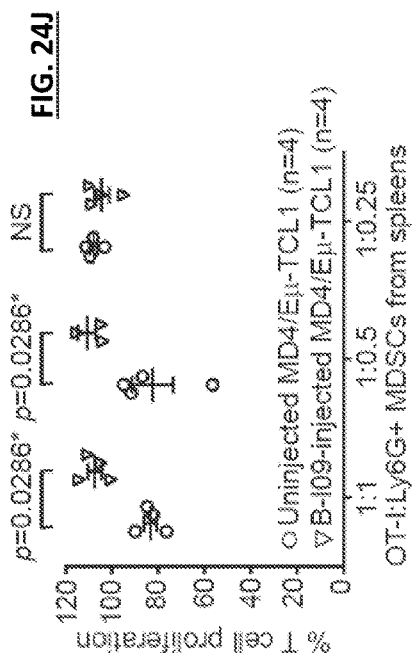

Example 18: Targeting XBP-1s Blocks the Levels of sIgM, Leading to Decreased Numbers and Suppressive Effects of CD11b+/Ly6G+ MDSCs in MD4$^{+/-}$/Eμ-TCL1$^{+/+}$ Mice XBP-1-deficient B cells and CLL cells produce significantly decreased sIgM, via activation of regulated IRE1-dependent decay (RIDD) to specifically cleave and degrade μS mRNA. To test whether deleting the XBP-1 gene from MD4$^{+/-}$/Eμ-TCL1$^{+/+}$ CLL cells could reduce the production of sIgM and lead to decreased numbers of MDSCs in MD4$^{+/-}$/Eμ-TCL1$^{+/+}$ mice, B cell-specific XBP-1$^{KO}$ mice were crossed with MD4$^{+/-}$/Eμ-TCL1$^{+/+}$ mice. Compared with MD4$^{+/-}$/Eμ-TCL1$^{+/+}$ mice, XBP-1$^{KO}$/MD4$^{+/-}$/Eμ-TCL1$^{+/+}$ mice produced significantly decreased levels of sIgM in the sera (FIG. 24A). As a result, significantly decreased percentages of CD11b+ myeloid cell populations and CD11b+/Ly6G+ granulocytic MDSCs were detected in the peripheral blood of XBP-1$^{KO}$/MD4$^{+/-}$/Eμ-TCL1$^{+/+}$ mice (FIGS. 24B-24D). When compared with granulocytic MDSCs in MD4$^{+/-}$/Eμ-TCL1$^{+/+}$ mice bearing similar burden of CLL, such MDSCs in XBP-1$^{KO}$/MD4$^{+/-}$/Eμ-TCL1$^{+/+}$ mice expressed significantly decreased levels of arginase-1 (Arg-1) and showed reduced activity in suppressing T cell proliferation (FIGS. 24E-24G).

Figure 24I:
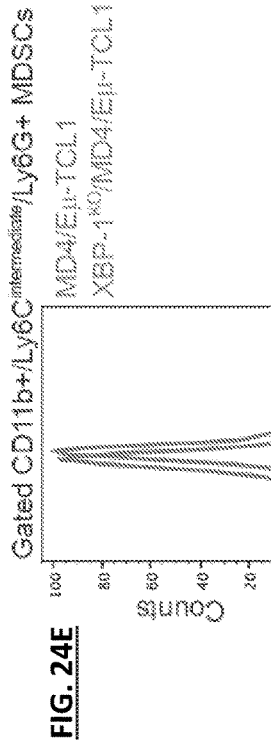
Figure 24H:
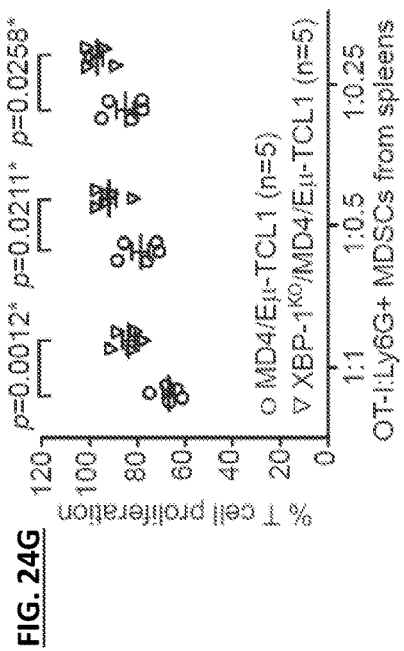
Figure 24J:
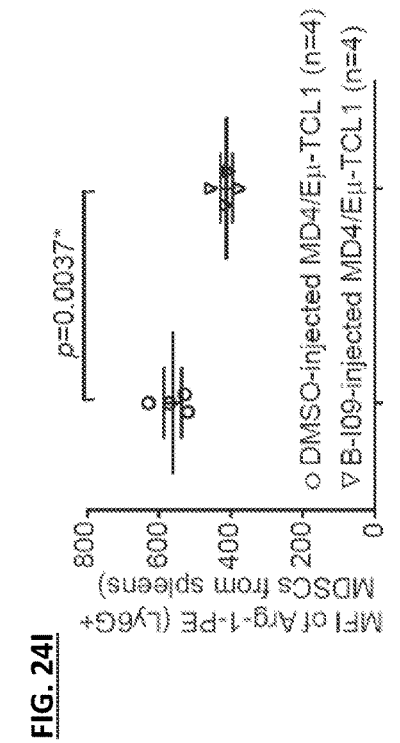

A small-molecule inhibitor, B-I09, can inhibit the expression of XBP-1s in CLL cells and retard the growth of CLL in Eμ-TCL1$^{+/+}$ mice. Similar to XBP-1-deficient B cells, B-I09-treated B cells are inefficient in producing sIgM. In certain embodiments, treatment with B-I09 can alter the function of MDSCs. MD4$^{+/-}$/Eμ-TCL1$^{+/+}$ mice were intraperitoneally injected with B-I09, and leukemic regression was observed (FIGS. 24H, 32C). When compared with CD11b+/Ly6G+ granulocytic MDSCs in DMSO-injected MD4$^{+/-}$/Eμ-TCL1$^{+/+}$ mice, such MDSCs in B-I09-injected MD4$^{+/-}$/Eμ-TCL1$^{+/+}$ mice expressed decreased levels of Arg-1 (FIG. 24I). While purified CD11b+/Ly6G+ granulocytic MDSCs from un-injected MD4$^{+/-}$/Eμ-TCL1$^{+/+}$ mice could suppress proliferation of T cells, those purified from B-I09-injected MD4$^{+/-}$/Eμ-TCL1$^{+/+}$ mice lost their immunosuppressive function (FIG. 24J).

Figure 25B:
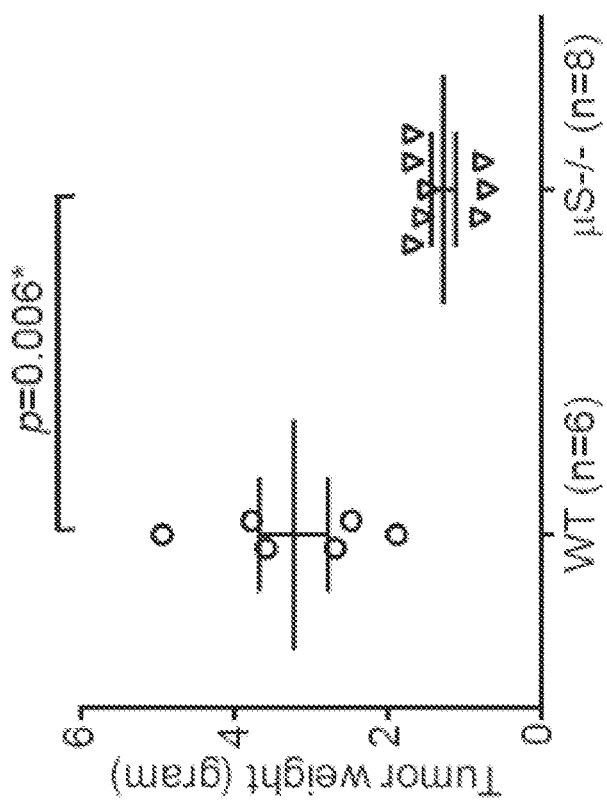
Figure 25A:
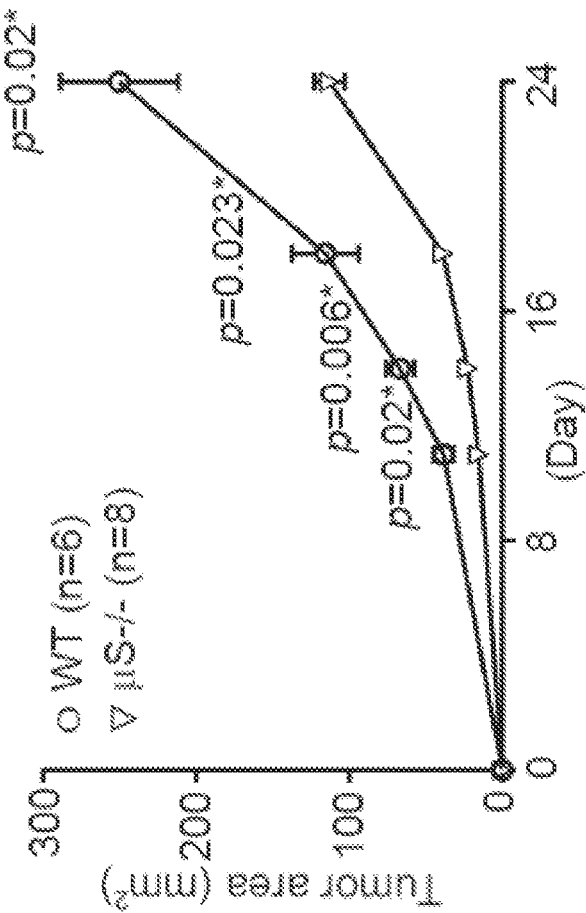
Figure 25C:
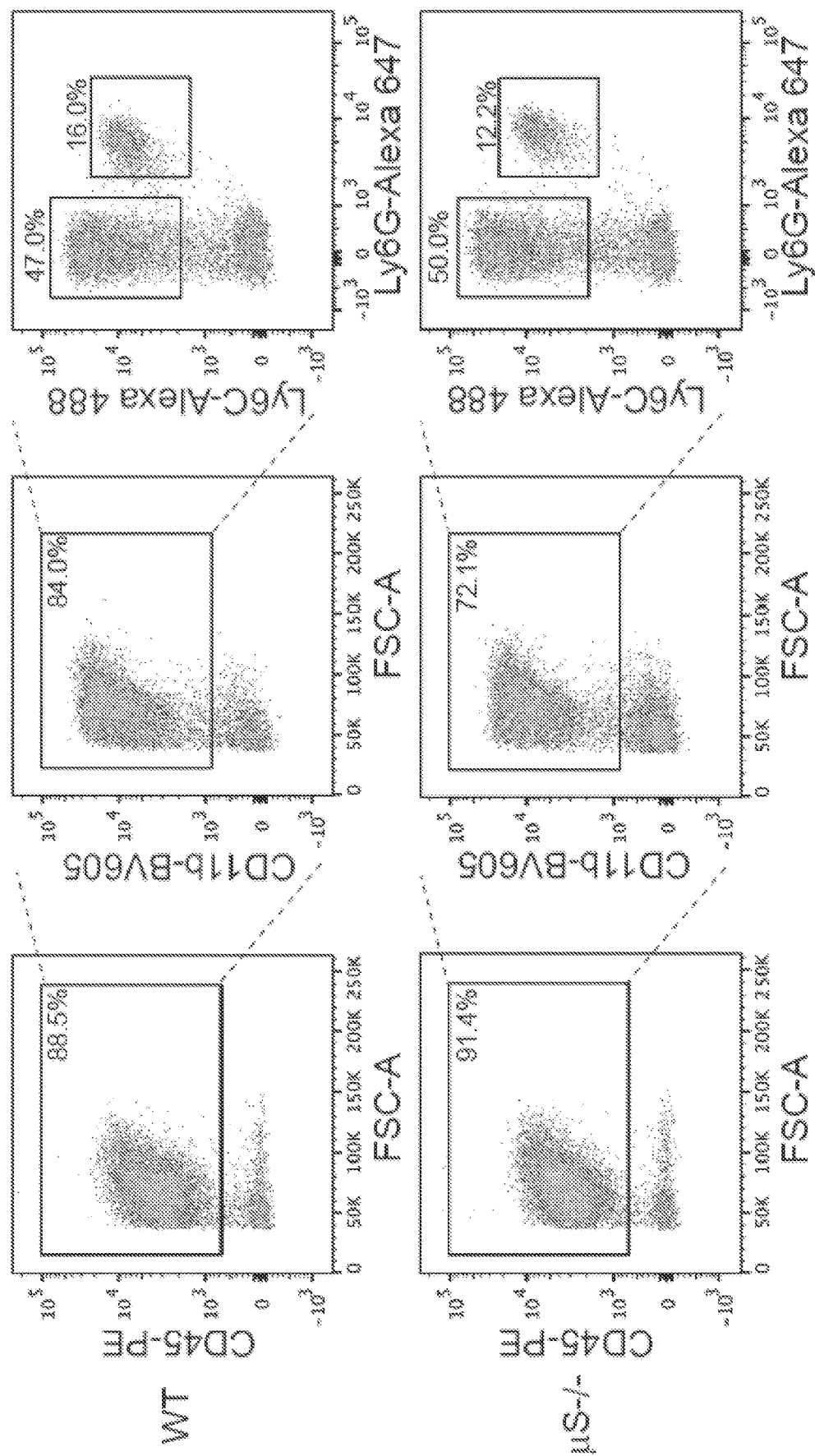
Figure 25I:
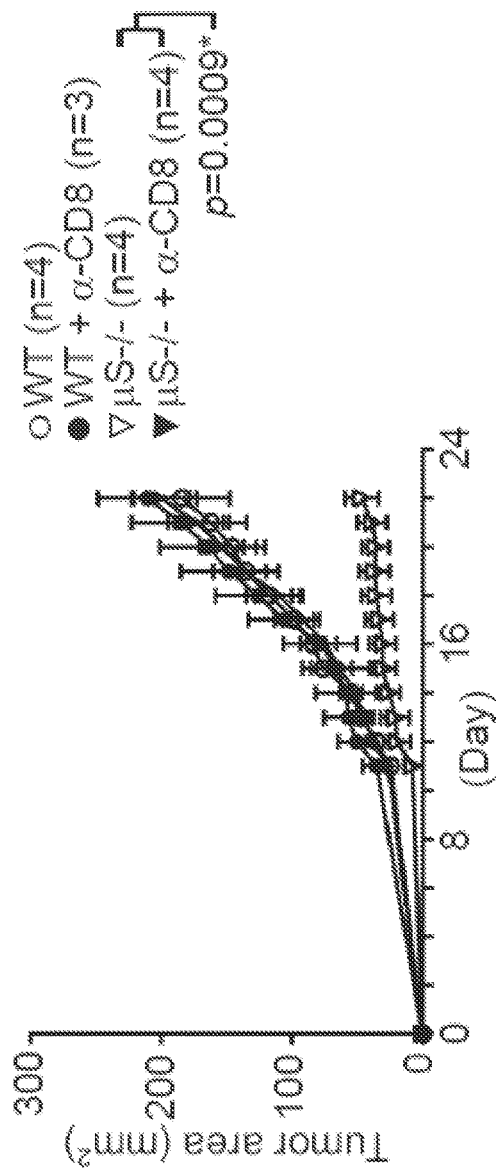
Figure 25J:
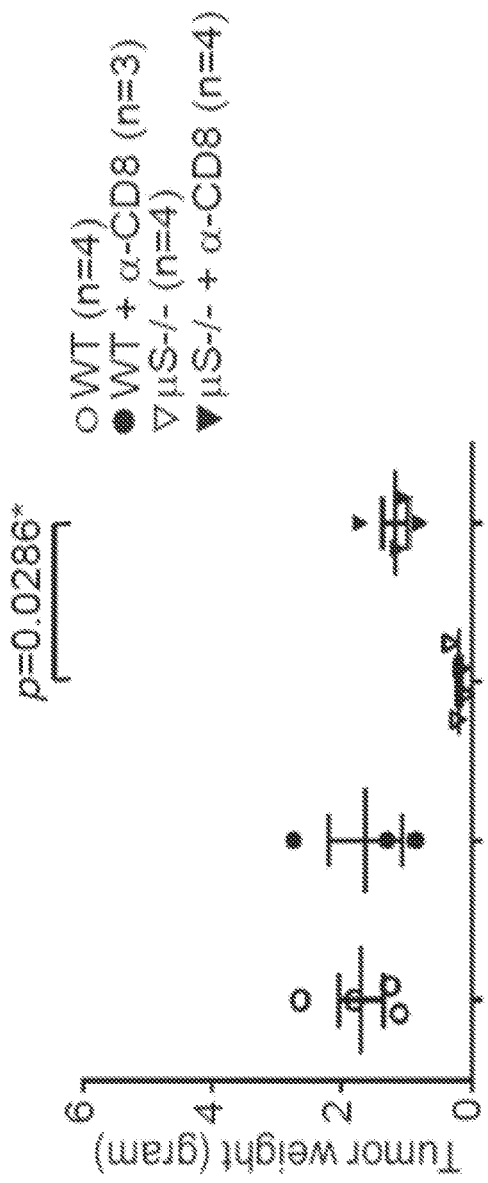

Example 19: Secretory IgM is Critical for the Function of MDSCs in Suppressing T Cell Proliferation To investigate whether sIgM is generally important in tumor microenvironments to induce accumulations of MDSCs, eight-week-old wild-type and μS$^{-/-}$ mice were grafted with mouse Lewis lung carcinoma (LLC), LL/2 cells, and significantly reduced tumor growth in μS$^{-/-}$ mice was found (FIGS. 25A-25B). There was no detectable level of sIgM in the sera of μS$^{-/-}$ mice grafted with LLC (FIG. 33A). Tumors were lysed, cells were stained with DAPI, CD45-PE, CD11b-BV605, Ly6C-Alexa 488 and Ly6G-Alexa 647. Live DAPI–/CD45+ immune cells were gated for CD11b+ myeloid cell populations, which were analyzed for their expression of Ly6C and Ly6G (FIG. 25C). Although there was a significant decrease of tumor-infiltrating CD11b+ myeloid cells in LLC-grafted μS$^{-/-}$ mice, there was no significant difference in the percentages of tumor-infiltrating CD11b+/Ly6G+ granulocytic or CD11b+/Ly6C+ monocytic MDSCs between LLC-grafted wild-type and μS$^{-/-}$ mice (FIGS. 25D-25F). However, while both monocytic and granulocytic MDSCs residing in LLC tumors of wild-type mice potently suppressed gp100-stimulated T cell proliferation, MDSCs residing in tumors of μS$^{-/-}$ mice lost their immunosuppressive functions (FIGS. 25G-25H), confirming the role of sIgM in mediating the functions of MDSCs. No difference in the percentages of infiltrating B cells between tumors in wild-type and μS$^{-/-}$ mice was detected (FIG. 33B), suggesting that the physical presence of B cells was not important in regulating the functions of MDSCs. In addition, CD11b+/Ly6G+ granulocytic MDSCs purified from the spleens or bone marrow of LLC-grafted wild-type and μS$^{-/-}$ mice had either small or no effect in suppressing gp100-stimulated T cell proliferation (FIGS. 33C-33D). To ascertain that the decreased LLC tumor growth in μS$^{-/-}$ mice was resulted from decreased capabilities of MDSCs in suppressing anti-tumor CD8 T cells in mice, LLC-grafted wild-type and μS$^{-/-}$ mice were intraperitoneally injected with an anti-CD8 antibody twice weekly to deplete CD8 T cells. When anti-tumor CD8 T cells were depleted, tumor growth in LLC-grafted μS$^{-/-}$ mice could no longer be suppressed (FIGS. 25I-25J).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

ENUMERATED EMBODIMENTS

The following enumerated embodiments are provided, the numbering of which is not to be construed as designating levels of importance.

Embodiment 1 provides a compound of formula (I), or a salt or solvate thereof:

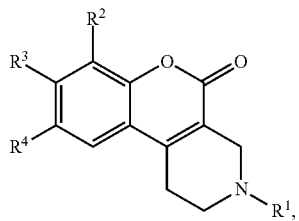

(I)

wherein in (I): $R^1$ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, ($C_3$-$C_8$ cycloalkyl)-C(=O)—, ($C_1$-$C_6$ alkyl)-OC(=O)—, ($C_2$-$C_6$ alkenyl)-OC(=O)—, ($C_2$-$C_6$ alkynyl)-OC(=O)—, and ($C_3$-$C_8$ cycloalkyl)-OC(=O)—, wherein the alkyl, alkenyl, alkynyl, or cycloalkyl are independently optionally substituted; $R^2$ is selected from the group consisting of optionally substituted 1,3-dioxolan-2-yl, optionally substituted 1,3-dioxan-2-yl, —CH=N—OR$^5$, and —CH=N—NR$^5$R$^6$, wherein: $R^5$ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, and ($C_3$-$C_8$ cycloalkyl)-C(=O)—, wherein the alkyl, alkenyl, alkynyl, or cycloalkyl are independently optionally substituted, and $R^6$ is selected from the group consisting of H and $C_1$-$C_6$ alkyl, wherein the alkyl is optionally substituted, or $R^5$ and $R^6$ combine with the N atom to which they are bound to form an optionally substituted heterocyclyl or heteroaryl; $R^3$ is a group that can be deprotected in vitro or in vivo to —OH; and $R^4$ is selected from the group consisting of H, —OH, $C_1$-$C_6$ alkoxy, $C_2$-$C_6$ alkenyloxy, $C_2$-$C_6$ alkynyloxy, $C_3$-$C_8$ cycloalkoxy, HC(=O)O—, ($C_1$-$C_6$ alkyl)-C(=O)O—, ($C_2$-$C_6$ alkenyl)-C(=O)O—, ($C_2$-$C_6$ alkynyl)-C(=O)O—, and ($C_3$-$C_8$ cycloalkyl)-C(=O)O—, wherein the alkyl, alkenyl, alkynyl, or cycloalkyl are independently optionally substituted.

Embodiment 2 provides a compound of formula (I), or a salt or solvate thereof:

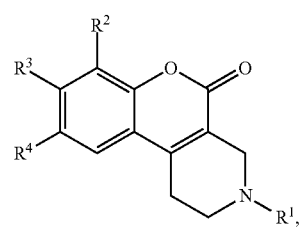

(I)

wherein in (I): $R^1$ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, ($C_3$-$C_8$ cycloalkyl)-C(=O)—, ($C_1$-$C_6$ alkyl)-OC(=O)—, ($C_2$-$C_6$ alkenyl)-OC(=O)—, ($C_2$-$C_6$ alkynyl)-OC(=O)—, and ($C_3$-$C_8$ cycloalkyl)-OC(=O)—, wherein the alkyl, alkenyl, alkynyl, or cycloalkyl are independently optionally substituted; $R^2$ is selected from the group consisting of optionally substituted 1,3-dioxolan-2-yl, optionally substituted 1,3-dioxan-2-yl, —CH=N—OR$^5$, and —CH=N—NR$^5$R$^6$, wherein: $R^5$ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, and ($C_3$-$C_8$ cycloalkyl)-C(=O)—, wherein the alkyl, alkenyl, alkynyl, or cycloalkyl are independently optionally substituted, and $R^6$ is selected from the group consisting of H and $C_1$-$C_6$ alkyl, wherein the alkyl is optionally substituted, or $R^5$ and $R^6$ combine with the N atom to which they are bound to form an optionally substituted heterocyclyl or heteroaryl; $R^3$ is —OH or a group that can be deprotected in vitro or in vivo to —OH; and $R^4$ is selected from the group consisting of $C_1$-$C_6$ alkoxy, $C_2$-$C_6$ alkenyloxy, $C_2$-$C_6$ alkynyloxy, $C_3$-$C_8$ cycloalkoxy, HC(=O)O—, ($C_1$-$C_6$ alkyl)-C(=O)O—, ($C_2$-$C_6$ alkenyl)-C(=O)O—, ($C_2$-$C_6$ alkynyl)-C(=O)O—, and ($C_3$-$C_8$ cycloalkyl)-C(=O)O—, wherein the alkyl, alkenyl, alkynyl, or cycloalkyl are independently optionally substituted.

Embodiment 3 provides the compound of any of Embodiments 1-2, wherein each heterocyclyl is independently selected from the group consisting of imidazolyl, dihydroimidazolyl, piperidinyl, piperazinyl, morpholinyl, pyrrolidinyl, and tetrahydropyrimidinyl.

Embodiment 4 provides the compound of any of Embodiments 1-3, wherein each heteroaryl is independently selected from the group consisting of pyridinyl, pyrimidinyl, pyrrolyl, oxazolyl, isoxazolyl, oxadiazolyl, imidazolyl, pyrazolyl, and triazolyl.

Embodiment 5 provides the compound of any of Embodiments 1-4, wherein each occurrence of alkyl, alkenyl, alkynyl, or cycloalkyl is independently optionally substituted with at least one substituent selected from the group consisting of $C_1$-$C_6$ alkyl, halo, —CN, —OR, phenyl, and —N(R)(R), wherein each occurrence of R is independently H, $C_1$-$C_6$ alkyl, or $C_3$-$C_8$ cycloalkyl.

Embodiment 6 provides the compound of any of Embodiments 1-5, wherein each occurrence of phenyl, heterocyclyl, or heteroaryl is independently optionally substituted with at least one substituent selected from the group consisting of $C_1$-$C_6$ alkyl, $C_1$-$C_6$ haloalkyl, $C_1$-$C_6$ alkoxy, $C_1$-$C_6$ haloalkoxy, halo, —CN, —C(=O)OR, —OR, —N(R)(R), —NO$_2$, —S(=O)$_2$N(R)(R), acyl, and $C_1$-$C_6$ alkoxycarbonyl, wherein each occurrence of R is independently H, $C_1$-$C_6$ alkyl, or $C_3$-$C_8$ cycloalkyl.

Embodiment 7 provides the compound of any of Embodiments 1-6, wherein R² is selected from the group consisting of:

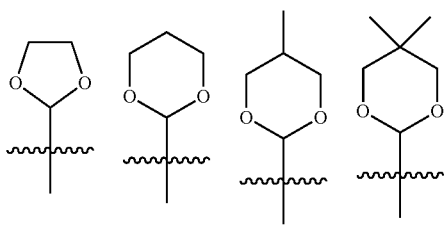

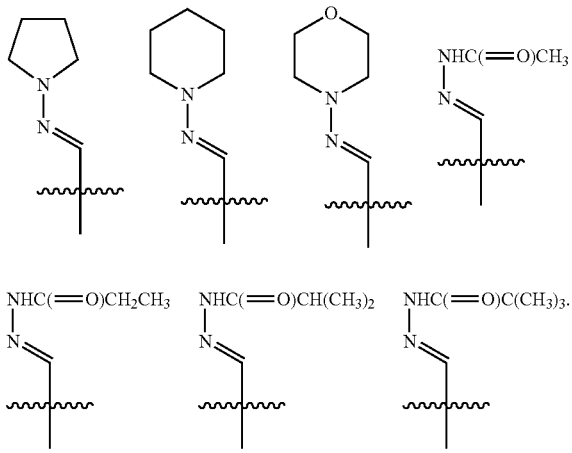

Embodiment 8 provides the compound of any of Embodiments 2-7, wherein R³ is a group that can be deprotected in vitro or in vivo to —OH.

Embodiment 9 provides the compound of any of Embodiments 2-8, wherein R³ is selected from the group consisting of optionally substituted o-nitrobenzyloxy groups, optionally substituted benzoin groups, (OH)₂B— and any ether derivatives thereof, optionally substituted boronobenzyl groups and any ether derivatives thereof, optionally substituted aryl-S(=O)₂O— or heteroaryl-S(=O)₂O— groups, and optionally substituted acyloxy or aroyloxy groups.

Embodiment 10 provides the compound of any of Embodiments 1-9, which is selected from the group consisting of:

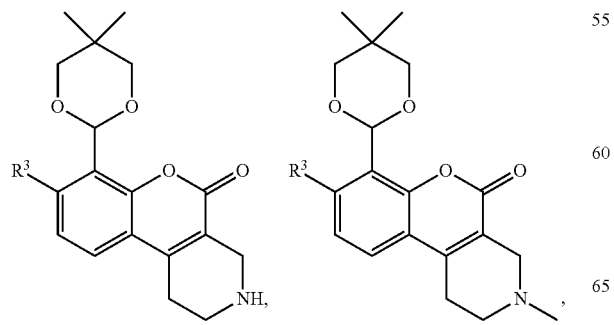

-continued

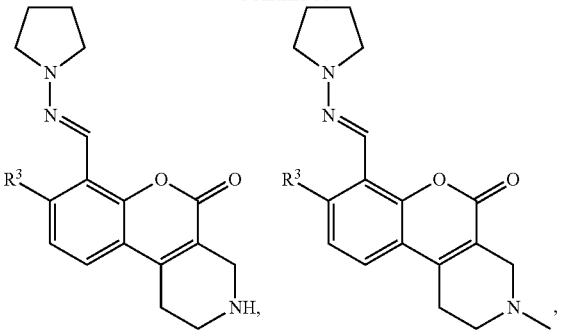

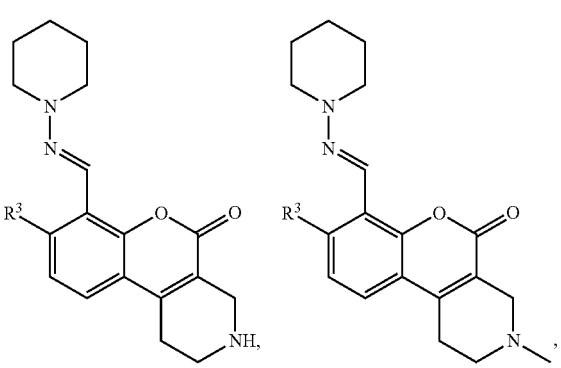

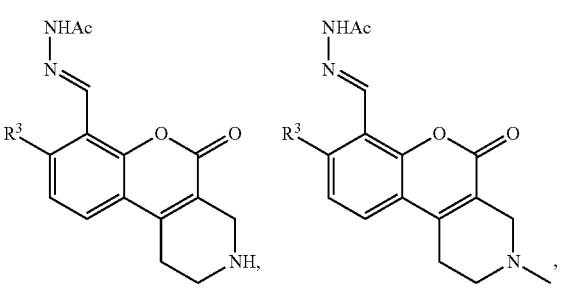

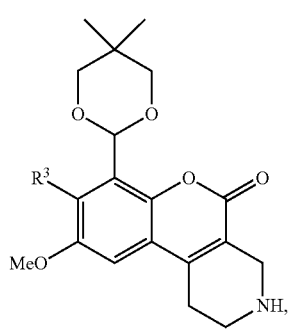

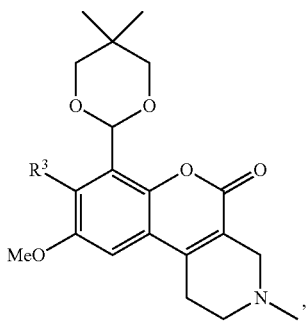

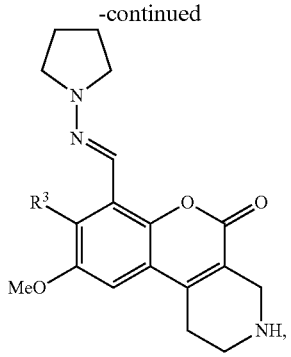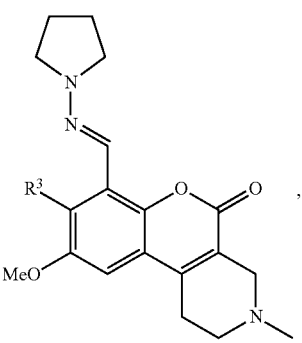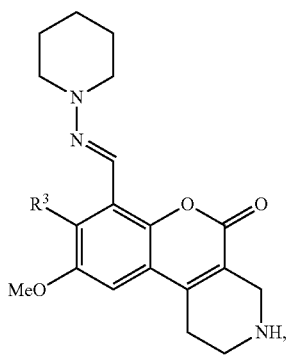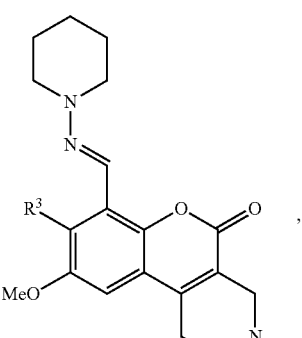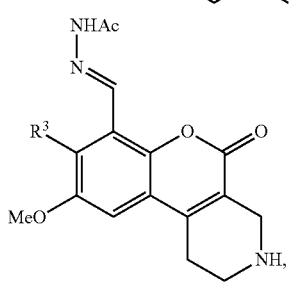
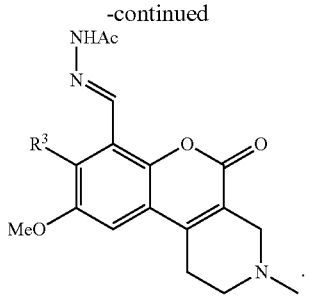
Embodiment 11 provides the compound of any of Embodiments 1-10, which is selected from the group consisting of:
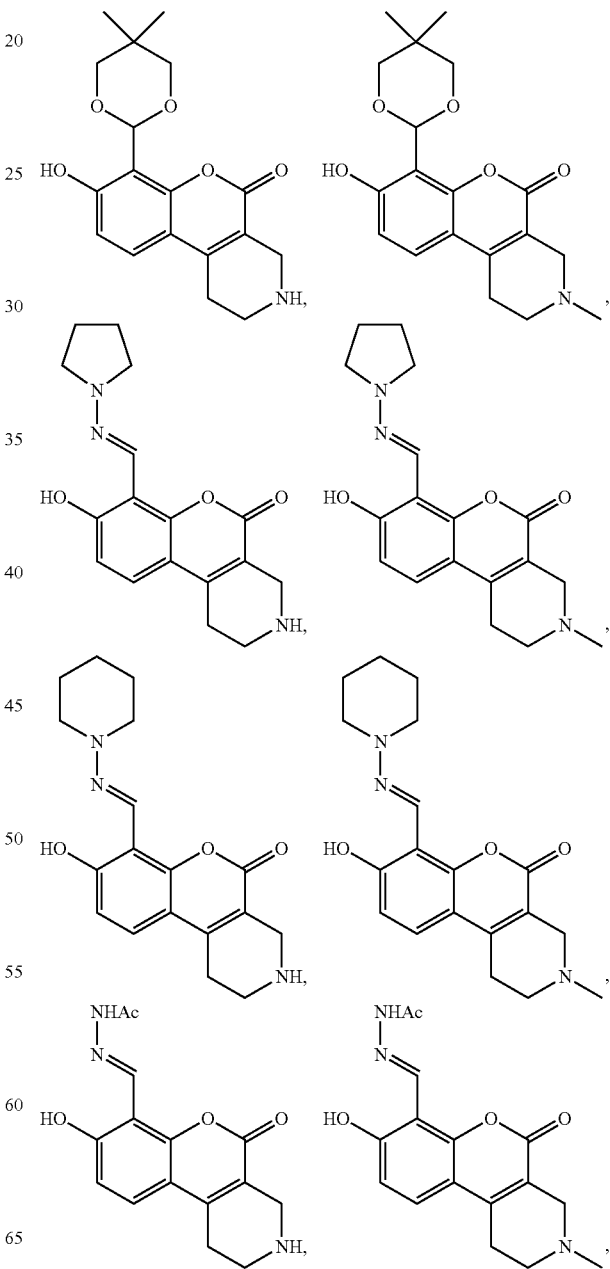

-continued

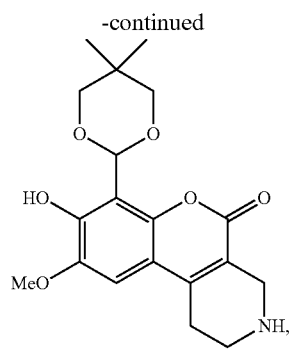

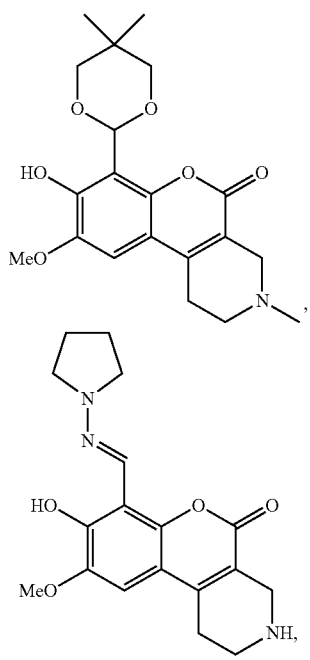

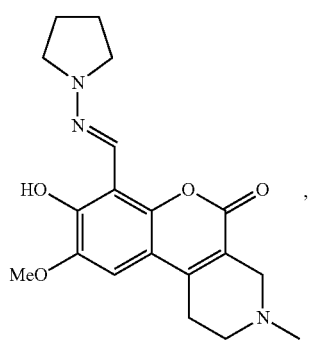

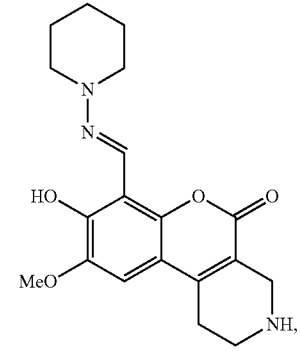

-continued

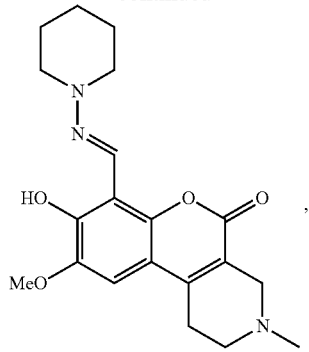

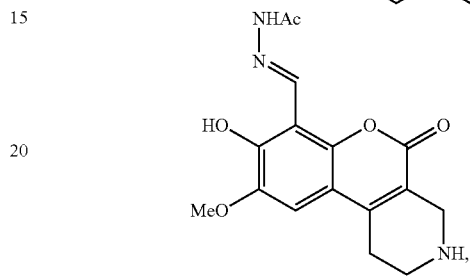

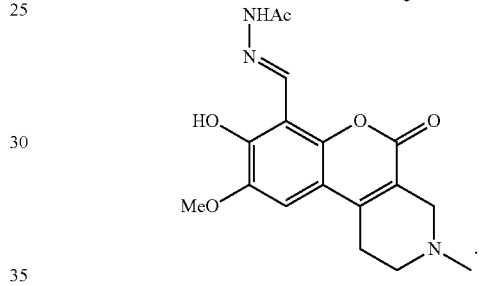

Embodiment 12 provides a pharmaceutical composition comprising at least one pharmaceutically acceptable carrier and the compound of any of Embodiments 1-11.

Embodiment 13 provides the composition of Embodiment 12, further comprising at least one additional anticancer agent.

Embodiment 14 provides the composition of Embodiment 13, wherein the at least one additional anticancer agent is ibrutinib, bortezomib, carfilzomib, ixazomib, lactacystin, disulfiram, epigallocatechin-3-gallate, marizomib, oprozomib (ONX-0912), delanzomib (CEP-18770), epoxomicin, beta-hydroxy beta-methylbutyrate, or a solvate or salt thereof.

Embodiment 15 provides a method of inhibiting IRE1's signaling in a cell, the method comprising contacting the cell with the compound of any of Embodiments 1-11 or the composition of any of Embodiments 12-14.

Embodiment 16 provides a method of inhibiting IRE1's RNase activity in a cell, the method comprising contacting the cell with the compound of any of Embodiments 1-11 or the composition of any of Embodiments 12-14.

Embodiment 17 provides a method of minimizing or abrogating thapsigargin (THG) inducible up-regulation of LOX-1 and T cells suppression in human normal polymorphonuclear cells (PMN) from healthy donors, the method comprising contacting the healthy donors' PMN cells with the compound of any of Embodiments 1-11 or the composition of any of Embodiments 12-14.

Embodiment 18 provides the method of any of Embodiments 15-17, wherein $R^3$ is a group that can be deprotected in vitro or in vivo to —OH, and wherein at least one applies: (a) the cell has a microenvironment that allows for deprotection of $R^3$ to —OH, or (b) the cell is further submitted to conditions that allow for deprotection of $R^3$ to —OH.

Embodiment 19 provides a method of inhibiting IRE1's RNase activity in a subject, the method comprising administering to the subject a therapeutically effective amount of the compound of any of Embodiments 1-11 or the composition of any of Embodiments 12-14.

Embodiment 20 provides a method of treating or preventing cancer in a subject, wherein the cancer is at least one selected from the group consisting of chronic lymphocytic leukemia (CLL), Burkitt's lymphoma, mantle cell lymphoma, breast cancer, and multiple myeloma, the method comprising administering to the subject a therapeutically effective amount of the compound of any of Embodiments 1-11 or the composition of any of Embodiments 12-14.

Embodiment 21 provides the method of Embodiment 20, wherein the cancer is c-myc positive and/or c-myc overexpressing.

Embodiment 22 provides the method of any of Embodiments 20-21, wherein the cancer is c-myc overexpressing Burkitt's lymphoma.

Embodiment 23 provides the method of any of Embodiments 20-21, wherein the cancer is myc-driven breast cancer.

Embodiment 24 provides the method of any of Embodiments 20-23, wherein the subject is further administered a BTK inhibitor.

Embodiment 25 provides the method of Embodiment 24, wherein the BTK inhibitor is ibrutinib.

Embodiment 26 provides a method of treating or preventing guest-versus-host disease (GVHD) in a subject, the method comprising administering to the subject a therapeutically effective amount of the compound of any of Embodiments 1-11 or the composition of any of Embodiments 12-14.

Embodiment 27 provides a method of enhancing efficacy of cancer immunotherapy in a subject, the method comprising administering to the subject a therapeutically effective amount of the compound of any of Embodiments 1-11 or the composition of any of Embodiments 12-14.

Embodiment 28 provides the method of Embodiment 27, wherein administration of the compound overcomes the immunosuppressive effect of UPR in a subject's tumor.

Embodiment 29 provides the method of any of Embodiments 27-28, wherein administration of the compound reprograms function of tumor-infiltrating myeloid cells in the subject.

Embodiment 30 provides the method of any of Embodiments 19-29, wherein $R^3$ is a group that can be deprotected in vitro or in vivo to —OH, and wherein at least one applies: (a) the cancer has a microenvironment that allows for deprotection of $R^3$ to —OH, or (b) the cancer is further submitted to conditions that allow for deprotection of $R^3$ to —OH.

Embodiment 31 provides the method of any of Embodiments 19-30, wherein the subject is a mammal.

Embodiment 32 provides a method of of reducing or minimizing production of secretory IgM (sIgM) in a cell, wherein the method comprises contacting the cell with an inositol-requiring enzyme 1 (IRE1 or IRE-1) RNAse inhibitor.

Embodiment 33 provides the method of Embodiment 32, wherein the cell is a B cell or a chronic lymphocytic leukemia (CLL) cell.

Embodiment 34 provides a method of reducing or minimizing levels and/or production of sIgM in a subject suffering from cancer, wherein the method comprises administering to the subject a therapeutically effective amount of a IRE1 RNAse inhibitor.

Embodiment 35 provides a method of minimizing or reducing number and/or activity of myeloid-derived suppressor cells (MDSCs) in a subject suffering from cancer, wherein the method comprises administering to the subject a therapeutically effective amount of a IRE1 RNAse inhibitor.

Embodiment 36 provides a method of treating or preventing a sIgM-assisted or sIgM-driven cancer in a subject, wherein the method comprises administering to the subject a therapeutically effective amount of a IRE1 RNAse inhibitor if levels of sIgM in a biological sample from the subject are higher than in a control biological sample.

Embodiment 37 provides a method of stimulating or increasing proliferation of anti-tumor T cells in a subject suffering from a sIgM-assisted or sIgM-driven cancer, wherein the method comprises administering to the subject a therapeutically effective amount of a IRE1 RNAse inhibitor.

Embodiment 38 provides a method of selecting a subject suffering from cancer for cancer treatment using a IRE1 RNAse inhibitor, wherein the method comprises: measuring levels of sIgM in a biological sample from the subject, and, if the levels of sIgM in the subject's biological sample are higher than in a control biological sample, the subject is selected for treatment with a IRE1 RNAse inhibitor.

Embodiment 39 provides the method of Embodiment 38, wherein the subject is administered a therapeutically effective amount of a IRE1 RNAse inhibitor.

Embodiment 40 provides the method of any of Embodiments 36 and 38-39, wherein the levels of sIgM in the subject's biological sample are higher than in a control biological sample by about 10%, 20%, 30%, 40%, 50%, 60%, 70%, 80%, 90%, 100%, 120%, 140%, 160%, 180%, 200%, 250%, 300%, 350%, 400%, 450%, 500%, or any fraction or multiple thereof.

Embodiment 41 provides the method of any of Embodiments 34-40, wherein the cancer comprises chronic lymphocytic leukemia (CLL) or lung cancer.

Embodiment 42 provides the method of Embodiment 41, wherein the lung cancer is Lewis lung carcinoma (LLC).

Embodiment 43 provides the method of any of Embodiments 32-42, wherein the IRE1 RNAse inhibitor is selected from the group consisting of:

(a) a compound of formula (I), or a salt or solvate thereof:

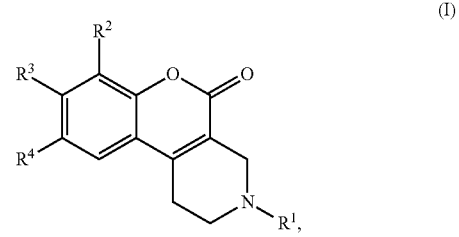

wherein in (I): $R^1$ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, ($C_3$-$C_8$ cycloalkyl)-C(=O)—, ($C_1$-$C_6$ alkyl)-OC(=O)—, ($C_2$-$C_6$ alkenyl)-OC (=O)—, (C₂-C₆ alkynyl)-OC(=O)—, and (C₃-C₈ cycloalkyl)-OC(=O)—, wherein the alkyl, alkenyl, alkynyl, or cycloalkyl are independently optionally substituted; $R^2$ is selected from the group consisting of optionally substituted 1,3-dioxolan-2-yl, optionally substituted 1,3-dioxan-2-yl, —CH=N—OR⁵, and —CH=N—NR⁵R⁶, wherein: $R^5$ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, and ($C_3$-$C_8$ cycloalkyl)-C(=O)—, wherein the alkyl, alkenyl, alkynyl, or cycloalkyl are independently optionally substituted, and $R^6$ is selected from the group consisting of H and $C_1$-$C_6$ alkyl, wherein the alkyl is optionally substituted, or $R^5$ and $R^6$ combine with the N atom to which they are bound to form an optionally substituted heterocyclyl or heteroaryl; $R^3$ is a group that can be deprotected in vitro or in vivo to —OH; and $R^4$ is selected from the group consisting of H, —OH, $C_1$-$C_6$ alkoxy, $C_2$-$C_6$ alkenyloxy, $C_2$-$C_6$ alkynyloxy, $C_3$-$C_8$ cycloalkoxy, HC(=O)O—, ($C_1$-$C_6$ alkyl)-C(=O)O—, ($C_2$-$C_6$ alkenyl)-C(=O)O—, ($C_2$-$C_6$ alkynyl)-C(=O)O—, and ($C_3$-$C_8$ cycloalkyl)-C(=O)O—, wherein the alkyl, alkenyl, alkynyl, or cycloalkyl are independently optionally substituted;

(b) a compound of formula:

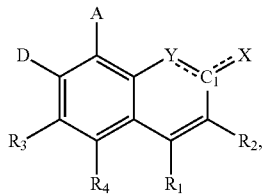

wherein: the dotted lines between Y and $C_1$ and between $C_1$ and X represent single or double bonds; A is a chalcogen containing moiety; D is selected from the group consisting of hydrogen, hydroxyl, carbonyl, alkoxy, halogen, thiol, thioalkyl, aryl, alkylaryl, and alkyl; $R^3$ and $R^4$ are independently selected from the group consisting of hydrogen, halogen, hydroxy, amino, alkyl, alkenyl, alkynyl, haloalkyl, cycloalkyl, heterocycloalkyl, alkylaryl, aryl, alkylheteroaryl, or heteroaryl, any of which is optionally substituted with carbonyl, alkyl, amino, amido, —NR⁶R⁷, —C(O)NR⁶R⁷, alkoxy, alkylhydroxy, cycloalkyl, heterocycloalkyl, aryl, heteroaryl, carbonyl, halo, hydroxy, thiol, cyano, and nitro; Y is selected from the group consisting of S, N, O, and C, wherein, when Y is C, the dotted line between Y and $C_1$ in the ring represents a double bond and the dotted line between $C_1$ and X is a single bond; and wherein, when Y is S, N, or O, the dotted line between Y and $C_1$ in the ring represents a single bond and the dotted line between $C_1$ and X represents a double bond; X is selected from the group consisting of hydrogen, oxygen, halogen, hydroxy, amino, thiol, thioalkyl, alkyl, alkenyl, alkynyl, haloalkyl, cycloalkyl, heterocycloalkyl, alkylaryl, aryl, alkylheteroaryl, or heteroaryl, any of which is optionally substituted with acetyl, alkyl, amino, amido, —NR⁶R⁷, —C(O)NR⁶R⁷, alkoxy, alkylhydroxy, cycloalkyl, heterocycloalkyl, aryl, heteroaryl, carbonyl, halo, hydroxy, thiol, cyano, and nitro; $R^1$ and $R^2$ are independently selected from the group consisting of hydrogen, benzoate, alkyl, heteroalkyl, alkenyl, heteroalkenyl, alkynyl, haloalkyl, cycloalkyl, heterocycloalkyl, alkylaryl, aryl, alkylheteroaryl, or heteroaryl, any of which is optionally substituted with acetyl, alkyl, amino, amido, NR⁶R⁷, C(O)NR⁶R⁷, alkoxy, alkylhydroxy, cycloalkyl, heterocycloalkyl, aryl, heteroaryl, carbonyl, halo, hydroxy, thiol, cyano, and nitro; or $R^1$ and $R^2$ together with the atoms to which they are attached form a 5-7 membered cyclic moiety wherein any of the additional atoms are optionally heteroatoms and the 5 to 7-membered ring is, optionally, a heterocyclic structure that is optionally substituted; and $R^6$ and $R^7$ are independently H or alkyl; or $R^6$ and $R^7$ together with the atoms to which they are attached form a 3-7 membered cyclic moiety wherein any of the additional atoms are optionally heteroatoms and the 3 to 7-membered ring is, optionally, a heterocyclic structure that is optionally substituted; or a pharmaceutically acceptable salt thereof;

(c) 1-[4-(8-amino-3-tert-butylimidazo[1,5-a]pyrazin-1-yl)naphthalen-1-yl]-3-[3-(trifluoromethyl)phenyl]urea, or a salt or solvate thereof, or any other IRE1 signaling inhibitor compound recited in US 20160024094A1;

(d) toyomycin (4-Aminopyrrolo[2,3-d]pyrimidine-5-carbonitrile 7-(β-D-ribofuranoside), 7-Deaza-7-cyanoadenosine), or a salt or solvate thereof;

(e) 4μ8C (7-hydroxy-4-methyl-2-oxo-2H-1-benzopyran-8-carboxaldehyde), or a salt or solvate thereof;

(f) STF-083010 (N-[2-Hydroxynaphthalen-1-yl)methylidene]thiophene-2-sulfonamide, N-[(2-Hydroxy-1-naphthyl)methylene]-2-thiophenesulfonamide), or a salt or solvate thereof;

(g) any IRE1 signaling inhibitor compound recited in WO 2017152117A1;

(h) any salicylaldehyde that acts as a IRE1-signaling inhibitor;

(i) MKC-3946 (2-hydroxy-6-(5-(4-methylpiperazine-1-carbonyl)thiophen-2-yl)-1-naphthaldehyde), or a salt or solvate thereof;

(j) any IRE1 signaling inhibitor compound recited in U.S. Pat. No. 9,359,299.

Embodiment 44 provides the method of Embodiment 43, wherein the compound is 7-(1,3-dioxan-2-yl)-8-hydroxy-1,2,3,4-tetrahydro-5H-chromeno[3,4-c]pyridin-5-one, or a salt or solvate thereof.

Embodiment 45 provides the method of any of Embodiments 34-44, wherein the subject is further administered at least one additional agent to treat or prevent the cancer.

Embodiment 46 provides the method of any of Embodiments 34-45, wherein the subject is a mammal.

Embodiment 47 provides the method of Embodiment 46, wherein the mammal is a human.

Embodiment 48 provides a kit for treating or preventing a sIgM-assisted or sIgM-driven cancer in a subject, the kit comprising: (a) at least one reagent to determine levels of sIgM in a biological sample of a subject; and (b) instructions reciting that, if levels of sIgM in the subject's biological sample are higher than in a reference sample, the subject is to be administered a therapeutically effective amount of a IRE1 RNAse inhibitor.

Embodiment 49 provides the kit of Embodiment 48, further comprising an amount of the IRE1 RNAse inhibitor.

What is claimed is:

1. A compound of formula (I), or a salt or solvate thereof:

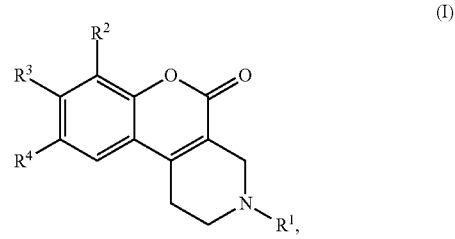

wherein:

R¹ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, ($C_3$-$C_8$ cycloalkyl)-C(=O)—, ($C_1$-$C_6$ alkyl)-OC(=O)—, ($C_2$-$C_6$ alkenyl)-OC(=O)—, ($C_2$-$C_6$ alkynyl)-OC(=O)—, and ($C_3$-$C_8$ cycloalkyl)-OC(=O)—, wherein the alkyl, alkenyl, alkynyl, or cycloalkyl are independently optionally substituted;

R² is selected from the group consisting of optionally substituted 1,3-dioxolan-2-yl, optionally substituted 1,3-dioxan-2-yl, —CH=N—OR⁵, and —CH=N—NR⁵R⁶, wherein:

R⁵ is selected from the group consisting of H, $C_1$-$C_6$ alkyl, $C_2$-$C_6$ alkenyl, $C_2$-$C_6$ alkynyl, $C_3$-$C_8$ cycloalkyl, HC(=O)—, ($C_1$-$C_6$ alkyl)-C(=O)—, ($C_2$-$C_6$ alkenyl)-C(=O)—, ($C_2$-$C_6$ alkynyl)-C(=O)—, and ($C_3$-$C_8$ cycloalkyl)-C(=O)—, wherein the alkyl, alkenyl, alkynyl, or cycloalkyl are independently optionally substituted, and R⁶ is selected from the group consisting of H and $C_1$-$C_6$ alkyl, wherein the alkyl is optionally substituted, or R⁵ and R⁶ combine with the N atom to which they are bound to form an optionally substituted heterocyclyl or heteroaryl;

R³ is —OH or a group that can be deprotected in vitro or in vivo to —OH; and

R⁴ is selected from the group consisting of $C_1$-$C_6$ alkoxy, $C_2$-$C_6$ alkenyloxy, $C_2$-$C_6$ alkynyloxy, $C_3$-$C_8$ cycloalkoxy, HC(=O)O—, ($C_1$-$C_6$ alkyl)-C(=O)O—, ($C_2$-$C_6$ alkenyl)-C(=O)O—, ($C_2$-$C_6$ alkynyl)-C(=O)O—, and ($C_3$-$C_8$ cycloalkyl)-C(=O)O—, wherein the alkyl, alkenyl, alkynyl, or cycloalkyl are independently optionally substituted.

2. The compound of claim 1, wherein at least one applies:

each heterocyclyl is independently selected from the group consisting of imidazolyl, dihydroimidazolyl, piperidinyl, piperazinyl, morpholinyl, pyrrolidinyl, and tetrahydropyrimidinyl;

each heteroaryl is independently selected from the group consisting of pyridinyl, pyrimidinyl, pyrrolyl, oxazolyl, isoxazolyl, oxadiazolyl, imidazolyl, pyrazolyl, and triazolyl.

3. The compound of claim 1, wherein at least one applies:

each occurrence of alkyl, alkenyl, alkynyl, or cycloalkyl is independently optionally substituted with at least one substituent selected from the group consisting of $C_1$-$C_6$ alkyl, halogen, —CN, —OR, phenyl, and —N(R)(R), wherein each occurrence of R is independently H, $C_1$-$C_6$ alkyl, or $C_3$-$C_8$ cycloalkyl;

each occurrence of phenyl, heterocyclyl, or heteroaryl is independently optionally substituted with at least one substituent selected from the group consisting of $C_1$-$C_6$ alkyl, $C_1$-$C_6$ haloalkyl, $C_1$-$C_6$ alkoxy, $C_1$-$C_6$ haloalkoxy, halogen, —CN, —C(=O)OR, —OR, —N(R)(R), —NO₂, —S(=O)₂N(R)(R), acyl, and $C_1$-$C_6$ alkoxycarbonyl, wherein each occurrence of R is independently H, $C_1$-$C_6$ alkyl, or $C_3$-$C_8$ cycloalkyl.

4. The compound of claim 1, wherein R² is selected from the group consisting of:

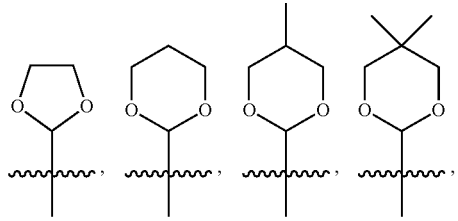

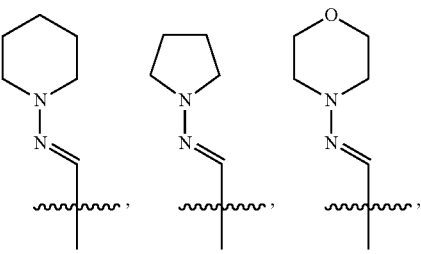

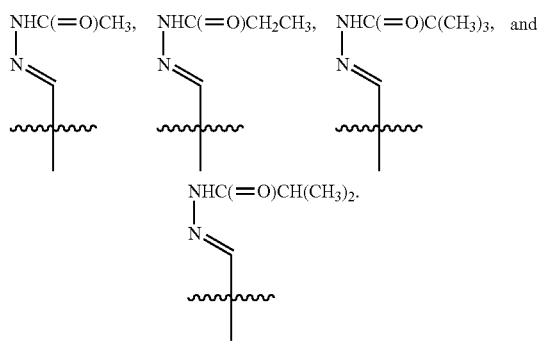

5. The compound of claim 1, wherein R³ is a group that can be deprotected in vitro or in vivo to —OH.

6. The compound of claim 5, wherein R³ is selected from the group consisting of optionally substituted o-nitrobenzyloxy groups, optionally substituted benzoin groups, (OH)₂B— and any ether derivatives thereof, optionally substituted boronobenzyl groups and any ether derivatives thereof, optionally substituted aryl-S(=O)₂O— or heteroaryl-S(=O)₂O— groups, and optionally substituted acyloxy or aryloxy groups.

7. The compound of claim 1, which is selected from the group consisting of:

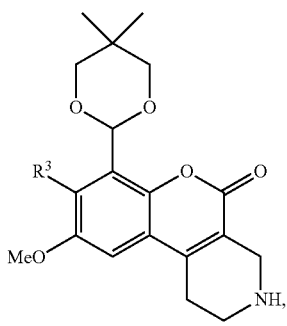

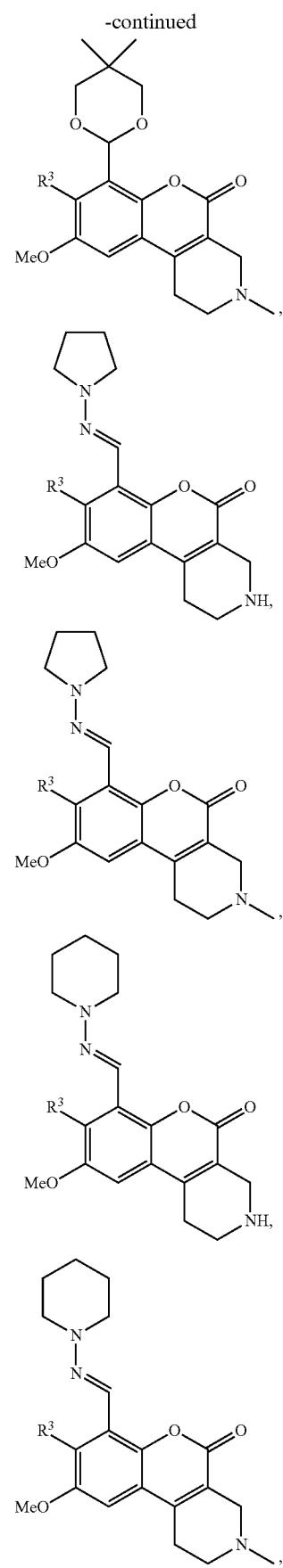
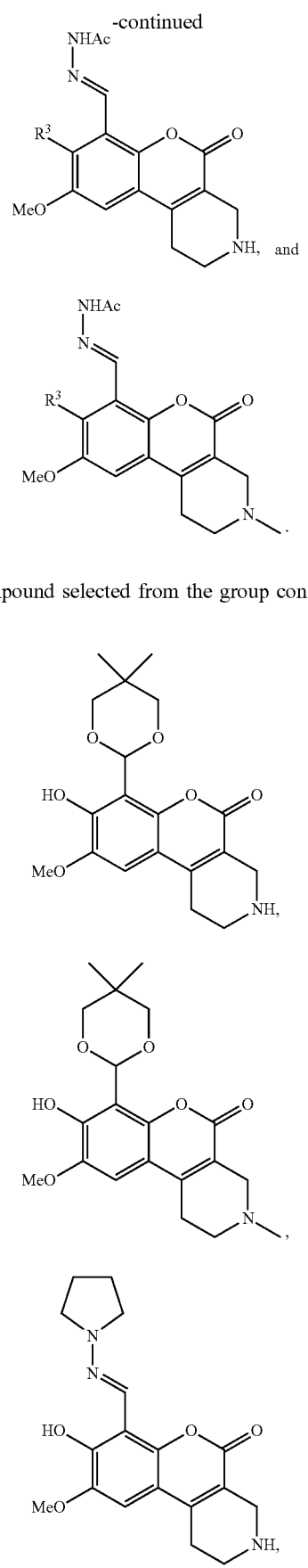
8. A compound selected from the group consisting of:

-continued

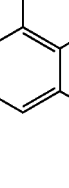

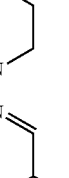

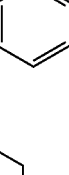

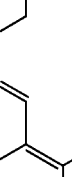

or a salt or solvate thereof.

9. A pharmaceutical composition comprising at least one pharmaceutically acceptable carrier and the compound of claim 1.

10. The pharmaceutical composition of claim 9, further comprising at least one additional anticancer agent selected from the group consisting of ibrutinib, bortezomib, carfilzomib, ixazomib, lactacystin, disulfiram, epigallocatechin-3-gallate, marizomib, oprozomib (ONX-0912), delanzomib (CEP-18770), epoxomicin, beta-hydroxy beta-methylbutyrate, or a solvate or salt thereof.

11. A compound of formula (I), or a salt or solvate thereof:

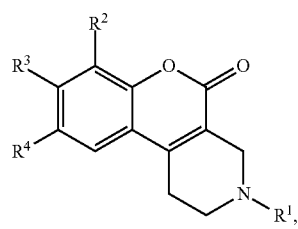

(I)

wherein:
R$^1$ is selected from the group consisting of H, C$_1$-C$_6$ alkyl, C$_2$-C$_6$ alkenyl, C$_2$-C$_6$ alkynyl, C$_3$-C$_8$ cycloalkyl, HC(=O)—, (C$_1$-C$_6$ alkyl)-C(=O)—, (C$_2$-C$_6$ alkenyl)-C(=O)—, (C$_2$-C$_6$ alkynyl)-C(=O)—, (C$_3$-C$_8$ cycloalkyl)-C(=O)—, (C$_1$-C$_6$ alkyl)-OC(=O)—, (C$_2$-C$_6$ alkenyl)-OC(=O)—, (C$_2$-C$_6$ alkynyl)-OC(=O)—, and (C$_3$-C$_8$ cycloalkyl)-OC(=O)—,
wherein the alkyl, alkenyl, alkynyl, or cycloalkyl are independently optionally substituted;
R$^2$ is selected from the group consisting of 1,3-dioxolan-2-yl, 5-methyl-1,3-dioxan-2-yl, 5,5-dimethyl-1,3-dioxan-2-yl, —CH=N—OR$^5$, and —CH=N—NR$^5$R$^6$, wherein:
R$^5$ is selected from the group consisting of H, C$_1$-C$_6$ alkyl, C$_2$-C$_6$ alkenyl, C$_2$-C$_6$ alkynyl, C$_3$-C$_8$ cycloalkyl, HC(=O)—, (C$_1$-C$_6$ alkyl)-C(=O)—, (C$_2$-C$_6$ alkenyl)-C(=O)—, (C$_2$-C$_6$ alkynyl)-C(=O)—, and (C$_3$-C$_8$ cycloalkyl)-C(=O)—,
wherein the alkyl, alkenyl, alkynyl, or cycloalkyl are independently optionally substituted, and
R$^6$ is selected from the group consisting of H and C$_1$-C$_6$ alkyl, wherein the alkyl is optionally substituted,
or R$^5$ and R$^6$ combine with the N atom to which they are bound to form an optionally substituted heterocyclyl or heteroaryl;
R$^3$ is —OH or a group that can be deprotected in vitro or in vivo to —OH; and
R$^4$ is selected from the group consisting of H, —OH, C$_1$-C$_6$ alkoxy, C$_2$-C$_6$ alkenyloxy, C$_2$-C$_6$ alkynyloxy, C$_3$-C$_8$ cycloalkoxy, HC(=O)O—, (C$_1$-C$_6$ alkyl)-C(=O)O—, (C$_2$-C$_6$ alkenyl)-C(=O)O—, (C$_2$-C$_6$ alkynyl)-C(=O)O—, and (C$_3$-C$_8$ cycloalkyl)-C(=O)O—,
wherein the alkyl, alkenyl, alkynyl, or cycloalkyl are independently optionally substituted.

12. The compound of claim 11, wherein at least one applies:
each heterocyclyl is independently selected from the group consisting of imidazolyl, dihydroimidazolyl, piperidinyl, piperazinyl, morpholinyl, pyrrolidinyl, and tetrahydropyrimidinyl;
each heteroaryl is independently selected from the group consisting of pyridinyl, pyrimidinyl, pyrrolyl, oxazolyl, isoxazolyl, oxadiazolyl, imidazolyl, pyrazolyl, and triazolyl.

13. The compound of claim 11, wherein at least one applies:

each occurrence of alkyl, alkenyl, alkynyl, or cycloalkyl is independently optionally substituted with at least one substituent selected from the group consisting of $C_1$-$C_6$ alkyl, halogen, —CN, —OR, phenyl, and —N(R)(R), wherein each occurrence of R is independently H, $C_1$-$C_6$ alkyl, or $C_3$-$C_8$ cycloalkyl;

each occurrence of phenyl, heterocyclyl, or heteroaryl is independently optionally substituted with at least one substituent selected from the group consisting of $C_1$-$C_6$ alkyl, $C_1$-$C_6$ haloalkyl, $C_1$-$C_6$ alkoxy, $C_1$-$C_6$ haloalkoxy, halogen, —CN, —C(=O)OR, —OR, —N(R)(R), —NO$_2$, —S(=O)$_2$N(R)(R), acyl, and $C_1$-$C_6$ alkoxycarbonyl,
   wherein each occurrence of R is independently H, $C_1$-$C_6$ alkyl, or $C_3$-$C_8$ cycloalkyl.

14. The compound of claim 11, wherein $R^2$ is selected from the group consisting of:

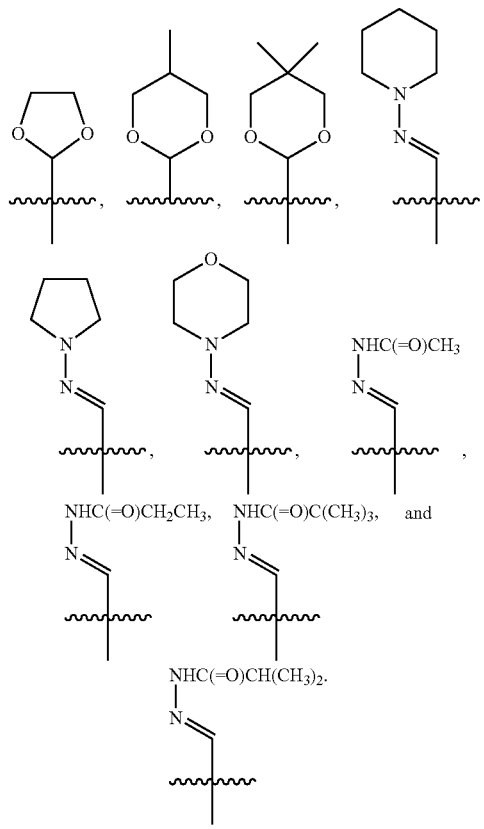

15. The compound of claim 11, wherein $R^3$ is a group that can be deprotected in vitro or in vivo to —OH.

16. The compound of claim 15, wherein $R^3$ is selected from the group consisting of optionally substituted o-nitrobenzyloxy groups, optionally substituted benzoin groups, (OH)$_2$B— and any ether derivatives thereof, optionally substituted boronobenzyl groups and any ether derivatives thereof, optionally substituted aryl-S(=O)$_2$O— or heteroaryl-S(=O)$_2$O— groups, and optionally substituted acyloxy or aryloxy groups.

17. The compound of claim 11, which is selected from the group consisting of:

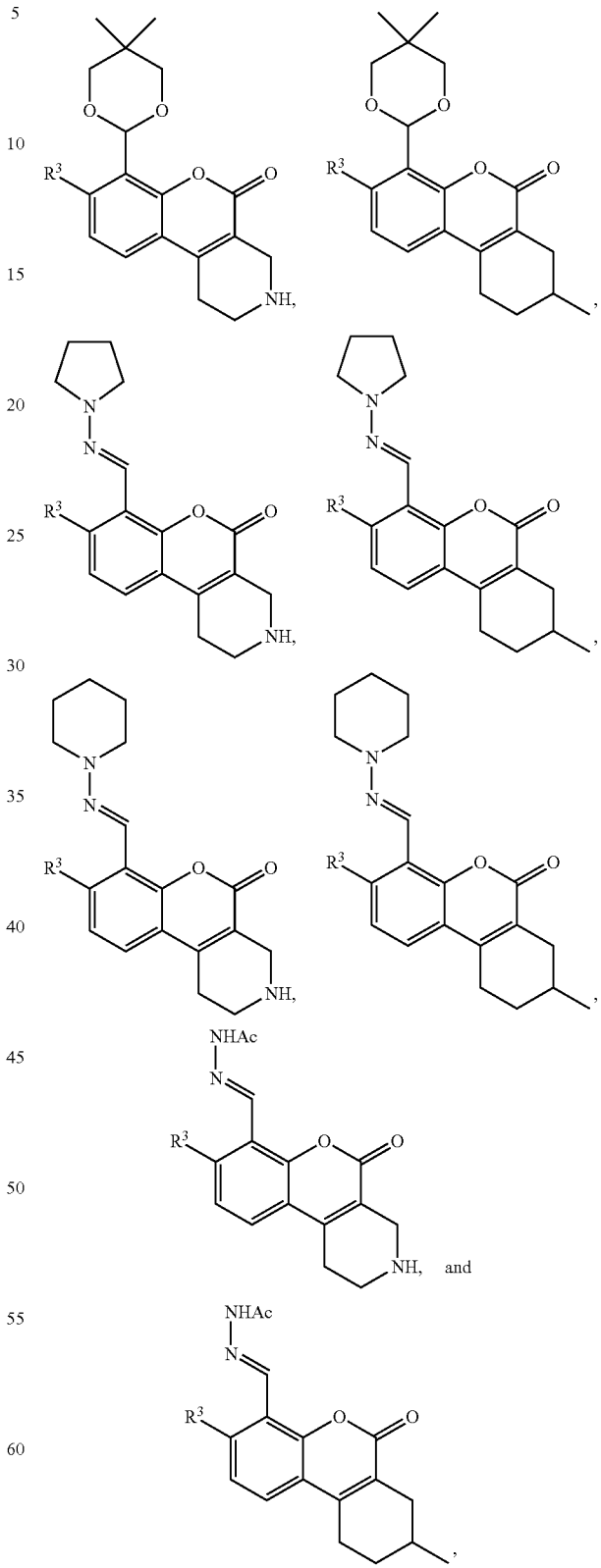

or a salt or solvate thereof.

18. A compound selected from the group consisting of

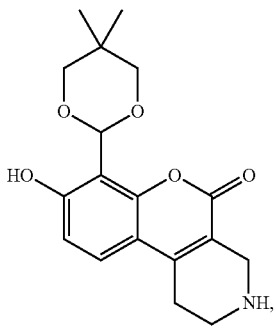

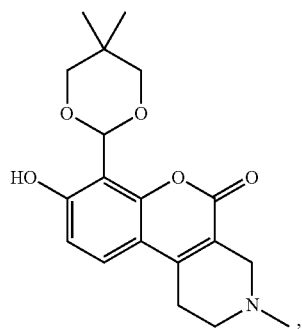

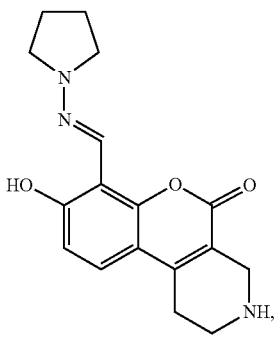

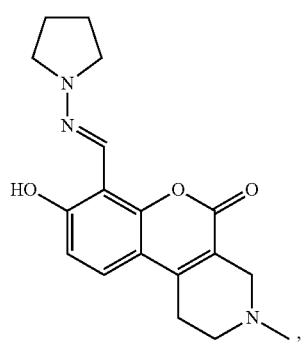

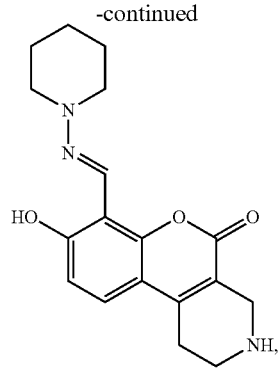

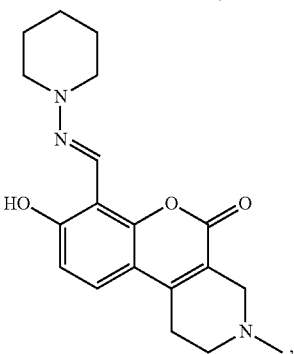

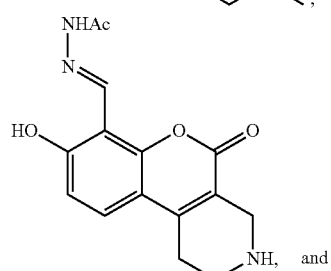

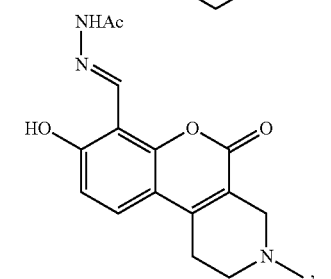 and

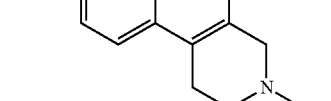

or a salt or solvate thereof.

19. A pharmaceutical composition comprising at least one pharmaceutically acceptable carrier and the compound of claim 11.

20. The pharmaceutical composition of claim 19, further comprising at least one additional anticancer agent selected from the group consisting of ibrutinib, bortezomib, carfilzomib, ixazomib, lactacystin, disulfiram, epigallocatechin-3-gallate, marizomib, oprozomib (ONX-0912), delanzomib (CEP-18770), epoxomicin, beta-hydroxy beta-methylbutyrate, or a solvate or salt thereof.

* * * * *